(12) United States Patent
Elban et al.

(10) Patent No.: US 11,945,826 B2
(45) Date of Patent: Apr. 2, 2024

(54) HYDROXYPYRIDOXAZEPINES AS NRF2 ACTIVATORS

(71) Applicant: GLAXOSMITHKLINE INTELLECTUAL PROPERTY DEVELOPMENT LIMITED, Middlesex (GB)

(72) Inventors: Mark Elban, Collegeville, PA (US); Michal Pawel Glogowski, Collegeville, PA (US); Michael Clinton Koetting, Collegeville, PA (US); Brian Griffin Lawhorn, Collegeville, PA (US); Jay M. Matthews, Collegeville, PA (US); Jaclyn Renee Patterson, Collegeville, PA (US)

(73) Assignee: GlaxoSmithKline Intellectual Property Development Limited, Stevenage (GB)

( * ) Notice: Subject to any disclaimer, the term of this patent is extended or adjusted under 35 U.S.C. 154(b) by 225 days.

(21) Appl. No.: 17/429,088

(22) PCT Filed: Feb. 11, 2020

(86) PCT No.: PCT/IB2020/051100
§ 371 (c)(1),
(2) Date: Aug. 6, 2021

(87) PCT Pub. No.: WO2020/165776
PCT Pub. Date: Aug. 20, 2020

(65) Prior Publication Data
US 2022/0204526 A1  Jun. 30, 2022

Related U.S. Application Data

(60) Provisional application No. 62/931,877, filed on Nov. 7, 2019, provisional application No. 62/806,201, filed on Feb. 15, 2019.

(51) Int. Cl.
*C07D 498/04* (2006.01)
*C07D 498/10* (2006.01)

(52) U.S. Cl.
CPC ......... *C07D 498/04* (2013.01); *C07D 498/10* (2013.01); *C07B 2200/13* (2013.01)

(58) Field of Classification Search
CPC .......................... C07D 498/04; C07D 498/10
See application file for complete search history.

(56) References Cited

U.S. PATENT DOCUMENTS

| 10,144,731 | B2 | 12/2018 | Davies et al. |
| 10,272,095 | B2 | 4/2019 | Kerns et al. |
| 10,485,806 | B2 | 11/2019 | Kerns et al. |
| 10,604,509 | B2 | 3/2020 | Kerns et al. |
| 11,028,099 | B2 | 6/2021 | Brooks et al. |

FOREIGN PATENT DOCUMENTS

| WO | WO 2015/092713 | 6/2015 |
| WO | WO 2016/202253 A1 | 12/2016 |
| WO | WO 2016/203400 | 12/2016 |
| WO | WO 2016/203401 | 12/2016 |
| WO | WO2018/104766 | 6/2018 |
| WO | WO2018/109646 | 6/2018 |

OTHER PUBLICATIONS

Co-pending U.S. Appl. No. 16/675,634, filed Nov. 6, 2019, now allowed.

*Primary Examiner* — Rebecca L Anderson
(74) *Attorney, Agent, or Firm* — Nora L. Stein

(57) ABSTRACT

The present invention relates hydroxypyridoxazepine compounds, methods of making them, pharmaceutical compositions containing them and their use as Nrf2 activators. In particular, the invention relates to compounds of Formula (I), and pharmaceutically acceptable salts thereof, or a tautomer thereof, or a hydrate thereof.

31 Claims, 12 Drawing Sheets

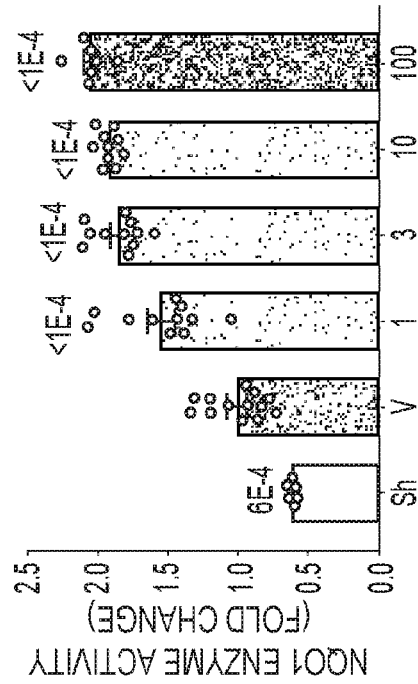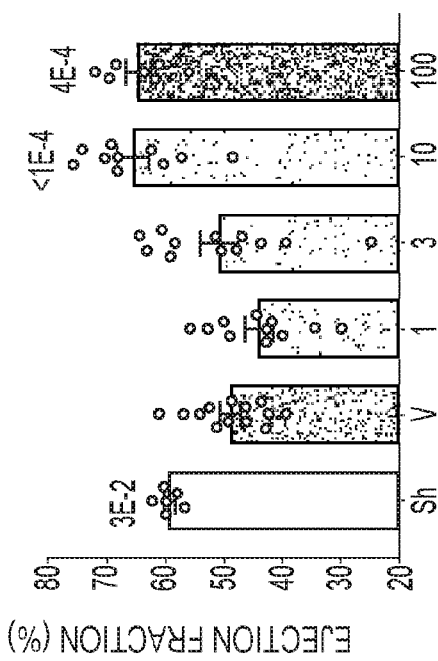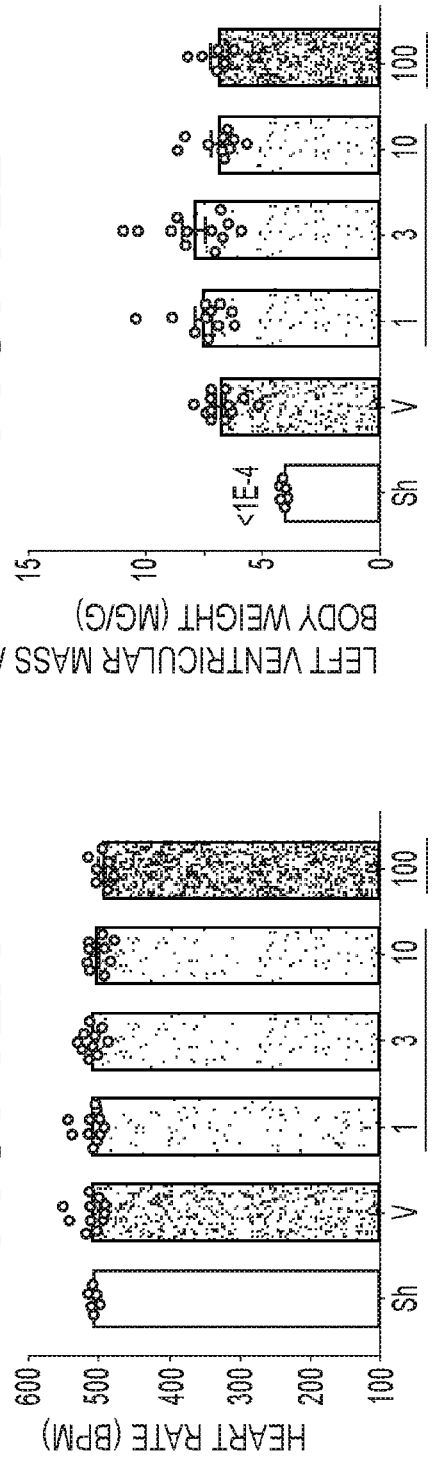

HYDROXYPYRIDOXAZEPINES AS NRF2 ACTIVATORS

This application is a § 371 national phase entry of International Application No. PCT/IB2020/051100, filed 11 Feb. 2020, which claims the benefit of U.S. Provisional Application Nos. 62/931,877, filed 7 Nov. 2019 and 62/806,201, filed 15 Feb. 2019.

FIELD OF THE INVENTION

The present invention relates to hydroxypyridoxazepine compounds, methods of making them, pharmaceutical compositions containing them and their use as Nrf2 activators.

BACKGROUND OF THE INVENTION

Nrf2 (NF-E2 related factor 2) is a member of the cap-n-collar family of transcription factors containing a characteristic basic-leucine zipper motif. Under basal conditions, Nrf2 levels are tightly controlled by the cytosolic actin-bound repressor, KEAP1 (Kelch-like ECH associating protein 1), which binds to Nrf2 and targets it for ubiquitylation and proteasomal degradation via the Cul3-based E3-ubiquitin ligase complex. Under conditions of oxidative stress, DJ1 (PARK7) is activated and stabilizes Nrf2 protein by preventing Nrf2 from interacting with KEAP1. Also, modification of reactive cysteines on KEAP1 can cause a conformational change in KEAP1 that alters Nrf2 binding and promotes Nrf2 stabilization. Thus, the levels of Nrf2 in the cell are usually kept low in normal conditions but the system is designed to respond quickly to environmental stress by increasing Nrf2 levels and thus downstream Nrf2 activity.

Inappropriately low Nrf2 activity in the face of on-going oxidative stress appears to be a pathological mechanism underlying chronic obstructive pulmonary disease (COPD). Yamada, K., et al. *BMC Pulmonary Medicine,* 2016, 16: 27. This may be a result of an altered equilibrium between Nrf2 activators with both inappropriate lack of positive activators such as DJ1, and overabundance of negative activators such as Keap1 and Bach1. Therefore, restoration of Nrf2 activity in the lungs of COPD patients should result in repair of the imbalance and mitigation of deleterious processes such as apoptosis of structural cells (including alveolar epithelial and endothelial cells) and inflammation. The results of these effects would be enhanced cytoprotection, preservation of lung structure, and structural repair in the COPD lung, thus slowing disease progression. Therefore, Nrf2 activators may treat COPD (Boutten, A., et al. 2011. *Trends Mol. Med.* 17:363-371) and other respiratory diseases, including asthma, Acute Lung Injury (ALI) (Cho, H. Y., and Kleeberger, S. R., 2015, *Arch Toxicol.* 89:1931-1957; Zhao, H. et al., 2017, *Am J Physiol Lung Clee Mol Physiol* 312:L155-L162, first published Nov. 18, 2016; doi:10.1152/ajplung.00449.2016), Acute Respiratory Distress Syndrome (ARDS) and pulmonary fibrosis (Cho, H. Y., and Kleeberger, S. R. 2010. *Toxicol. Appl. Pharmacol.* 244:43-56).

The therapeutic potential of an Nrf2 activator is exemplified in pulmonary macrophages from COPD patients where Nrf2 pathway appears maladaptive. These cells have impaired bacterial phagocytosis compared with similar cells from control patients, and this effect is reversed by the addition of Nrf2 activators in vitro. Therefore, in addition to the effects mentioned above, restoration of appropriate Nrf2 activity could also rescue COPD exacerbations by reducing lung infection.

This is demonstrated by the Nrf2 activator, Sulforaphane, which increases the expression of Macrophage Receptor with Collagenous structure (MARCO) by COPD macrophages and alveolar macrophages from cigarette smoke-exposed mice, thereby improving in these cells' bacterial phagocytosis (*Pseudomonas aeruginosa,* non-typable *Haemophilus influenzae*) and bacterial clearance both ex vivo and in vivo. (Harvey, C. J., et al. 2011. *Sci. Transl. Med.* 3:78ra32).

The therapeutic potential of targeting Nrf2 in the lung is not limited to COPD. Rather, targeting the Nrf2 pathway could provide treatments for other human lung and respiratory diseases that exhibit oxidative stress components such as chronic asthma and acute asthma, lung disease secondary to environmental exposures including but not limited to ozone, diesel exhaust and occupational exposures, fibrosis, acute lung infection (e.g., viral (Noah, T. L. et al. 2014. PLoS ONE 9(6): e98671), bacterial or fungal), chronic lung infection, α1 antitrypsin disease, ALI, ARDS and cystic fibrosis (C F, Chen, J. et al. 2008. *PLoS One.* 2008; 3(10): e3367).

A therapy that targets the Nrf2 pathway also has many potential uses outside the lung and respiratory system. Many of the diseases for which an Nrf2 activator may be useful are autoimmune diseases (psoriasis, IBD, MS), suggesting that an Nrf2 activator may be useful in autoimmune diseases in general.

In the clinic, a drug targeting the Nrf2 pathway (bardoxolone methyl) has shown efficacy in diabetic patients with diabetic nephropathy/chronic kidney disease (CKD) (Aleksunes, L. M., et al. 2010. *J. Pharmacol. Exp. Ther.* 335:2-12), though phase III trials with this drug in patients with the most severe stage of CKD were terminated. Furthermore, there is evidence to suspect that such a therapy would be effective in sepsis-induced acute kidney injury, other acute kidney injury (AKI) (Shelton, L. M., et al. 2013. *Kidney International.* June 19. doi: 10.1038/ki.2013.248.), and kidney disease or malfunction seen during kidney transplantation.

In the cardiac area, bardoxolone methyl is currently under investigation in patients with Pulmonary Arterial Hypertension and so a drug targeting Nrf2 by other mechanisms may also be useful in this disease area. Oxidative stress is increased in the diseased myocardium, resulting in accumulation of reactive oxygen species (ROS) which impairs cardiac function [*Circ* (1987) 76(2); 458-468] and increases susceptibility to arrhythmia [*J of Mol & Cell Cardio* (1991) 23(8); 899-918] by a direct toxic effect of increased necrosis and apoptosis [*Circ Res* (2000) 87(12); 1172-1179]. In a mouse model of pressure overload (TAC), Nrf2 gene and protein expression is increased during the early stage of cardiac adaptive hypertrophy but decreased in the later stage of maladaptive cardiac remodeling associated with systolic dysfunction [*Arterioscler Thromb Vasc Biol* (2009) 29(11); 1843-5 1850; *PLOS ONE* (2012) 7(9); e44899]. In addition, Nrf2 activation has been shown to suppress myocardial oxidative stress as well as cardiac apoptosis, fibrosis, hypertrophy, and dysfunction in mouse models of pressure overload [*Arterioscler Thromb Vasc Biol* (2009) 29(11); *J of Mol & Cell Cardio* (2014) 72; 305-315; and 1843-1850; *PLOS ONE* (2012) 7(9); e44899]. Nrf2 activation has also been shown to protect against cardiac I/R injury in mice 10 [*Circ Res* (2009) 105(4); 365-374; *J of Mol & Cell Cardio* (2010) 49(4); 576-586] and reduce myocardial oxidative damage following cardiac I/R injury in rat. Therefore, a drug targeting Nrf2 by other mechanisms may be useful in a variety of cardiovascular diseases including but not limited to atherosclerosis, hypertension, and heart failure (Oxidative Medicine and Cellular Longevity Volume 2013 (2013), Article ID 104308, 10 pages), acute coronary syndrome, myocardial infarction, myocardial repair, cardiac remodeling, cardiac arrhythmias, heart failure with preserved ejection fraction, heart failure with reduced ejection fraction and diabetic cardiomyopathy. Recently, improvement in left ventricular function was shown in rats with ischemic cardiac injury using Nrf2 activator bardoxolone methyl [Tian, C, et al., JPET, doi: 10.1124/jpet.119.261792 (Oct. 10, 2019)].

A drug activating the Nrf2 pathway could also be useful for treatment of several neurodegenerative diseases including Parkinson's disease (PD), Alzheimer's disease (AD), amyotrophic lateral sclerosis (ALS) (Brain Res. 2012 Mar. 29; 1446:109-18. 2011.12.064. Epub 2012 Jan. 12.), Huntington's disease (HD), multiple sclerosis (MS), spinal cord injury, traumatic brain injury, ischemic stroke, stroke, Creutzfeldt-Jakob Disease, fatal familial insomnia, Gerstmann-Sträussler-Scheinker syndrome, and related prion diseases, progressive supranuclear palsy, chronic traumatic encephalopathy (CTE), neurodegeneration, dementias, frontotemporal dementias, tauopathies, retinitis pigmentosa, Pick's disease, Neimann-Pick's disease, amyloidosis, and cognitive impairment (FEBS 201 8, doi: 10.1111/febs.14379, Pharmacology & Therapeutics 2016, 157, 84-104). Multiple in vivo models have shown that Nrf2 KO mice are more sensitive to neurotoxic insults than their wild-type counterparts. Treatment of rats with the Nrf2 activator tert-butylhydroquinone (tBHQ) reduced cortical damage in rats in a cerebral ischemia-reperfusion model, and cortical glutathione levels were increased in Nrf2 wild-type but not KO mice after administration of tBHQ (Shih, A. Y., et al. 2005. *J. Neurosci.* 25: 10321-10335). Tecfidera™ (dimethyl fumarate), which activates Nrf2 among other targets, is approved in the U.S. to treat relapsing-remitting multiple sclerosis (MS). Activation of Nrf2 may also help treat cases of Friedreich's Ataxia, where increased sensitivity to oxidative stress and impaired Nrf2 activation has been reported (Paupe V., et al, 2009. PLoS One; 4(1):e4253. Omaveloxolone (RTA-408) is also in clinical trials for Friedreich's Ataxia.

There is preclinical evidence of the specific protective role of the Nrf2 pathway in models of inflammatory bowel disease (IBD, Crohn's Disease and Ulcerative Colitis) and/or colon cancer (Khor, T. O., et al 2008. *Cancer Prev. Res. (Phila)* 1:187-191).

Age-related macular degeneration (AMD) is a common cause of vision loss in people over the age of 50. Cigarette smoking is a major risk factor for the development of non-neovascular (dry) AMD and perhaps also neovascular (wet) AMD. Findings in vitro and in preclinical species support the notion that the Nrf2 pathway is involved in the anti-oxidant response of retinal epithelial cells and modulation of inflammation in pre-clinical models of eye injury (Schimel, et al. 2011. *Am. J. Pathol.* 178:2032-2043). Fuchs Endothelial Corneal Dystrophy (FECD) is a progressive, blinding disease characterized by corneal endothelial cells apoptosis. It is a disease of aging and increased oxidative stress related to low levels of Nrf2 expression and/or function (Biter, M. S., et al. 2012. *Invest Ophthalmol. Vis. Sci.* Aug. 24, 2012 vol. 53 no. 9 5806-5813). In addition, an Nrf2 activator may be useful in uveitis or other inflammatory eye conditions.

Non-alcoholic steatohepatitis (NASH) is a disease of fat deposition, inflammation, and damage in the liver that occurs in patients who drink little or no alcohol. In pre-clinical models, development of NASH is greatly accelerated in KO mice lacking Nrf2 when challenged with a methionine- and choline-deficient diet (Chowdhry S., et al. 2010. *Free Rad. Biol. & Med.* 48:357-371). Administration of the Nrf2 activators oltipraz and NK-252 in rats on a choline-deficient L-amino acid-defined diet significantly attenuated progression of histologic abnormalities, especially hepatic fibrosis (Shimozono R. et al. 2012. *Molecular Pharmacology.* 84:62-70). Other liver diseases that may be amenable to Nrf2 modulation are toxin-induced liver disease (e.g., acetaminophen-induced hepatic disease), viral hepatitis, and cirrhosis (Oxidative Medicine and Cellular Longevity Volume 2013 (2013), Article ID 763257, 9 page).

Recent studies have also begun to elucidate the role of ROS in skin diseases such as psoriasis. A study in psoriasis patients showed an increase in serum malondialdehyde and nitric oxide end products and a decrease in erythrocyte-superoxide dismutase activity, catalase activity, and total antioxidant status that correlated in each case with disease severity index (Dipali P. K., et al. Indian J Clin Biochem. 2010 October; 25(4): 388-392). Also, an Nrf2 activator may be useful in treating the dermatitis/topical effects of radiation (Schäfer, M. et al. 2010. *Genes & Devl.* 24:1045-1058), and the immunosuppression due to radiation exposure (Kim, J. H. et al., J. Clin. Invest. 2014 Feb. 3; 124(2):730-41).

There are also data suggesting that an Nrf2 activator may be beneficial in preeclampsia, a disease that occurs in 2-5% of pregnancies and involves hypertension and proteinuria (*Annals of Anatomy—Anatomischer Anzeiger Volume* 196, *Issue* 5, September 2014, Pages 268-277).

Preclinical data has shown that compounds with Nrf2 activating activity are better at reversing high altitude-induced damage than compounds without Nrf2 activity, using animal and cellular models of Acute Mountain Sickness (Lisk C. et al, 2013, Free Radic Biol Med. October 2013; 63: 264-273.)

Nrf2 regulators have been disclosed in WO 2015/092713, published Jun. 25, 2015, in co-pending patent applications WO 2016/203400, published Dec. 22, 2016; WO 2016/203401, published Dec. 22, 2016; WO2018/104766; published Jun. 14, 2018; WO 2016/202253, published Dec. 22, 2016; and in WO2018/109646, published Jun. 21, 2018.

SUMMARY OF THE INVENTION

In one aspect, this invention provides for hydroxypyridoxazepine analogs, or a salt, particularly a pharmaceutically acceptable salt thereof, or a tautomer thereof, or a hydrate thereof, and pharmaceutical compositions containing them. In particular, the compounds of this invention include a compound of Formula (I):

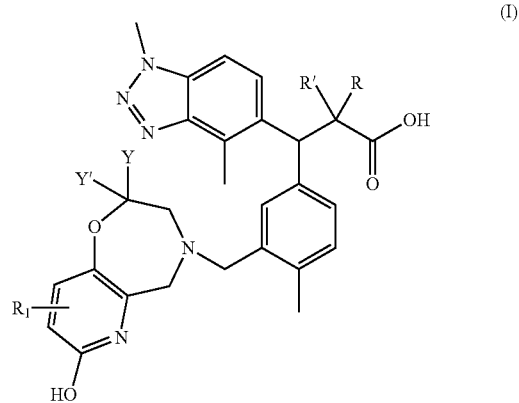

wherein:
R is hydrogen or methyl;
R' is hydrogen or methyl;
$R_1$ is hydrogen, —OH, —$C_{1-3}$alkyl, —$CF_3$, difluoromethyl, or halo;
Y is hydrogen, —$C_{1-5}$alkyl, —$C_{3-7}$cycloalkyl, —$CF_3$, —$CHF_2$, or —$CH_2CF_3$; and
Y' is hydrogen, —$C_{1-5}$alkyl, —$C_{3-7}$cycloalkyl, —$CF_3$, —$CHF_2$, or —$CH_2CF_3$;
or Y and Y' together form —$C_{3-7}$cycloalkyl;
or a pharmaceutically acceptable salt thereof, or a tautomer thereof, or a hydrate thereof.

In another aspect, this invention provides a compound of Formula (I), or a salt, particularly a pharmaceutically acceptable salt thereof, or a tautomer thereof, or a hydrate thereof, for use in medical therapy. This invention provides a compound of Formula (I), or a salt, particularly a pharmaceutically acceptable salt thereof, or a tautomer thereof, or a hydrate thereof, for use in therapy, particularly in treating an Nrf2-regulated disease of disorder. In a further aspect, this invention provides a compound of Formula (I), or a salt, particularly a pharmaceutically acceptable salt thereof, or a tautomer thereof, or a hydrate thereof, for use in therapy wherein the Nrf2-regulated disease or disorder is a respiratory or non-respiratory disorder, selected from COPD, asthma, ALI, ARDS, fibrosis, chronic asthma and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, heart failure with preserved ejection fraction, heart failure with reduced ejection fraction, diabetic cardiomyopathy, SCD, Progeria and CRS, Parkinson's disease (PD), Alzheimer's disease (AD), Friedreich's Ataxia (FA), amyotrophic lateral sclerosis (ALS), multiple sclerosis (MS), Huntington's disease (HD), spinal cord injury, traumatic brain injury, ischemic stroke, stroke, Creutzfeldt-Jakob Disease, fatal familial insomnia, Gerstmann-Sträussler-Scheinker syndrome, and related prion diseases, progressive supranuclear palsy, chronic traumatic encephalopathy (CTE), neurodegeneration, dementias, frontotemporal dementias, tauopathies, retinitis pigmentosa, Pick's disease, Neimann-Pick's disease, amyloidosis, cognitive impairment, inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In one aspect, this invention provides a compound of Formula (I), or a salt, particularly a pharmaceutically acceptable salt thereof, or a tautomer thereof, or a hydrate thereof, for use in treating an Nrf2-regulated disease or disorder. In a further aspect, this invention provides a compound of Formula (I), or a salt, particularly a pharmaceutically acceptable salt thereof, or a tautomer thereof, or a hydrate thereof, for use in treating a disease or disorder which is a respiratory or non-respiratory disorder, selected from COPD, asthma, ALI, ARDS, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, heart failure with preserved ejection fraction, heart failure with reduced ejection fraction, diabetic cardiomyopathy, SCD, Progeria and CRS, Parkinson's disease (PD), Alzheimer's disease (AD), Friedreich's Ataxia (FA), amyotrophic lateral sclerosis (ALS), multiple sclerosis (MS), Huntington's disease (HD), spinal cord injury, traumatic brain injury, ischemic stroke, stroke, Creutzfeldt-Jakob Disease, fatal familial insomnia, Gerstmann-Sträussler-Scheinker syndrome, and related prion diseases, progressive supranuclear palsy, chronic traumatic encephalopathy (CTE), neurodegeneration, dementias, frontotemporal dementias, tauopathies, retinitis pigmentosa, Pick's disease, Neimann-Pick's disease, amyloidosis, cognitive impairment, inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In a further aspect, this invention provides for a method of treating an Nrf2-regulated disease or disorder, which disease or disorder is a respiratory or non-respiratory disorder, selected from COPD, asthma, ALI, ARDS, fibrosis, chronic asthma and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, heart failure with preserved ejection fraction, heart failure with reduced ejection fraction, diabetic cardiomyopathy, sickle cell disease (SCD), Progeria and cardiorenal syndrome (CRS), Parkinson's disease (PD), Alzheimer's disease (AD), Friedreich's Ataxia (FA), amyotrophic lateral sclerosis (ALS), multiple sclerosis (MS), Huntington's disease (HD), spinal cord injury, traumatic brain injury, ischemic stroke, stroke, Creutzfeldt-Jakob Disease, fatal familial insomnia, Gerstmann-Sträussler-Scheinker syndrome, and related prion diseases, progressive supranuclear palsy, chronic traumatic encephalopathy (CTE), neurodegeneration, dementias, frontotemporal dementias, tauopathies, retinitis pigmentosa, Pick's disease, Neimann-Pick's disease, amyloidosis, cognitive impairment, inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness, which comprises administering to a subject in need thereof, a therapeutically effective amount of a compound of Formula (I), or a salt, particularly a pharmaceutically acceptable salt thereof, or a tautomer thereof, or a hydrate thereof.

In a further aspect, this invention relates to the use of a compound of Formula (I), or a salt, particularly a pharmaceutically acceptable salt thereof, or a tautomer thereof, or a hydrate thereof, in the manufacture of a medicament for the treatment of an Nrf2-regulated disease or disorder. In a further aspect, the Nrf2-regulated disease or disorder is a respiratory or non-respiratory disorder, selected from COPD, asthma, ALI, ARDS, fibrosis, chronic asthma and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, heart failure with preserved ejection fraction, heart failure with reduced ejection fraction, diabetic cardiomyopathy, SCD, Progeria and CRS, Parkinson's disease (PD), Alzheimer's disease (AD), Friedreich's Ataxia (FA), amyotrophic lateral sclerosis (ALS), multiple sclerosis (MS), Huntington's disease (HD), spinal cord injury, traumatic brain injury, ischemic stroke, stroke, Creutzfeldt-Jakob Disease, fatal familial insomnia, Gerstmann-Sträussler-Scheinker syndrome, and related prion diseases, progressive supranuclear palsy, chronic traumatic encephalopathy (CTE), neurodegeneration, dementias, frontotemporal dementias, tauopathies, retinitis pigmentosa, Pick's disease, Neimann-Pick's disease, amyloidosis, cognitive impairment, inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In another aspect, this invention provides a compound of Formula (I) or a salt, particularly a pharmaceutically acceptable salt thereof, or a tautomer thereof, or a hydrate thereof, for use as an Nrf2 activator in treating diseases or disorders as recited herein.

Accordingly, the present invention is also directed to a method of regulating Nrf2 which method comprises contacting a cell with a compound according to Formula (I) or a salt, particularly a pharmaceutically acceptable salt, or a tautomer, or a hydrate thereof.

In one aspect, the invention provides a pharmaceutical composition comprising a compound of the invention according to Formula (I) or a salt, particularly a pharmaceutically acceptable salt thereof, or a tautomer thereof, or a hydrate thereof, and one or more pharmaceutically acceptable excipients.

In another aspect, this invention is directed to a pharmaceutical composition for the treatment of an Nrf2 regulated disease or disorder, wherein the composition comprises a compound according to Formula (I), or a salt, particularly a pharmaceutically acceptable salt thereof, or a tautomer thereof, or a hydrate thereof, and one or more pharmaceutically acceptable excipients.

Other aspects and advantages of the present invention are described further in the following detailed description of the embodiments thereof.

DESCRIPTION OF FIGURES

FIG. 12 depicts the effect of the KEAP1 blockers/Nrf2 activators (R)-3-(1,4-dimethyl-1H-benzo[d][1,2,3]triazol-5- yl)-3-(3-(((R)-2-ethyl-7-hydroxy-2,3-dihydropyrido[2,3-f][1,4]oxazepin-4(5H)-yl)methyl)-4-methylphenyl)propanoic acid, hydrochloride, or a tautomer thereof (Compound of Example 1) and (S)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid (Compound B) on cardiac function and remodeling in the murine TAC model. Studies utilized high rigor & reproducibility design standards (layered blinding and appropriate power). Data represented as mean (±s.e.m). All p-values in comparison to vehicle, one-way ANOVA.

Figure 1:
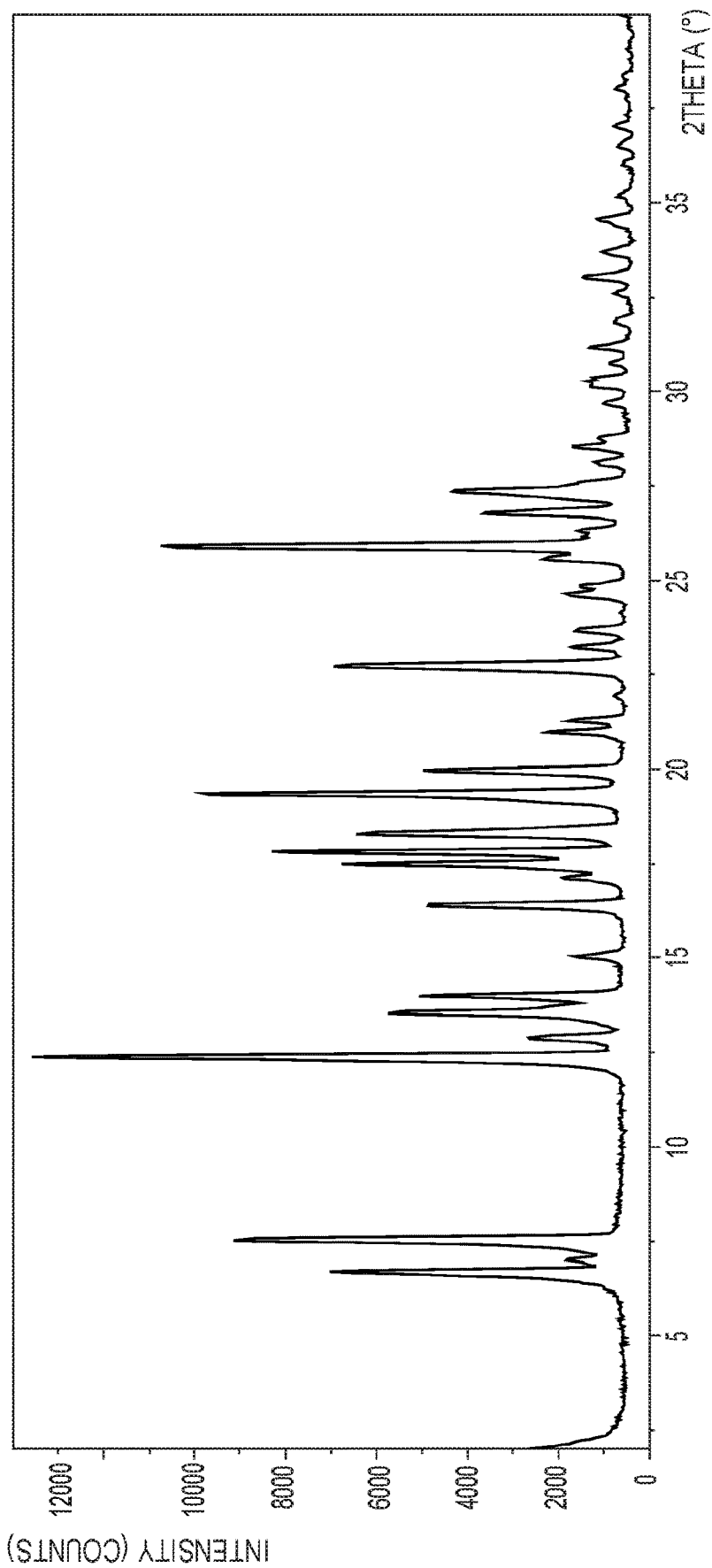
FIG. 1 depicts a Powder X-Ray Diffraction pattern (XRPD) of a crystalline form of anhydrous (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4 (5H)-yl)methyl)-4-methylphenyl)propanoic acid (free form), or a tautomer thereof.

FIG. 12 legend: Sh (sham, n=6), V (TAC without drug, n=13), EX 1 [TAC+(R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, hydrochloride, or a tautomer thereof at 1 mg/kg (n=11), 3 mg/kg (n=12) and 10 mg/kg (n=10)], EX B [TAC+(S)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid at 100 mg/kg, n=7].

FIG. 12(A) depicts ejection fraction, percent of LV ejection volume. (EX 1 results are shown at bars graphs labelled 1, 3 and 10; EX B results are shown at bar graph labelled 100).

FIG. 12(B) depicts left ventricular NQO1 enzyme activity, fold change relative to vehicle. (EX 1 results are shown at bars graphs labelled 1, 3 and 10; EX B results are shown at bar graph labelled 100).

FIG. 12(C) depicts heart rate, beats per min (bpm). (EX 1 results are shown at bars graphs labelled 1, 3 and 10; EX B results are shown at bar graph labelled 100).

FIG. 12(D) depicts left ventricular mass (hypertrophy) normalized to body weight. (EX 1 results are shown at bars graphs labelled 1, 3 and 10; EX B results are shown at bar graph labelled 100).

DETAILED DESCRIPTION OF THE INVENTION

The present invention provides for compounds of Formula (I):

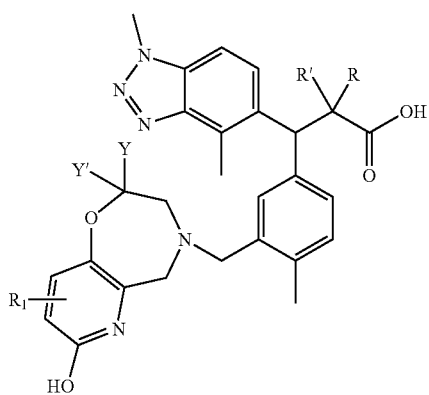

(I)

wherein:
R is hydrogen or methyl;
R' is hydrogen or methyl;
$R_1$ is hydrogen, —OH, —$C_{1-3}$alkyl, —$CF_3$, difluoromethyl, or halo;
Y is hydrogen, —$C_{1-5}$alkyl, —$C_{3-7}$cycloalkyl, —$CF_3$, —$CHF_2$, or —$CH_2CF_3$;
Y' is hydrogen, —$C_{1-5}$alkyl, —$C_{3-7}$cycloalkyl, —$CF_3$, —$CHF_2$, or —$CH_2CF_3$;
or Y and Y' together form —$C_{3-7}$cycloalkyl;
or a pharmaceutically acceptable salt thereof, or a tautomer thereof, or a hydrate thereof.

"Alkyl" refers to a monovalent saturated hydrocarbon chain having the specified number of carbon member atoms. For example, $C_{1-3}$alkyl refers to an alkyl group having from 1 to 3 carbon member atoms. Alkyl groups may be straight or branched. Representative branched alkyl groups have one, two, or three branches. Alkyl includes methyl, ethyl, propyl, (n-propyl and isopropyl), butyl (n-butyl, isobutyl, s-butyl, and t-butyl), pentyl (n-pentyl, tert-pentyl, iso-pentyl), and hexyl (n-hexyl, isohexyl, ter-hexyl).

"Cycloalkyl" refers to a monovalent saturated or unsaturated hydrocarbon ring having the specified number of carbon member atoms. For example, $C_{3-7}$cycloalkyl refers to a cycloalkyl group having from 3- to 7-carbon member atoms, unless otherwise limited. In one embodiment, $C_{5-7}$cycloalkyl refers to a cycloalkyl group having from 3- to 5-carbon member atoms. Unsaturated cycloalkyl groups have one or more carbon-carbon double bonds within the ring. Cycloalkyl groups are not aromatic. Cycloalkyl includes cyclopropyl, cyclopropenyl, cyclobutyl, cyclobutenyl, cyclopentyl, cyclopentenyl, cyclohexyl, and cyclohexenyl.

When used herein, the terms 'halogen' and 'halo' include fluorine, chlorine, bromine and iodine, and fluoro, chloro, bromo, and iodo, respectively.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e., one that does not spontaneously undergo transformation such as by rearrangement, cyclization, or elimination and that is sufficiently robust to survive isolation from a reaction mixture). When it is stated that a group may contain one or more substituents, one or more (as appropriate) member atoms within the group may be substituted. In addition, a single member atom within the group may be substituted with more than one substituent as long as such substitution is in accordance with the permitted valence of the atom. Suitable substituents are defined herein for each substituted or optionally substituted group.

The term "independently" means that where more than one substituent is selected from a number of possible substituents, those substituents may be the same or different. That is, each substituent is separately selected from the entire group of recited possible substituents.

The invention also includes various isomers of the compounds of Formula (I) and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers). The compounds according to Formula (I) contain one or more asymmetric centers, also referred to as chiral centers, and may, therefore, exist as individual enantiomers, diastereomers, or other stereoisomeric forms, or as mixtures thereof. All such isomeric forms are included within the present invention, including mixtures thereof.

Chiral centers may also be present in a substituent such as an alkyl group. Where the stereochemistry of a chiral center present in Formula (I), or in any chemical structure illustrated herein, is not specified the structure is intended to encompass any stereoisomer and all mixtures thereof. Thus, compounds according to Formula (I) containing one or more chiral centers may be used as racemic mixtures, enantiomerically enriched mixtures, or as enantiomerically pure individual stereoisomers.

Individual stereoisomers of a compound according to Formula (I) which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

For compounds falling within the scope of the invention, the structural conventions used in the Examples are as follows: (a) absolute stereochemistry is defined by the structure; (b) when annotated by "or", then stereochemistry is unknown but resolved; and (c) when annotated by "&" or "and", then stereochemistry is relative, but racemic.

It is to be understood that the references herein to a compound of Formula (I) or a salt thereof includes a compound of Formula (I) as a free base [or acid, as appropriate], or as a salt thereof, for example as a pharmaceutically acceptable salt thereof. Thus, in one embodiment, the invention is directed to a compound of Formula (I). In another embodiment, the invention is directed to a salt of a compound of Formula (I). In a further embodiment, the invention is directed to a pharmaceutically acceptable salt of a compound of Formula (I). In another embodiment, the invention is directed to a compound of Formula (I) or a salt thereof. In a further embodiment, the invention is directed to a compound of Formula (I) or a pharmaceutically acceptable salt thereof.

If a compound of Formula (I) has both a basic amine group and a carboxylic acid group and can consequently be in the form of a zwitterion, also known as an inner salt. Therefore, in an embodiment the compound of Formula (I) is in a zwitterion form.

As used herein, "pharmaceutically acceptable" refers to those compounds (including salts), materials, compositions, and dosage forms which are, within the scope of sound medical judgment, suitable for use in contact with the tissues of subjects without excessive toxicity, irritation, or other problem or complication, commensurate with a reasonable benefit/risk ratio, specifically, a compound which is suitable for pharmaceutical use. Salts and solvates (e.g., hydrates and hydrates of salts) of the compounds of the invention which are suitable for use in medicine are those wherein the counterion or associated solvent is pharmaceutically acceptable. Salts and solvates having non-pharmaceutically acceptable counterions or associated solvents are within the scope of the present invention, for example, for use as intermediates in the preparation of other compounds of the invention and their salts and solvates.

Pharmaceutically acceptable salts include, amongst others, those described in Berge, J. Pharm. Sci., 1977, 66, 1-19, or those listed in P H Stahl and C G Wermuth, editors, *Handbook of Pharmaceutical Salts; Properties, Selection and Use, Second Edition* Stahl/Wermuth: Wiley-VCH/VHCA, 2011 (see http://www.wiley.com/WileyCDA/Wiley-Title/productCd-3906390519.html).

These pharmaceutically acceptable salts may be prepared in situ during the final isolation and purification of the compound, or by separately treating the purified compound in its free acid or free base form with a suitable base or acid, respectively. If a basic compound of Formula (I) is isolated as a salt, the corresponding free base form of that compound may be prepared by any suitable method known to the art, including treatment of the salt with an inorganic or organic base, suitably an inorganic or organic base having a higher $pK_a$ than the free base form of the compound. Similarly, if a disclosed compound containing a carboxylic acid or other acidic functional group is isolated as a salt, the corresponding free acid form of that compound may be prepared by any suitable method known to the art, including treatment of the salt with an inorganic or organic acid, suitably an inorganic or organic acid having a lower $pK_a$ than the free acid form of the compound. This invention also provides for the conversion of one salt of a compound of this invention, e.g., a hydrochloride salt, into another salt of a compound of this invention, e.g., a sulfate salt.

It will be understood that if a compound of Formula (I) contains two or more basic moieties, the stoichiometry of salt formation may include 1, 2 or more equivalents of acid. Such salts would contain 1, 2 or more acid counterions, for example, a dihydrochloride salt.

Stoichiometric and non-stoichiometric forms of a pharmaceutically acceptable salt of a compound of Formula (I) are included within the scope of the invention, including sub-stoichiometric salts, for example where a counterion contains more than one acidic proton.

Salts of the compounds of Formula (I), containing a basic amine or other basic functional group may be prepared by any suitable method known in the art, such as treatment of the free base with an acid. Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Salts of the disclosed compounds containing a carboxylic acid or other acidic functional group can be prepared by reacting with a suitable base. Such a pharmaceutically acceptable salt may be made with a base which affords a pharmaceutically acceptable cation. Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl)amine, bismuth, calcium, chloroprocaine, choline, clemizole (1-p chlorobenzyl-2-pyrrolildine-1'-ylmethylbenzimidazole),
cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

In one embodiment, the invention provides a compound of Formula (I) which is a hydrate, or a tautomer thereof. In another embodiment, the invention provides (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid hydrate, or a tautomer thereof. In yet another embodiment, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid hydrate, or a tautomer thereof. In still another embodiment, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid hydrate, or a tautomer thereof, characterized by the XRPD pattern substantially in accordance with that shown in FIG. 4. In a further embodiment, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid hydrate, or a tautomer thereof, characterized by having at least 5 peaks selected from the diffraction data in Table 4. In still a further embodiment, the invention provides a crystalline form of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid hydrate, or a tautomer thereof, having an x-ray powder diffraction pattern comprising peaks at 15.76°, 7.86°, 9.58°, and 19.07°±0.2° 2θ as measured by x-ray powder diffraction using an x-ray wavelength of 1.5406 Å.

In one embodiment, the invention provides a compound of Formula (I) which is a besylate salt thereof, or a tautomer thereof. In a second embodiment, the invention provides a compound which is:

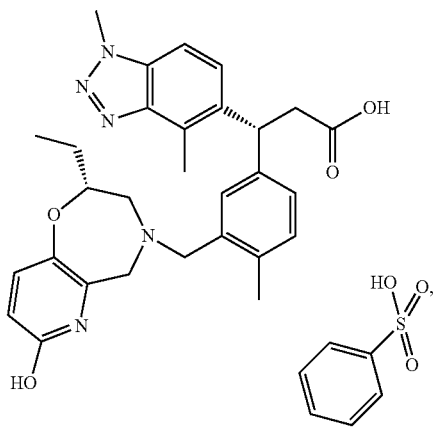 [SMILES: CC[C@@H]1CN(Cc2cc([C@@H](CC(=O)O)c3ccc4c(nnn4C)c3C)ccc2C)Cc2nc(O)ccc2O1 ; O=S(=O)(O)c1ccccc1]

or a tautomer thereof. In yet another embodiment, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid besylate salt, or a tautomer thereof. In yet another embodiment, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid besylate salt, or a tautomer thereof. In still another embodiment, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid besylate salt, or a tautomer thereof, characterized by the XRPD pattern substantially in accordance with that shown in FIG. 8. In a further embodiment, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid besylate salt, or a tautomer thereof, characterized by having at least 5 peaks selected from the diffraction data in Table 5. In still a further embodiment, the invention provides a crystalline form of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid besylate salt, or a tautomer thereof, having an x-ray powder diffraction pattern comprising peaks at 25.18°, 22.53°, 16.66°, and 7.82°±0.2° 2θ as measured by x-ray powder diffraction using an x-ray wavelength of 1.5406 Å.

In another embodiment, the invention provides a compound of Formula (I) which is a mesylate salt thereof, or a tautomer thereof. In a second embodiment, the invention provides a compound of Formula (I) which is a hydrate of a mesylate salt thereof, or a tautomer thereof. In another embodiment, the invention provides a compound which is:

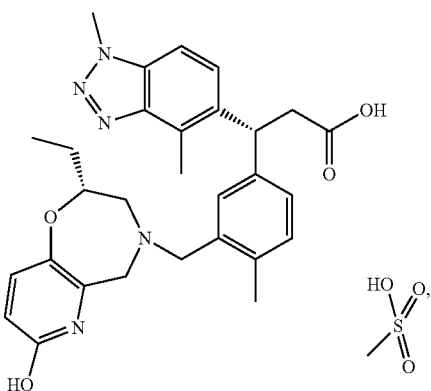

or a tautomer thereof. In another embodiment, the invention provides (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid mesylate salt hydrate, or a tautomer thereof. In yet another embodiment, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid mesylate salt hydrate, or a tautomer thereof. In still another embodiment, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid mesylate salt hydrate, or a tautomer thereof, characterized by the XRPD pattern substantially in accordance with that shown in FIG. 9. In a further embodiment, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid mesylate salt hydrate, or a tautomer thereof, characterized by having at least 5 peaks selected from the diffraction data in Table 6. In still a further embodiment, the invention provides a crystalline form of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid mesylate salt hydrate, or a tautomer thereof, having an x-ray powder diffraction pattern comprising peaks at 19.84°, 17.25°, 21.06°, and 13.45°±0.2° 2θ as measured by x-ray powder diffraction using an x-ray wavelength of 1.5406 Å.

As used herein, the term "a compound of Formula (I)" or "the compound of Formula (I)" or "compound(s) of the invention" or "compound(s) of this invention" refers to one or more compounds according to Formula (I). The compound(s) of Formula (I) may exist in any form, i.e., any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms), and mixtures of various forms. The skilled artisan will appreciate that pharmaceutically acceptable hydrates may be formed from crystalline compounds wherein water molecules are incorporated into the crystalline lattice during crystallization. Hydrates include stoichiometric hydrates as well as compositions containing variable amounts of water. The invention includes all such hydrates.

The skilled artisan will further appreciate that certain compounds of the invention that exist in crystalline form, including the various solvates thereof, may exhibit polymorphism (i.e., the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

It is well known and understood to those skilled in the art that the apparatus employed, humidity, temperature, orientation of the powder crystals, and other parameters involved in obtaining a powder X-ray diffraction (XRPD) pattern may cause some variability in the appearance, intensities, and positions of the lines in the diffraction pattern. A powder X-ray diffraction pattern that is "substantially in accordance" with that of a Figure provided herein is an XRPD pattern that would be considered by one skilled in the art to represent a compound possessing the same crystal form as the compound that provided the XRPD pattern of the Figure. For example, the XRPD pattern may be identical to that of FIG. 1, or more likely it may be somewhat different. Such an XRPD pattern may not necessarily show each of the lines of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns. For example, one skilled in the art can overlay an XRPD pattern of a sample of a crystalline form of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form) with the XRPD pattern of FIG. 1, and using expertise and knowledge in the art, readily determine whether the XRPD pattern of the sample is substantially in accordance with the XRPD pattern of FIG. 1. If the XRPD pattern is substantially in accordance with FIG. 1, the sample form can be readily and accurately identified as having the same form as the crystalline form of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form) described herein. Similarly, a person skilled in the art is capable of determining if a given diffraction angle (expressed in °2θ) obtained from an XRPD pattern is at about the same position as a recited value. In one aspect, the invention provides a compound of Formula (I), or a salt, particularly a pharmaceutically acceptable salt thereof, or a tautomer thereof, or a hydrate thereof, wherein the compound can be identified as being the same form as a known crystalline form thereof, characterized by having at least 5 peaks selected from an XRPD diffraction pattern of the known crystalline form.

In one aspect, the invention is directed to a compound, or a salt thereof, particularly, a pharmaceutically acceptable salt thereof, or a tautomer thereof, which is (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid with the structure

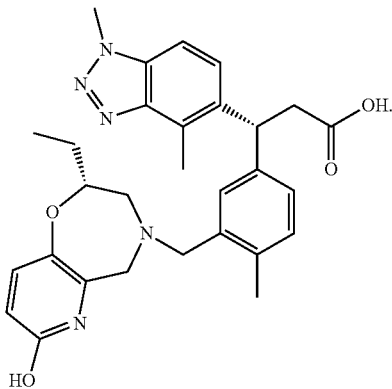 [SMILES: CC[C@@H]1CN(Cc2cc([C@@H](CC(=O)O)c3ccc4c(nnn4C)c3C)ccc2C)Cc2nc(O)ccc2O1]

In one embodiment, this invention provides a crystalline compound of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, as a non-hydrated, non-solvated, crystal form (Form 1), also referred to as crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof. In one embodiment, this invention provides isolated crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof. In a further embodiment, this invention provides substantially pure crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof.

Crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, is characterized by an XRPD pattern substantially in accordance with that shown in FIG. 1. Crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, is characterized by the diffraction data in Table 3. In one embodiment, the invention provides a crystalline form of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, having an x-ray powder diffraction pattern comprising peaks at 12.38°, 25.90°, 19.35°, and 7.54°±0.2° 2θ as measured by x-ray powder diffraction using an x-ray wavelength of 1.5406 Å.

In one aspect, this invention provides a substantially pure compound of Formula (I), or a salt, particularly a pharmaceutically acceptable salt thereof, or a tautomer thereof, or a hydrate thereof. In one embodiment, the invention provides a substantially pure compound, or a salt, particularly a pharmaceutically acceptable salt thereof, or a tautomer thereof, or a hydrate thereof, which is (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid. In another embodiment, this invention provides substantially pure crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof.

In one aspect, this invention provides an isolated compound of Formula (I), or a salt, particularly or a pharmaceutically acceptable salt thereof, or a tautomer thereof, or a hydrate thereof. In one embodiment, the invention provides an isolated compound, or a salt, particularly a pharmaceutically acceptable salt thereof, or a tautomer thereof, or a hydrate thereof, which is (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid. In another embodiment, this invention provides isolated crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof.

It will be appreciated by those skilled in the art that in certain instances chemical naming programs may name a structurally depicted compound as a tautomer of that compound. It is to be understood that any reference to a named compound or a structurally depicted compound is intended to encompass all tautomers of such compounds and any mixtures of tautomers thereof.

In one embodiment, the invention is directed to a compound of Formula (I) with the following tautomers:

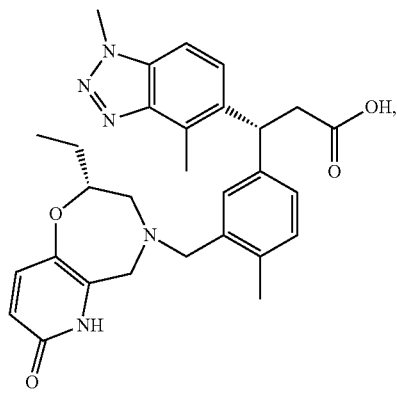 [SMILES: CC[C@@H]1CN(Cc2cc([C@@H](CC(=O)O)c3ccc4c(nnn4C)c3C)ccc2C)Cc2[nH]c(=O)ccc2O1]

namely, (R)-3-(1,4-dimethyl-1H-benzo[d][1,2,3]triazol-5-yl)-3-(3-(((R)-2-ethyl-7-oxo-2,3,6,7-tetrahydropyrido[2,3-f][1,4]oxazepin-4(5H)-yl)methyl)-4-methylphenyl)propanoic acid; and

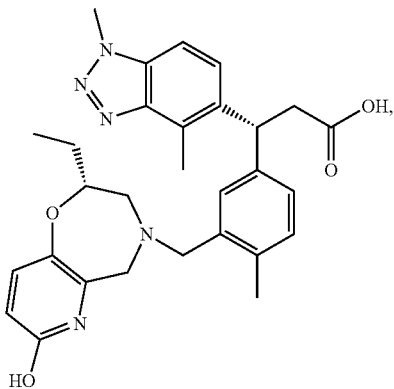 [SMILES: CC[C@@H]1CN(Cc2cc([C@@H](CC(=O)O)c3ccc4c(nnn4C)c3C)ccc2C)Cc2nc(O)ccc2O1]

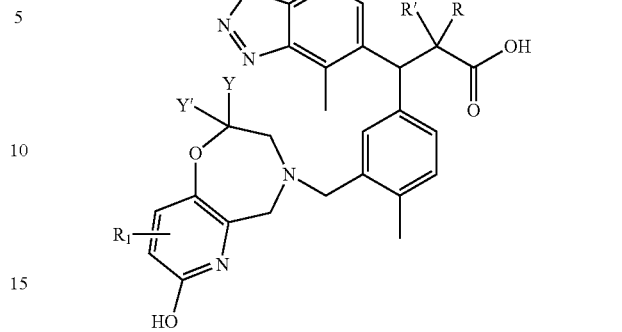

namely, (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid.

The subject invention also includes isotopically-labelled compounds, which are identical to those recited in Formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}F$, $^{35}S$, $^{18}F$, $^{36}Cl$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of Formula (I) and following of this invention can generally be prepared by carrying out the procedures disclosed in the Schemes and/or in the Examples below, by substituting a readily available isotopically labelled reagent for a non-isotopically labelled reagent.

Representative Embodiments

The invention is directed to a compound of Formula (I), which is:

wherein:
R is hydrogen or methyl;
R' is hydrogen or methyl;
$R_1$ is hydrogen, —OH, —$C_{1-3}$alkyl, —$CF_3$, difluoromethyl, or halo;
Y is hydrogen, —$C_{1-5}$alkyl, —$C_{3-7}$cycloalkyl, —$CF_3$, —$CHF_2$, or —$CH_2CF_3$; and
Y' is hydrogen, —$C_{1-5}$alkyl, —$C_{3-7}$cycloalkyl, —$CF_3$, —$CHF_2$, or —$CH_2CF_3$;
or Y and Y' together form —$C_{3-7}$cycloalkyl;
or a salt thereof, particularly a pharmaceutically acceptable salt thereof, or a tautomer thereof, or a hydrate thereof.

Suitably, the compounds of the invention are wherein, R is hydrogen or methyl; R' is hydrogen or methyl; $R_1$ is hydrogen, —OH, —$C_{1-3}$alkyl, —$CF_3$, difluoromethyl, or halo; Y is hydrogen, —$C_{1-5}$alkyl, —$C_{3-7}$cycloalkyl, —$CF_3$, —$CHF_2$, or —$CH_2CF_3$; Y' is hydrogen, —$C_{1-5}$alkyl, —$C_{3-7}$cycloalkyl, —$CF_3$, —$CHF_2$, or —$CH_2CF_3$; or Y and Y' together form —$C_{3-7}$cycloalkyl; and a salt thereof, or a pharmaceutically acceptable salt thereof, or a tautomer thereof, or a hydrate thereof.

In one embodiment of the compounds of this invention, R is hydrogen or methyl. In a specific embodiment, R is hydrogen. In another embodiment, R' is methyl.

In one embodiment of the compounds of this invention, R' is hydrogen or methyl. In a specific embodiment, R' is hydrogen. In another embodiment, R is methyl.

In one embodiment of the compounds of this invention, R and R' are independently hydrogen or methyl. In a specific embodiment, R and R' are both hydrogen. In another embodiment, R and R' are both methyl. In yet another embodiment, R is methyl and R' is hydrogen. In still another embodiment, R is hydrogen and R' is methyl.

In one embodiment of the compounds of this invention, $R_1$ is hydrogen, —OH, —$C_{1-3}$alkyl, —$CF_3$, difluoromethyl, or halo. In a specific embodiment, $R_1$ is hydrogen. In another embodiment, $R_1$ is —$C_{1-3}$alkyl. In yet another embodiment, $R_1$ is halo. In another embodiment, $R_1$ is methyl. In still another embodiment, $R_1$ is fluorine.

In one embodiment of the compounds of this invention, Y is hydrogen, —$C_{1-5}$alkyl, —$C_{3-7}$cycloalkyl, —$CF_3$, —$CHF_2$, or —$CH_2CF_3$. In one embodiment, Y is —$C_{1-5}$alkyl, —$C_{3-5}$cycloalkyl or —$CF_3$. In another specific embodiment, Y is methyl, ethyl, isopropyl, or —$CF_3$. In yet another specific embodiment, Y is methyl, ethyl or isopropyl. In another embodiment, Y is methyl. In still another embodiment, Y is ethyl. In a further embodiment, Y is isopropyl. In still another embodiment, Y is —$CF_3$.

In one embodiment of the compounds of this invention, Y' is hydrogen, —$C_{1-5}$alkyl, —$C_{3-7}$cycloalkyl, —$CF_3$, —$CHF_2$, or —$CH_2CF_3$. In one embodiment, Y' is hydrogen or —$C_{1-5}$alkyl. In another embodiment, Y' is hydrogen, methyl or ethyl. In yet another embodiment, Y' is methyl or ethyl. In another embodiment, Y' is methyl. In still another embodiment, Y' is ethyl. In a further specific embodiment, Y' is hydrogen.

Suitably, when Y is methyl, ethyl, isopropyl or —$CF_3$, Y' is hydrogen or methyl. In one embodiment, Y is methyl, ethyl, isopropyl or —$CF_3$, and Y' is hydrogen. In another embodiment, Y is methyl, ethyl, isopropyl or —$CF_3$, and Y' is methyl. In a specific embodiment, Y is methyl and Y' is hydrogen. In another specific embodiment, Y is ethyl and Y' is hydrogen. In yet another specific embodiment, Y is isopropyl and Y' is hydrogen. In still yet another specific embodiment, Y is —$CF_3$ and Y' is hydrogen. In yet another specific embodiment, Y is methyl and Y' is methyl.

In a particular embodiment of the invention, R is hydrogen, R' is hydrogen, $R_1$ is hydrogen, Y is ethyl and Y' is hydrogen.

In one embodiment of the invention, the compound of Formula (I) is as follows:
R is hydrogen or methyl;
R' is hydrogen or methyl;
$R_1$ is hydrogen, —$C_{1-3}$alkyl or halo;
Y is —$C_{1-5}$alkyl, —$C_{3-5}$cycloalkyl or —$CF_3$; and
Y' is hydrogen;
or a salt thereof, particularly a pharmaceutically acceptable salt thereof, or a tautomer thereof, or a hydrate thereof.

In one embodiment of the invention, the compound of Formula (I) is as follows:
R is hydrogen or methyl;
R' is hydrogen or methyl;
$R_1$ is hydrogen, —$C_{1-3}$alkyl or halo;
Y is —$C_{1-5}$alkyl, —$C_{3-5}$cycloalkyl or —$CF_3$; and
Y' is methyl;
or a salt thereof, particularly a pharmaceutically acceptable salt thereof, or a tautomer thereof, or a hydrate thereof.

In another embodiment of the invention, the compound of Formula (I) is as follows:
R is hydrogen or methyl;
R' is hydrogen or methyl;
$R_1$ is hydrogen, methyl or fluorine;
Y is methyl, ethyl, isopropyl, or —$CF_3$; and
Y' is hydrogen;
or a salt thereof, particularly a pharmaceutically acceptable salt thereof, or a tautomer thereof, or a hydrate thereof.

In still another embodiment of the invention, the compound of Formula (I) is as follows:
R is hydrogen or methyl;
R' is hydrogen or methyl;
$R_1$ is hydrogen, methyl or fluorine;
Y is methyl, ethyl, isopropyl, or —$CF_3$; and
Y' is methyl;
or a salt thereof, particularly a pharmaceutically acceptable salt thereof, or a tautomer thereof, or a hydrate thereof.

In yet another embodiment of the invention, the compound of Formula (I) is as follows:
R is hydrogen or methyl;
R' is hydrogen or methyl;
$R_1$ is hydrogen;
Y is methyl, ethyl, isopropyl, or —$CF_3$; and
Y' is hydrogen;
or a salt thereof, particularly a pharmaceutically acceptable salt thereof, or a tautomer thereof, or a hydrate thereof.

In another embodiment of the invention, the compound of Formula (I) is as follows:
R is hydrogen or methyl;
R' is hydrogen or methyl;
$R_1$ is hydrogen;
Y is methyl, ethyl, isopropyl, or —$CF_3$; and
Y' is methyl;
or a salt thereof, particularly a pharmaceutically acceptable salt thereof, or a tautomer thereof, or a hydrate thereof.

In still another embodiment of the invention, the compound of Formula (I) is as follows:
R is methyl;
R' is methyl
$R_1$ is hydrogen;
Y is methyl, ethyl, isopropyl, or —$CF_3$; and
Y' is hydrogen;
or a salt thereof, particularly a pharmaceutically acceptable salt thereof, or a tautomer thereof, or a hydrate thereof.

In still another embodiment of the invention, the compound of Formula (I) is as follows:
R is methyl;
R' is methyl
$R_1$ is hydrogen;
Y is methyl, ethyl, isopropyl, or —$CF_3$; and
Y' is methyl;
or a salt thereof, particularly a pharmaceutically acceptable salt thereof, or a tautomer thereof, or a hydrate thereof.

In still another embodiment of the invention, the compound of Formula (I) is as follows:
R is hydrogen;
R' is hydrogen;
$R_1$ is hydrogen;
Y is methyl, ethyl, isopropyl, or —$CF_3$; and
Y' is hydrogen;
or a salt thereof, particularly a pharmaceutically acceptable salt thereof, or a tautomer thereof, or a hydrate thereof.

In still another embodiment of the invention, the compound of Formula (I) is as follows:
R is hydrogen;
R' is hydrogen;
$R_1$ is hydrogen;
Y is methyl, ethyl, isopropyl, or —$CF_3$; and
Y' is methyl;
or a salt thereof, particularly a pharmaceutically acceptable salt thereof, or a tautomer thereof, or a hydrate thereof.

In yet another embodiment of the invention, the compound of Formula (I) is as follows:
R is methyl;
R' is methyl
$R_1$ is hydrogen;
Y is methyl, ethyl or isopropyl; and
Y' is hydrogen;
or a salt thereof, particularly a pharmaceutically acceptable salt thereof, or a tautomer thereof, or a hydrate thereof.

In yet another embodiment of the invention, the compound of Formula (I) is as follows:
R is methyl;
R' is methyl
$R_1$ is hydrogen;
Y is methyl, ethyl or isopropyl; and
Y' is methyl;
or a salt thereof, particularly a pharmaceutically acceptable salt thereof, or a tautomer thereof, or a hydrate thereof.

In still yet another embodiment of the invention, the compound of Formula (I) is as follows:
R is hydrogen;
R' is hydrogen;
$R_1$ is hydrogen;
Y is methyl, ethyl or isopropyl; and
Y' is hydrogen;
or a salt thereof, particularly a pharmaceutically acceptable salt thereof, or a tautomer thereof, or a hydrate thereof.

In still yet another embodiment of the invention, the compound of Formula (I) is as follows:
R is hydrogen;
R' is hydrogen;
$R_1$ is hydrogen;
Y is methyl, ethyl or isopropyl; and
Y' is methyl;
or a salt thereof, particularly a pharmaceutically acceptable salt thereof, or a tautomer thereof, or a hydrate thereof.

In a further embodiment of the invention, the compound of Formula (I) is as follows:
R is methyl;
R' is methyl
$R_1$ is hydrogen;
Y is methyl; and
Y' is hydrogen;
or a salt thereof, particularly a pharmaceutically acceptable salt thereof, or a tautomer thereof, or a hydrate thereof.

In a further embodiment of the invention, the compound of Formula (I) is as follows:
R is methyl;
R' is methyl
$R_1$ is hydrogen;
Y is methyl; and
Y' is methyl;
or a salt thereof, particularly a pharmaceutically acceptable salt thereof, or a tautomer thereof, or a hydrate thereof.

In another embodiment of the invention, the compound of Formula (I) is as follows:
R is hydrogen;
R' is hydrogen;
$R_1$ is hydrogen;
Y is methyl; and
Y' is hydrogen;
or a salt thereof, particularly a pharmaceutically acceptable salt thereof, or a tautomer thereof, or a hydrate thereof.

In another embodiment of the invention, the compound of Formula (I) is as follows:
R is hydrogen;
R' is hydrogen;
$R_1$ is hydrogen;
Y is methyl; and
Y' is methyl;
or a salt thereof, particularly a pharmaceutically acceptable salt thereof, or a tautomer thereof, or a hydrate thereof.

In a further embodiment of the invention, the compound of Formula (I) is as follows:
R is methyl;
R' is methyl
$R_1$ is hydrogen;
Y is ethyl; and
Y' is hydrogen;
or a salt thereof, particularly a pharmaceutically acceptable salt thereof, or a tautomer thereof, or a hydrate thereof.

In a further embodiment of the invention, the compound of Formula (I) is as follows:
R is methyl;
R' is methyl
$R_1$ is hydrogen;
Y is ethyl; and
Y' is methyl;
or a salt thereof, particularly a pharmaceutically acceptable salt thereof, or a tautomer thereof, or a hydrate thereof.

In another embodiment of the invention, the compound of Formula (I) is as follows:
R is hydrogen;
R' is hydrogen;
$R_1$ is hydrogen;
Y is ethyl; and
Y' is hydrogen;
or a salt thereof, particularly a pharmaceutically acceptable salt thereof, or a tautomer thereof, or a hydrate thereof.

In another embodiment of the invention, the compound of Formula (I) is as follows:
R is hydrogen;
R' is hydrogen;
$R_1$ is hydrogen;
Y is ethyl; and
Y' is methyl;
or a salt thereof, particularly a pharmaceutically acceptable salt thereof, or a tautomer thereof, or a hydrate thereof.

In a further embodiment of the invention, the compound of Formula (I) is as follows:
R is methyl;
R' is methyl
$R_1$ is hydrogen;
Y is isopropyl; and
Y' is hydrogen;
or a salt thereof, particularly a pharmaceutically acceptable salt thereof, or a tautomer thereof, or a hydrate thereof.

In a further embodiment of the invention, the compound of Formula (I) is as follows:
R is methyl;
R' is methyl
$R_1$ is hydrogen;
Y is isopropyl; and
Y' is methyl;
or a salt thereof, particularly a pharmaceutically acceptable salt thereof, or a tautomer thereof, or a hydrate thereof.

In another embodiment of the invention, the compound of Formula (I) is as follows:
R is hydrogen;
R' is hydrogen;

R₁ is hydrogen;
Y is isopropyl; and
Y' is hydrogen;
or a salt thereof, particularly a pharmaceutically acceptable salt thereof, or a tautomer thereof, or a hydrate thereof.

In another embodiment of the invention, the compound of Formula (I) is as follows:
R is hydrogen;
R' is hydrogen;
R₁ is hydrogen;
Y is isopropyl; and
Y' is methyl;
or a salt thereof, particularly a pharmaceutically acceptable salt thereof, or a tautomer thereof, or a hydrate thereof.

It is to be understood that the present invention covers all combinations of the embodiments and particular groups described hereinabove.

Specific examples of compounds of the present invention include the following:

(R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid;

(R)-3-(1,4-dimethyl-1H-benzo[d][1,2,3]triazol-5-yl)-3-(3-(((S)-7-hydroxy-2-isopropyl-2,3-dihydropyrido[2,3-f][1,4]oxazepin-4(5H)-yl)methyl)-4-methylphenyl)propanoic acid;

(R)-3-(1,4-dimethyl-1H-benzo[d][1,2,3]triazol-5-yl)-3-(3-(((R)-7-hydroxy-2-isopropyl-2,3-dihydropyrido[2,3-f][1,4]oxazepin-4(5H)-yl)methyl)-4-methylphenyl)propanoic acid;

(R)-3-(1,4-dimethyl-1H-benzo[d][1,2,3]triazol-5-yl)-3-(3-(((R)-7-hydroxy-2-methyl-2,3-dihydropyrido[2,3-f][1,4]oxazepin-4(5H)-yl)methyl)-4-methylphenyl)propanoic acid;

(R)-3-(1,4-dimethyl-1H-benzo[d][1,2,3]triazol-5-yl)-3-(3-((7-hydroxy-2,2-dimethyl-2,3-dihydropyrido[2,3-f][1,4]oxazepin-4(5H)-yl)methyl)-4-methylphenyl)propanoic acid;

(R)-3-(1,4-dimethyl-1H-benzo[d][1,2,3]triazol-5-yl)-3-(3-(((S)-7-hydroxy-2-(trifluoromethyl)-2,3-dihydropyrido[2,3-f][1,4]oxazepin-4(5H)-yl)methyl)-4-methylphenyl)propanoic acid;

(R)-3-(1,4-dimethyl-1H-benzo[d][1,2,3]triazol-5-yl)-3-(3-(((S)-2-ethyl-7-hydroxy-2,3-dihydropyrido[2,3-f][1,4]oxazepin-4(5H)-yl)methyl)-4-methylphenyl)propanoic acid;

(S)-3-(1,4-dimethyl-1H-benzo[d][1,2,3]triazol-5-yl)-3-(3-(((R)-7-hydroxy-2-isopropyl-2,3-dihydropyrido[2,3-f][1,4]oxazepin-4(5H)-yl)methyl)-4-methylphenyl)propanoic acid;

(S)-3-(1,4-dimethyl-1H-benzo[d][1,2,3]triazol-5-yl)-3-(3-(((S)-7-hydroxy-2-isopropyl-2,3-dihydropyrido[2,3-f][1,4]oxazepin-4(5H)-yl)methyl)-4-methylphenyl)propanoic acid;

(S)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid;

(S)-3-(1,4-dimethyl-1H-benzo[d][1,2,3]triazol-5-yl)-3-(3-((7-hydroxy-2,2-dimethyl-2,3-dihydropyrido[2,3-f][1,4]oxazepin-4(5H)-yl)methyl)-4-methylphenyl)propanoic acid;

(S)-3-(1,4-dimethyl-1H-benzo[d][1,2,3]triazol-5-yl)-3-(3-(((S)-2-ethyl-7-hydroxy-2,3-dihydropyrido[2,3-f][1,4]oxazepin-4(5H)-yl)methyl)-4-methylphenyl)propanoic acid;

(S)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)-2,2-dimethyl propanoic acid;

(S)-3-(1,4-dimethyl-1H-benzo[d][1,2,3]triazol-5-yl)-3-(3-(((R)-7-hydroxy-2-methyl-2,3-dihydropyrido[2,3-f][1,4]oxazepin-4(5H)-yl)methyl)-4-methylphenyl)-2,2-dimethylpropanoic acid;

(S)-3-(1,4-dimethyl-1H-benzo[d][1,2,3]triazol-5-yl)-3-(3-(((R)-7-hydroxy-2-isopropyl-2,3-dihydropyrido[2,3-f][1,4]oxazepin-4(5H)-yl)methyl)-4-methylphenyl)-2,2-dimethylpropanoic acid;

(S)-3-(1,4-dimethyl-1H-benzo[d][1,2,3]triazol-5-yl)-3-(3-(((S)-7-hydroxy-2-isopropyl-2,3-dihydropyrido[2,3-f][1,4]oxazepin-4(5H)-yl)methyl)-4-methylphenyl)-2,2-dimethylpropanoic acid;

(S)-3-(1,4-dimethyl-1H-benzo[d][1,2,3]triazol-5-yl)-3-(3-((7-hydroxy-2,2-dimethyl-2,3-dihydropyrido[2,3-f][1,4]oxazepin-4(5H)-yl)methyl)-4-methylphenyl)-2,2-dimethylpropanoic acid;

(S)-3-(1,4-dimethyl-1H-benzo[d][1,2,3]triazol-5-yl)-3-(3-(((S)-2-ethyl-7-hydroxy-2,3-dihydropyrido[2,3-f][1,4]oxazepin-4(5H)-yl)methyl)-4-methylphenyl)-2,2-dimethylpropanoic acid;

(S)-3-(1,4-dimethyl-1H-benzo[d][1,2,3]triazol-5-yl)-3-(3-(((S)-7-hydroxy-2-(trifluoromethyl)-2,3-dihydropyrido[2,3-f][1,4]oxazepin-4(5H)-yl)methyl)-4-methylphenyl)-2,2-dimethylpropanoic acid;

(R)-3-(1,4-dimethyl-1H-benzo[d][1,2,3]triazol-5-yl)-3-(3-(((R)-7-hydroxy-2-(trifluoromethyl)-2,3-dihydropyrido[2,3-f][1,4]oxazepin-4(5H)-yl)methyl)-4-methylphenyl)propanoic acid;

(S)-3-(1,4-dimethyl-1H-benzo[d][1,2,3]triazol-5-yl)-3-(3-(((R)-7-hydroxy-2-(trifluoromethyl)-2,3-dihydropyrido[2,3-f][1,4]oxazepin-4(5H)-yl)methyl)-4-methylphenyl)-2,2-dimethylpropanoic acid;

(R)-3-(1,4-dimethyl-1H-benzo[d][1,2,3]triazol-5-yl)-3-(3-(((R)-2-ethyl-8-fluoro-7-hydroxy-2,3-dihydropyrido[2,3-f][1,4]oxazepin-4(5H)-yl)methyl)-4-methylphenyl)propanoic acid;

(S)-3-(1,4-dimethyl-1H-benzo[d][1,2,3]triazol-5-yl)-3-(3-(((S)-7-hydroxy-2-methyl-2,3-dihydropyrido[2,3-f][1,4]oxazepin-4(5H)-yl)methyl)-4-methylphenyl)-2,2-dimethylpropanoic acid;

(S)-3-(1,4-dimethyl-1H-benzo[d][1,2,3]triazol-5-yl)-3-(3-((7-hydroxy-2,3-dihydropyrido[2,3-f][1,4]oxazepin-4(5H)-yl)methyl)-4-methylphenyl)-2,2-dimethylpropanoic acid;

(S)-3-(1,4-dimethyl-1H-benzo[d][1,2,3]triazol-5-yl)-3-(3-(((S)-7-hydroxy-2-(trifluoromethyl)-2,3-dihydropyrido[2,3-f][1,4]oxazepin-4(5H)-yl)methyl)-4-methylphenyl)propanoic acid;

(R)-3-(1,4-dimethyl-1H-benzo[d][1,2,3]triazol-5-yl)-3-(3-(((R)-2-ethyl-7-hydroxy-2-methyl-2,3-dihydropyrido[2,3-f][1,4]oxazepin-4(5H)-yl)methyl)-4-methylphenyl)propanonic acid;

(R)-3-(1,4-dimethyl-1H-benzo[d][1,2,3]triazol-5-yl)-3-(3-(((S)-2-ethyl-7-hydroxy-2-methyl-2,3-dihydropyrido[2,3-f][1,4]oxazepin-4(5H)-yl)methyl)-4-methylphenyl)propanonic acid;

(S)-3-(1,4-dimethyl-1H-benzo[d][1,2,3]triazol-5-yl)-3-(3-(((R)-7-hydroxy-2-(trifluoromethyl)-2,3-dihydropyrido [2,3-f][1,4]oxazepin-4(5H)-yl)methyl)-4-methylphenyl) propanoic acid;

(R)-3-(1,4-dimethyl-1H-benzo[d][1,2,3]triazol-5-yl)-3-(3-((7'-hydroxy-3'H-spiro[cyclobutane-1,2'-pyrido[2,3-f][1, 4]oxazepin-4'(5H)-yl)methyl)-4-methylphenyl)propanonic acid; and (R)-3-(3-(((R)-2-(tert-butyl)-7-hydroxy-2,3-dihydropyrido [2,3-f][1,4]oxazepin-4(5H)-yl)methyl)-4-methylphenyl)-3-(1,4-dimethyl-1H-benzo[d][1,2,3]triazol-5-yl)propanoic acid;

or a salt thereof, particularly a pharmaceutically acceptable salt thereof, or a tautomer thereof, or a hydrate thereof.

Because the compounds of this invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Compound Preparation

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

The synthesis of the compounds of the general Formula (I) and pharmaceutically acceptable derivatives and salts thereof may be accomplished as outlined below in Schemes A thru F. In the following description, the groups are as defined above for compounds of Formula (I) unless otherwise indicated. Abbreviations are as defined in the Examples section. Starting materials are commercially available or are made from commercially available starting materials using methods known to those skilled in the art.

General Synthetic Methods

The compounds I and II are either commercially available or may be prepared by known methods described in the scientific literature. In Scheme A, the compound I may be reacted in the presence of reducing agent, such as borane-tetrahydrofuran, borane-dimethylsulfide, or lithium aluminum hydride to give a compound II, which, upon treatment with base, such as sodium hydride, followed by alkylation with p-methoxybenzyl chloride forms intermediate III.

Scheme A

Conditions: a) BH$_3$-DMS; b) NaH, PMB-Cl.

Scheme B illustrates a route for the synthesis of a compound of formula XIV. A compound IV may be converted to a compound V using methyl amine in a polar protic solvent. A compound V may be brominated in the presence of N-bromosuccinimide to form a compound VI. A compound VI may be treated with reducing agent, such as iron in the presence of an acid, such as hydrochloric acid, to form a compound of the formula VII, which in turn can be treated with tert-butyl nitrite and tetrafluoro boric acid, in a polar aprotic solvent to a form a compound VIII. A compound VIII may be treated with an acrylate, such as methyl acrylate, ethyl acrylate or tert-butyl acrylate, in the presence of palladium source, such as palladium acetate, combined with a phosphine ligand, such as triphenylphosphine or tri-o-tolylphosphine, to form a compound IX. A compound IX may be treated with base, such as lithium hydroxide or sodium hydroxide, or acid, such as trifluoroacetic acid, to form a compound X. Treatment of compound X with pivaloyl chloride in the presence of base, such as triethylamine or diisopropylamine, in a polar aprotic solvent at reduced temperature, followed by addition of lithium chloride and (S)-4-phenyloxazolidin-2-one to form a compound XI. A compound XI can be converted to a compound XII by forming a Grignard reagent of compound III, using either magnesium metal, reike metal or turbo (isopropylmagnesium chloride lithium chloride complex) reagent, with a metal scrub in the form of iodine, dibromoethane, methyl iodide or diisobutylaluminum hydride, whereas the formed Grignard reagent can subsequently be used in the presence of a copper source, such as copper bromide, copper iodide, or copper cyanide to form compound XII. A compound XII can be converted to a compound XIII using magnesium bromide in a polar protic solvent, such as ethanol or methanol, and compound XIII can be subsequently deprotected under oxidative conditions to compound XIV using DDQ in a polar aprotic solvent.

Scheme B

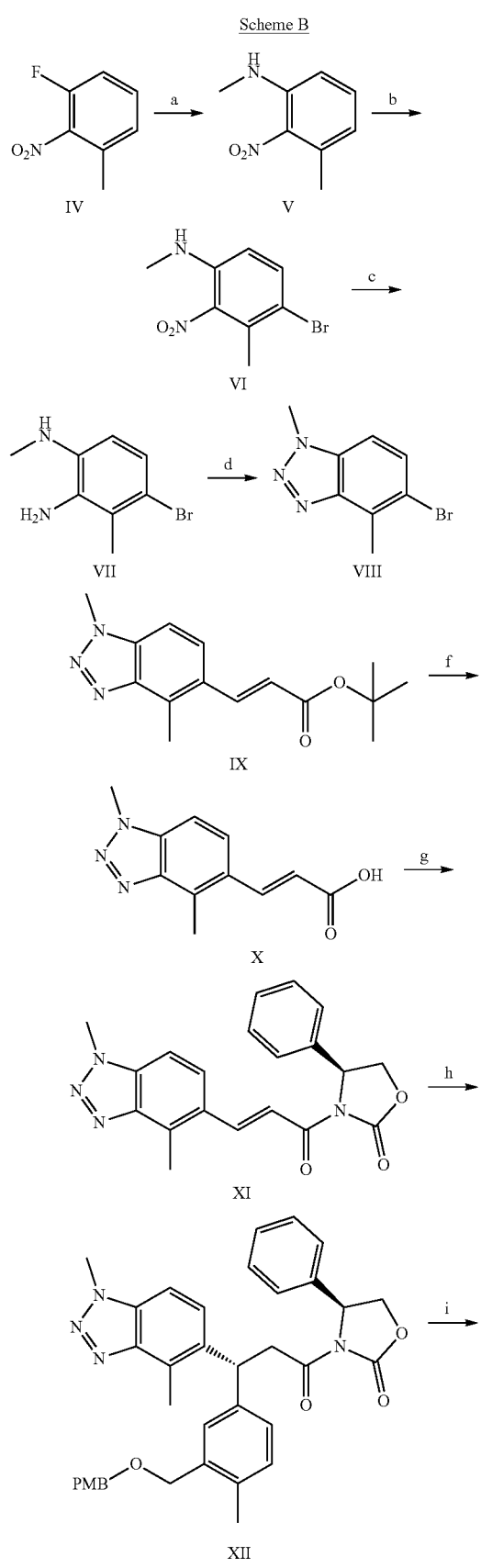

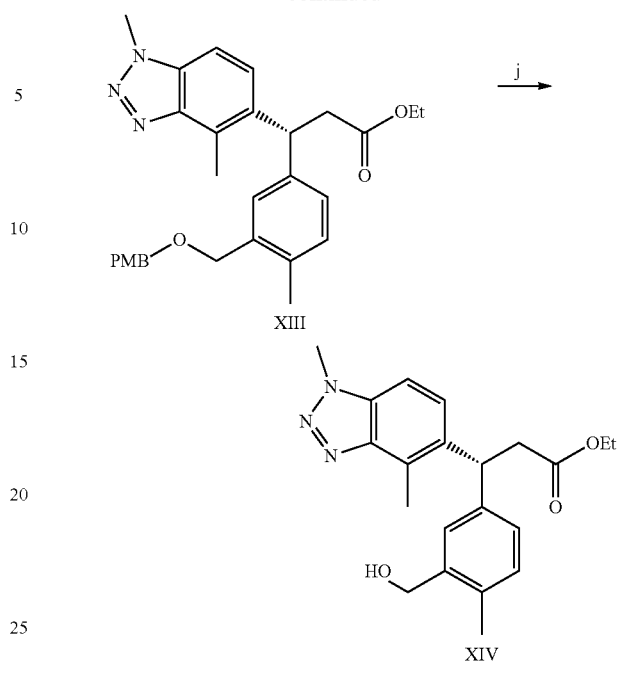

Conditions: a) MeNH₂, EtOH; b) NBS; c) Fe, HCl; d) t-BuONO, HF-BF₃; e) t-Bu-acrylate, Pd(OAc)₂, P(o-tol)₃; f) TFA; g) THF, PivCl, TEA, -25° C.; 2. LiCl, (S)-4-phenyloxazolidin-2-one; h) 1. THF, Mg, III; 2. CuBr-DMS, -40 to -30° C.; i) EtOH, MgBr; j) DCM, DDQ.

Scheme C illustrates a route for the synthesis of a compound of formula XVIII. A compound X can be converted to a compound XV using pivaloyl chloride in the presence of base, such as triethylamine or diisopropylamine, in a polar aprotic solvent at reduced temperature, followed by addition of lithium chloride and (R)-4-phenyloxazolidin-2-one. A compound XV can be converted to a compound XVI by forming a Grignard reagent of compound III, using either magnesium metal, reike metal or turbo reagent, with a metal scrub in the form of iodine, dibromoethane, methyl iodide or diisobutylaluminum hydride, whereas the formed Grignard reagent can subsequently be used in the presence of a copper source, such as copper bromide, copper iodide, or copper cyanide to form a compound XVI. A compound XVI can be converted to a compound XVII using magnesium bromide in a polar protic solvent, such as ethanol or methanol, and compound XVII can be subsequently deprotected under oxidative conditions to compound XVIII using DDQ in a polar aprotic solvent.

Scheme C

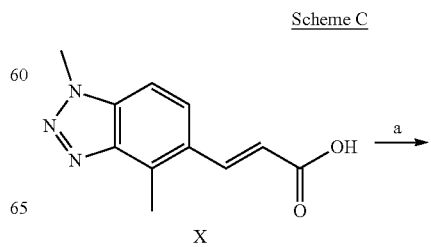

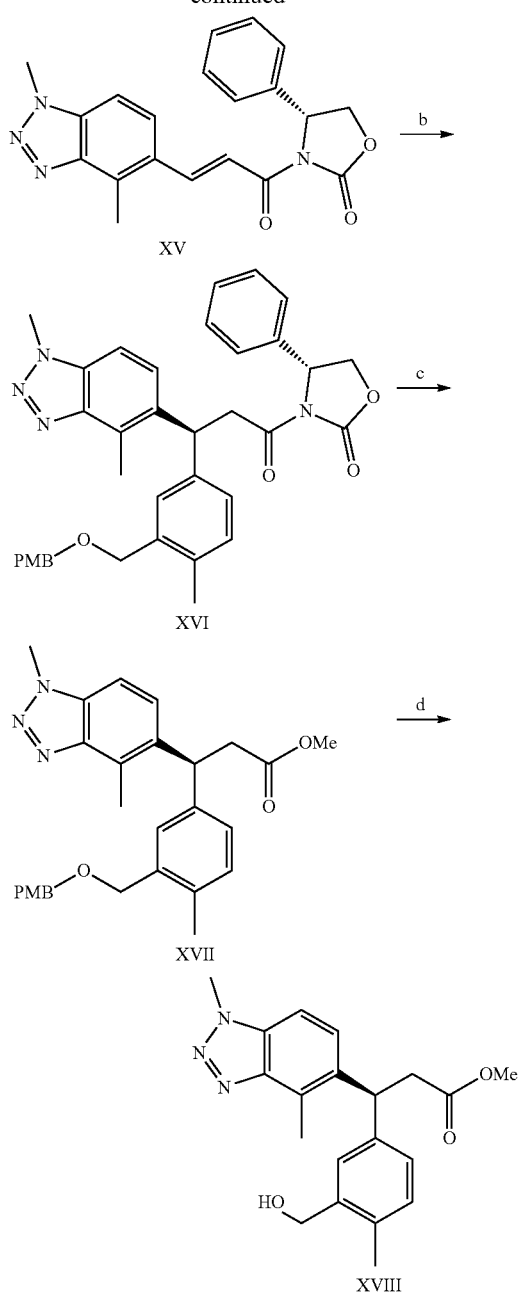

XV

XVI

XVII

XVIII

Conditions: a) 1. THF, PivCl, TEA, −25° C.; 2. LiCl, (R)-4-phenyloxazolidin-2-one; b) 1. THF, Mg, A3; 2. CuBr-DMS, −40 to −30° C.; c) MeOH, MgBr; d) DCM, DDQ.

Scheme D illustrates a route for the synthesis of a compound of formula XX. A compound XVIII can be converted to a compound XIX using a strong base, such as lithium bis(trimethylsilyl)amide or sodium bis(trimethylsilyl)amide, in the presence methyl iodide, in a polar aprotic solvent, which can subsequently be converted to a compound XX under oxidative conditions using DDQ in a polar aprotic solvent.

Scheme D

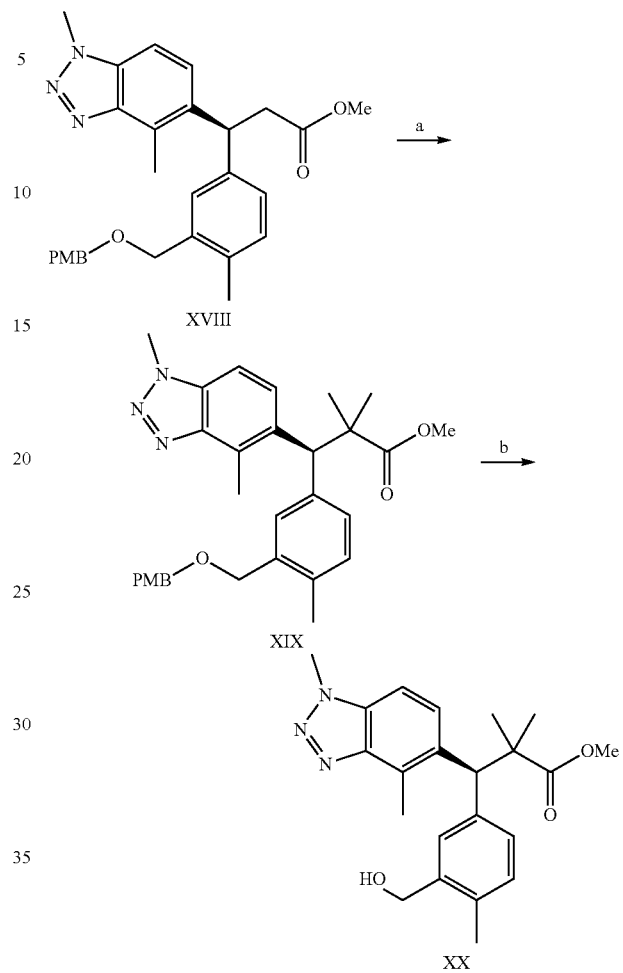

XVIII

XIX

XX

Conditions: a) 1. THF, NaHMDS, MeI, RT; 2. NaHMDS, MeI, 5° C.; b) DCM, H₂O, DDQ.

In Scheme E, the compounds XXI and XXII are either commercially available or may be prepared by known methods described in the scientific literature. The compound XXI may be treated with an amine source, such as ammonia, in a polar protic solvent, such as methanol or ethanol, to give a compound of formula XXII, wherein Y is previously defined. A compound XXII can be treated with an appropriately substituted pyridyl carboxaldehyde, using a reducing agent such as sodium borohydride, sodium cyanoborohydride or sodium triacetoxyborohydride in a polar aprotic solvent to give a compound XXIII, wherein R' is as previously defined. Alternatively, a compound XXII can be converted to a compound XXIII by treatment with a pyridyl carboxaldehyde, using a reducing agent such as sodium borohydride in the presence of a drying agent, such as molecular sieves or magnesium sulfate in a polar protic solvent. A compound XXIII can be cyclized to a compound XXIV upon heating in a polar aprotic solvent, in the presence of a strong base, such as potassium t-butoxide, followed by addition of boc-anhydride. In the event each Y is not the same, a compound XXIV can be converted to a compound XXV by performing chiral chromatography, followed by substitution of the hydroxyl group using a palladium catalyst, such as bis(dibenzylideneacetone)dipalladium(0) or tris(dibenzylideneacetone)dipalladium(0), in the presence of a ligand, such as bippyphos, XPhos, or tBuX-Phos, and a hydroxide source, such as potassium hydroxide or cesium hydroxide. A compound XXV can be deprotected to a compound XXVI under acidic conditions, using trifluoroacetic acid or hydrochloric acid in a non-polar solvent.

elevated temperatures. Conversely, if R is Me, hydrolysis conditions are performed in a high boiling non-polar solvent, such as dioxane, using base, such as lithium hydroxide or sodium hydroxide at high temperatures or in a combination of polar protic solvents, such as methanol and water under microwave irradiation.

Scheme E

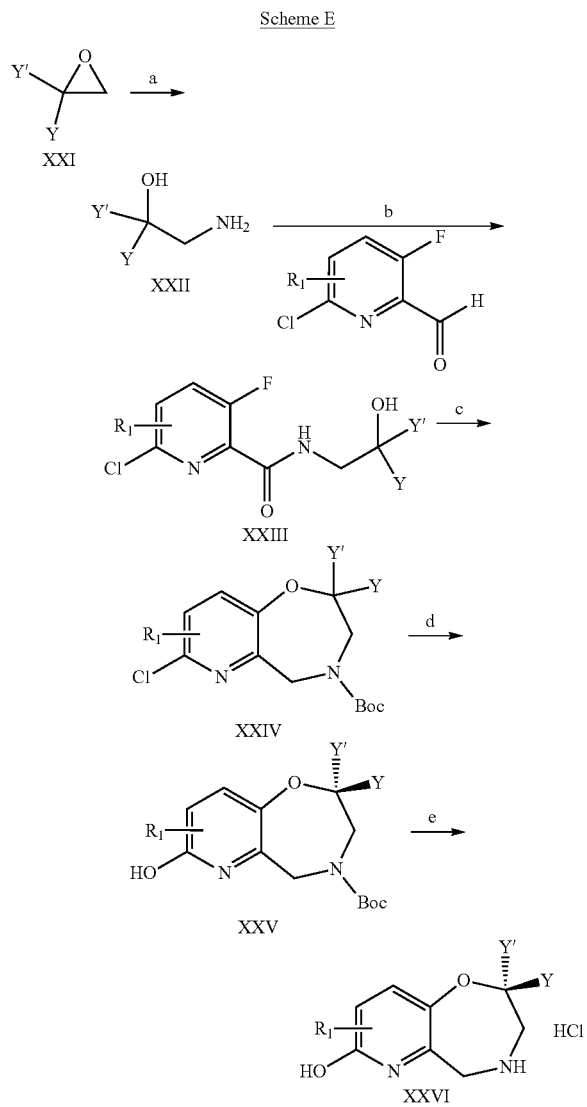

Conditions: a) NH$_3$, MeOH; b) NaBH(OAc)$_3$, THF or MeOH, MgSO$_4$, NaBH$_4$; c) 1. KOtBu, DMSO, 100° C.; 2. Boc$_2$O; d) 1. Chiral chromatography; 2. CsOH, Pd(dba)$_2$, Bippyphos, 90° C.; e) HCl/dioxane.

Scheme F illustrates a route for the synthesis of a compound of formula XXIX, wherein Y, R and R' are previously defined. A compound of XXVII can be converted to a compound XXVIII by treatment with a chlorinating source, such as thionyl chloride, in the presence of a polar aprotic solvent, followed by alkylation with XXVI, in the presence of base, such as triethylamine or diisopropylamine, in a polar aprotic solvent at elevated temperatures. A compound of formula XXIX can be prepared from compound XXVIII by a variety of hydrolysis conditions, pending nature of R. For example, if R is H, hydrolysis conditions are performed with a base, such as lithium hydroxide or sodium hydroxide, in a polar protic solvent, such as methanol or ethanol, at Scheme F

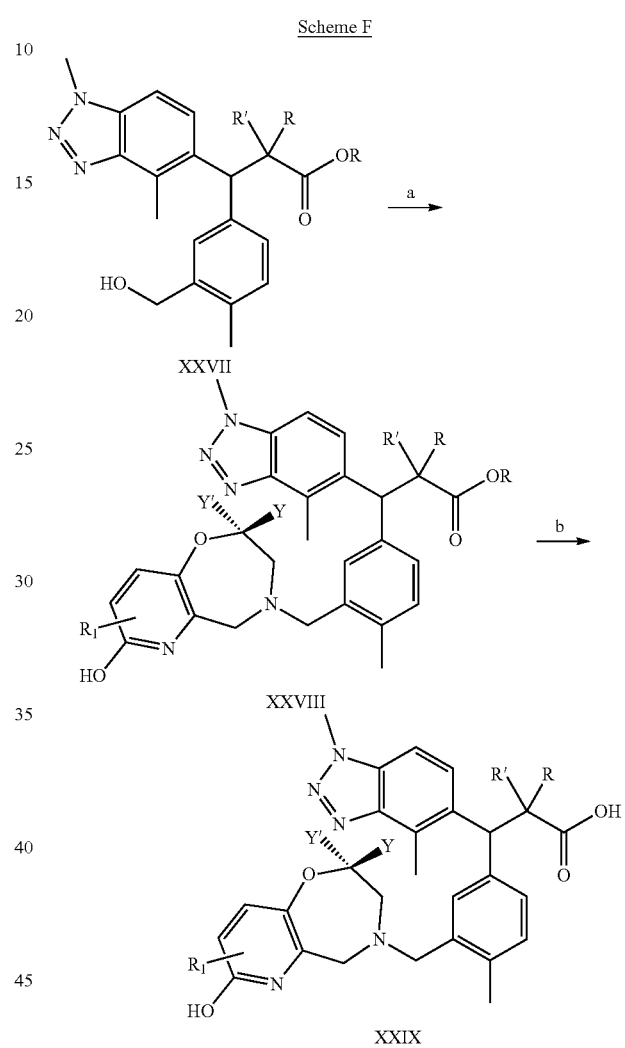

Conditions: a) 1. DCM, S(O)Cl$_2$; 2. MeCN, XXVI, DIEA, 55° C.; b) ROH, aq. NaOH, 55° C. (R = H) or Dioxane, 5N NaOH, 100° C. (R = Me) or MeOH, LiOH, 120° C.

Scheme G

In Scheme G, pyridyl carboxaldehydes are either commercially available or may be prepared by known methods described in the scientific literature. The pyridyl carboxaldehyde may be treated with an amine source to serve as a protecting group, 2-methoxy benzyl amine, 2,4-dimethoxy benzyl amine, or the like, in a polar aprotic solvent, such as dichloromethane, using a reducing agent such as sodium borohydride, sodium cyanoborohydride or sodium triacetoxyborohydride, to give a compound of formula XXX, wherein X is a halogen such as chlorine or bromine and R$_1$ was previously defined. A compound XXX can be treated with an epoxide XXI, wherein Y was previously defined, in a polar protic solvent, such as methanol, to give a compound XXXI. A compound XXXI can be cyclized to a compound XXXII upon heating in a polar aprotic solvent, in the presence of a strong base, such as potassium t-butoxide, sodium hydride, or the like. A compound XXXII can be treated with a hydroxide source, such as potassium hydroxide or cesium hydroxide, in the presence of a palladium catalyst, such as bis(dibenzylideneacetone)dipalladium(0) or tris(dibenzylideneacetone)dipalladium(0), and a ligand, such as bippyphos, XPhos, or ᵗBuXPhos, to give a compound XXXIII. A compound XXXIII can be deprotected to a compound XXVI under acidic conditions, using trifluoroacetic acid or hydrochloric acid in a non-polar solvent.

Scheme G

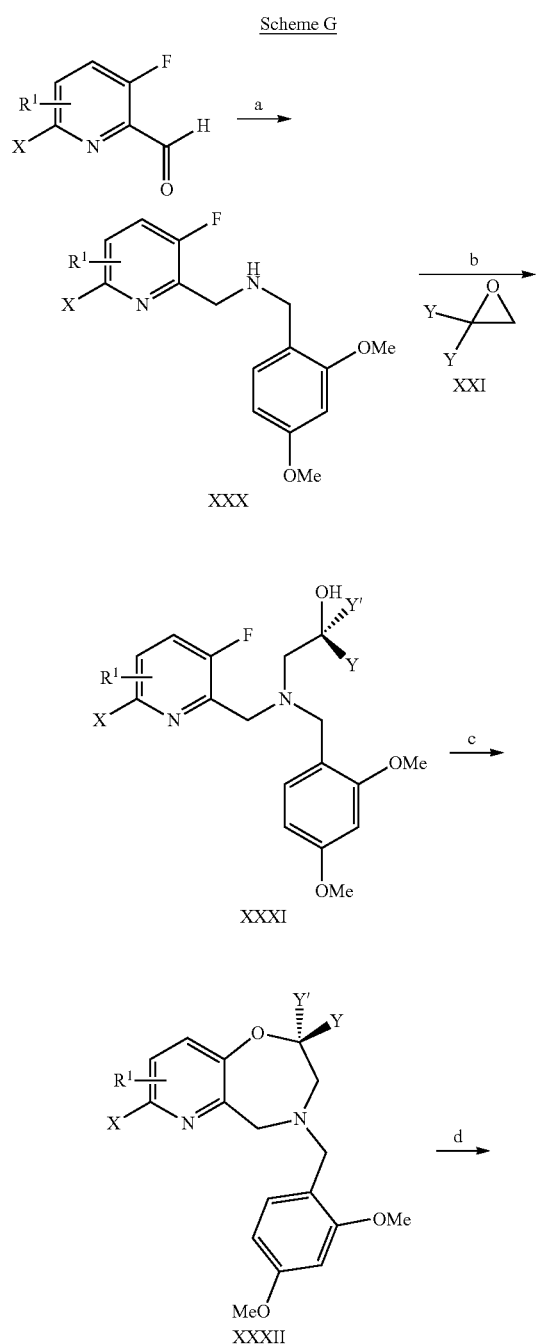

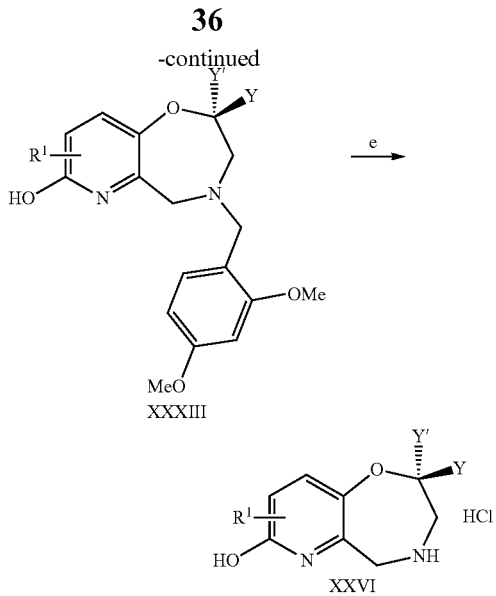

Conditions: a) NaBH(OAc)₃, DCM, HOAc; b) XXI, MeOH, 40° C.; c) NaH, DMF; d) Pd₂(dba)₃, ᵗBuXPhos, KOH, Dioxane, H₂O, 100° C.; d) 1. TFA, 80° C.; 2. HCl, dioxane.

In Scheme H, the compound II may be reacted with 4,4,4',4',5,5,5',5'-octamethyl-2,2'-bi(1,3,2-dioxaborolane), in the presence of a palladium catalyst, such as PdCl₂(dppf)-CH₂Cl₂ adduct and a base, such as potassium acetate, to give a compound of formula XXIV.

Scheme H

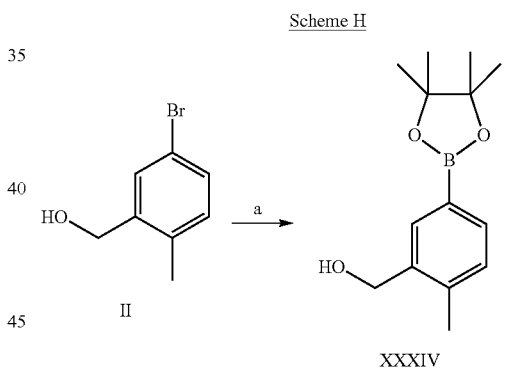

Conditions: a) 4, 4, 4', 4', 5, 5, 5', 5', -octamethyl-2, 2'-bi(1, 3, 2-dioxaborolane), PdCl₂(dppf)-CH₂Cl₂ adduct, KOAc, dioxane.

Biological Activity

As stated above, the compounds according to Formula I are Nrf2 activators, useful in treating an Nrf2-regulated disease or disorder. In a further aspect, the Nrf2-regulated disease or disorder is a human disease or disorder that exhibits oxidative stress components such as respiratory and non-respiratory disorders, selected from COPD, asthma, ALI, ARDS, fibrosis, chronic and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, heart failure with preserved ejection fraction, heart failure with reduced ejection fraction, diabetic cardiomyopathy, SCD, Progeria and CRS, Parkinson's disease (PD), Alzheimer's disease (AD), Friedreich's Ataxia (FA), amyotrophic lateral sclerosis (ALS), multiple sclerosis (MS), Huntington's disease (HD), spinal cord injury, traumatic brain injury, ischemic stroke, stroke, Creutzfeldt-Jakob Disease, fatal familial insomnia, Gerstmann-Stráussler-Scheinker syndrome, and related prion diseases, progressive supranuclear palsy, chronic traumatic encephalopathy (CTE), neurodegeneration, dementias, frontotemporal dementias, tauopathies, retinitis pigmentosa, Pick's disease, Neimann-Pick's disease, amyloidosis, cognitive impairment, inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

The biological activity of the compounds according to Formula I can be determined using any suitable assay for determining the activity of a candidate compound as a Nrf2 activator, as well as tissue and in vivo models.

The biological activity of the compounds of Formula (I) are demonstrated by the following tests.

BEAS-2B NQO1 MTT Assay

NAD(P)H:quinone oxidoreductase 1 (NQO1), also called DT diaphorase, is a homodimeric FAD-containing enzyme that catalyzes obligatory NAD(P)H-dependent two-electron reductions of quinones and protects cells against the toxic and neoplastic effects of free radicals and reactive oxygen species arising from one-electron reductions. The transcription of NQO1 is finely regulated by Nrf2, and thus NQO1 activity is a good marker for Nrf2 activation. On day one, frozen BEAS-2B cells (ATCC) were thawed in a water bath, counted, and re-suspended at a concentration of 250,000 cells/mL. Fifty microliters of cells were plated in 384 well black clear-bottomed plates. Plates were incubated at 37° C., 5% $CO_2$ overnight. On day two, plates were centrifuged and 50 nL of compound or controls were added to the cells. Plates were then incubated at 37° C., 5% $CO_2$ for 48 hours. On day four, medium was aspirated from the plate and crude cell lysates were made by adding 13 μL of 1× Cell Signalling Technologies lysis buffer with 1 Complete, Mini, EDTA-free Protease Inhibitor Tablet (Roche) for each 10 mL of lysis buffer. After lysis plates were incubated for 20 minutes at room temperature. Two microliters of lysate were removed for use in Cell Titer Glo assay (Promega) and MTT cocktail was prepared (Prochaska et. al. 1998) for measurement of NQO1 activity. Fifty microliters of MTT cocktail was added to each well, plate was centrifuged, and analyzed on an Envision plate reader (Perkin Elmer) using Absorbance 570 nm label for 30 minutes. Product formation was measured kinetically and the $pEC_{50}$ of NQO1 specific activity induction was calculated by plotting the change in absorbance (Delta OD/min) versus the log of compound concentration followed by 3-parameter fitting.

All examples described herein possessed activity in the BEAS-2B cell assay unless otherwise noted (see Table 1). $EC_{50}$s<1 nM (+++++), $EC_{50}$s 1 nM-10 nM (++++), $EC_{50}$s 10 nM-100 nM (+++), $EC_{50}$s 100 nM-1 μM (++), $EC_{50}$s 1 μM-10 μM (+).

TABLE 1

| Ex | $EC_{50}$ |
|---|---|
| 1 | +++ |
| 2 | ++ |
| 3 | ++++ |
| 4 | +++ |
| 5 | +++ |
| 6 | +++ |
| 7 | ++ |
| 8 | +++ |
| 9 | ++ |
| 10 | +++ |
| 11 | ++ |
| 12 | + |
| 13 | +++++ |
| 14 | ++++ |
| 15 | +++++ |
| 16 | ++++ |
| 17 | ++++ |
| 18 | ++++ |
| 19 | +++++ |
| 20 | + |
| 21 | +++ |
| 22 | ++++ |
| 23 | +++ |
| 24 | +++ |
| 25 | +++ |
| 26 | ++ |
| 27 | +++ |
| 28 | + |
| 29 | +++ |
| 30 | +++ |

Human PXR Activation Assay

Transactivation activity of PXR ligands was measured in a human hepatocellular carcinoma line (HepG2) batch transiently transfected using FuGENE™ with expression vectors containing full length human PXR and the human CYP3A4 promoter driving luciferase expression. Following transfection, cells are frozen until required for assay.

On day of assay, cells were recovered, counted on a CEDEX instrument then resuspended to a density of 50,000 cells/mL in phenol red-free DMEM-F12 supplemented with 10% charcoal/dextran-treated FBS. 20 μl of cell suspension was then dispensed to each well of white Nunc 384-well plates, containing 0.1 mL of test compounds in DMSO. Cells were incubated for 24 h in the presence compound after which time 10 mL of Steady-Lite™ luciferase substrate was added to each well. Luciferase activity was quantified by measurement on the Pherastar™ imager and activity was expressed as percent maximum induction as compared to induction by 10 μM rifampicin.

Monkey PK Study

All studies were conducted after review by the GSK Institutional Animal Care and Use Committee and in accordance with the GSK Policy on the Care, Welfare and Treatment of Laboratory Animals. A pre-study health examination that included a physical exam and complete blood count was performed on the animals prior to use on study. A catheter was temporarily placed in a cephalic or saphenous vein for sample collection on the study day. The animals were fasted overnight prior to dosing; food provided after the 4-hour blood sample was collected. The intravenous and oral solution pharmacokinetic studies were carried out using a non-crossover design; a total of four male cynomolgus monkeys were used, two per route of administration.

The compounds used in this study were the compound of Example 1, herein, and Compound A (the compound of Example 1 of WO 2018/109646).

The dose for intravenous administration was prepared as a cassette of up to five test compounds in 20% Cavitron™ and 5% DMSO. The intravenous dose formulation was filtered through a 0.22-micron polytetrafluoroethylene (PTFE) filter prior to administration. The dose for oral solution administration was prepared as a cassette of up to five compounds in 6% Cavitron™ and 5% DMSO and was filtered through a 0.22-micron VWR PTFE filter prior to administration.

Each animal received a nominal dose of 1 mg/kg/compound (4 mL/kg dose volume) either as a 60-minute intravenous infusion or as an oral gavage. Blood samples (approximately 0.25 mL each) were collected from a cephalic or saphenous vein. Blood samples from animals that received the intravenous dose were collected prior to dosing and at target times of 15, 30, 45, 60 (before termination of the infusion), 62, 65, 75, 90, 120, 180, 240, 360, 480, 600, and 1440 minutes following the initiation of the intravenous infusion. For animals that received the oral dose, blood samples were collected prior to dosing and at target times of 5, 15, 30, 45, 60, 90, 120, 180, 240, 360, 480, 600, and 1440 minutes following oral gavage. Plasma was isolated from blood by centrifugation and a 30 μL aliquot was transferred to a non-heparinized tube, quick frozen on solid carbon dioxide and stored at approximately −80° C. until analyzed by liquid chromatography/tandem mass spectroscopy (LC/MS/MS) for test compound concentration.

Mouse PK Study

All studies were conducted after review by the GSK Institutional Animal Care and Use Committee and in accordance with the GSK Policy on the Care, Welfare and Treatment of Laboratory Animals. The oral suspension pharmacokinetic study was carried out on a single study day; a total of three male CD1 mice were used.

The compounds used in this study were the compound of Example 1, herein, and Compound A (the compound of Example 1 of WO 2018/109646).

The oral suspension dose was prepared in 1% aqueous methylcellulose. Each animal received a nominal dose of 30 mg/kg (10 mL/kg dose volume) as an oral gavage. Blood samples (approximately 0.025 mL each) were collected from a tail vein. Blood samples were collected prior to dosing and at target times of 15, 30, 60, 120, 240, 480, and 1440 minutes following oral gavage. A 25 μL aliquot was added to a non-heparinized tube containing 25 μL water and quick frozen on solid carbon dioxide and stored at approximately −80° C. until analyzed by liquid chromatography/tandem mass spectroscopy (LC/MS/MS) for test compound concentration.

Rat PK Study

All studies were conducted after review by the GSK Institutional Animal Care and Use Committee and in accordance with the GSK Policy on the Care, Welfare and Treatment of Laboratory Animals. This study was conducted with a crossover design on two study days with a one-day recovery period between each study day. At least three days prior to the start of the study, three rats received surgically implanted femoral vein, femoral artery, and gastric catheters for infusion of test molecules, blood sampling, and oral dose administration, respectively. Dose solutions were filtered prior to administration and the actual dosage administered to the animals was quantified. All PK parameters were calculated based on the actual dosage administered to each animal. Urine was collected from 0-24 h following iv administration from each animal for determination of renal clearance.

The compounds used in this study were the compound of Example 1, herein, and Compound A (the compound of Example 1 of WO 2018/109646).

The dose for intravenous administration was prepared in 20% Cavitron™ and 5% DMSO. The intravenous dose formulation was filtered through a 0.22-micron polytetrafluoroethylene (PTFE) filter prior to administration. The dose for oral solution administration was prepared in 6% Cavitron™ and 5% DMSO and was filtered through a 0.22-micron VWR PTFE filter prior to administration.

Each animal received a nominal dose of 1 mg/kg (4 mL/kg dose volume) as a 30-minute intravenous infusion on study day one. On study day two, each animal received a nominal dose of 2 mg/kg (16 mL/kg dose volume) as an oral gavage. Blood samples (approximately 0.11 mL each) were collected from the femoral artery catheter. Blood samples from animals that received the intravenous dose were collected prior to dosing and at target times of 5, 15, 29, (before termination of the infusion), 32, 35, 45, 60, 90, 120, 180, 240, 360, 480, 720, 960, 1200, and 1440 minutes following the initiation of the intravenous infusion. For animals that received the oral dose, blood samples were collected prior to dosing and at target times of 5, 15, 30, 45, 60, 90, 120, 180, 240, 360, 480, 720, 960, 1200, and 1440 minutes following oral gavage. Plasma was isolated from blood by centrifugation and a 30 μL aliquot was transferred to a non-heparinized tube, quick frozen on solid carbon dioxide and stored at approximately −80° C. until analyzed by liquid chromatography/tandem mass spectroscopy (LC/MS/MS) for test compound concentration.

Pharmacokinetic parameters for all in vivo PK studies were calculated using non-compartmental methods with Phoenix WinNonlin version 6.1.0 or 8.1.0. All parameters were calculated using actual blood sampling times and actual dosages for each animal. The extrapolated area under the curve ($AUC_{0-inf}$) was determined using unweighted linear regression analysis of at least three log transformed concentrations visually assessed to be on the linear portion of the terminal elimination slope. Oral solution bioavailability was calculated in a non-crossover fashion using the mean intravenous dose and $AUC_{0-inf}$ values from the two intravenously dosed animals for the monkey PK study and in a crossover fashion for the rat PK study.

Mouse Plasma Protein Binding Study

Stock solutions of the compound of Example 1, herein, and Compound A (the compound of Example 1 of WO 2018/109646), were prepared in dimethyl sulfoxide (DMSO) at a concentration of 1 mg/mL. Incubation mixtures were prepared by diluting the stock solution into heparinized mouse plasma to a concentration of 2000 ng/mL. The final concentration of DMSO was 0.2%. The thawed plasma was centrifuged to remove any debris. If necessary, the pH of the plasma sample was adjusted to approximately 7.5 with 1% aqueous phosphoric acid prior to use. Incubation mixtures were prepared. Triplicate 10 μL aliquots of each incubation mixture were collected and analyzed to verify initial compound concentration. Four aliquots of each incubation mixture were placed into separate polyallomer ultracentrifuge tubes. The incubation mixtures were centrifuged in a Beckman Type 42.2 Ti rotor at 42,000 rpm (214,361×g) at 37° C. for 3 hours with maximum acceleration and deceleration. Following centrifugation, one 50 μL aliquot was collected from the topmost layer of supernatant from three tubes. The contents of the remaining tube were mixed until homogeneous, and three 10 μL aliquots were collected to determine recovery of compound from the centrifugation tubes. The samples were quick frozen on solid carbon dioxide and stored at approximately −80° C. until analyzed by liquid chromatography/tandem mass spectroscopy (LC/MS/MS) for test compound concentration. Total recovery of compound from the ultracentrifugation tubes was calculated with the following formula:

$$Recovery = \frac{Cplas}{Cinit} * 100,$$

where Cplas is the post-centrifugation mixed plasma compound concentration and Cinit is the mean initial (pre-centrifugation) compound concentration.

Percent unbound (Fu) by ultracentrifugation was calculated with the following formula:

$$Fu = \frac{Csup}{Cinit} * 100,$$

where Csup is the post-centrifugation plasma supernatant compound concentration and Cinit is the mean initial (pre-centrifugation) compound concentration.

mL/min/kg in cynomolgus monkey. There was an ~11-fold improvement in mean residence time (MRT) for the compound of Example 1, herein, which demonstrated MRT of 18 h, while Compound A demonstrated MRT of 1.6 h in cynomolgus monkey. The reduced CL and longer MRT provide a PK profile which indicates the compound of Example 1 herein, could be administered at lower doses in the clinic with a preferred once daily regimen.

In the mouse, Example 1 (Clearance/Bioavailability=15.6 mL/min/kg) and Compound A (Clearance/Bioavailability=31 mL/min/kg) gave similar exposures in blood after oral dosing. However, Compound A was found to be highly bound to mouse plasma proteins (99.7%) while Example 1 displayed dramatically less plasma protein binding (91.6%). The reduced plasma protein binding of Example 1 suggests it will have greater efficacy than Compound A at a given dose.

Activity against human preganane X-receptor (PXR) is another key criterion used in the selection of compounds for progression to the clinic as PXR activators may cause

TABLE 2

|  | Compound A | Example 1 |
|---|---|---|
| Compound Structure | (structure image) | (structure image) |
| Nrf2 BEAS-2B NQO1 $EC_{50}$ | 16 nM | 13 nM |
| Human PXR $EC_{50}/E_{max}$ | 25,000 nM/56% | >50,000 nM/10% |
| Rat Pharmacokinetics | | |
| Total Clearance | 1.9 mL/min/kg | 5.2 mL/min/kg |
| MRT | 4.0 h | 6.5 h |
| Monkey Pharmacokinetics | | |
| Total Clearance | 10.9 mL/min/kg | 0.41 mL/min/kg |
| MRT | 1.6 h | 18 h |
| Mouse Pharmacokinetics | | |
| Clearance/Bioavailability | 31 mL/min/kg | 15.6 mL/min/kg |
| Plasma Protein Binding, % bound | 99.7% | 91.6% |

As shown in Table 2, Example 1 ($EC_{50}$=13 nM) and Compound A ($EC_{50}$=16 nM) exhibit comparable activation of the Nrf2 pathway in cells and show similar pharmacokinetic parameters in rats. However, Example 1 shows differences compared to Compound A when assessed in monkey and mouse pharmacokinetic studies.

Pharmacokinetic (PK) parameters in cynomolgus monkey are key criteria used in the selection of compounds for progression to the clinic as they inform the likelihood of achieving drug exposures required to produce a pharmacologic effect in humans with a suitable dosing regimen. There was a ~27-fold reduction in total clearance (CL) for the compound of Example 1, herein, with a demonstrated CL of 0.41 mL/min/kg, while Compound A (the compound of Example 1 of WO 2018/109646) demonstrated CL of 10.9 drug-drug interactions that can render other co-administered drugs ineffective. The lack of measurable PXR activity ($EC_{50}$>50,0000 nM) for the compound of Example 1, herein, indicates the compounds of this invention have a reduced risk of encountering clinical drug-drug interactions.

Mouse Transverse Aortic Constriction (TAC) Left Ventricular Pressure Overload Model Male C57BLK/6J mice (10-12 weeks old) were individually housed and acclimated to a standard powdered rodent diet for 1-3 days. Water was offered ad libitum throughout the study. Mice were initially anesthetized in a chamber using an 3% isoflurane with oxygen (1.0 L/min), and then maintained at 1.5% via nose cone (without intubation). A small incision (~5 mm) was made just left of midline and just above the rib cage at the level of the suprasternal notch.

The muscle tissue was retracted to expose the area above the pleural cavity. The lobes of the thymus were separated and retracted to expose the aortic arch. Fine surgical forceps with blunted tips were used to expose a region above and below the aorta. A micro blunt hook tied with 7-0 silk surgical suture was looped under the aorta and the suture pulled through. The suture was tied-off against a small piece of blunted 27 G needle and the needle was then removed creating the aortic constriction (a 60-70% constriction of the lumen). The incision was closed using 6-0 silk suture for the muscle layer, then the skin with Medbond. The sham procedure was identical without ligation of aorta. Depending on the individual study designs, drug administration began either on the day of surgery, or 1-2 weeks after surgery (detailed in figure legends) and continued until the end of study. Compounds were administered in the mouse chow unless otherwise noted in FIG. 12 legends. TAC study duration was either 6 weeks or 10 weeks in duration. All TAC study endpoints were collected at the end of study. Following heart dissections, samples were either snap frozen in liquid nitrogen and stored at −80° C. or placed in 10% neutral buffered formalin until analysis.

Echocardiography: For mouse TAC studies, echocardiography was performed on a Vevo 2100 high frequency imaging system. Animals were anesthetized with 2-3% isoflurane and sedation maintained with 1% isoflurane with animals on a heating pad. B-mode imaging of three cardiac cycles was used to assess ejection fraction (EF), end diastolic volume (EDV), end systolic volume (ESV), LV mass, and heart rate. ECG was used to measure heart rate during the echocardiography procedure.

NADPH dehydrogenase [quinone]-1 (NQO1) activity: Left ventricular (LV) tissue NQO1 activity was determined using an NQO1 assay kit per manufacturer's protocol (Abcam, Cambridge MA)

The KEAP1 blockers/Nrf2 activators, (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, hydrochloride, or a tautomer thereof (Example 1) (in dose-response) and (S)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid (Example B) were evaluated in a 10-week mouse TAC model of severe hemodynamic stress. Both compounds, administered daily for eight weeks, and initiated after cardiac function had declined, elicited a full normalization of cardiac function as assessed by ejection fraction, significant dose-related elevations in NAD(P)H quinone oxidoreductase 1 (NQO1; an antioxidant enzyme and Nrf2 target gene product) in the LV, and did not influence cardiac hypertrophy, nor did the ejection fraction change occur by unloading the heart (i.e., lowering blood pressure) or increasing the heart rate, the mechanism by which many established HF therapies (ACEi/ARBs, β-blockers, inotropes) improve cardiac function but also increase the risk for hypotension and arrhythmias. See FIG. 12.

FIG. 12 depicts the effect of the KEAP1-kelch domain blockers/Nrf2 activators (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, hydrochloride, or a tautomer thereof (Compound of Example 1) and (S)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid (Compound B) on cardiac function, remodeling, and NQO1 enzyme activity in the murine 10-week TAC model. All compounds were dosed in chow beginning 2-weeks after TAC. Figures labeled as follows: Sh (sham, n=6), V (TAC and chow no drug, n=13), EX1 [TAC and (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, hydrochloride, or a tautomer thereof, in chow at 1.0 mg/kg/d (n=11), 3.0 mg/kg/d (n=12) and 10 mg/kg/d (n=10)], EXB [TAC and (S)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid in chow at 100 mg/kg/d, n=7]. (12A) Ejection fraction, percent of left ventricular volume; (12B) Left ventricular NQO1 enzyme activity, vehicle value set at 100%; (12C) Heart rate, (bpm) beats per min.; and (12D) Left ventricular weights normalized to tibia length Data are represented as mean (±s.e.m). P-values were determined by one-way ANOVA with Dunnett's multiple comparison test. All p-values (top of bars) in comparison to vehicle. (EX 1 results are shown at bars graphs labelled 1, 3 and 10; EX B results are shown at bar graph labelled 100).

Methods of Use

The compounds of the invention are Nrf2 activators, and are useful in the treatment or prevention of respiratory and non-respiratory disorders, selected from COPD, asthma, ALI, ARDS, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, heart failure with preserved ejection fraction, heart failure with reduced ejection fraction, diabetic cardiomyopathy, SCD, Progeria and CRS, Parkinson's disease (PD), Alzheimer's disease (AD), Friedreich's Ataxia (FA), amyotrophic lateral sclerosis (ALS), multiple sclerosis (MS), Huntington's disease (HD), spinal cord injury, traumatic brain injury, ischemic stroke, stroke, Creutzfeldt-Jakob Disease, fatal familial insomnia, Gerstmann-Sträussler-Scheinker syndrome, and related prion diseases, progressive supranuclear palsy, chronic traumatic encephalopathy (CTE), neurodegeneration, dementias, frontotemporal dementias, tauopathies, retinitis pigmentosa, Pick's disease, Neimann-Pick's disease, amyloidosis, cognitive impairment, inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

Accordingly, in one aspect, the invention provides methods of treating such conditions.

The methods of treatment of the invention comprise administering a therapeutically effective amount of a compound according to Formula I or a salt thereof, particularly, a pharmaceutically acceptable salt thereof, or a tautomer thereof, or a hydrate thereof, to a patient in need thereof.

In one embodiment, this invention provides a compound of Formula (I), or a salt, particularly a pharmaceutically acceptable salt thereof, or a tautomer thereof, or a hydrate thereof, for use in the treatment of Pulmonary Arterial Hypertension. In another embodiment, this invention provides a compound of Formula (I), or a salt, particularly a pharmaceutically acceptable salt thereof, or a tautomer thereof, or a hydrate thereof, for use in the treatment of atherosclerosis. In another embodiment, this invention provides a compound of Formula (I), or a salt, particularly a pharmaceutically acceptable salt thereof, or a tautomer thereof, or a hydrate thereof, for use in the treatment of hypertension. In another embodiment, this invention provides a compound of Formula (I), or a salt, particularly a pharmaceutically acceptable salt thereof, or a tautomer thereof, or a hydrate thereof, for use in the treatment of acute coronary syndrome. In another embodiment, this invention provides a compound of Formula (I), or a salt, particularly a pharmaceutically acceptable salt thereof, or a tautomer thereof, or a hydrate thereof, for use in the treatment of myocardial infarction. In another embodiment, this invention provides a compound of Formula (I), or a salt, particularly a pharmaceutically acceptable salt thereof, or a tautomer thereof, or a hydrate thereof, for use in the treatment of myocardial repair. In another embodiment, this invention provides a compound of Formula (I), or a salt, particularly a pharmaceutically acceptable salt thereof, or a tautomer thereof, or a hydrate thereof, for use in the treatment of cardiac remodelling. In another embodiment, this invention provides a compound of Formula (I), or a salt, particularly a pharmaceutically acceptable salt thereof, or a tautomer thereof, or a hydrate thereof, for use in the treatment of cardiac arrhythmias. In another embodiment, this invention provides a compound of Formula (I), or a salt, particularly a pharmaceutically acceptable salt thereof, or a tautomer thereof, or a hydrate thereof, for use in the treatment of diabetic cardiomyopathy. In another embodiment, this invention provides a compound of Formula (I), or a salt, particularly a pharmaceutically acceptable salt thereof, or a tautomer thereof, or a hydrate thereof, for use in the treatment of sickle cell disease. In another embodiment, this invention provides a compound of Formula (I), or a salt, particularly a pharmaceutically acceptable salt thereof, or a tautomer thereof, or a hydrate thereof, for use in the treatment of Progeria and cardiorenal syndrome. In another embodiment, this invention provides a compound of Formula (I), or a salt, particularly a pharmaceutically acceptable salt thereof, or a tautomer thereof, or a hydrate thereof, for use in the treatment of Parkinson's disease. In another embodiment, this invention provides a compound of Formula (I), or a salt, particularly a pharmaceutically acceptable salt thereof, or a tautomer thereof, or a hydrate thereof, for use in the treatment of Alzheimer's disease. In another embodiment, this invention provides a compound of Formula (I), or a salt, particularly a pharmaceutically acceptable salt thereof, or a tautomer thereof, or a hydrate thereof, for use in the treatment of Friedreich's Ataxia. In another embodiment, this invention provides a compound of Formula (I), or a salt, particularly a pharmaceutically acceptable salt thereof, or a tautomer thereof, or a hydrate thereof, for use in the treatment of amyotrophic lateral sclerosis. In another embodiment, this invention provides a compound of Formula (I), or a salt, particularly a pharmaceutically acceptable salt thereof, or a tautomer thereof, or a hydrate thereof, for use in the treatment of multiple sclerosis. In another embodiment, this invention provides a compound of Formula (I), or a salt, particularly a pharmaceutically acceptable salt thereof, or a tautomer thereof, or a hydrate thereof, for use in the treatment of Huntington's disease. In another embodiment, this invention provides a compound of Formula (I), or a salt, particularly a pharmaceutically acceptable salt thereof, or a tautomer thereof, or a hydrate thereof, for use in the treatment of spinal cord injury. In another embodiment, this invention provides a compound of Formula (I), or a salt, particularly a pharmaceutically acceptable salt thereof, or a tautomer thereof, or a hydrate thereof, for use in the treatment of traumatic brain injury. In another embodiment, this invention provides a compound of Formula (I), or a salt, particularly a pharmaceutically acceptable salt thereof, or a tautomer thereof, or a hydrate thereof, for use in the treatment of ischemic stroke. In another embodiment, this invention provides a compound of Formula (I), or a salt, particularly a pharmaceutically acceptable salt thereof, or a tautomer thereof, or a hydrate thereof, for use in the treatment of stroke.

In one aspect, this invention provides a method of treating COPD comprising administering to a subject in need thereof, a therapeutically effective amount of a compound of Formula (I), or a salt, particularly a pharmaceutically acceptable salt thereof, or a tautomer thereof, or a hydrate thereof. Specifically, the invention provides a method of treating COPD comprising administering to a subject in need thereof, a therapeutically effective amount of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof.

In one aspect, this invention provides a method of treating heart failure, comprising administering to a subject in need thereof, a therapeutically effective amount of a compound of Formula (I), or a salt, particularly a pharmaceutically acceptable salt thereof, or a tautomer thereof, or a hydrate thereof. In one embodiment, the invention provides a method of treating heart failure comprising administering to a subject in need thereof, a therapeutically effective amount of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof. In another embodiment, this invention provides a method of treating heart failure comprising administering to a subject in need thereof, a therapeutically effective amount of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof. In a further embodiment, this invention provides a method of treating heart failure comprising administering to a subject in need thereof, a therapeutically effective amount of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, or a hydrate thereof.

In one aspect, this invention relates to a method for treating heart failure with reduced ejection fraction comprising administering to a subject in need thereof, a therapeutically effective amount of a compound of Formula (I), or a salt, particularly a pharmaceutically acceptable salt thereof, or a tautomer thereof, or a hydrate thereof. In one embodiment, the invention relates to a method of treating heart failure with reduced ejection fraction comprising administering to a subject in need thereof, a therapeutically effective amount of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof. In another embodiment, this invention provides a method of treating heart failure with reduced ejection fraction comprising administering to a subject in need thereof, a therapeutically effective amount of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof. In a further embodiment, this invention provides a method of treating heart failure with reduced ejection fraction comprising administering to a subject in need thereof, a therapeutically effective amount of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, or a hydrate thereof.

In one aspect, this invention relates to a method for treating heart failure with preserved ejection fraction, which comprises administering to a subject in need thereof, a therapeutically effective amount of a compound of Formula (I), or a salt, particularly a pharmaceutically acceptable salt thereof, or a tautomer thereof, or a hydrate thereof. In one embodiment, the invention relates to a method of treating heart failure with preserved ejection fraction comprising administering to a subject in need thereof, a therapeutically effective amount of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a salt thereof, particularly a pharmaceutically acceptable salt thereof, or a tautomer thereof, or a hydrate thereof. In another embodiment, this invention provides a method of treating heart failure with preserved ejection fraction comprising administering to a subject in need thereof, a therapeutically effective amount of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof. In a further embodiment, this invention provides a method of treating heart failure with preserved ejection fraction comprising administering to a subject in need thereof, a therapeutically effective amount of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, or a hydrate thereof.

In one aspect, the invention provides a method of improving or alleviating the symptoms of heart failure as a result of non-ischemic injury, comprising administering to a subject in need thereof, a therapeutically effective amount of a compound of Formula (I), or a salt thereof, particularly a pharmaceutically acceptable salt thereof, or a tautomer thereof, or a hydrate thereof. In one embodiment, the invention provides a method of improving or alleviating the symptoms of heart failure as a result of non-ischemic injury, comprising administering to a subject in need thereof, a therapeutically effective amount of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof. In a further embodiment, the invention provides a method of improving or alleviating the symptoms of heart failure as a result of non-ischemic injury, comprising administering to a subject in need thereof, a therapeutically effective amount of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof. In yet another embodiment, the invention provides a method of improving or alleviating the symptoms of heart failure as a result of non-ischemic injury, comprising administering to a subject in need thereof, a therapeutically effective amount of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid hydrate, or a tautomer thereof. In each of these embodiments, the symptoms of heart failure as a result of non-ischemic injury include, but are not limited to, increased heart rate, hypotension, swollen ankles, shortness of breath, fatigue, excess fluids or fluid retention, and the like.

In one aspect, the invention provides a method of treating heart failure as a result of ischemic injury comprising administering to a subject in need thereof, a therapeutically effective amount of a compound of Formula (I), or a salt thereof, particularly a pharmaceutically acceptable salt thereof, or a tautomer thereof, or a hydrate thereof. In one embodiment, the invention provides a method of treating heart failure as a result of ischemic injury comprising administering to a subject in need thereof, a therapeutically effective amount of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof. In a further embodiment, the invention provides a method of treating heart failure as a result of ischemic injury comprising administering to a subject in need thereof, a therapeutically effective amount of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof. In yet another embodiment, the invention provides a method of treating heart failure as a result of ischemic injury comprising administering to a subject in need thereof, a therapeutically effective amount of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid hydrate, or a tautomer thereof.

In one aspect, the invention provides a compound of Formula (I), or a salt thereof, particularly a pharmaceutically acceptable salt thereof, or a tautomer thereof, or a hydrate thereof, for use in treating and/or preventing conditions associated with Nrf2 regulation. In one embodiment, the invention provides (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, for use in treating and/or preventing conditions associated with Nrf2 regulation. In another embodiment, this invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, for use in treating conditions associated with Nrf2 regulation. In a further embodiment, this invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, or a hydrate thereof, for use in treating conditions associated with Nrf2 regulation.

In one aspect, the invention provides a method of regulating Nrf2 which method comprises contacting a cell with a compound of Formula (I), or a salt, particularly a pharmaceutically acceptable salt thereof, or a tautomer thereof, or a hydrate thereof. In one embodiment, the invention provides a method of regulating Nrf2 which method comprises contacting a cell with (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof. In another embodiment, this invention provides a method of regulating Nrf2 which method comprising contacting a cell with crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof. In a further embodiment, this invention provides a method of regulating Nrf2 which method comprising contacting a cell with crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, or a hydrate thereof.

In one aspect, this invention provides a compound of the invention for use in therapy. In one embodiment, his invention provides a compound of Formula (I), or a salt, particularly a pharmaceutically acceptable salt thereof, or a tautomer thereof, or a hydrate thereof, for use in therapy. In another embodiment, this invention provides (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, for use in therapy. In a further embodiment, this invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, for use in therapy. In still another embodiment, this invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, or a hydrate thereof, for use in therapy.

In one aspect, the invention provides a compound of Formula (I), or a salt, particularly a pharmaceutically acceptable salt thereof, or a tautomer thereof, or a hydrate thereof, for use as an Nrf2 activator. In one embodiment, the invention provides (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, for use as an Nrf2 activator. In another embodiment, this invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, for use as an Nrf2 activator. In a further embodiment, this invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, or a hydrate thereof, for use as an Nrf2 activator.

In one aspect, this invention relates to the use of a compound of Formula (I), or a salt, particularly a pharmaceutically acceptable salt thereof, or a tautomer thereof, or a hydrate thereof, for the treatment of COPD. Specifically, the invention relates to the use of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, for the treatment of COPD.

In one aspect, this invention provides the use of a compound of Formula (I), or a salt, particularly a pharmaceutically acceptable salt thereof, or a tautomer thereof, or a hydrate thereof, for the treatment of heart failure. In one embodiment, the invention provides the use of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, for the treatment of heart failure. In another embodiment, this invention provides the use of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, for the treatment of heart failure.

In a further embodiment, this invention provides the use of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, or a hydrate thereof, for the treatment of heart failure.

In one aspect, this invention provides the use of a compound of Formula (I), or a salt, particularly a pharmaceutically acceptable salt thereof, or a tautomer thereof, or a hydrate thereof, for the treatment of heart failure with reduced ejection fraction. In one embodiment, this invention provides the use of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, for the treatment of heart failure with reduced ejection fraction. In another embodiment, this invention provides the use of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, for the treatment of heart failure with reduced ejection fraction. In a further embodiment, this invention provides the use of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, or a hydrate thereof, for the treatment of heart failure with reduced ejection fraction.

In one aspect, this invention provides the use of a compound of Formula (I), or a salt, particularly a pharmaceutically acceptable salt thereof, or a tautomer thereof, or a hydrate thereof, for the treatment of heart failure with preserved ejection fraction. In one embodiment, the invention provides the use of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4- methylphenyl)propanoic acid, or a salt thereof, particularly a pharmaceutically acceptable salt thereof, or a tautomer thereof, or a hydrate thereof, for the treatment of heart failure with preserved ejection fraction. In another embodiment, this invention provides the use of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, for the treatment of heart failure with preserved ejection fraction. In a further embodiment, this invention provides the use of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, or a hydrate thereof, for the treatment of heart failure with preserved ejection fraction.

In one aspect, this invention provides the use of a compound of Formula (I), or a salt, particularly a pharmaceutically acceptable salt thereof, or a tautomer thereof, or a hydrate thereof, in the manufacture of a medicament for the treatment of COPD. Specifically, the invention provides the use of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, in the manufacture of a medicament for the treatment of COPD.

In one aspect, this invention provides the use of a compound of Formula (I), or a salt, particularly a pharmaceutically acceptable salt thereof, or a tautomer thereof, or a hydrate thereof, in the manufacture of a medicament for the treatment of heart failure. In one embodiment, this invention provides the use of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, in the manufacture of a medicament for the treatment of heart failure. In another embodiment, the invention provides the use of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, in the manufacture of a medicament for the treatment of heart failure. In a further embodiment, the invention provides the use of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, or a hydrate thereof, in the manufacture of a medicament for the treatment of heart failure.

In one aspect, this invention provides the use of a compound of Formula (I), or a salt, particularly a pharmaceutically acceptable salt thereof, or a tautomer thereof, or a hydrate thereof, in the manufacture of a medicament for the treatment of heart failure with reduced ejection fraction. In one embodiment, this invention provides the use of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, in the manufacture of a medicament for the treatment of heart failure with reduced ejection fraction. In another embodiment, the invention provides the use of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, in the manufacture of a medicament for the treatment of heart failure with reduced ejection fraction. In a further embodiment, the invention provides the use of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, or a hydrate thereof, in the manufacture of a medicament for the treatment of heart failure with reduced ejection fraction.

In one aspect, this invention provides the use of a compound of Formula (I), or a salt, particularly a pharmaceutically acceptable salt thereof, or a tautomer thereof, or a hydrate thereof, in the manufacture of a medicament for the treatment of heart failure with preserved ejection fraction. In one embodiment, this invention provides the use of (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, in the manufacture of a medicament for the treatment of heart failure with preserved ejection fraction. In another embodiment, the invention provides the use of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, in the manufacture of a medicament for the treatment of heart failure with preserved ejection fraction. In a further embodiment, the invention provides the use of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, or a hydrate thereof, in the manufacture of a medicament for the treatment of heart failure with preserved ejection fraction.

In one aspect, this invention provides a compound of Formula (I), or a salt, particularly a pharmaceutically acceptable salt thereof, or a tautomer thereof, or a hydrate thereof, for use in the treatment of COPD. Specifically, the invention relates to (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, for use in treating COPD.

In one aspect, this invention provides a compound of Formula (I), or a salt, particularly a pharmaceutically acceptable salt thereof, or a tautomer thereof, or a hydrate thereof, for use in the treatment of heart failure. In one embodiment, the compound of Formula (I) is (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, for use in the treatment of heart failure. In another embodiment, this invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, for use in the treatment of heart failure. In a further embodiment, this invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid hydrate, or a tautomer thereof, for use in the treatment of heart failure.

In one aspect, this invention provides a compound of Formula (I), or a salt, particularly a pharmaceutically acceptable salt thereof, or a tautomer thereof, or a hydrate thereof, for use in the treatment of heart failure with reduced ejection fraction. In one embodiment, this invention provides (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, for use in the treatment of heart failure with reduced ejection fraction. In another embodiment, this invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, for use in the treatment of heart failure with reduced ejection fraction. In a further embodiment, this invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid hydrate, or a tautomer thereof, for use in the treatment of heart failure with reduced ejection fraction.

In one aspect, this invention provides a compound of Formula (I), or a salt, particularly a pharmaceutically acceptable salt thereof, or a tautomer thereof, or a hydrate thereof, for use in the treatment of heart failure with preserved ejection fraction. In one embodiment, the invention provides (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, for use in the treatment of heart failure with preserved ejection fraction. In another embodiment, this invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, for use in the treatment of heart failure with preserved ejection fraction. In a further embodiment, this invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid hydrate, or a tautomer thereof, for use in the treatment of heart failure with preserved ejection fraction.

In a setting of heart failure with reduced ejection fraction, the compounds of Formula (I), or a salt, particularly a pharmaceutically acceptable salt thereof, or a tautomer thereof, or a hydrate thereof, show improvement in cardiac function and restore lost ejection fraction. In one aspect, the invention provides a compound of Formula (I), or a salt, particularly a pharmaceutically acceptable salt thereof, or a tautomer thereof, or a hydrate thereof, for use in improving cardiac function and restoring lost ejection fraction. In one embodiment, the invention provides (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, for use in improving cardiac function and restoring lost ejection fraction. In another embodiment, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, for use in improving cardiac function and restoring lost ejection fraction. In yet another aspect, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid hydrate, or a tautomer thereof, for use in improving cardiac function and restoring lost ejection fraction.

Treatment of heart failure may be symptomatic or may be disease modifying. In one aspect of the invention, treatment of heart failure refers to disease modifying. In another aspect of the invention, treatment of heart failure refers to symptomatic treatment. In a further aspect of the invention, treatment refers to improvement or alleviation of symptoms in a subject with heart failure as a result of non-ischemic injury. It will be understood by the skilled artisan that hypertension can be a cause of heart failure in non-ischemic injury. In a further aspect of the invention, treatment refers to improvement or alleviation of symptoms existing in a subject with heart failure as a result of non-ischemic injury, which symptoms include, but are not limited to, increased heart rate, hypotension, swollen ankles, shortness of breath, fatigue, excess fluids or fluid retention, and the like.

In one aspect, the invention provides a compound of Formula (I), or a salt thereof, particularly a pharmaceutically acceptable salt thereof, or a tautomer thereof, or a hydrate thereof, for use in improving or alleviating symptoms existing in a subject with heart failure as a result of non-ischemic injury. In one embodiment, the invention provides (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, for use in improving or alleviating symptoms existing in a subject with heart failure as a result of non-ischemic injury. In a further embodiment, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, for use in improving or alleviating symptoms existing in a subject with heart failure as a result of non-ischemic injury. In yet another embodiment, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid hydrate, or a tautomer thereof, for use in improving or alleviating symptoms existing in a subject with heart failure as a result of non-ischemic injury. In each of these embodiments, the symptoms of heart failure as a result of non-ischemic injury include, but are not limited to, increased heart rate, hypotension, swollen ankles, shortness of breath, fatigue, excess fluids or fluid retention, and the like.

In one embodiment, the invention provides a compound of Formula (I), or a salt thereof, particularly a pharmaceutically acceptable salt thereof, or a tautomer thereof, or a hydrate thereof, for use in improving or alleviating symptoms existing in a subject with heart failure as a result of non-ischemic injury, which symptoms include, but are not limited to, increased heart rate, hypotension, swollen ankles, shortness of breath, fatigue, excess fluids or fluid retention, and the like. In another embodiment, the invention provides (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, for use in improving or alleviating the symptoms existing in a subject with heart failure as a result of non-ischemic injury, which symptoms include, but are not limited to, increased heart rate, hypotension, swollen ankles, shortness of breath, fatigue, excess fluids or fluid retention, and the like. In yet another embodiment, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, for use in improving or alleviating the symptoms existing in a subject with heart failure as a result of non-ischemic injury, which symptoms include, but are not limited to, increased heart rate, hypotension, swollen ankles, shortness of breath, fatigue, excess fluids or fluid retention, and the like. In still another embodiment, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid hydrate, or a tautomer thereof, for use in improving or alleviating the symptoms existing in a subject with heart failure as a result of non-ischemic injury, which symptoms include, but are not limited to, increased heart rate, hypotension, swollen ankles, shortness of breath, fatigue, excess fluids or fluid retention, and the like.

In one aspect, the invention provides a compound of Formula (I), or a salt thereof, particularly a pharmaceutically acceptable salt thereof, or a tautomer thereof, or a hydrate thereof, for use in treating a subject with heart failure as a result of ischemic injury. In one embodiment, the invention provides (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, for use in treating a subject with heart failure as a result of ischemic injury. In a further embodiment, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, for use in treating a subject with heart failure as a result of ischemic injury. In yet another embodiment, the invention provides crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid hydrate, or a tautomer thereof, for use in treating a subject with heart failure as a result of ischemic injury.

It will be understood by the skilled artisan that heart failure and congestive heart failure are used interchangeably.

As used herein, "treat", "treating" or "treatment" is intended to mean at least: (1) to ameliorate, mitigate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition. The methods of treatment for mitigation of a disease or disorder include the use of the compounds in this invention in any conventionally acceptable manner, for example for prevention, retardation, prophylaxis, therapy or cure of a Nrf2-mediated disease or disorder, as described hereinabove.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "therapeutically effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. Thus, e.g., a therapeutically effective amount of a compound of Formula (I), or a salt thereof, particularly a pharmaceutically acceptable salt thereof, or a tautomer thereof, or a hydrate thereof, is a quantity of an inventive agent that, when administered to a subject in need thereof, is sufficient to modulate and/or activate the activity of Nrf2 such that a disease condition which is mediated by that activity is treated, including reduced, alleviated or prevented. A therapeutically effective amount of a compound will vary with the particular compound chosen (e.g., consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" or "subject" refers to a human.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person. In one embodiment of the invention, administration of a compound of Formula (I), or a salt, particularly a pharmaceutically acceptable salt thereof, or a tautomer thereof, or a hydrate thereof, is twice per day. In another embodiment of the invention, administration of a compound of Formula (I), or a salt, particularly a pharmaceutically acceptable salt thereof, or a tautomer thereof, or a hydrate thereof, is once per day. In a further embodiment, administration of a compound of Formula (I), or a salt, particularly a pharmaceutically acceptable salt thereof, or a tautomer thereof, or a hydrate thereof, is less than once per day.

Compositions

The compounds of the invention will normally, but not necessarily, be formulated into pharmaceutical compositions prior to administration to a patient. Accordingly, in another aspect, the invention is directed to pharmaceutical compositions comprising a compound of the invention and one or more pharmaceutically-acceptable excipients. According to one aspect, the invention provides a pharmaceutical composition comprising a compound of the invention and a pharmaceutically acceptable excipient.

The pharmaceutical compositions of the invention may be prepared and packaged in bulk form wherein a therapeutically effective amount of a compound of the invention can be extracted and then given to the patient such as with powders or syrups. Alternatively, the pharmaceutical compositions of the invention may be prepared and packaged in unit dosage form wherein each physically discrete unit contains a therapeutically effective amount of a compound of the invention. When prepared in unit dosage form, the pharmaceutical compositions of the invention typically contain from 1 mg to 1000 mg. Therefore, in one aspect, the invention provides a pharmaceutical composition comprising 1-1000 mg of a compound of the invention.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule. Suitable pharmaceutically acceptable excipients for oral administration of a compound of the invention, include a diluent or filler. Suitable diluents and fillers include lactose, sucrose, dextrose, mannitol, sorbitol, starch (e.g. corn starch, potato starch, and pre-gelatinized starch), cellulose and its derivatives (e.g., microcrystalline cellulose), calcium sulfate, and dibasic calcium phosphate. The oral solid dosage form may further comprise a binder. Suitable binders include starch (e.g., corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

Specifically, the invention provides a pharmaceutical composition comprising a compound of Formula (I), or a salt, particularly a pharmaceutically acceptable salt thereof, or a tautomer thereof, or a hydrate thereof, and one or more pharmaceutically acceptable excipients. In one embodiment, the invention provides (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, and one or more pharmaceutically acceptable excipients. In another embodiment, this invention provides a pharmaceutical composition comprising crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, and one or more pharmaceutically acceptable excipients. In still another embodiment, this invention provides a pharmaceutical composition comprising crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, or a hydrate thereof, and one or more pharmaceutically acceptable excipients.

In one aspect, the invention provides a pharmaceutical composition comprising a compound of Formula (I), or a salt, particularly a pharmaceutically acceptable salt thereof, or a tautomer thereof, or a hydrate thereof, and one or more pharmaceutically acceptable excipients, for oral administration. In one embodiment, the invention provides a pharmaceutical composition comprising (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, and one or more pharmaceutically acceptable excipients, for oral administration. In another embodiment, the invention provides a pharmaceutical composition comprising crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), and one or more pharmaceutically acceptable excipients, for oral administration. In a further embodiment, this invention provides a pharmaceutical composition comprising crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, or a hydrate thereof, and one or more pharmaceutically acceptable excipients, for oral administration.

In one aspect, this invention provides a pharmaceutical composition for the treatment of an Nrf2 regulated disease or disorder, wherein the composition comprises a compound of Formula (I), or a salt, particularly a pharmaceutically acceptable salt thereof, or a tautomer thereof, or a hydrate thereof. In one embodiment, this invention provides a pharmaceutical composition for the treatment of an Nrf2 regulated disease or disorder, wherein the composition comprises (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a salt thereof, particularly a pharmaceutically acceptable salt thereof, or a tautomer thereof, or a hydrate thereof, and one or more pharmaceutically acceptable excipients. In another embodiment, this invention provides a pharmaceutical composition for the treatment of an Nrf2-regulated disease or disorder, wherein the composition comprises crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, and one or more pharmaceutically acceptable excipients. In a further embodiment, this invention provides a pharmaceutical composition for the treatment of an Nrf2-regulated disease or disorder, wherein the composition comprises crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, or a hydrate thereof, and one or more pharmaceutically acceptable excipients.

In one embodiment, the invention provides a pharmaceutical composition comprising crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof, (free form) having substantially the same XRPD pattern of FIG. 1 and one or more pharmaceutically acceptable excipients. In one embodiment, the invention provides a pharmaceutical composition comprising crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, or a tautomer thereof (free form), having substantially the same XRPD pattern of FIG. 1 and one or more pharmaceutically acceptable excipients, for oral administration.

In another aspect, the invention is directed to a dosage form adapted for administration to a patient parenterally including subcutaneous, intramuscular, intravenous or intradermal. Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise a compound of the invention as a finely divided powder together with one or more pharmaceutically acceptable excipients as finely divided powders. Pharmaceutically acceptable excipients particularly suited for use in dry powders are known to those skilled in the art and include lactose, starch, mannitol, and mono-, di-, and polysaccharides.

A compound of the invention that enhances Nrf2 target gene expression may offer additional benefits when combined with a therapy that inhibits cell stress responses. The unfolded protein response (UPR) and integrated stress response (ISR) are critical protective pathways that can become maladaptive under conditions of chronic stress and aging (Martinez et al, 2017. Aging Cell, 1-9.; Pakos-Zebrucka et al, 2016. EMBO Reports. DOI 10.15252/embr.201642195). Both the UPR and ISR pathways repress global protein translation through the phosphorylation of the alpha subunit of eukaryotic initiation factor-2 (eIF2α), effected by a family of four eIF2α kinases (PERK, PKR, HRI, and GCN2). Increased eIF2α phosphorylation and a corresponding decrease in protein synthesis is observed broadly in neurodegenerative diseases, which can significantly impact synaptic plasticity and contribute to cognitive decline (Moon et al. 2018. Trends Mol. Med. https://doi.org/10.1016/j.molmed.2018.04.001; Trinh and Klann, 2013. Neurobio Learning Memory, 105, 93-99). Moreover, pathological hallmarks of UPR and ISR activation found in brain specimens are frequently associated with oxidative stress and in diseases of aging and neurodegeneration (Hoozemans et al, 2005. Acta Neuropathol 110, 165-172; Scheper and Hoozemans, 2016. Acta Neuropath, DOI 10.1007/s00401-015-1462-8; Stutzbach et al. 2013. Acta Neuropathol Comm, 1, 31, http://www.actaneurocomms.org/content/1/1/31). Hence, compounds that block stress response signaling and translational repression, such as UPR inhibitors, eIF2α kinase inhibitors, or enhancers of eIF2B activity have emerged as potential therapies for neurodegenerative diseases and cognitive disorders. (Smith and Mallucci, 2016. Brain, doi:10.1093/brain/aww101; Freeman and Mallucci, 2016. Brain Res. http://dx.doi.org/10.1016/j.brainres.2016.03.029; Sidrauski et al., 2013. eLIFE, 2:e00498, DOI: 10.7554/eLife.00498).

Nrf2 is a protective stress-responsive protein activated during the UPR with reported dependence on PERK kinase activity (Cullinan et al., 2003. Mol Cell Biol, 23, 7198-7209). However, in disease relevant situations of chronic stress and maladaptive UPR signaling, Nrf2 function can be exhausted or compromised by defective nuclear trafficking. For example, evidence of Nrf2 localization defects have been reported in Alzheimer's disease, Lewy body dementia, and progeria (Ramsey et al., 2007. J Neuropathol Exp Neurol, 66, 75-85; Kubben et al., 2016. Cell, 165, 1361-1374). The loss of Nrf2 target gene transcription during chronic UPR and ISR activation when protein synthesis is repressed may further enhance or accelerate disease pathogenesis, making cells and neurons more vulnerable to apoptosis. Thus, an activator of Nrf2 activity in combination with a stress response inhibitor could provide significant therapeutic benefit by increasing both the protective antioxidant response and sustaining synaptic plasticity through restoration of global translation.

Suitably, for the treatment of asthma, compounds or pharmaceutical formulations of the invention may be administered together with an anti-inflammatory agent such as, for example, a corticosteroid, or a pharmaceutical formulation thereof. For example, a compound of the invention may be formulated together with an anti-inflammatory agent, such as a corticosteroid, in a single formulation, such as a dry powder formulation for inhalation. Alternatively, a pharmaceutical formulation comprising a compound of the invention may be administered in conjunction with a pharmaceutical formulation comprising an anti-inflammatory agent, such as a corticosteroid, either simultaneously or sequentially. In one embodiment, a pharmaceutical formulation comprising a compound of the invention and a pharmaceutical formulation comprising an anti-inflammatory agent, such as a corticosteroid, may each be held in device suitable for the simultaneous administration of both formulations via inhalation.

Suitable corticosteroids for administration together with a compound of the invention include, but are not limited to, fluticasone furoate, fluticasone propionate, beclomethasone diproprionate, budesonide, ciclesonide, mometasone furoate, triamcinolone, flunisolide and prednisolone. In one embodiment of the invention a corticosteroid for administration together with a compound of the invention via inhalation includes fluticasone furoate, fluticasone propionate, beclomethasone diproprionate, budesonide, ciclesonide, mometasone furoate, and, flunisolide.

Suitably, for the treatment of COPD, compounds or pharmaceutical formulations of the invention may be administered together with one or more bronchodilators, or pharmaceutical formulations thereof. For example, a compound of the invention may be formulated together with one or more bronchodilators in a single formulation, such as a dry powder formulation for inhalation. Alternatively, a pharmaceutical formulation comprising a compound of the invention may be administered in conjunction with a pharmaceutical formulation comprising one or more bronchodilators, either simultaneously or sequentially. In a further alternative, a formulation comprising a compound of the invention and a bronchodilator may be administered in conjunction with a pharmaceutical formulation comprising a further bronchodilator. In one embodiment, a pharmaceutical formulation comprising a compound of the invention and a pharmaceutical formulation comprising one or more bronchodilators may each be held in device suitable for the simultaneous administration of both formulations via inhalation. In a further embodiment, a pharmaceutical formulation comprising a compound of the invention together with a bronchodilator and a pharmaceutical formulation comprising a further bronchodilator may each be held in one or more devices suitable for the simultaneous administration of both formulations via inhalation.

Suitable bronchodilators for administration together with a compound of the invention include, but are not limited to, $\beta_2$-adrenoreceptor agonists and anticholinergic agents. Examples of $\beta_2$-adrenoreceptor agonists, include, for example, vilanterol, salmeterol, salbutamol, formoterol, salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt of salbutamol or the fumarate salt of formoterol. Suitable anticholinergic agents include umeclidinium (for example, as the bromide), ipratropium (for example, as the bromide), oxitropium (for example, as the bromide) and tiotropium (for example, as the bromide). In one embodiment of the invention, a compound of the invention may be administered together with a $\beta_2$-adrenoreceptor agonist, such as vilanterol, and an anticholinergic agent, such as, umeclidinium.

The compounds may also be used in combination with agents for aiding transplantation including Cyclosporines, Tacrolimus, Mycophenolate mofetil, Prednisone, Azathioprine, Sirolimus, Daclizumab, Basiliximab and OKT3.

The compounds of the invention may be used in combination with antihypertensive medicines such as diuretics, ACE inhibitors, beta blockers, ARBS, calcium channel blockers, and mineralocorticoid receptor antagonists (MRA).

The compounds of the invention may be used in combination with another heart failure medicine such as neprilysin.

The compounds of the invention may be used in combination with an anti-diabetic medicine such as an SGLT2 antagonist.

One embodiment of the invention encompasses combinations comprising one or two other therapeutic agents. It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. The invention thus provides, in a further aspect, a pharmaceutical composition comprising a combination of a compound of the invention together with another therapeutically active agent.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

All temperatures are given in degrees Celsius, all solvents are highest available purity and all reactions run under anhydrous conditions in an argon (Ar) or nitrogen ($N_2$) atmosphere where necessary.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. The CombiFlash® system used for purification in this application was purchased from Isco, Inc. CombiFlash® purification was carried out using prepacked silica gel columns, a detector with UV wavelength at 254 nm and a variety of solvents or solvent combinations.

Preparative HPLC was performed using a Gilson Preparative System with variable wavelength UV detection or an Agilent Mass Directed AutoPrep (MDAP) system with both mass and variable wavelength UV detection or Waters Preparative System with UV/PDA detection or an Shimadzu PREP LC 20AP. A variety of reverse phase columns, e.g., Luna 5 m C18(2) 100A, SunFire C18, XBridge C18, Atlantics T3, Kromasil C18, Xbridge Phenyl-Hexyl, were used in the purification with the choice of column support dependent upon the conditions used in the purification. The compounds are eluted using a gradient of $CH_3CN$ and water. Neutral conditions used an $CH_3CN$ and water gradient with no additional modifier, acidic conditions used an acid modifier, 0.1% TFA (added to both the $CH_3CN$ and water) or 0.1% formic acid, and basic conditions used a basic modifier, usually 0.1% $NH_4OH$ (added to the water) or 10 mM ammonium bicarbonate (added to the water), or 0.05% $NH_4HCO_3$ (added to water).

Analytical HPLC was run using an Agilent system, Shimadzu/Sciex LCMS with variable wavelength UV detection using reverse phase chromatography with a $CH_3CN$ and water gradient with a 0.02 or 0.1% TFA modifier (added to each solvent). LC-MS was determined using either a PE Sciex Single Quadrupole 150EX LC-MS, or Waters ZQ Single Quadrupole LC-MS or Agilent 1200 series SL (detectors: Agilent 6140 single quadrupole and Agilent 1200 MWD SL) instruments. The compound is analyzed using a reverse phase column, e.g., Thermo Hypersil Gold C18, eluted using a gradient of $CH_3CN$ and water with a low percentage of an acid modifier such as 0.02% TFA or 0.1% formic acid or a base modifier such as 5 mM ammonium bicarbonate (adjusted to pH 10 with aqueous ammonia). When specified "acid method" refers to 0.1% formic acid in water and $CH_3CN$ gradient (1.8 min. 0.9 mL/min flow) with a Waters Acquity UPLC HSS C18; 1.8μ; 2.1×50 mm at 50° C.; "basic method" refers to 95:5 $H_2O$+0.1% $NH_4OH$:$CH_3CN$ (pH=9.4) and water gradient (1.8 min. 0.9 mL/min flow) with a Waters Acquity UPLC BEH C18; 1.7μ; 2.1×50 mm at 50° C. and "overnight basic method" refers to 95:5 $H_2O$+0.1% $NH_4OH$:$CH_3CN$ (pH=9.4) and water gradient (16 min. 0.8 mL/min flow) with a Waters Acquity UPLC BEH C18; 1.7μ; 2.1×50 mm at 50° C.

Preparative Chiral SFC was performed using a Thar/Waters Preparative SFC System with single wavelength UV detection system or PDA detector. A variety of chiral SFC columns, e.g. Chiralpak IA, IC, AY, AD. OD, OJ, C2 were used in the purification. The compounds are eluted using supercritical fluid $CO_2$ and co-solvents, such as MeOH, EtOH, IPA, and combination of these solvent in different ratio based on the compound selectivity. Modifiers (0.1% of TFA, $NH_4OH$, DEA, or DIA) would be used as needed.

Analytical Chiral SFC was run using a Thar/Waters SFC system with variable wavelength UV detection or PDA detector. A variety of chiral SFC columns, e.g. Chiralpak IA, IB, IC, ID, AY, AD, AS, CCL4 were used in the purification. The compounds are eluted using supercritical fluid $CO_2$ and co-solvents, such as MeOH, EtOH, IPA, and combination of these solvent in different ratio based on the compound selectivity. Modifiers (0.1% of TFA, $NH_4OH$, DEA) would be used as needed.

Celite® is a filter aid composed of acid-washed diatomaceous silica, and is a registered trademark of Manville Corp., Denver, Colorado Isolute® is a functionalized silica gel-based sorbent, and is a registered trademark of Biotage AB Corp., Sweden.

Nuclear magnetic resonance spectra were recorded at 400 MHz using a Bruker AVANCE 400 or Brucker DPX400 or Varian MR400 400 MHz spectrometer. $CDCl_3$ is deuteriochloroform, DMSO-$D_6$ is hexadeuteriodimethylsulfoxide, and Methanol-$d_4$ is tetradeuteriomethanol. Chemical shifts are reported in parts per million (δ) downfield from the internal standard tetramethylsilane (TMS) or calibrated to the residual proton signal in the NMR solvent (e.g., $CHCl_3$ in $CDCl_3$). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz.

Heating of reaction mixtures with microwave irradiations was carried out on a Biotage Initiator® or CEM microwave reactor, typically employing the high absorbance setting.

Cartridges or columns containing polymer based functional groups (acid, base, metal chelators, etc) can be used as part of compound workup. The "amine" columns or cartridges are used to neutralize or basify acidic reaction mixtures or products. These include $NH_2$ Aminopropyl SPE-ed SPE Cartridges available from Applied Separations and diethylamino SPE cartridges available from United Chemical Technologies, Inc.

FT-Raman Spectroscopy. Raman spectra were collected with a Nicolet NXR9650 or NXR 960 spectrometer (Thermo Electron) equipped with 1064 nm Nd:$YVO_4$ excitation laser, InGaAs and liquid-$N_2$ cooled Ge detectors, and a Micro-Stage. All spectra were acquired at 4 $cm^{-1}$ resolution, 64 scans, using Happ-Genzel apodization function and 2-level zero-filling.

Powder X-Ray Diffraction (XRPD) PANalytical. XRPD diffractograms were acquired on PANalytical X'Pert Pro diffractometer using Ni-filtered Cu Kα (45 kV/40 mA, 1.5406 Å wavelength) radiation and a step size of 0.03° 2θ and X'celerator™ RTMS (Real Time Multi-Strip) detector. Configuration on the incidental beam side: variable divergence slits (10 mm irradiated length), 0.04 rad Soller slits, fixed anti-scatter slit (0.50°), and 10 mm beam mask. Configuration on the diffracted beam side: variable anti-scatter slit (10 mm observed length) and 0.04 rad Soller slit. Samples were mounted flat on zero-background Si wafers.

Powder X-Ray Diffraction (XRPD) Bruker. XRPD diffractograms may be acquired on a Bruker D8 Advance system (SN:2631), using Cu Kα (40 kV/40 mA) radiation and a step size of 0.03° 2θ and LynxEye detector. Configuration on the incident beam side: Goebel mirror, mirror exit slit (0.2 mm), 2.5 deg Soller slits, beam knife. Configuration on the diffracted beam side: anti-scatter slit (8 mm) and 2.5 deg. Soller slit. Samples are mounted flat on zero-background Si wafers.

Differential Scanning calorimetry (DSC). DSC was conducted with a TA Instruments Q100 or Q2000 differential scanning calorimeter equipped with an autosampler and a refrigerated cooling system under 40 mL/min $N_2$ purge. DSC thermograms were obtained at 15° C./min in crimped Al pans unless noted otherwise.

| Table of Abbreviations |
|---|
| ° C.: degree Celsius |
| aq = aqueous |
| 'BuXPhos: 2-Di-tert-butylphosphino-2',4',6'-triisopropylbiphenyl |
| $CHCl_3$: chloroform |
| $CH_3CN$: acetonitrile |
| DCM: dichloromethane |
| DDQ: 2,3-dichloro-5,6-dicyano-1,4-benzoquinone |
| DMF: N,N-dimethylformamide |
| DMSO: dimethyl sulfoxide |
| TEA: triethylamine |
| EtOAc: ethyl acetate |
| EtOH: ethanol |
| g: gram(s) |
| h: hour(s) |
| $H_2SO_4$: sulfuric acid |
| HCl: hydrochloric acid |
| HOAc: acetic acid |
| HPLC: high performance liquid chromatography |
| IPA: isopropyl alcohol |

| Table of Abbreviations |
|---|
| J: coupling constant |
| KOAc: potassium acetate |
| LC: liquid chromatography |
| LC-MS: liquid chromatography-mass spectroscopy |
| NaHMDS: sodium hexamethyldisilazane |
| L: Liters |
| LiOH: lithium hydroxide |
| M: molar |
| MeCN: acetonitrile |
| MeI: methyl iodide |
| MeOH: methanol |
| mg: milligram(s) |
| Hz: megahertz |
| min: minute(s) |
| mL: milliliter(s) |
| mmol: millimole(s) |
| MS: mass spectroscopy |
| m/z: mass to charge ratio |
| N: Normality |
| $N_2$: nitrogen gas |
| $NaBH(OAc)_3$: sodium triacetoxyborohydride |
| NaH: sodium hydride |
| NaHMDS: sodium hexamethyldisilazane |
| $NaHSO_3$: sodium bisulfate |
| $NaNO_2$: sodium nitrite |
| NaOH: sodium hydroxide |
| NBS: N-bromosuccinimide |
| NCS: N-chlorosuccinimide |
| $NH_4HCO_3$: ammonium bicarbonate |
| $NH_4OH$: ammonium hydroxide |
| NMR: nuclear magnetic resonance |
| $PdCl_2(dppf)$: [1,1'-Bis(diphenylphosphino)ferrocene]dichloropalladium(II) |
| $Pd_2(dba)_3$: tris(dibenzylideneacetone)-dipalladium(0) |
| $Pd(OAc)_2$: palladium acetate |
| $P(o-tol)_3$: Tri(o-tolyl)-phosphine |
| $[Rh(COD)Cl]_2$: Chloro(1,5-cyclooctadiene)rhodium(I) dimer |
| RT: room temperature |
| rt: retention time |
| TEA: triethylamine |
| TFA: trifluoroacetic acid |
| THF: tetrahydrofuran |
| UV: ultraviolet |
| wt %: weight percent |
| XPhos: 2-Dicyclohexylphosphino-2',4',6'-triisopropylbiphenyl |

Intermediates

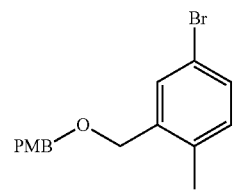

III

Step A: (5-bromo-2-methylphenyl)methanol (II)

A stirred solution of 5-bromo-2-methylbenzoic acid (100 g, 465 mmol) in tetrahydrofuran (1.2 L) was cooled in an ice bath to 0° C. 2N borane-methyl sulfide complex in THF (302 mL, 605 mmol) was added dropwise via additional funnel over 90 min. The reaction mixture was allowed to warm to room temperature and was stirred for 24 h. Reaction mixture was cooled to 0° C., quenched with methanol (200 mL) and was stirred for 1 h. The solvents were removed under reduced pressure and the resultant oil was partitioned between diethyl ether (1 L) and 1N HCl (1 L). The layers were separated and the aqueous extracted with diethyl ether (2×500 mL). The combined organic extracts were washed with 1N HCl (2×500 ml), brine, dried over sodium sulfate, filtered and concentrated to afford a compound II as a yellow solid (97 g, 100% yield). $^1$H NMR (CHCl$_3$-d) δ: 7.54 (s, 1H), 7.33 (d, J=8.0 Hz, 1H), 7.05 (d, J=8.3 Hz, 1H), 4.66 (s, 2H), 2.28 (s, 3H), 1.99 (br. s., 1H). LC-MS: rt=0.74 mins (UPLC), m/z 183.0 [M-OH]$^+$ Step B: 4-bromo-2-(((4-methoxybenzyl)oxy)methyl)-1-methylbenzene (III)

A stirred suspension of 60% sodium hydride in mineral oil (24.83 g, 621 mmol) in tetrahydrofuran (800 mL) was cooled to 0° C. A solution of compound II (96 g, 477 mmol) in tetrahydrofuran (100 mL) was added dropwise over 90 minutes and was then stirred for 15 minutes. 1-(chloromethyl)-4-methoxybenzene (71.5 mL, 525 mmol) was added dropwise over 10 minutes. The resultant was allowed to warm to room temperature and was stirred for 24 h. After 3 h, DMF (200 mL) was added to the reaction mixture. After 24 h, piperazine (8.23 g, 95 mmol) was added and the mixture stirred for 1 h. The reaction mixture was cooled to 0° C. and quenched with water (200 mL) and then diluted with diethyl ether (1.5 L) and water (1 L) and the layers were separated. The aqueous layer was extracted with diethyl ether (500 mL). The combined organic extracts were washed with water (2×500 mL), 1N HCl (2×500 mL), brine, dried over sodium sulfate and concentrated under reduced pressure to afford a yellow oil. The oil was purified by silica gel chromatography (0-20% ethyl acetate/hexane) to afford compound III as a colorless oil (145 g, 95% yield). $^1$H NMR (DMSO-d$_6$) δ: 7.49 (m, 1H), 7.38 (m, 1H), 7.24-7.33 (m, 2H), 7.14 (m, 1H), 6.88-6.97 (m, 2H), 4.48 (m, 4H), 3.70 (s, 3H), 2.20 (s, 3H). LC-MS: rt=2.93 mins (UPLC), m/z=321.0 [M+H]$^+$

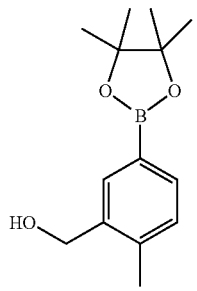

XXXIV

Step A: (2-methyl-5-(4,4,5,5-tetramethyl-1,3,2-dioxaborolan-2-yl)phenyl)methanol (XXXIV)

A stirred solution of compound II (70 g, 348 mmol) in 1,4-dioxane (400 mL) was added potassium acetate (34.2 g, 348 mmol) followed by 4,4,4',4',5,5,5',5'-octamethyl-2,2'-bi(1,3,2-dioxaborolane) (80 g, 315 mmol) and the reaction mixture was degassed with argon for 30 min. PdCl$_2$(dppf)-CH$_2$Cl$_2$ adduct (17.0 g, 20.9 mmol) was added to the reaction mixture and the reaction mixture heated at 100° C. for 16 h. The reaction mixture was allowed to cool to room temperature, was filtered through a pad of celite and the filtrate concentrated under reduced pressure. The oil was purified by silica gel chromatography (4:1 petroleum ether-EtOAc) to afford compound XXXIV as a yellow solid (60 g, 64% yield). $^1$H NMR (CDCl$_3$) δ 7.80 (d, J=31.6 Hz, 1H), 7.64 (dd, J=16.3, 7.5 Hz, 1H), 7.23-7.08 (m, 1H), 4.73 (t, J=92.0 Hz, 2H), 2.51-2.23 (m, 3H), 1.33 (d, J=6.4 Hz, 12H). LC-MS: rt=2.93 mins (UPLC), m/z 231.3 [M-OH]$^+$

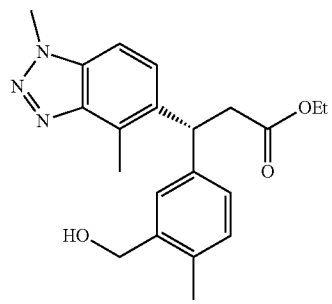

XIV

Step A: N,3-dimethyl-2-nitroaniline (V)

1-Fluoro-3-methyl-2-nitrobenzene (50 g, 322 mmol) was dissolved in ethanol (250 mL) and 40% methanamine in water (98 mL, 1128 mmol) was added. The reaction mixture was heated to reflux for 8 h and then cooled back to room temperature. The reaction mixture was filtered to afford compound V as an orange solid (47.9 g, 89% yield). $^1$H NMR (DMSO-d$_6$) δ: 7.29 (t, J=8.0 Hz, 1H), 6.70 (d, J=8.5 Hz, 1H), 6.55 (d, J=7.3 Hz, 1H), 6.51 (d, J=4.3 Hz, 1H), 2.78 (d, J=4.8 Hz, 3H), 2.30 (s, 3H). LC-MS: rt=1.47 mins (UPLC), m/z 167.2 [M+H]$^+$ Step B: 4-bromo-N,3-dimethyl-2-nitroaniline (VI)

Compound V (47.9 g, 288 mmol) was dissolved in N,N-dimethylformamide (250 mL) and the reaction mixture was cooled to 5° C. N-Bromosuccinimide (51.3 g, 288 mmol), dissolved in N,N-dimethylformamide (150 mL) was added dropwise via an addition funnel and was stirred at room temperature for 24 h. The reaction mixture was poured into water (1.5 L) and filtered to afford compound VI as an orange solid (73.5 g, 99% yield). $^1$H NMR (DMSO-d$_6$) δ: 7.56 (d, J=9.3 Hz, 1H), 6.66 (d, J=9.3 Hz, 1H), 6.26 (d, J=4.5 Hz, 1H), 2.73 (d, J=4.8 Hz, 3H), 2.25 (s, 3H). LC-MS: rt=1.47 mins (UPLC), m/z 247.0 [M+H]$^+$ Step C: 4-bromo-N1,3-dimethylbenzene-1,2-diamine (VII)

To a solution of compound VI (78.4 g, 320 mmol) in acetic acid (500 mL) and ethanol (500 mL) at 0° C. was added iron powder (89 g, 1600 mmol) followed by 2N HCl (320 mL, 640 mmol). The mixture was stirred for 1 h and then filtered through celite and the filtrate concentrated to remove the majority of ethanol. The residue was diluted with ethyl acetate (800 mL) and water (800 mL) and the layers separated. The organic extract was washed with water (500 mL), 10% sodium bicarbonate solution (500 mL), brine and concentrated under reduced pressure to afford compound VII as a red oil (67 g, 97% yield). $^1$H NMR (DMSO-d$_6$) δ: 6.75 (d, J=8.5 Hz, 1H), 6.22 (d, J=8.5 Hz, 1H), 4.48-4.90 (m, 2H), 2.69 (s, 3H), 2.17 (s, 3H). LC-MS: rt=0.38 mins (UPLC), m/z=215.2 [M+H]$^+$ Step D: 5-bromo-1,4-dimethyl-1H-benzo[d][1,2,3]triazole (VIII)

Tert-butyl nitrite (61.5 mL, 467 mmol, 90% tech grade) and tetrafluoroboric acid (97 mL, 623 mmol, 48% aqueous solution) were dissolved in 50 mL of acetonitrile and cooled to 0° C. A solution of compound VII (67 g, 311 mmol), dissolved in a solution of acetonitrile (200 mL) and tetrafluoroboric acid (97 mL, 623 mmol, 48% aqueous solution), was added dropwise to maintain the internal temperature below 5° C. The reaction mixture was stirred at 5° C. for 2 h and then room temperature for 1 h. The reaction mixture was poured into a stirred solution of sodium hydroxide (100 g, 2500 mmol) in water (4 L). Sodium chloride was added until the solution reached saturation. The resulting solid was collected by filtration and washed with water (2×3 L), air dried and purified by silica gel column chromatography (25-100% ethyl acetate/hexanes) to afford compound VIII as a light yellow solid (61 g, 86% yield). $^1$H NMR (DMSO-$d_6$) δ: 7.66 (m, 2H), 4.30 (s, 3H), 2.70 (s, 3H). LC-MS: rt=1.03 mins (UPLC), m/z=226.0 [M+H]$^+$

Step E: tert-butyl (E)-3-(1,4-dimethyl-1H-benzo[d][1,2,3]triazol-5-yl)acrylate (IX)

A solution of compound VIII (100 g, 443 mmol) and N,N-dimethylformamide (1000 mL) was purged with nitrogen for 30 min. Tri-o-tolylphosphine (27.0 g, 89 mmol), Pd(OAc)$_2$ (9.95 g, 44.3 mmol), potassium carbonate (184 g, 1330 mmol) and tert-butyl acrylate (130 mL, 886 mmol) were added and the reaction mixture was heated at 100° C. for 24 h under a nitrogen atmosphere. The reaction mixture was cooled to room temperature, diluted with water (1 L) and ethyl acetate (1 L) and the layers separated. The aqueous layer was extracted with ethyl acetate (2×1 L) and then the combined organic extracts were washed with water (2×), brine, dried over sodium sulfate, filtered and the solvent evaporated under reduced pressure. The crude dark solid was triturated with diethyl ether, filtered and dried under vacuum to afford compound IX as a light brown solid (109.3 g, 89% yield). $^1$H NMR (DMSO-$d_6$) δ: 7.89-8.00 (m, 2H), 7.67 (m, 1H), 6.54 (d, J=15.8 Hz, 1H), 4.29 (s, 3H), 2.79 (s, 3H), 1.51 (s, 9H). LCMS: rt=1.45 mins (UPLC), m/z 274.2 [M+H]$^+$

Step F: (E)-3-(1,4-dimethyl-1H-benzo[d][1,2,3]triazol-5-yl)acrylic acid (X)

To a solution of compound IX (107 g, 391 mmol) in dichloromethane (300 mL) was added cold trifluoroacetic acid (250 mL) and the reaction mixture was stirred at room temperature for 2 h.

The solvent was evaporated under reduced pressure and then azeotroped with chloroform. The resulting solid was triturated with diethyl ether to afford compound X as a beige solid (80 g, 94% yield). $^1$H NMR (DMSO-$d_6$) δ: 7.90-8.02 (m, 2H), 7.69 (m, 1H), 6.55 (d, J=16.1 Hz, 1H), 4.30 (s, 3H), 2.80 (s, 3H). LC-MS: rt=0.66 mins (UPLC), m/z 218.2 [M+H]$^+$

Step G: (S,E)-3-(3-(1,4-dimethyl-1H-benzo[d][1,2,3]triazol-5-yl)acryloyl)-4-phenyl-oxazolidin-2-one (XI)

To a suspension of compound X (82 g, 376 mmol) in tetrahydrofuran (1.5 L) was added triethylamine (131 mL, 939 mmol). The reaction mixture was cooled to −25° C. and pivaloyl chloride (46 mL, 376 mmol) was added dropwise and stirred for 30 min at −25° C. Lithium chloride (17.52 g, 413 mmol) was added in one-portion, followed by (S)-4-phenyloxazolidin-2-one (58.8 g, 361 mmol) and the reaction mixture was allowed to warm to room temperature and was stirred for 1 h. The mixture was re-cooled to −25° C. and additional pivaloyl chloride (12 ml, 98 mmol) was added dropwise and allowed to stir for an additional 1 h. THF (300 mL) was added followed by (S)-4-phenyloxazolidin-2-one (10 g, 61 mmol) and pivaloyl chloride (18 mL, 147 mmol) and the mixture was stirred at 10° C. for 1 h and then room temperature for 18 h. The reaction mixture was diluted with ethyl acetate (1 L) and washed with 5% NaHSO$_3$ (1 L). The resulting solid was collected by filtration and washed with water and diethyl ether to afford compound XI as a light yellow solid (104.4 g, 77% yield). $^1$H NMR (DMSO-$d_6$) δ: 8.05 (d, J=15.8 Hz, 1H), 7.71-7.88 (m, 3H), 7.30-7.45 (m, 5H), 5.61 (m, 1H), 4.83 (m, 1H), 4.30 (s, 3H), 4.24 (m, 1H), 2.78 (s, 3H). LC-MS: rt=1.29 mins (UPLC), m/z 363.2 [M+H]$^+$

Step H: (S)-3-((R)-3-(1,4-dimethyl-1H-benzo[d][1,2,3]triazol-5-yl)-3-(3-(((4-methoxybenzyl)oxy)methyl)-4-methylphenyl)propanoyl)-4-phenyloxazolidin-2-one (XII)

A mixture of magnesium (4.87 g, 200 mmol) and iodine (0.141 g, 0.556 mmol) was heated to 75° C. for 5 min. A solution of compound III (50.0 g, 156 mmol) in THF (200 mL) was added portion wise over 15 min and the mixture was stirred at reflux for 1 h and then cooled to room temperature to afford solution A. Separately, a mixture of copper(I) bromide-dimethyl sulfide complex (16.0 g, 78 mmol) in tetrahydrofuran (150 mL) was cooled to −40° C. and treated with dimethyl sulfide (41.1 mL, 556 mmol). The reaction mixture was stirred at −40° C. for 25 min. The cooled solution A was added dropwise over 1 h maintaining a temperature between −35 to −45° C. The reaction mixture was allowed to warm to −20° C. and then compound XI (20.2 g, 55.6 mmol) was added in one portion. The resultant mixture was stirred at −20° C. for 30 min, then allowed to warm to −10° C. and was stirred for 30 minutes. Saturated aq. ammonium chloride solution was added followed by ethyl acetate (1.5 L) and the layers were separated. The organic extract was washed with water (4×500 mL), brine, dried over sodium sulfate, filtered and the solvent evaporated to afford an oil which was purified by silica gel chromatography (0-100% ethyl acetate/hexane) to afford compound XII as a white foam (24.5 g, 73% yield). $^1$H NMR (DMSO-$d_6$) δ: 7.56 (m, 1H), 7.41 (d, 1H), 7.21-7.25 (m, 3H), 7.16-7.20 (m, 3H), 7.04-7.16 (m, 4H), 6.82-6.89 (m, 2H), 5.36 (m, 1H), 4.91 (m, 1H), 4.69 (m, 1H), 4.34-4.41 (m, 4H), 4.24 (s, 3H), 4.10 (m, 1H), 3.88 (m, 1H), 3.74 (s, 3H), 3.60 (m, 1H), 2.70 (s, 3H), 2.18 (s, 3H). LC-MS: rt=1.81 mins (UPLC), m/z 605.2 [M+H]$^+$

Step I: Ethyl (R)-3-(1,4-dimethyl-1H-benzo[d][1,2,3]triazol-5-yl)-3-(3-(((4-methoxybenzyl)oxy)methyl)-4-methylphenyl)propanoate (XIII)

To a solution of compound XII (2.140 g, 3.54 mmol) in ethanol (30 mL) was added magnesium bromide (1.629 g, 8.85 mmol) and the reaction mixture was stirred for 4 h. Additional magnesium bromide (0.81 g, 4.5 mmol) was added and the mixture was stirred for 18 h. Saturated aq. ammonium chloride solution was added and the resultant white precipitate was collected and washed with ethanol to afford compound XIII as a viscous oil (1.46 g, 85% yield). $^1$H NMR (DMSO-$d_6$) δ: 7.56-7.62 (m, 1H), 7.48 (m, 1H), 7.12-7.22 (m, 4H), 7.05-7.11 (m, 1H), 6.83-6.90 (m, 2H), 4.84 (m, 1H), 4.39 (m, 4H), 4.24 (s, 3H), 3.87-3.97 (m, 2H), 3.75 (s, 3H), 3.08-3.23 (m, 2H), 2.75 (s, 3H), 2.18 (s, 3H), 1.01 (m, 3H). LC-MS: rt=1.77 mins (UPLC), m/z=488.2 [M+H]⁺

Step J: Ethyl (R)-3-(1,4-dimethyl-1H-benzo[d][1,2,3]triazol-5-yl)-3-(3-(hydroxy-methyl)-4-methylphenyl)propanoate (XIV)

To a solution of compound XIII (53.6 g, 110 mmol), in dichloromethane (700 mL) was added water (35 mL) and the reaction mixture cooled to 0° C. DDQ (37.4 g, 165 mmol) was added and the reaction mixture was stirred at 0° C. for 2 h. The reaction mixture was diluted with 10% sodium bicarbonate solution (1 L) and dichloromethane (750 mL) and filtered. The filtrate was separated and the aqueous layer extracted with dichloromethane (3×750 mL). The combined organic extracts were washed with water, brine, dried over sodium sulfate and concentrated under reduced pressure. The residue was purified by silica gel chromatography (0-100% ethyl acetate/hexanes) to afford compound XIV as an orange oil (38.1 g, 94% yield). $^1$H NMR (DMSO-$d_6$) δ: 7.55-7.63 (m, 1H), 7.46-7.52 (m, 1H), 7.26 (s, 1H), 7.07-7.14 (m, 1H), 6.99-7.06 (m, 1H), 4.98 (m, 1H), 4.85 (m, 1H), 4.41 (m, 2H), 4.25 (s, 3H), 3.94 (m, 2H), 3.07-3.21 (m, 2H), 2.76 (s, 3H), 2.16 (s, 3H), 1.03 (m, 3H). LC-MS: rt=1.20 mins (UPLC), m/z=368.2 [M+H]⁺

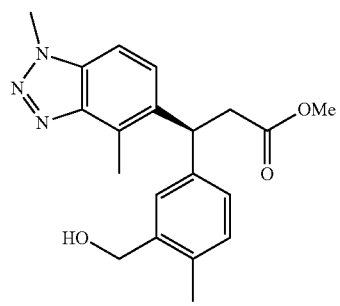

XVIII

Step A: (R,E)-3-(3-(1,4-dimethyl-1H-benzo[d][1,2,3]triazol-5-yl)acryloyl)-4-phenyl-oxazolidin-2-one (XV)

Compound XV was prepared according to scheme B, step G, replacing (S)-4-phenyloxazolidin-2-one with (R)-4-phenyloxazolidin-2-one to afford a yellow solid (195 g, 81% yield). $^1$H NMR (CDCl$_3$-d) δ: 8.20-8.25 (d, 1H), 7.80-7.88 (m, 2H), 7.25-7.45 (m, 6H), 5.60 (m, 1H), 4.67-4.81 (t, 1H), 4.25-4.28 (m, 1H), 4.23 (s, 3H), 2.82 (s, 3H). LC-MS: rt m/z=363.0 [M+H]⁺

Step B: (R)-3-((S)-(3-(1,4-dimethyl-1H-benzo[d][1,2,3]triazol-5-yl)-3-(3-(((4-methoxy-benzyl)oxy)methyl)-4-methylphenyl)propanoyl)-4-phenyloxazolidin-2-one (XVI)

Compound XVI was prepared according to scheme B, step H, replacing compound XI with compound XV to afford a white solid (104 g, 59% yield). $^1$H NMR (DMSO-$d_6$): 7.50-7.60 (d, 1H), 7.38-7.42 (d, 1H), 7.10-7.22 (m, 10H), 6.80-6.90 (d, 2H), 5.35-5.42 (m, 1H), 4.84-4.97 (t, 1H), 4.62-4.72 (t, 1H), 4.38-4.40 (d, 4H), 4.25 (s, 3H), 4.08-4.18 (m, 1H), 3.80-3.90 (m, 1H), 3.75 (s, 3H), 3.50-3.62 (m, 1H), 2.70 (s, 3H), 2.20 (s, 3H). LC-MS: rt=1.81 mins (UPLC), m/z=605.2 [M+H]⁺

Step C: Methyl (S)-3-(1,4-dimethyl-1H-benzo[d][1,2,3]triazol-5-yl)-3-(3-(((4-methoxybenzyl)oxy)methyl)-4-methylphenyl)propanoyl)-4-phenyloxazolidin-2-one (XVII)

Compound XVII was prepared according to scheme B, step I, replacing compound XII with compound XVI and swapping ethanol for methanol to afford a white solid (148 g, 92% yield). $^1$H NMR (DMSO-$d_6$) δ: 7.50-7.60 (d, 1H), 7.45-7.48 (d, 1H), 7.10-7.21 (m, 4H), 7.05-7.09 (m, 1H), 6.81-6.85 (d, 2H), 4.81-4.90 (t, 1H), 4.30-4.42 (d, 4H), 4.21 (s, 3H), 3.74 (s, 3H), 3.50 (s, 3H), 3.08-3.22 (m, 2H), 2.77 (s, 3H), 2.18 (s, 3H). LC-MS: rt=1.66 mins (UPLC), m/z=474.2 [M+H]⁺

Step D: (S)-methyl-3-(1,4-dimethyl-1H-benzo[d][1,2,3]triazol-5-yl)-3-(3-(hydroxymethyl)-4-methylphenyl)-propanoate (XVIII)

Compound XVIII was prepared according to scheme B, step J, replacing compound XIII with compound XVII to afford a white solid (5.2 g, 67% yield). $^1$H NMR (DMSO-$d_6$) δ: 7.46-7.61 (m, 2H), 7.26 (d, J=1.5 Hz, 1H), 7.08-7.14 (m, 1H), 7.01-7.07 (m, 1H), 5.01 (t, J=5.4 Hz, 1H), 4.85 (t, J=7.9 Hz, 1H), 4.41 (d, J=5.3 Hz, 2H), 4.25 (s, 3H), 3.49 (s, 3H), 3.17 (dd, J=7.9, 2.8 Hz, 2H), 2.76 (s, 3H), 2.17 (s, 3H). LC-MS: rt=0.82 mins (UPLC), m/z=354.2 [M+H]⁺

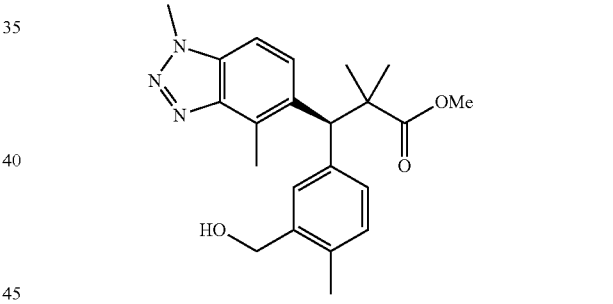

XX

Step A: (S)-methyl-3-(1,4-dimethyl-1H-benzo[d][1,2,3]triazol-5-yl)-3-(3-(((4-methoxybenzyl)-oxy)methyl)-4-methylphenyl)-2,2-dimethylpropanoate (XIX)

To a solution of compound XVIII (21.5 g, 45.4 mmol) in THF (175 mL), purged with N$_2$, was added a 1M solution of NaHMDS in THF (91 mL, 91 mmol), in one-portion. The reaction mixture was stirred at RT for 25 min to which was added MeI (1.35 mL, 21.5 mmol) in one-portion and the reaction mixture was stirred for 25 min. The reaction mixture was concentrated under reduced pressure to a thick oil, to which was added a 1M solution of NaHMDS in THF (363 mL, 363 mmol) and the reaction mixture was stirred at RT for 25 min, cooled in an ice bath to 5° C., to which was added MeI (28.4 mL, 454 mmol) in a slow stream. The ice bath was removed, and the reaction mixture was stirred for 1 h. The reaction mixture was cooled in an ice bath to 5° C., quenched with saturated ammonium chloride, extracted with EtOAc (5×), the organic extracts combined, washed with water, brine, dried over sodium sulfate, filtered and the solvent evaporated under reduced pressure. Multiple batches were purified as one-batch by silica gel chromatography (0-40% ethyl acetate/hexane) to afford compound XIX as a white foam (13.4 g, 59% yield). ¹H NMR (DMSO-d₆) δ: 7.55-7.64 (m, 2H), 7.11-7.24 (m, 4H), 7.03-7.09 (m, 1H), 6.84-6.91 (m, 2H), 4.79 (s, 1H), 4.34-4.46 (m, 4H), 4.25 (s, 3H), 3.75 (s, 3H), 3.42 (s, 3H), 2.70 (s, 3H), 2.18 (s, 3H), 1.20-1.36 (m, 6H). LC-MS: rt=1.79 mins (UPLC), m/z=502.2 [M+H]⁺

Step B: (S)-methyl-3-(1,4-dimethyl-1H-benzo[d][1,2,3]triazol-5-yl)-3-(3-(hydroxymethyl)-4-methylphenyl)-2,2-dimethylpropanoate (XX)

To a solution of compound XIX (26.4 g, 52.6 mmol), in dichloromethane (400 mL) was added water (20 mL) and the reaction mixture cooled to 0° C. DDQ (17.9 g, 79 mmol) was added in two equal portions and the reaction mixture was stirred at 0° C. for 1.5 h. The reaction mixture was poured into a solution of 10% sodium bicarbonate solution (1 L), the black solid filtered, washed with water and DCM. The combined organic phases were separated, and the aqueous phase extracted with DCM (3×750 mL). The organic extracts were combined, washed with water, brine, dried over sodium sulfate and concentrated under reduced pressure. The residue was combined with multiple batches and purified by silica gel chromatography (20-100% ethyl acetate/hexanes) to afford compound XX as a white solid (48.5 g, 57% yield). ¹H NMR (DMSO-d₆) δ: 7.55-7.68 (m, 2H), 7.27 (s, 1H), 6.98-7.13 (m, 2H), 4.99 (t, J=5.4 Hz, 1H), 4.78 (s, 1H), 4.42 (d, J=5.3 Hz, 2H), 4.25 (s, 3H), 3.43 (s, 3H), 2.70 (s, 3H), 2.16 (s, 3H), 1.21-1.36 (m, 6H). LC-MS: rt=1.25 mins (UPLC), m/z=382.2 [M+H]⁺

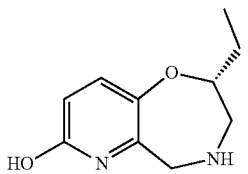

XXVI-1

Step A: (R)-1-aminobutan-2-ol (XXII-1)

To a 2 L-roundbottom flask containing (R)-ethyloxirane (74.4 g, 1.03 mol) was added a 7M solution of ammonia in methanol (1 L, 6.99 mol) and the reaction mixture was cooled to 5° C., through which was bubble ammonia gas for 30 min, then the reaction was sealed and stirred for 48 h. The reaction mixture was re-cooled to 5° C., through which was bubbled ammonia gas for 30 min, the reaction sealed and stirred for an additional 72 h at RT. The reaction mixture was concentrated under reduced pressure, the resultant oil dissolved in DCM and evaporated (3×) and dried under vacuum to afford XXII-1 as a clear oil (101 g, 62% yield, 56% pure). ¹H NMR (METHANOL-d₄) δ: 3.44-3.47 (tdd, J=8.0, 4.5, 3.6 Hz, 1H), 2.68-2.72 (dd, J=13.1, 3.5 Hz, 1H), 2.52-2.57 (m, 1H), 1.41-1.53 (m, 2H), 0.97-1.00 (t, 3H).

Step B: (R)-1-(((6-chloro-3-fluoropyridin-2-yl)methyl)amino)butan-2-ol (XXIII-1)

To a solution of compound XXII-1 (17.6 g, 197 mmol) in THF (200 mL) was added 6-chloro-3-fluoropicolinaldehyde (10.5 g, 65.8 mmol) followed by sodium triacetoxyborohydride (34.9 g, 165 mmol) and the reaction mixture was stirred at RT for 4 h. The reaction mixture was quenched with 10% sodium bicarbonate solution, extracted with EtOAc, the organic phase washed with water, dried over sodium sulfate, filtered and the solvent evaporated under reduced pressure. The crude material was purified by silica gel chromatography (0-70% 3:1 EtOAc-EtOH/hexanes) to afford compound XXIII-1 as a beige solid (6.73 g, 44% yield). ¹H NMR (DMSO-d₆) δ: 7.81 (t, J=8.7 Hz, 1H), 7.51 (dd, J=8.6, 3.3 Hz, 1H), 4.49 (d, J=4.8 Hz, 1H), 3.72-3.91 (m, 2H), 3.29-3.51 (m, 1H), 2.55 (s, 1H), 2.39-2.47 (m, 1H), 2.16 (br. s., 1H), 1.35-1.47 (m, 1H), 1.23-1.35 (m, 1H), 0.85 (t, J=7.5 Hz, 3H). LC-MS: rt=0.32 mins (UPLC), m/z=233.1/235.1 [M+H]⁺

Step C: (R)-tert-butyl-7-chloro-2-ethyl-2,3-dihydropyrido[2,3-f][1,4]oxazepine-4(5H)-carboxylate (XXIV-1)

To a solution of compound XXIII-1 (6.73 g, 28.9 mmol) in DMSO (55 mL) was added potassium tert-butoxide (4.87 g, 43.4 mmol) and the reaction mixture was stirred at 90° C. for 3 h. The reaction mixture was cooled to RT, diluted with EtOAc (600 mL), washed with water (3×), brine, dried over sodium sulfate, filtered and the solvent evaporated under reduced pressure. The residue was dissolved in DCM (200 mL) to which was added TEA (6.05 mL, 43.4 mmol) followed by boc-anhydride (7.58 g, 34.7 mmol) and the reaction mixture was stirred for 5 h. The reaction mixture was washed with water, dried over sodium sulfate, filtered and the solvent evaporated under reduced pressure. The crude residue was purified by silica gel chromatography (0-50% EtOAc/hexanes) to afford compound XXIV-1 as a yellow solid (4.71 g, 52% yield). ¹H NMR (DMSO-d₆) δ: 7.45 (d, J=8.4 Hz, 1H), 7.33 (d, J=8.6 Hz, 1H), 4.39-4.74 (m, 2H), 3.90-4.15 (m, 1H), 3.50-3.75 (m, 2H), 1.54-1.67 (m, 2H), 1.21-1.42 (m, 9H), 1.01 (t, J=6.7 Hz, 3H). LC-MS: rt=1.15 mins (UPLC), m/z=313.1/315.1 [M+H]⁺

Step D: (R)-tert-butyl 2-ethyl-7-hydroxy-2,3-dihydropyrido[2,3-f][1,4]oxazepine-4(5H)-carboxylate (XXV-1)

To a solution of compound XXIV-1 (8.32 g, 26.6 mmol) in dioxane (120 mL), purged with N₂, was added Pd(dba)₂ (0.612 g, 1.064 mmol), 5-(di-tert-butylphosphanyl)-1',3',5'-triphenyl-1H-1,4'-bipyrazole (Bippyphos) (1.078 g, 2.128 mmol), and cesium hydroxide monohydrate (13.40 g, 80 mmol) and the reaction mixture was stirred at 100° C. for 5 h. The reaction mixture was cooled to RT and concentrated under reduced pressure. Water (20 mL) was added and the pH of the aq. phase adjusted to ~pH 7 using 5N HCl, the aqueous phase extracted with EtOAc (2×300 mL), the extracts combined, dried over sodium sulfate, filtered and the solvent evaporated under reduced pressure. The crude residue was dissolved in DCM and purified by silica gel chromatography (0-60% 3:1 EtOAc-EtOH/heptanes) to afford compound XXV-1 as a beige solid (5.5 g, 70% yield). ¹H NMR (METHANOL-d₄) δ: 7.41 (d, J=9.6 Hz, 1H), 6.41 (d, J=9.4 Hz, 1H), 4.28-4.69 (m, 2H), 3.83-4.00 (m, 1H), 3.70 (br. s., 1H), 3.36-3.48 (m, 1H), 1.55-1.72 (m, 2H), 1.44 (br. s., 9H), 1.10 (t, J=7.4 Hz, 3H). LC-MS: rt=0.76 mins (UPLC), m/z=295.1 [M+H]⁺

Step E: (R)-2-ethyl-2,3,4,5-tetrahydropyrido[2,3-f][1,4]oxazep-7-ol dihydrochloride, (XXVI-1)

To a solution of compound XXV-1 (5.50 g, 18.7 mmol) in dichloromethane (20 mL) was added a solution of 4N HCl in dioxane (75 mL, 2.46 mol) and the reaction mixture was stirred at RT for 5 h. The reaction mixture was evaporated under reduced pressure, the solid triturated with diethyl ether, filtered, washed with diethyl ether and dried under vacuum with a nitrogen stream to afford compound XXVI-1 as a white solid (4.79 g, 91% yield). $^1$H NMR (METHANOL-d$_4$) δ: 7.93 (d, J=9.4 Hz, 1H), 7.06 (d, J=9.4 Hz, 1H), 4.49-4.68 (m, 2H), 4.12-4.24 (m, 1H), 3.64-3.79 (m, 1H), 3.51 (dd, J=13.7, 10.4 Hz, 1H), 1.69-1.91 (m, 2H), 1.17 (t, J=7.4 Hz, 3H). LC-MS: rt 0.24 mins (UPLC), m/z=177.0 [M−H$_2$O]$^+$

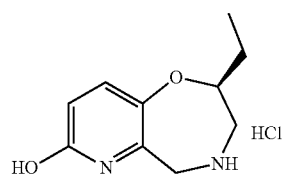

XXVI-2

Step A: (S)-1-aminobutan-2-ol (XXII-2)

Compound XXII-2 was prepared according to scheme E, step A, replacing (R)-ethyloxirane with (S)-ethyloxirane to afford a clear oil (28.9 g, 71% yield, 75% pure). $^1$H NMR (METHANOL-d$_4$) δ: 3.46 (tdd, J=8.0, 4.6, 3.7 Hz, 1H), 2.70 (dd, J=12.9, 3.5 Hz, 1H), 2.54 (dd, J=13.1, 8.0 Hz, 1H), 1.35-1.60 (m, 2H), 0.93-1.06 (m, 3H).

Step B: (S)-1-(((6-chloro-3-fluoropyridin-2-yl)methyl)amino)butan-2-ol (XXIII-2)

Compound XXIII-2 was prepared according to scheme E, step B, replacing compound XXII-1 with compound XXII-2 to afford a clear oil (7.4 g, 48% yield). $^1$H NMR (DMSO-d$_6$) δ: 7.81 (t, J=8.7 Hz, 1H), 7.51 (dd, J=8.6, 3.3 Hz, 1H), 4.49 (d, J=5.1 Hz, 1H), 3.74-3.88 (m, 2H), 3.42 (td, J=7.5, 4.3 Hz, 1H), 2.54-2.55 (m, 1H), 2.39-2.46 (m, 1H), 2.16 (br. s., 1H), 1.35-1.46 (m, 1H), 1.23-1.35 (m, 1H), 0.85 (t, J=7.5 Hz, 3H). LC-MS: rt=0.37 mins (UPLC), m/z=233.2 [M+H]$^+$

Step C: (S)-tert-butyl 7-chloro-2-ethyl-2,3-dihydropyrido[2,3-f][1,4]oxazepine-4(5H)-carboxylate (XXIV-2)

Compound XXIV-2 was prepared according to scheme E, step C, replacing compound XXIII-1 with compound XXIII-2 to afford a clear oil (5.2 g, 53% yield). $^1$H NMR (DMSO-d$_6$) δ: 7.45 (d, J=8.62 Hz, 1H), 7.33 (d, J=8.36 Hz, 1H), 4.44-4.69 (m, 2H), 3.93-4.11 (m, 1H), 3.51-3.75 (m, 2H), 1.52-1.69 (m, 2H), 1.15-1.45 (m, 9H), 1.02 (t, J=6.72 Hz, 3H). LC-MS: rt=1.24 mins (UPLC), m/z=257.2/259.2 [M+H]$^+$

Step D: (S)-tert-butyl 2-ethyl-7-hydroxy-2,3-dihydropyrido[2,3-f][1,4]oxazepine-4(5H)-carboxylate (XXV-2)

Compound XXV-2 was prepared according to scheme E, step D, replacing compound XXIV-1 with compound XXIV-2 to afford a clear oil (0.80 g, 34% yield). $^1$H NMR (DMSO-d$_6$) δ: 11.12 (br. s., 1H), 7.23 (d, J=9.1 Hz, 1H), 6.26 (d, J=9.1 Hz, 1H), 4.48 (d, J=9.6 Hz, 1H), 4.27-4.39 (m, 1H), 3.74 (br. s., 1H), 3.29-3.47 (m, 2H), 1.46-1.59 (m, 2H), 1.36 (d, J=17.5 Hz, 9H), 1.00 (t, J=7.4 Hz, 3H). LC-MS: rt=0.77 mins (UPLC), m/z=295.3 [M+H]$^+$

Step E: (S)-2-ethyl-2,3,4,5-tetrahydropyrido[2,3-f][1,4]oxazep-7-ol dihydrochloride, (XXVI-2)

Compound XXVI-2 was prepared according to scheme E, step E, replacing compound XXV-1 with compound XXV-2 to afford a clear oil (0.63 g, 82% yield). $^1$H NMR (METHANOL-d$_4$) δ: 7.99 (d, J=9.4 Hz, 1H), 7.12 (d, J=9.1 Hz, 1H), 4.54-4.72 (m, 2H), 4.22 (tdd, J=8.3, 4.1, 2.2 Hz, 1H), 3.75 (dd, J=13.7, 2.0 Hz, 1H), 3.53 (dd, J=13.8, 10.5 Hz, 1H), 1.69-1.92 (m, 2H), 1.17 (t, J=7.4 Hz, 3H). LC-MS: rt=0.29 mins (UPLC), m/z=195.3 [M+H]$^+$

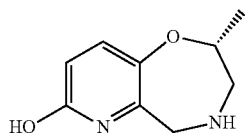

XXVI-3

Step A: (R)-1-(((6-chloro-3-fluoropyridin-2-yl)methyl)amino)propan-2-ol (XXIII-3)

Compound XXIII-3 was prepared according to scheme E, step B, replacing compound XXII-2 with (R)-1-aminopropan-2-ol to afford an orange oil (36.0 g, >100% yield). $^1$H NMR (DMSO-d$_6$) δ: 7.82 (t, J=8.9 Hz, 1H), 7.51 (dd, J=8.6, 3.3 Hz, 1H), 3.94 (br. s., 1H), 3.83 (dd, J=5.7, 1.9 Hz, 2H), 3.69 (dd, J=11.4, 6.3 Hz, 1H), 2.41-2.49 (m, 2H), 1.03 (d, J=6.3 Hz, 3H). LC-MS: rt m/z=219.1 [M+H]$^+$

Step B: (R)-tert-butyl-7-chloro-2-methyl-2,3-dihydropyrido[2,3-f][1,4]oxazepine-4(5H)-carboxylate (XXIV-3)

Compound XXIV-3 was prepared according to scheme E, step C, replacing compound XXIII-1 with compound XXIII-3 to afford a clear oil (9.5 g, 23% yield). $^1$H NMR (DMSO-d$_6$) δ: 7.38-7.45 (m, 1H), 7.31-7.35 (m, 1H), 4.43-4.69 (m, 2H), 4.20-4.42 (m, 1H), 3.52-3.70 (m, 2H), 1.15-1.46 (m, 12H). LC-MS: rt=1.05 mins (UPLC), m/z=299.0 [M+H]$^+$

Step C: (R)-tert-butyl-7-hydroxy-2-methyl-2,3-dihydropyrido[2,3-f][1,4]oxazepine-4(5H)-carboxylate (XXV-3)

Compound XXV-3 was prepared according to scheme E, step D, replacing compound XXIV-1 with compound XXIV-3 to afford an orange solid (6.8 g, 73% yield). $^1$H NMR (DMSO-d$_6$) δ: 11.13 (br. s., 1H), 7.21 (d, J=9.4 Hz, 1H), 6.25 (d, J=8.9 Hz, 1H), 4.44-4.54 (m, 1H), 4.27-4.41 (m, 1H), 3.89-4.08 (m, 1H), 3.70 (d, J=14.2 Hz, 1H), 3.40 (br. s., 1H), 1.36 (d, J=15.7 Hz, 9H), 1.21 (br. s., 3H). LC-MS: rt=0.65 mins (UPLC), m/z=281.1 [M+H]$^+$

Step D: (R)-2-methyl-2,3,4,5-tetrahydropyrido[2,3-f][1,4]oxazep-7-ol dihydrochloride (XXVI-3)

Compound XXVI-3 was prepared according to scheme E, step E, replacing compound XXV-1 with compound XXV-3 to afford a beige solid (6.2 g, 96% yield). $^1$H NMR (DMSO-d$_6$) δ: 9.44 (br. s., 2H), 7.47 (d, J=9.1 Hz, 1H), 6.65 (d, J=9.1

Hz, 1H), 4.29 (d, J=8.6 Hz, 1H), 4.13-4.25 (m, 2H), 3.45-3.54 (m, 1H), 3.18 (d, J=12.9 Hz, 1H), 1.33 (d, J=6.3 Hz, 3H). LC-MS: rt=0.15 mins (UPLC), m/z=181.1 [M+H]⁺

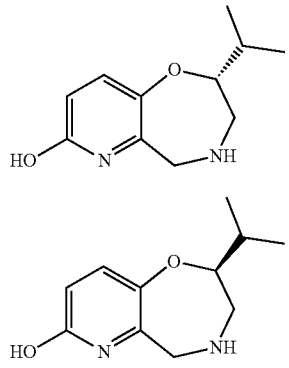

XXVI-4-a

XXVI-4-b

Step A: 1-(((6-chloro-3-fluoropyridin-2-yl)methyl)amino)-3-methylbutan-2-ol (XXIII-4)

Compound XXIII-4 was prepared according to scheme E, step B, replacing compound XXII-1 with 1-amino-3-methylbutan-2-ol to afford an off-white solid (14.4 g, 88% yield). ¹H NMR (DMSO-d₆) δ: 7.81 (t, J=8.87 Hz, 1H), 7.50 (dd, J=3.30, 8.62 Hz, 1H), 4.45 (d, J=5.07 Hz, 1H), 3.74-3.88 (m, 2H), 3.20-3.29 (m, 1H), 2.57 (dd, J=3.55, 11.66 Hz, 1H), 2.44 (dd, J=8.24, 11.53 Hz, 1H), 2.17 (br. s., 1H), 1.52-1.63 (m, 1H), 0.83 (dd, J=3.68, 6.72 Hz, 6H). LC-MS: rt=0.41 mins (UPLC), m/z=247.2 [M+H]⁺

Step B: tert-butyl-7-chloro-2-isopropyl-2,3-dihydropyrido[2,3-f][1,4]oxazepine-4(5H)-carboxylate (XXIV-4)

Compound XXIV-4 was prepared according to scheme E, step C, replacing compound XXIII-1 with compound XXIII-4 to afford a clear oil (22.1 g, 84% yield). ¹H NMR (DMSO-d₆) δ: 7.43 (d, J=8.36 Hz, 1H), 7.32 (d, J=8.36 Hz, 1H), 4.60-4.72 (m, 1H), 4.43-4.55 (m, 1H), 3.58-3.85 (m, 3H), 1.88 (qd, J=6.59, 13.18 Hz, 1H), 1.18-1.42 (m, 9H), 1.01 (dd, J=6.59, 18.00 Hz, 6H). LC-MS: rt=1.25 mins (UPLC), m/z=271.1 [(M-tBu)+H]⁺. Compound XXIII-4 was dissolved in EtOH (70 mL) and the enantiomers separated by SCF chiral purification (Chiralpak IG, 30×250 mm, 5µ) eluting with 20% EtOH, to afford compound XXIV-4-a as a yellow oil (10.3 g, 46%) and compound XXIV-4-b as a yellow oil (10.3 g, 46%).

(R)-tert-butyl-7-chloro-2-isopropyl-2,3-dihydropyrido[2,3-f][1,4]oxazepine-4(5H)-carboxylate (XXIV-4-a)

¹H NMR (DMSO-d₆) δ: 7.44 (d, J=8.62 Hz, 1H), 7.32 (d, J=8.36 Hz, 1H), 4.60-4.72 (m, 1H), 4.43-4.55 (m, 1H), 3.57-3.85 (m, 3H), 1.88 (qd, J=6.59, 13.18 Hz, 1H), 1.17-1.43 (m, 9H), 1.01 (dd, J=6.84, 18.00 Hz, 6H). LC-MS: rt=1.25 mins (UPLC), m/z=271.1 [(M-tBu)+H]⁺

(S)-tert-butyl-7-chloro-2-isopropyl-2,3-dihydropyrido[2,3-f][1,4]oxazepine-4(5H)-carboxylate (XXIV-4-b)

¹H NMR (DMSO-d₆) δ: 7.44 (d, J=8.36 Hz, 1H), 7.32 (d, J=8.36 Hz, 1H), 4.61-4.72 (m, 1H), 4.44-4.54 (m, 1H), 4.36 (t, J=5.07 Hz, 1H), 3.78 (dd, J=5.83, 11.15 Hz, 1H), 3.57-3.74 (m, 2H), 3.45 (dq, J=5.20, 6.97 Hz, 1H), 1.83-1.93 (m, 1H), 1.18-1.42 (m, 9H), 0.94-1.10 (m, 6H). LC-MS: rt=1.25 mins (UPLC), m/z=271.1 [(M-tBu)+H]⁺

Step C: (R)-tert-butyl-7-hydroxy-2-isopropyl-2,3-dihydropyrido[2,3-f][1,4]oxazepine-4(5H)-carboxylate (XXV-4-a)

Compound XXV-4-a was prepared according to scheme E, step D, replacing compound XXIV-1 with compound XXIV-4-a to afford a white solid (4.4 g, 46% yield). ¹H NMR (DMSO-d₆) δ: 10.86-11.34 (m, 1H), 7.22 (d, J=9.12 Hz, 1H), 6.24 (d, J=9.12 Hz, 1H), 4.43-4.61 (m, 1H), 4.21-4.36 (m, 1H), 3.69-3.90 (m, 1H), 3.39 (br. s., 2H), 1.74-1.86 (m, 1H), 1.26-1.42 (m, 9H), 0.92-1.05 (m, 6H). LC-MS: rt=0.86 mins (UPLC), m/z=309.2 [M+H]⁺

(S)-tert-butyl-7-hydroxy-2-isopropyl-2,3-dihydropyrido[2,3-f][1,4]oxazepine-4(5H)-carboxylate (XXV-4-b)

Compound XXV-4-b was prepared according to scheme E, step D, replacing compound XXIV-1 with compound XXIV-4-b to afford a beige solid (2.9 g, 72% yield). ¹H NMR (DMSO-d₆) δ: 11.06 (br. s., 1H), 7.22 (d, J=9.29 Hz, 1H), 6.25 (d, J=9.03 Hz, 1H), 4.43-4.62 (m, 1H), 4.20-4.36 (m, 1H), 3.70-3.91 (m, 1H), 3.34-3.54 (m, 2H), 1.72-1.90 (m, 1H), 1.35 (d, J=18.57 Hz, 9H), 0.90-1.10 (m, 6H). LC-MS: rt=0.87 mins (UPLC), m/z=309.3 [M+H]⁺

Step D: (R)-2-isopropyl-2,3,4,5-tetrahydropyrido[2,3-f][1,4]oxazep-7-ol dihydrochloride (XXVI-4-a)

Compound XXVI-4-a was prepared according to scheme E, step E, replacing compound XXV-1 with compound XXV-4-a to afford a white solid (1.0 g, 94% yield). ¹H NMR (METHANOL-d₄) δ: 7.79 (d, J=9.38 Hz, 1H), 6.93 (d, J=9.38 Hz, 1H), 4.54 (d, J=7.60 Hz, 2H), 3.99 (ddd, J=2.53, 5.39, 8.05 Hz, 1H), 3.69-3.80 (m, 1H), 3.57 (dd, J=10.77, 13.56 Hz, 1H), 2.03 (d, J=5.58 Hz, 1H), 1.13 (t, J=6.59 Hz, 6H). LC-MS: rt=0.35 mins (UPLC), m/z=209.3 [M+H]⁺

(S)-2-isopropyl-2,3,4,5-tetrahydropyrido[2,3-f][1,4]oxazep-7-ol, dihydrochloride (XXVI-4-b)

Compound XXVI-4-b was prepared according to scheme E, step E, replacing compound XXV-1 with compound XXV-4-b to afford a white solid (2.4 g, 86% yield). ¹H NMR (METHANOL-d₄) δ: 7.89 (d, J=9.12 Hz, 1H), 7.03 (d, J=9.38 Hz, 1H), 4.60 (s, 2H), 4.07 (ddd, J=2.03, 5.32, 10.65 Hz, 1H), 3.77 (dd, J=2.15, 13.56 Hz, 1H), 3.59 (dd, J=10.77, 13.56 Hz, 1H), 1.95-2.14 (m, 1H), 1.03-1.23 (m, 6H). LC-MS: rt=0.36 mins (UPLC), m/z=209.0 [M+H]⁺

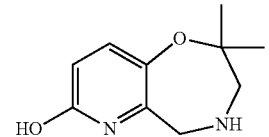

XXVI-5

Step A: 1-(((6-chloro-3-fluoropyridin-2-yl)methyl)amino)-2-methylprop-2-ol (XXIII-5)

Compound XXIII-5 was prepared according to scheme E, step B, replacing compound XXII-1 with 1-amino-2-methylpropan-2-ol to afford an off-white solid (38.2 g, 85% yield). ¹H NMR (CDCl₃) δ: 7.34-7.39 (t, 1H), 7.20-7.24 (m, 1H), 3.99 (s, 2H), 2.56 (s, 2H), 1.34 (s, 6H). LC-MS: rt=0.83 mins (UPLC), m/z=233.2 [M+H]⁺

Step B: tert-butyl-7-chloro-2,2-dimethyl-2,3-dihydropyrido[2,3-f][1,4]oxazepine-4(5H)-carboxylate (XXIV-5)

Compound XXIV-5 was prepared according to scheme E, step C, replacing compound XXIII-1 with compound XXIII-5 to afford a yellow solid (3.0 g, 65% yield). ¹H NMR (CDCl₃) δ: 7.13-7.23 (m, 2H), 4.58-4.63 (d, 2H), 3.59-3.63 (m, 2H), 1.46 (s, 9H), 1.22 (s, 6H). LC-MS: rt=1.13 mins (UPLC), m/z=313.0 [M+H]⁺

Step C: tert-butyl-7-hydroxy-2,2-dimethyl-2,3-dihydropyrido[2,3-f][1,4]oxazepine-4(5H)-carboxylate (XXV-5)

Compound XXV-5 was prepared according to scheme E, step D, replacing compound XXIV-1 with compound XXIV-5 to afford a light yellow solid (2.5 g, 53% yield). ¹H NMR (DMSO-d₆) δ: 7.57-7.18 (m, 1H), 6.24-6.27 (d, 1H), 4.36 (s, 2H), 3.52 (s, 2H), 1.37 (s, 9H), 1.13 (s, 6H). LC-MS: rt=0.82 mins (UPLC), m/z=295.2 [M+H]⁺

Step D: 2,2-dimethyl-2,3,4,5-tetrahydropyrido[2,3-f][1,4]oxazep-7-ol, dihydrochloride (XXVI-5)

Compound XXVI-5 was prepared according to scheme E, step E, replacing compound XXV-1 with compound XXV-5 to afford a white solid (9.4 g, 93% yield). ¹H NMR (DMSO-d₆) δ: 11.19 (s, 2H), 10.26 (s, 2H), 7.46 (d, J=9.2 Hz, 1H), 6.74 (d, J=8.8 Hz, 1H), 4.23 (s, 2H), 3.33 (s, 2H), 1.30 (s, 6H). LC-MS: rt=0.62 mins (UPLC), m/z=195.0 [M+H]⁺

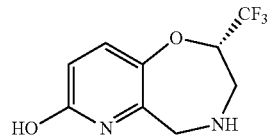

XXVI-6

Step A: (S)-3-(((6-chloro-3-fluoropyridin-2-yl)methyl)amino)-1,1,1-trifluoropropan-2-ol (XXIII-6)

Compound XXIII-6 was prepared according to scheme E, step B, replacing compound XXII-1 with (S)-3-amino-1,1,1-trifluoropropan-2-ol to afford a white solid (5.5 g, 87% yield). ¹H NMR (DMSO-d₆) δ: 7.82 (t, J=8.7 Hz, 1H), 7.52 (dd, J=8.6, 3.3 Hz, 1H), 6.31 (d, J=6.3 Hz, 1H), 4.02-4.14 (m, 1H), 3.81-3.94 (m, 2H), 2.76-2.85 (m, 1H), 2.65-2.74 (m, 1H), 2.35 (br. s., 1H). LC-MS: rt=0.36 mins (UPLC), m/z=273.1/275.1 [M+H]⁺

Step B: (S)-tert-butyl-7-chloro-2-(trifluoromethyl)-2,3-dihydropyrido[2,3-f][1,4]oxazepine-4(5H)-carboxylate (XXIV-6)

Compound XXIV-6 was prepared according to scheme E, step C, replacing compound XXIII-1 with compound XXIII-6 to afford a yellow solid (2.7 g, 38% yield). ¹H NMR (DMSO-d₆) δ: 7.58 (d, J=8.6 Hz, 1H), 7.42 (d, J=8.4 Hz, 1H), 5.05 (d, J=6.3 Hz, 1H), 4.67-4.78 (m, 1H), 4.52-4.65 (m, 1H), 3.85-4.04 (m, 2H), 1.11-1.49 (m, 9H). LC-MS: rt=1.20 mins (UPLC), m/z=353.2/355.2 [M+H]⁺

Step C: (S)-tert-butyl-7-hydroxy-2-(trifluoromethyl)-2,3-dihydropyrido[2,3-f][1,4]oxazepine-4(5H)-carboxylate (XXV-6)

Compound XXV-6 was prepared according to scheme E, step D, replacing compound XXIV-1 with compound XXIV-6 to afford an off-white solid (0.54 g, 30% yield). ¹H NMR (DMSO-d₆) δ: 11.27 (br. s., 1H), 7.31 (d, J=9.1 Hz, 1H), 6.33 (d, J=9.1 Hz, 1H), 4.53-4.75 (m, 2H), 4.36-4.47 (m, 1H), 3.98 (d, J=12.4 Hz, 1H), 3.74 (d, J=9.4 Hz, 1H), 1.37 (d, J=19.8 Hz, 9H). LC-MS: rt=0.85 mins (UPLC), m/z=335.3 [M+H]⁺

Step D: (S)-2-(trifluoromethyl)-2,3,4,5-tetrahydropyrido[2,3-f][1,4]oxazepin-7-ol, dihydrochloride (XXVI-6)

Compound XXVI-6 was prepared according to scheme E, step E, replacing compound XXV-1 with compound XXV-6 to afford a beige solid (0.33 g, 66% yield). ¹H NMR (METHANOL-d₄) δ: 7.56 (d, J=9.1 Hz, 1H), 6.70 (d, J=9.1 Hz, 1H), 4.77-4.86 (m, 1H), 4.57-4.63 (m, 1H), 4.41-4.48 (m, 1H), 3.99 (d, J=2.0 Hz, 1H), 3.95 (d, J=2.0 Hz, 1H), 3.79 (s, 1H), 3.76 (d, J=2.8 Hz, 1H), 3.73 (s, 1H). LC-MS: rt=0.30 mins (UPLC), m/z=235.2 [M+H]⁺

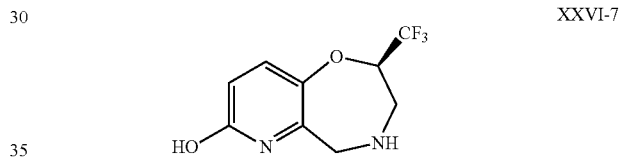

XXVI-7

Step A: (R)-3-(((6-bromo-3-fluoropyridin-2-yl)methyl)amino)-1,1,1-trifluoropropan-2-ol (XXIII-7)

Compound XXIII-7 was prepared according to scheme E, step B, replacing compound XXII-1 with (R)-3-amino-1,1,1-trifluoropropan-2-ol to afford a colorless solid (16.6 g, 97% yield). ¹H NMR (DMSO-d₆) δ: 7.69-7.77 (m, 1H), 7.62-7.66 (m, 1H), 6.29 (d, J=6.4 Hz, 1H), 4.07 (td, J=11.3, 3.3 Hz, 1H), 3.88 (br. s., 2H), 2.75-2.85 (m, 1H), 2.65-2.74 (m, 1H), 2.34 (d, J=1.7 Hz, 1H). LC-MS: rt=0.41 mins (UPLC), m/z=319.0 [M+H]⁺

Step B: (R)-tert-butyl-7-bromo-2-(trifluoromethyl)-2,3-dihydropyrido[2,3-f][1,4]oxazepine-4(5H)-carboxylate (XXIV-7)

Compound XXIV-7 was prepared according to scheme E, step D, replacing compound XXIII-1 with compound XXIII-7 to afford a yellow oil (3.79 g, 18% yield). ¹H NMR (DMSO-d₆) δ: 7.51-7.56 (m, 1H), 7.45-7.49 (m, 1H), 5.07 (br. s., 1H), 4.59 (br. s., 1H), 3.92 (d, J=8.6 Hz, 1H), 2.68 (s, 1H), 2.33 (d, J=2.0 Hz, 1H), 1.15-1.48 (m, 9H). LC-MS: rt=1.22 mins (UPLC), m/z=342.9 [M-ᵗBu]⁺

Step C: (R)-tert-butyl-7-hydroxy-2-(trifluoromethyl)-2,3-dihydropyrido[2,3-f][1,4]oxazepine-4(5H)-carboxylate (XXV-7)

Compound XXV-7 was prepared according to scheme E, step D, replacing compound XXIV-1 with compound XXIV-7 to afford a beige solid (2.66 g, 83% yield). $^1$H NMR (DMSO-d$_6$) δ: 10.81-11.85 (m, 1H), 7.30 (d, J=9.0 Hz, 1H), 6.33 (br. s., 1H), 4.52-4.75 (m, 2H), 4.36-4.46 (m, 1H), 3.98 (d, J=13.2 Hz, 1H), 3.72 (br. s., 1H), 1.36 (d, J=18.3 Hz, 9H). LC-MS: rt=0.84 mins (UPLC), m/z=335.1 [M+H]$^+$

Step D: (R)-2-(trifluoromethyl)-2,3,4,5-tetrahydropyrido[2,3-f][1,4]oxazepin-7-ol, dihydrochloride (XXVI-7)

Compound XXVI-7 was prepared according to scheme E, step E, replacing compound XXV-1 with compound XXV-7 to afford a beige solid (2.24 g, 92% yield). $^1$H NMR (METHANOL-d$_4$) δ: 7.61 (d, J=9.0 Hz, 1H), 6.76 (d, J=9.3 Hz, 1H), 4.82 (ddd, J=10.9, 6.2, 2.2 Hz, 1H), 4.39-4.67 (m, 2H), 3.97 (dd, J=13.6, 2.1 Hz, 1H), 3.77 (dd, J=13.7, 11.0 Hz, 1H), 3.68 (s, 2H). LC-MS: rt=0.31 mins (UPLC), m/z=235.1 [M+H]$^+$

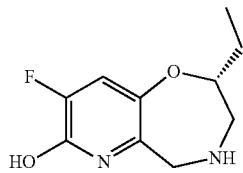

XXVI-8

Step A: (R)-1-(((6-chloro-3,5-difluoropyridin-2-yl)methyl)amino)butan-2-ol (XXIII-8)

Compound XXIII-8 was prepared according to scheme E, step B, replacing 6-chloro-3-fluoropicolinaldehyde with 6-chloro-3,5-difluoropicolinaldehyde to afford a yellow solid (2.3 g, 31% yield). $^1$H NMR (CDCl$_3$) δ: 7.31-7.35 (t, 1H), 4.15 (br. s., 2H), 3.97-4.01 (m, 2H), 3.65-3.71 (m, 1H), 2.80-2.84 (dd, 1H), 2.55-2.66 (dd, 1H), 1.47-1.58 (m, 2H), 1.26-1.28 (t, 3H). LC-MS: rt=0.78 mins (UPLC), m/z=251.0 [M+H]$^+$

Step B: tert-butyl (R)-7-chloro-2-ethyl-8-fluoro-2,3-dihydropyrido[2,3-f][1,4]oxazepine-4(5H)-carboxylate (XXIV-8)

Compound XXIV-8 was prepared according to scheme E, step D, replacing compound XXIII-1 with compound XXIII-8 to afford a brown oil (1.43 g, 62% yield). $^1$H NMR (CDCl$_3$) δ: 7.15-7.18 (d, 1H), 4.73-4.78 (m, 1H), 4.44-4.49 (m, 1H), 3.87-3.99 (m, 2H), 3.47-3.50 (m, 1H), 1.61-1.78 (m, 2H), 1.42 (s, 9H), 1.08-1.13 (t, 3H). LC-MS: rt=1.95 mins (UPLC), m/z=275.1 [M-$^t$Bu]$^+$

Step C: tert-butyl (R)-2-ethyl-8-fluoro-7-hydroxy-2,3-dihydropyrido[2,3-f][1,4]oxazepine-4(5H)-carboxylate (XXV-8)

Compound XXV-8 was prepared according to scheme E, step D, replacing compound XXIV-1 with compound XXIV-8 to afford a white solid (1.1 g, 90% yield). $^1$H NMR (CDCl$_3$) δ: 7.14-7.16 (d, 1H), 4.75-4.79 (d, 1H), 4.25-4.33 (dd, 2H), 3.63-3.68 (m, 1H), 3.14-3.20 (m, 1H), 3.14-3.20 (m, 1H), 1.59-1.70 (m, 2H), 1.43 (s, 9H), 1.07-1.11 (t, 3H). LC-MS: rt=1.24 mins (UPLC), m/z=313.1 [M+H]$^+$

Step D: (R)-2-ethyl-8-fluoro-2,3,4,5-tetrahydropyrido[2,3-f][1,4]oxazepin-7-ol, dihydrochloride (XXVI-8)

Compound XXVI-8 was prepared according to scheme E, step E, replacing compound XXV-1 with compound XXV-8 to afford a white solid (0.70 g, 96% yield). $^1$H NMR (METHANOL-d$_4$) δ: 7.36-7.38 (m, 1H), 4.40-4.44 (m, 1H), 4.27-4.30 (m, 1H), 3.91-3.96 (m, 1H), 3.60-3.63 (m, 1H), 3.35-3.41 (m, 1H), 1.69-1.76 (m, 2H), 1.11-1.16 (m, 3H). LC-MS: rt=0.58 mins (UPLC), m/z=213.1 [M+H]$^+$

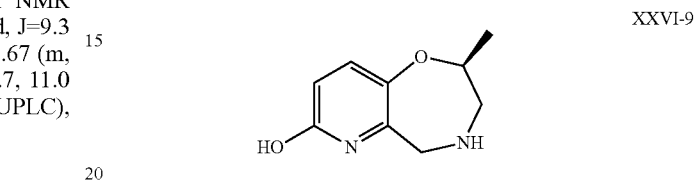

XXVI-9

Step A: (S)-1-(((6-bromo-3-fluoropyridin-2-yl)methyl)amino)propan-2-ol (XXIII-9)

Compound XXIII-9 was prepared according to scheme E, step B, replacing 6-chloro-3-fluoropicolinaldehyde with 6-bromo-3-fluoropicolinaldehyde and XXII-1 with (S)-1-aminopropan-2-ol to afford a colorless solid (22.6 g, 70% yield). $^1$H NMR (DMSO-d$_6$) δ: 7.68-7.74 (m, 1H), 7.59-7.65 (m, 1H), 4.49 (d, J=4.4 Hz, 1H), 3.81 (d, J=3.7 Hz, 2H), 3.62-3.72 (m, 1H), 2.39-2.47 (m, 3H), 1.03 (d, J=6.4 Hz, 3H). LC-MS: rt=0.31 mins (UPLC), m/z=263.1/265.1 [M+H]$^+$

Step B: tert-butyl (S)-7-bromo-2-methyl-2,3-dihydropyrido[2,3-f][1,4]oxazepine-4(5H)-carboxylate (XXIV-9)

Compound XXIV-9 was prepared according to scheme E, step D, replacing compound XXIII-1 with compound XXIII-9 to afford a yellow oil (1.3 g, 4% yield). $^1$H NMR (DMSO-d$_6$) δ: 7.45 (d, J=8.3 Hz, 1H), 7.32 (d, J=8.3 Hz, 1H), 4.57-4.70 (m, 1H), 4.19-4.43 (m, 1H), 3.51-3.70 (m, 2H), 3.34 (s, 1H), 1.21-1.41 (m, 12H). LC-MS: rt=1.09 mins (UPLC), m/z=345.1 [M+H]$^+$;

Step C: tert-butyl (S)-7-hydroxy-2-methyl-2,3-dihydropyrido[2,3-f][1,4]oxazepine-4(5H)-carboxylate (XXV-9)

Compound XXV-9 was prepared according to scheme E, step D, replacing compound XXIV-1 with compound XXIV-9 to afford a beige solid (0.64 g, 60% yield). $^1$H NMR (DMSO-d$_6$) δ: 11.19 (br. s., 1H), 7.21 (d, J=9.3 Hz, 1H), 6.24 (d, J=8.1 Hz, 1H), 4.42-4.55 (m, 1H), 4.24-4.41 (m, 1H), 3.88-4.09 (m, 1H), 3.69 (d, J=13.9 Hz, 1H), 3.40 (d, J=10.5 Hz, 1H), 1.35 (d, J=15.9 Hz, 9H), 1.20 (br. s., 3H). LC-MS: rt=0.67 mins (UPLC), m/z=281.2 [M+H]$^+$

Step D: (S)-2-methyl-2,3,4,5-tetrahydropyrido[2,3-f][1,4]oxazepin-7-ol, hydrochloride (XXVI-9)

Compound XXVI-9 was prepared according to scheme E, step E, replacing compound XXV-1 with compound XXV-9 to afford a beige solid (0.45 g, 92% yield). $^1$H NMR (DMSO-d$_6$) δ 9.94 (br. s., 1H), 9.59 (br. s., 1H), 7.36 (d, J=9.0 Hz, 1H), 6.50 (d, J=9.0 Hz, 1H), 4.30 (dd, J=14.4, 9.0

Hz, 1H), 4.04-4.18 (m, 2H), 3.52 (br. s., 1H), 3.13-3.27 (m, 1H), 1.33 (d, J=6.4 Hz, 3H). LC-MS: rt=0.21 mins (UPLC), m/z=181.0 [M+H]

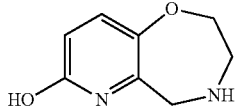

XXVI-10

Step A: 1-(((6-chloro-3-fluoropyridin-2-yl)methyl)amino)ethan-2-ol (XXIII-10)

Compound XXIII-10 was prepared according to scheme E, step B, replacing XXII-1 with 2-aminopropan-1-ol to afford a yellow solid (3.37 g, 52% yield). $^1$H NMR (DMSO-$d_6$) δ: 7.81 (t, J=8.74 Hz, 1H), 7.50 (dd, J=3.30, 8.62 Hz, 1H), 4.53 (t, J=5.07 Hz, 1H), 3.82 (d, J=2.03 Hz, 2H), 3.46 (q, J=5.32 Hz, 2H), 2.61 (t, J=5.70 Hz, 2H), 2.19 (br. s., 1H). LC-MS: rt=0.17 mins (UPLC), m/z=205.3 [M+H]$^+$

Step B: tert-butyl 7-chloro-2,3-dihydropyrido[2,3-f][1,4]oxazepine-4(5H)-carboxylate (XXIV-10)

Compound XXIV-10 was prepared according to scheme E, step D, replacing compound XXIII-1 with compound XXIII-10 to afford a light yellow solid (2.09 g, 43% yield). $^1$H NMR (DMSO-$d_6$) δ: 7.43 (d, J=8.62 Hz, 1H), 7.31-7.36 (m, 1H), 4.63 (d, J=19.77 Hz, 2H), 4.25 (br. s., 2H), 3.74 (br. s., 2H), 1.13-1.48 (m, 9H). LC-MS: rt=0.97 mins (UPLC), m/z=229.2 ((M-tBu)+).

Step C: tert-butyl 7-hydroxy-2,3-dihydropyrido[2,3-f][1,4]oxazepine-4(5H)-carboxylate (XXV-10)

Compound XXV-10 was prepared according to scheme E, step D, replacing compound XXIV-1 with compound XXIV-10 to afford a beige solid (1.16 g, 63% yield). $^1$H NMR (DMSO-$d_6$) δ: 11.13 (br. s., 1H), 7.22 (d, J=9.3 Hz, 1H), 6.25 (d, J=9.0 Hz, 1H), 4.43 (br. s., 2H), 4.00 (br. s., 2H), 3.66 (br. s., 2H), 1.35 (d, J=15.4 Hz, 9H). LC-MS: rt=0.58 mins (UPLC), m/z=267.2 [M+H]$^+$

Step D: 2,3,4,5-tetrahydropyrido[2,3-f][1,4]oxazepin-7-ol, dihydrochloride (XXVI-10)

Compound XXVI-10 was prepared according to scheme E, step E, replacing compound XXV-1 with compound XXVI-10 to afford a white solid (1.03 g, 96% yield). $^1$H NMR (DMSO-$d_6$) δ: 6.96 (d, J=9.3 Hz, 1H), 6.10 (d, J=9.3 Hz, 1H), 3.99-4.19 (m, 5H), 3.55 (dt, J=4.5, 2.4 Hz, 2H), 2.90 (dt, J=4.5, 2.4 Hz, 2H). LC-MS: rt=0.09 mins (UPLC), m/z=167.2 [M+H]$^+$

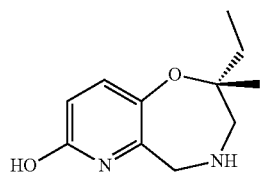

XXVI-11-a

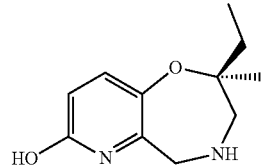

XXVI-11-b

Step A: 1-(((6-chloro-3-fluoropyridin-2-yl)methyl)amino)-2-methylbutan-2-ol (XXIII-11)

Compound XXIII-11 was prepared according to scheme E, step B, replacing compound XXII-1 with 1-amino-2-methylbutan-2-ol to afford an brown oil (12 g, 83% yield). $^1$H NMR (CDCl$_3$) δ: 7.37-7.42 (t, 1H), 7.24-7.27 (dd, 1H), 5.20 (br. S, 2H), 4.03-4.03 (d, 2H), 2.57-2.76 (q, 2H), 1.46-1.59 (m, 2H), 1.17 (s, 3H), 0.85-0.98 (t, 3H). LC-MS: rt=0.72 mins (UPLC), m/z=247.0 [M+H]$^+$

Step B: tert-butyl 7-chloro-2-ethyl-2-methyl-2,3-dihydropyrido[2,3-f][1,4]oxazepine-4(5H)-carboxylate (XXIV-11)

Compound XXIV-11 was prepared according to scheme E, step C, replacing XXIII-1 with compound XXIII-11 to afford a brown oil (8.0 g, 66% yield). Compound XXIV-11 was used as is in Step C.

Step C: tert-butyl 2-ethyl-7-hydroxy-2-methyl-2,3-dihydropyrido[2,3-f][1,4]oxazepine-4(5H)-carboxylate (XXV-11)

Compound XXV-11 was prepared according to scheme E, step D, replacing compound XXIV-1 with compound XXIV-11 to afford a yellow solid (0.64 g, 26% yield). $^1$H NMR (CDCl$_3$) δ: 7.18-7.24 (m, 1H), 6.39-6.43 (m, 1H), 4.59-4.63 (d, 1H), 4.36-4.40 (d, 1H), 3.64-3.83 (dd, 1H), 3.43-3.48 (d, 1H), 1.50-1.66 (m, 2H), 1.44 (s, 9H), 1.09-1.11 (d, 3H), 0.99-1.02 (t, 3H). LC-MS: rt=0.92 mins (UPLC), m/z=309.1 [M+H]$^+$. Compound XXIV-11 was dissolved in MeOH and the enantiomers separated by Chiral HPLC (Lux 5µ Celluloes-3, AXIA) eluting with a hexanes-MeOH gradient, to afford compound XXIV-11-a as a yellow solid (0.27 g, 42%) and compound XXIV-11-b as a yellow solid (0.265 g, 41%).

tert-butyl (R)-2-ethyl-7-hydroxy-2-methyl-2,3-dihydropyrido[2,3-f][1,4]oxazepine-4(5H)-carboxylate (XXIV-11-a)

$^1$H NMR (CDCl$_3$) δ: 7.18-7.25 (m, 1H), 6.40-6.44 (m, 1H), 4.57-4.62 (m, 1H), 4.35-4.39 (d, 1H), 3.64-3.84 (dd, 1H), 3.42-3.48 (m, 1H), 1.50-1.67 (m, 2H), 1.45 (s, 9H), 1.09-1.11 (m, 3H), 0.90-1.05 (t, 3H). LC-MS: rt=0.98 mins (UPLC), m/z=253.2 [(M-tBu)+H]$^+$ tert-butyl (S)-2-ethyl-7-hydroxy-2-methyl-2,3-dihydropyrido[2,3-f][1,4]oxazepine-4(5H)-carboxylate (XXIV-11-b)

$^1$H NMR (CDCl$_3$) δ: 7.22-7.27 (m, 1H), 6.47-6.49 (d, 1H), 4.56-4.62 (m, 1H), 4.34-4.40 (d, 1H), 3.65-3.85 (dd, 1H), 3.44-3.49 (m, 1H), 1.54-1.67 (m, 2H), 1.46 (s, 9H), 1.10-1.11 (m, 3H), 0.99-1.03 (t, 3H). LC-MS: rt=0.98 mins (UPLC), m/z=253.2 [(M-tBu)+H]$^+$ Step D: (R)-2-ethyl-2-methyl-2,3,4,5-tetrahydro-pyrido[2,3-f][1,4]oxazepin-7-ol, dihydrochloride (XXVI-11-a)

Compound XXVI-11-a was prepared according to scheme E, step E, replacing compound XXV-1 with compound XXV-11-a to afford a white solid (0.173 g, 81% yield). $^1$H NMR (CD$_3$OD) δ: 7.78 (d, J=4.0 Hz, 1H), 6.96 (d, J=4.0 Hz, 1H), 4.35-4.54 (m, 2H), 3.56 (s, 2H), 1.60-1.85 (m, 2H), 1.33 (s, 3H), 1.04-1.19 (m, 3H). LC-MS: rt=0.54 mins (UPLC), m/z=209.1 [M+H]$^+$ (S)-2-ethyl-2-methyl-2,3,4,5-tetrahydropyrido[2,3-f][1,4]oxazepin-7-ol, dihydrochloride (XXVI-11-b)

Compound XXVI-11-b was prepared according to scheme E, step E, replacing compound XXV-1 with compound XXV-11-b to afford a white solid (0.179 g, 81% yield). $^1$H NMR (CD$_3$OD) δ: 7.88 (d, J=4.0 Hz, 1H), 7.06 (d, J=4.0 Hz, 1H), 4.45-4.58 (m, 2H), 3.57 (s, 2H), 1.68-1.87 (m, 2H), 1.34 (s, 3H), 1.04-1.08 (m, 3H). LC-MS: rt=0.54 mins (UPLC), m/z=209.1 [M+H]$^+$

XXVI-12

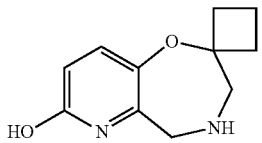

Step A: 1-(6-bromo-3-fluoropyridin-2-yl)-N-(2,4-dimethoxybenzyl)methanamine (XXX)

To a solution of (2,4-dimethoxyphenyl)methanamine (10.6 g, 63.4 mmol) in dichloromethane (150 mL) was added 6-bromo-3-fluoropicolinaldehyde (11.7 g, 57.6 mmol), followed by acetic acid (3.30 mL, 57.6 mmol), the reaction mixture was cooled in an ice bath, to which was added sodium triacetoxyborohydride (18.3 g, 86 mmol). The ice bath was removed, and the reaction mixture was stirred at RT for 2 h. The reaction mixture was carefully quenched with saturated Na$_2$CO$_3$ until reaching pH 7, the layers separated, the aqueous phase extracted with DCM, the organics combined, dried over Na$_2$SO$_4$, filtered, and the solvent evaporated under reduced pressure. The crude solid was purified by flash column chromatography (100% hexanes to 50% EtOAc) to afford compound XXX as a light-yellow oil (12.6 g, 62%). $^1$H NMR (DMSO-d$_6$) δ: 7.63-7.69 (m, 1H), 7.56-7.60 (m, 1H), 7.18 (d, J=8.3 Hz, 1H), 6.50 (d, J=2.4 Hz, 1H), 6.45 (dd, J=8.2, 2.3 Hz, 1H), 3.71-3.78 (m, 9H), 3.62 (s, 2H), 2.39 (br. s., 1H). LC-MS: rt=0.59 mins (UPLC), m/z=355.1 [M+H]$^+$ Step B: 1-((((6-bromo-3-fluoropyridin-2-yl)methyl)(2,4-dimethoxybenzyl)amino)-methyl)cyclobutan-1-ol (XXXI-1)

To a solution of compound XXX (1.99 g, 5.60 mmol), in methanol (9 mL) was added 1-oxaspiro[2.3]hexane (0.66 g, 7.84 mmol) and the reaction mixture was stirred at 60° C. for 3 h. The solvent was evaporated under reduced pressure and the residue dried overnight under high vacuum to afford compound XXXI-1 as a light-yellow oil (2.3 g, 93%). $^1$H NMR (DMSO-d$_6$) δ: 7.58-7.68 (m, 2H), 7.30 (d, J=8.3 Hz, 1H), 6.46-6.49 (m, 1H), 6.45 (d, J=2.4 Hz, 1H), 4.84 (s, 1H), 3.78 (d, J=1.2 Hz, 2H), 3.74 (s, 3H), 3.70 (s, 3H), 3.68 (s, 2H), 2.63 (s, 2H), 1.73-1.90 (m, 4H), 1.42-1.57 (m, 1H), 1.08 (dt, J=10.6, 8.9 Hz, 1H). LC-MS: rt=0.78 mins (UPLC), m/z=441.1 [M+H]$^+$ Step C: 7'-bromo-4'-(2,4-dimethoxybenzyl)-4',5'-dihydro-3'H-spiro[cyclobutane-1,2'-pyrido[2,3-f][1,4]oxazepine] (XXXII-1)

To a solution of compound XXXI-1 (2.30 g, 5.24 mmol), in N,N-dimethylformamide (20 mL), cooled to 0° C., was added 60% sodium hydride (0.314 g, 7.85 mmol) in one portion, the ice bath removed, and the reaction mixture stirred at RT for 24 h. The reaction mixture was quenched with H$_2$O, extracted with EtOAc (2×), the organic extracts combined, washed with brine, dried over Na$_2$SO$_4$, filtered and the solvent evaporated under reduced pressure. The crude residue was purified by flash column chromatography (100% hexanes to 100% EtOAc) to afford compound XXXII-1 as a yellow oil (1.61 g, 73%). $^1$H NMR (DMSO-d$_6$) δ: 7.35-7.50 (m, 2H), 7.23 (d, J=8.3 Hz, 1H), 6.57 (d, J=2.2 Hz, 1H), 6.52 (dd, J=8.3, 2.4 Hz, 1H), 3.77 (d, J=4.6 Hz, 6H), 3.67 (s, 4H), 2.91 (s, 2H), 1.88-2.03 (m, 4H), 1.75-1.87 (m, 1H), 1.51 (dt, J=10.9, 8.7 Hz, 1H). LC-MS: rt=0.72 mins (UPLC), m/z=421.3 [M+H]$^+$ Step D: 4'-(2,4-dimethoxybenzyl)-4',5'-dihydro-3'H-spiro[cyclobutane-1,2'-pyrido[2,3-f][1,4]oxazepin]-7'-ol (XXXIII-1)

To a 100 mL flask, purged with N$_2$, was added Pd$_2$(dba)$_3$ (0.176 g, 0.192 mmol) and $^t$BuXPhos (0.326 g, 0.768 mmol) followed by a solution of compound XXXII-1 (1.610 g, 3.84 mmol), in dioxane (15 mL) and KOH (0.646 g, 11.52 mmol) in water (15 mL), and the reaction mixture was heated under N$_2$ at 100° C. for 18 h. The reaction mixture was cooled to RT, concentrated under reduced pressure, diluted with H$_2$O and the pH of the aqueous phase adjusted to ~6 with 1N HCl. The aqueous phase was extracted with EtOAc (3×), the combined extracts dried over Na$_2$SO$_4$, filtered and the solvent evaporated under reduced pressure. The crude residue was purified by flash column chromatography (100% hexanes to 100% 3:1 EtOAc-EtOH/heptanes) to afford compound XXXIII-1 as a tan solid (311.7 mg, 23%). $^1$H NMR (DMSO-d$_6$) δ: 11.06 (br. s., 1H), 7.15-7.29 (m, 2H), 6.46-6.61 (m, 2H), 6.22 (d, J=9.0 Hz, 1H), 3.77 (d, J=2.7 Hz, 6H), 3.61 (s, 2H), 3.50 (s, 2H), 2.82 (s, 2H), 1.84-1.99 (m, 4H), 1.72-1.84 (m, 1H), 1.40-1.56 (m, 1H). LC-MS: rt=0.55 mins (UPLC), m/z=357.2 [M+H]$^+$ Step E: 4',5'-dihydro-3'H-spiro[cyclobutane-1,2'-pyrido[2,3-f][1,4]oxazepin]-7'-ol, dihydrochloride (XXVI-12)

To compound XXXIII-1 (300 mg, 0.842 mmol) was added trifluoroacetic acid (3 mL) and the reaction mixture was heated at 80° C. for 2 h. The reaction mixture was cooled to RT and concentrated under reduced pressure and azeotroped with CHCl$_3$ (2×). The crude purple solid was partitioned between EtOAc and 6N HCl, a suspension was filtered, washed with H$_2$O and EtOAc, the layers separated, and the aqueous phase evaporated under reduced pressure. The purple solid was dissolved in MeOH, evaporated under reduced pressure 2×, the solid dissolved in a minimum amt of MeOH, to which was added diethyl ether, the solvent evaporated under reduced pressure and the foam dried under vacuo to afford compound XXVI-12 as a purple solid (237 mg, 101%). ¹H NMR (METHANOL-d₄) δ: 7.86 (d, J=9.3 Hz, 1H), 6.95 (d, J=9.3 Hz, 1H), 4.44 (s, 2H), 3.75 (s, 2H), 2.24-2.35 (m, 2H), 2.14-2.23 (m, 2H), 1.97-2.09 (m, 1H), 1.76-1.90 (m, 1H). LC-MS: rt=0.30 mins (UPLC), m/z=207.2 [M+H]⁺

XXVI-13

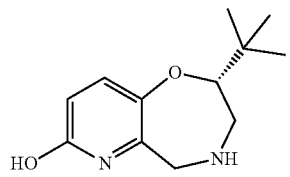

Step A: (R)-1-(((6-bromo-3-fluoropyridin-2-yl) methyl)(2,4-dimethoxybenzyl)amino)-3,3-dimethylbutan-2-ol (XXXI-2)

Compound XXXI-2 was prepared according to scheme G, step B, replacing compound 1-oxaspiro[2.3]hexane with (R)-2-(tert-butyl)oxirane to afford compound XXXI-2 as a white solid (13.4 g, 92%). ¹H NMR (DMSO-d₆) δ: 7.58-7.70 (m, 2H), 7.21 (d, J=8.3 Hz, 1H), 6.50 (d, J=2.4 Hz, 1H), 6.45 (dd, J=8.2, 2.3 Hz, 1H), 4.03 (d, J=2.0 Hz, 1H), 3.76-3.82 (m, 1H), 3.72 (d, J=13.2 Hz, 6H), 3.52-3.69 (m, 3H), 3.21-3.27 (m, 1H), 2.60 (dd, J=12.8, 2.8 Hz, 1H), 2.36 (dd, J=12.8, 9.9 Hz, 1H), 0.75 (s, 9H). LC-MS: rt=0.78 mins (UPLC), m/z=457.3 [M+H]⁺

Step B: (R)-7-bromo-2-(tert-butyl)-4-(2,4-dimethoxybenzyl)-2,3,4,5-tetrahydropyrido[2,3-f][1,4]oxazepine (XXXII-2)

Compound XXXII-2 was prepared according to scheme G, step C, replacing compound XXXI-1 with compound XXXI-2 to afford compound XXXII-2 as a yellow oil (4.69 g, 22%), contaminated with 25% of compound XXXI-2. ¹H NMR (DMSO-d₆) δ: 7.58-7.69 (m, 1H), 7.31-7.47 (m, 2H), 7.21 (d, J=8.3 Hz, 1H), 7.17 (d, J=8.3 Hz, 1H), 6.54 (d, J=2.2 Hz, 1H), 6.47-6.51 (m, 1H), 6.45 (dd, J=8.2, 2.3 Hz, 1H), 3.87 (s, 2H), 3.75 (d, J=5.4 Hz, 7H), 3.71 (s, 2H), 3.63 (dd, J=8.4, 1.6 Hz, 1H), 3.56 (s, 2H), 3.05 (d, J=12.5 Hz, 1H), 2.85 (dd, J=13.7, 10.3 Hz, 1H), 2.60 (dd, J=12.7, 2.7 Hz, 1H), 2.37 (dd, J=12.8, 9.9 Hz, 1H), 0.96 (s, 9H), 0.75 (s, 4H). LC-MS: rt=0.84 mins (UPLC), m/z=437.3 [M+H]⁺

Step C: (R)-2-(tert-butyl)-4-(2,4-dimethoxybenzyl)-2,3,4,5-tetrahydropyrido[2,3-f][1,4]oxazepin-7-ol (XXXIII-2)

Compound XXXIII-2 was prepared according to scheme G, step D, replacing compound XXXII-1 with compound XXXII-2 to afford compound XXXIII-2 as a yellow solid (1.78 g, 45%). ¹H NMR (METHANOL-d₄) δ: 7.43 (d, J=9.5 Hz, 1H), 7.21 (d, J=8.1 Hz, 1H), 6.50-6.58 (m, 2H), 6.41 (d, J=9.5 Hz, 1H), 3.85-3.94 (m, 1H), 3.81 (s, 6H), 3.69 (d, J=2.0 Hz, 2H), 3.58 (dd, J=10.1, 1.3 Hz, 1H), 3.20 (d, J=13.9 Hz, 1H), 2.85 (dd, J=14.1, 10.1 Hz, 1H), 1.00 (s, 9H). LC-MS: rt=0.66 mins (UPLC), m/z=377.3 [M+H]⁺

Step D: (R)-2-(tert-butyl)-2,3,4,5-tetrahydropyrido[2,3-f][1,4]oxazepin-7-ol (XXVI-13)

Compound XXVI-13 was prepared according to scheme G, step E, replacing compound XXXIII-1 with compound XXXIII-2 to afford compound XXVI-13 as a light pink foam (1.20 g, 92%). ¹H NMR (METHANOL-d₄) δ: 7.83 (d, J=9.3 Hz, 1H), 6.96 (d, J=9.3 Hz, 1H), 4.58 (s, 2H), 3.96 (dd, J=11.0, 2.2 Hz, 1H), 3.81 (dd, J=13.4, 2.4 Hz, 1H), 3.60 (dd, J=13.4, 11.0 Hz, 1H), 1.13 (s, 9H). LC-MS: rt=0.43 mins (UPLC), m/z=223.3 [M+H]⁺

EXAMPLES

Example 1

(R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid Example 1

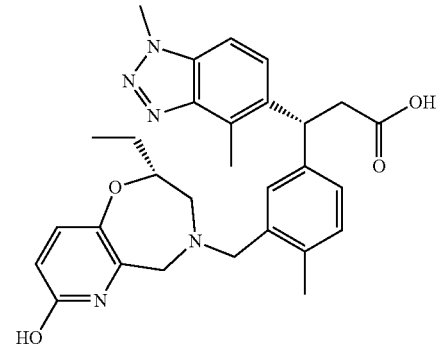

Step A: Ethyl (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoate (XXVIII-1)

To a solution of compound XIV (2.64 g, 7.18 mmol) in dichloromethane (20 mL) was added thionyl chloride (1.05 mL, 14.3 mmol) and the reaction mixture was stirred at RT for 4 h. The solvent was evaporated under reduced pressure and azeotroped using chloroform (3×). The residue was dissolved in acetonitrile (20 mL) to which was added XXVI-1 (2.32 g, 10.06 mmol) followed by diisopropylamine (6.27 mL, 35.9 mmol) and the reaction mixture was stirred at 60° C. for 48 h. The reaction mixture was cooled to RT and the solvent evaporated under reduced pressure. The residue was dissolved in ethyl acetate, washed with water (2×) and brine, dried over sodium sulfate, filtered and the solvent evaporated under reduced pressure. The residue was dissolved in DCM, absorbed onto a silica gel prepacked column and purified by flash chromatography (SiO₂, 120 g, Gold) eluting with a 50% hexanes-3:1 EtOAc/EtOH to 100% 3:1 EtOAc/EtOH gradient (20 min) to afford compound XXVIII-1 as a white foam (3.70 g, 95% yield). ¹H NMR (DMSO-d₆) δ: 11.13 (br. s., 1H), 7.42-7.57 (m, 2H), 7.26 (d, J=9.1 Hz, 1H), 7.09-7.13 (m, 2H), 7.04-7.08 (m, 1H), 6.25 (d, J=9.1 Hz, 1H), 4.83 (t, J=8.0 Hz, 1H), 4.24 (s, 3H), 3.92 (q, J=7.1 Hz, 2H), 3.87 (d, J=14.7 Hz, 1H), 3.64-3.74 (m, 2H), 3.45-3.58 (m, 2H), 3.06-3.22 (m, 2H), 2.75 (s, 3H), 2.54-2.71 (m, 2H), 2.21 (s, 3H), 1.28-1.41 (m, 1H), 1.05-1.15 (m, 1H), 1.01 (t, J=7.1 Hz, 3H), 0.80 (t, J=7.4 Hz, 3H). LC-MS: rt=0.74 mins (UPLC), m/z=544.2 [M+H]⁺

Step B: (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid To a solution of compound XXVIII-1 (3.70 g, 6.81 mmol) in ethanol (30 mL) was added a 5M solution of NaOH (5.44 mL, 27.2 mmol) and the reaction mixture was stirred at 60° C. for 24 h. The reaction mixture was allowed to cool to RT and the solvent evaporated under reduced pressure. The resultant solid was dissolved in $H_2O$ (approx. 20 mL), cooled to 5° C., and the pH adjusted to pH 5-6 using a solution of 6N HCl (dropwise addition). The solid was filtered, washed with $H_2O$, and dried under vacuo to afford Example 1 as a white solid (3.21 g, 91% yield). $^1$H NMR (METHANOL-$d_4$) δ: 7.52 (q, J=8.8 Hz, 2H), 7.45 (d, J=9.4 Hz, 1H), 7.14-7.23 (m, 3H), 6.48 (d, J=9.4 Hz, 1H), 4.96 (t, J=7.9 Hz, 1H), 4.30 (s, 3H), 4.08 (d, J=13.4 Hz, 1H), 3.83 (d, J=4.8 Hz, 4H), 3.03-3.22 (m, 3H), 2.94 (br. s., 1H), 2.78 (s, 3H), 2.34 (s, 3H), 1.44-1.59 (m, 1H), 1.23-1.38 (m, 1H), 0.96 (t, J=7.4 Hz, 3H). LC-MS: rt=0.62 mins (UPLC), m/z=516.2 [M+H]$^+$ Following the procedure described above for Example 1 and substituting the appropriate reagents, starting materials and purification methods known to those skilled in the art, the following compounds of the present invention were prepared:

Example 2

(R)-3-(1,4-dimethyl-1H-benzo[d][1,2,3]triazol-5-yl)-3-(3-(((S)-7-hydroxy-2-isopropyl-2,3-dihydropyrido[2,3-f][1,4]oxazepin-4(5H)-yl)methyl)-4-methylphenyl)propanoic acid

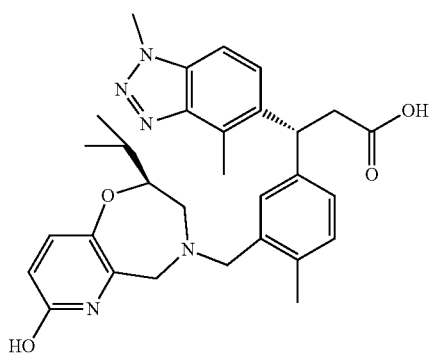

Example 2

Step A: Ethyl (R)-3-(1,4-dimethyl-1H-benzo[d][1,2,3]triazol-5-yl)-3-(3-(((S)-7-hydroxy-2-isopropyl-2,3-dihydropyrido[2,3-f][1,4]oxazepin-4(5H)-yl)methyl)-4-methylphenyl)propanoate (XXVIII-4)

Compound XXVIII-4 was prepared according to scheme F, step A, replacing compound XXVI-1 with XXV1-4-b to afford a yellow solid (0.181 g, 68% yield). $^1$H NMR (DMSO-$d_6$) δ: 7.45-7.59 (m, 2H), 7.24 (d, J=9.3 Hz, 1H), 7.03-7.14 (m, 3H), 6.25 (br. s., 1H), 4.80 (t, J=7.9 Hz, 1H), 4.24 (s, 3H), 3.65-3.96 (m, 4H), 3.44-3.57 (m, 3H), 3.13 (d, J=7.8 Hz, 2H), 2.59-2.77 (m, 5H), 2.21 (s, 3H), 1.41-1.53 (m, 1H), 1.00 (t, J=7.2 Hz, 3H), 0.65-0.88 (m, 6H). LCMS: rt=1.16 mins (UPLC), m/z=558.3 [M+H]$^+$

Step B: (R)-3-(1,4-dimethyl-1H-benzo[d][1,2,3]triazol-5-yl)-3-(3-(((S)-7-hydroxy-2-isopropyl-2,3-dihydropyrido[2,3-f][1,4]oxazepin-4(5H)-yl)methyl)-4-methylphenyl)propanoic acid Example 2 was prepared according to Scheme F, step B, replacing compound XXVIII-1 with XXVIII-4 to afford a yellow solid (0.057 g, 60% yield). $^1$H NMR (DMSO-$d_6$) δ: 11.63 (br. s., 2H), 7.44-7.57 (m, 2H), 7.25 (d, J=9.29 Hz, 1H), 7.09-7.15 (m, 1H), 7.07 (br. s., 2H), 6.24 (d, J=9.29 Hz, 1H), 4.78 (t, J=7.78 Hz, 1H), 4.24 (s, 3H), 3.66-3.90 (m, 2H), 3.44-3.57 (m, 3H), 3.04 (d, J=7.53 Hz, 2H), 2.60-2.76 (m, 5H), 2.21 (s, 3H), 1.47 (dd, J=6.27, 12.80 Hz, 1H), 0.82 (d, J=6.78 Hz, 3H), 0.69 (d, J=6.78 Hz, 3H). LC-MS: rt=0.950 mins (UPLC), m/z=530.2 [M+H]$^+$

Example 3

(R)-3-(1,4-dimethyl-1H-benzo[d][1,2,3]triazol-5-yl)-3-(3-(((R)-7-hydroxy-2-isopropyl-2,3-dihydropyrido[2,3-f][1,4]oxazepin-4(5H)-yl)methyl)-4-methylphenyl)propanoic acid

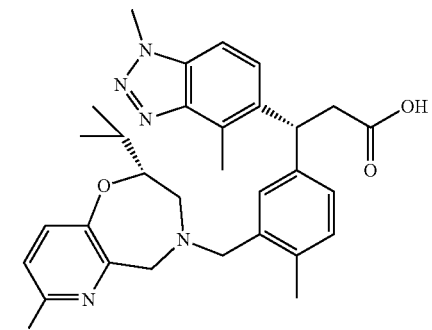

Example 3

Step A: Ethyl (R)-3-(1,4-dimethyl-1H-benzo[d][1,2,3]triazol-5-yl)-3-(3-(((R)-7-hydroxy-2-isopropyl-2,3-dihydropyrido[2,3-f][1,4]oxazepin-4(5H)-yl)methyl)-4-methylphenyl)propanoate (XXVIII-5)

Compound XXVIII-5 was prepared according to Scheme F, step A, replacing compound XXVI-1 with XXV1-4-a to afford a white solid (0.104 g, 70% yield). $^1$H NMR (DMSO-$d_6$) δ: 11.30 (br. s., 1H), 7.40-7.57 (m, 2H), 7.24 (d, J=9.3 Hz, 1H), 7.03-7.15 (m, 3H), 6.24 (br. s., 1H), 4.82 (t, J=8.0 Hz, 1H), 4.23 (s, 3H), 3.92 (q, J=7.0 Hz, 2H), 3.86 (d, J=14.8 Hz, 1H), 3.69 (d, J=14.8 Hz, 1H), 3.44-3.57 (m, 3H), 3.08-3.16 (m, 2H), 2.73 (s, 3H), 2.65 (br. s., 2H), 2.21 (s, 3H), 1.37 (d, J=6.5 Hz, 1H), 1.00 (t, J=7.0 Hz, 3H), 0.78 (d, J=6.5 Hz, 3H), 0.66 (d, J=6.8 Hz, 3H). LC-MS: rt=1.14 mins (UPLC), m/z=558.2 [M+H]$^+$

Step B: (R)-3-(1,4-dimethyl-1H-benzo[d][1,2,3]triazol-5-yl)-3-(3-(((R)-7-hydroxy-2-isopropyl-2,3-dihydropyrido[2,3-f][1,4]oxazepin-4(5H)-yl)methyl)-4-methylphenyl)propanoic acid Example 3 was prepared according to Scheme F, step B, replacing compound XXVIII-1 with XXVIII-5 to afford a yellow solid (0.054 g, 54% yield). ¹H NMR (DMSO-d₆) δ: 11.66 (br. s., 2H), 7.39-7.57 (m, 2H), 7.24 (d, J=9.3 Hz, 1H), 7.03-7.14 (m, 3H), 6.24 (d, J=9.3 Hz, 1H), 4.80 (t, J=7.9 Hz, 1H), 4.23 (s, 3H), 3.64-3.90 (m, 2H), 3.44-3.57 (m, 3H), 3.03 (t, J=7.2 Hz, 2H), 2.73 (s, 3H), 2.65 (br. s., 2H), 2.22 (s, 3H), 1.29-1.41 (m, 1H), 0.78 (d, J=6.8 Hz, 3H), 0.65 (d, J=6.5 Hz, 3H). LC-MS: rt=0.877 mins (UPLC), m/z=504.2 [M+H]⁺

Example 4

(R)-3-(1,4-dimethyl-1H-benzo[d][1,2,3]triazol-5-yl)-3-(3-(((R)-7-hydroxy-2-methyl-2,3-dihydropyrido[2,3-f][1,4]oxazepin-4(5H)-yl)methyl)-4-methylphenyl)propanoic acid

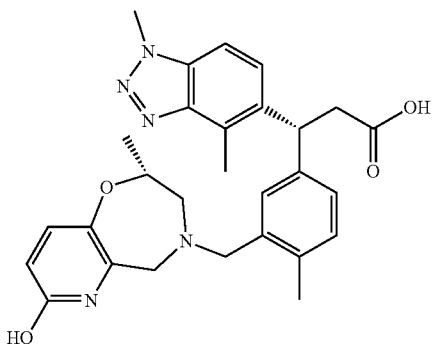

Example 4

Step A: Ethyl (R)-3-(1,4-dimethyl-1H-benzo[d][1,2,3]triazol-5-yl)-3-(3-(((R)-7-hydroxy-2-methyl-2,3-dihydropyrido[2,3-f][1,4]oxazepin-4(5H)-yl)methyl)-4-methylphenyl)propanoate (XXVIII-6)

Compound XXVIII-6 was prepared according to Scheme F, step A, replacing compound XXVI-1 with XXV1-3 to afford a light orange foam (0.196 g, 100% yield). ¹H NMR (DMSO-d₆) δ: 7.47-7.58 (m, 2H), 7.26 (d, J=9.4 Hz, 1H), 7.15 (s, 1H), 7.03-7.11 (m, 2H), 6.24 (d, J=7.6 Hz, 1H), 4.83 (t, J=8.0 Hz, 1H), 4.24 (s, 3H), 3.96-4.08 (m, 1H), 3.93 (q, J=7.1 Hz, 2H), 3.86 (d, J=14.7 Hz, 1H), 3.68 (d, J=14.7 Hz, 1H), 3.52 (s, 2H), 3.15 (dd, J=8.0, 3.4 Hz, 2H), 2.75 (s, 3H), 2.55-2.73 (m, 2H), 2.20 (s, 3H), 0.98-1.05 (m, 6H). LC-MS: rt=0.69 mins (UPLC), m/z=530.2 [M+H]⁺

Step B: (R)-3-(1,4-dimethyl-1H-benzo[d][1,2,3]triazol-5-yl)-3-(3-(((R)-7-hydroxy-2-methyl-2,3-dihydropyrido[2,3-f][1,4]oxazepin-4(5H)-yl)methyl)-4-methylphenyl)propanoic acid Example 4 was prepared according to Scheme F, step B, replacing compound XXVIII-1 with XXVIII-6 to afford an orange oil (0.136 g, 95% yield). ¹H NMR (DMSO-d₆) δ: 11.65 (br. s., 1H), 7.53-7.57 (m, 1H), 7.45-7.49 (m, 1H), 7.27 (d, J=9.4 Hz, 1H), 7.14 (s, 1H), 7.03-7.11 (m, 2H), 6.25 (d, J=9.1 Hz, 1H), 4.81 (t, J=7.9 Hz, 1H), 4.24 (s, 3H), 3.96-4.06 (m, 1H), 3.87 (d, J=15.0 Hz, 1H), 3.67 (d, J=14.7 Hz, 1H), 3.53 (s, 2H), 3.18 (s, 2H), 2.97-3.13 (m, 2H), 2.74 (s, 3H), 2.66-2.73 (m, 1H), 2.60 (dd, J=14.2, 9.4 Hz, 1H), 2.20 (s, 3H), 1.02 (d, J=6.3 Hz, 3H). LC-MS: rt=0.57 mins (UPLC), m/z=502.2 [M+H]⁺

Example 5

(R)-3-(1,4-dimethyl-1H-benzo[d][1,2,3]triazol-5-yl)-3-(3-((7-hydroxy-2,2-dimethyl-2,3-dihydropyrido[2,3-f][1,4]oxazepin-4(5H)-yl)methyl)-4-methylphenyl)propanoic acid

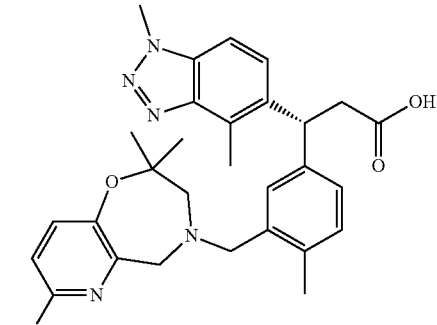

Example 5

Step A: Ethyl (R)-3-(1,4-dimethyl-1H-benzo[d][1,2,3]triazol-5-yl)-3-(3-((7-hydroxy-2,2-dimethyl-2,3-dihydropyrido[2,3-f][1,4]oxazepin-4(5H)-yl)methyl)-4-methylphenyl)propanoate (XXVIII-12)

Compound XXVIII-12 was prepared according to Scheme F, step A, replacing compound XXVI-1 with XXV1-5 to afford an orange oil (0.152 g, 100% yield). ¹H NMR (DMSO-d₆) δ: 7.49-7.55 (m, 1H), 7.41-7.46 (m, 1H), 7.04-7.17 (m, 4H), 6.24 (br. s., 1H), 4.83 (t, J=8.0 Hz, 1H), 4.23 (s, 3H), 3.93 (q, J=7.1 Hz, 2H), 3.53 (d, J=6.6 Hz, 4H), 3.15 (dd, J=10.0, 8.2 Hz, 2H), 2.71 (s, 3H), 2.21 (s, 3H), 0.93-1.05 (m, 9H). LC-MS: rt=0.81 mins (UPLC), m/z=544.3 [M+H]⁺

Step B: (R)-3-(1,4-dimethyl-1H-benzo[d][1,2,3]triazol-5-yl)-3-(3-((7-hydroxy-2,2-dimethyl-2,3-dihydropyrido[2,3-f][1,4]oxazepin-4(5H)-yl)methyl)-4-methylphenyl)propanoic acid Example 5 was prepared according to Scheme F, step B, replacing compound XXVIII-1 with XXVIII-12 to afford a light orange solid (0.140 g, 76% yield). ¹H NMR (DMSO-d₆) δ: 11.58 (br. s., 2H), 7.50-7.54 (m, 1H), 7.42 (d, J=8.6 Hz, 1H), 7.04-7.16 (m, 4H), 6.24 (d, J=9.1 Hz, 1H), 4.81 (t, J=7.9 Hz, 1H), 4.23 (s, 3H), 3.53 (d, J=6.8 Hz, 4H), 3.35 (br. s., 2H), 2.93-3.14 (m, 2H), 2.71 (s, 3H), 2.21 (s, 3H), 0.97 (d, J=13.2 Hz, 6H). LC-MS: rt=0.66 mins (UPLC), m/z=516.4 [M+H]⁺

Example 6

(R)-3-(1,4-dimethyl-1H-benzo[d][1,2,3]triazol-5-yl)-3-(3-(((S)-7-hydroxy-2-(trifluoromethyl)-2,3-dihydropyrido[2,3-f][1,4]oxazepin-4(5H)-yl)methyl)-4-methylphenyl)propanoic acidacid

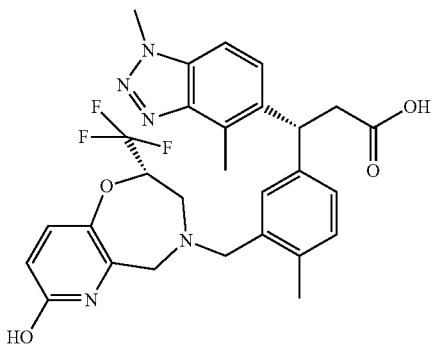

Example 6

Step A: Ethyl (R)-3-(1,4-dimethyl-1H-benzo[d][1,2,3]triazol-5-yl)-3-(3-(((S)-7-hydroxy-2-(trifluoromethyl)-2,3-dihydropyrido[2,3-f][1,4]oxazepin-4(5H)-yl)methyl)-4-methylphenyl)propanoate (XXVIII-16)

Compound XXVIII-16 was prepared according to Scheme F, step A, replacing compound XXVI-1 with XXV1-6 to afford a yellow oil (0.159 g, 83% yield). $^1$H NMR (DMSO-d$_6$) δ: 11.32 (br. s., 1H), 7.51-7.59 (m, 2H), 7.39 (d, J=9.1 Hz, 1H), 7.28 (s, 1H), 7.03-7.14 (m, 2H), 6.34 (br. s., 1H), 4.77-4.90 (m, 2H), 4.24 (s, 3H), 4.04-4.13 (m, 1H), 3.91 (q, J=7.1 Hz, 2H), 3.79 (d, J=15.2 Hz, 1H), 3.51-3.65 (m, 2H), 3.05-3.22 (m, 2H), 2.95 (br. s., 2H), 2.74 (s, 3H), 2.22 (s, 3H), 1.00 (t, J=7.1 Hz, 3H). LC-MS: rt=1.06 mins (UPLC), m/z=584.4 [M+H]$^+$

Step B: (R)-3-(1,4-dimethyl-1H-benzo[d][1,2,3]triazol-5-yl)-3-(3-(((S)-7-hydroxy-2-(trifluoromethyl)-2,3-dihydropyrido[2,3-f][1,4]oxazepin-4(5H)-yl)methyl)-4-methylphenyl)propanoic acid Example 6 was prepared according to Scheme F, step B, replacing compound XXVIII-1 with XXVIII-16 to afford a white solid (0.072 g, 49% yield). $^1$H NMR (DMSO-d$_6$) δ: 11.80 (br. s., 2H), 7.53 (q, J=8.79 Hz, 2H), 7.38 (d, J=9.38 Hz, 1H), 7.27 (s, 1H), 7.03-7.12 (m, 2H), 6.33 (d, J=9.38 Hz, 1H), 4.72-4.92 (m, 2H), 4.24 (s, 3H), 4.06 (d, J=15.21 Hz, 1H), 3.78 (d, J=14.95 Hz, 1H), 3.52-3.64 (m, 2H), 2.92-3.10 (m, 4H), 2.73 (s, 3H), 2.22 (s, 3H). LC-MS: rt=0.94 mins (UPLC), m/z=556.4 [M+H]$^+$

Example 7

(R)-3-(1,4-dimethyl-1H-benzo[d][1,2,3]triazol-5-yl)-3-(3-(((S)-2-ethyl-7-hydroxy-2,3-dihydropyrido[2,3-f][1,4]oxazepin-4(5H)-yl)methyl)-4-methylphenyl)propanoic acid

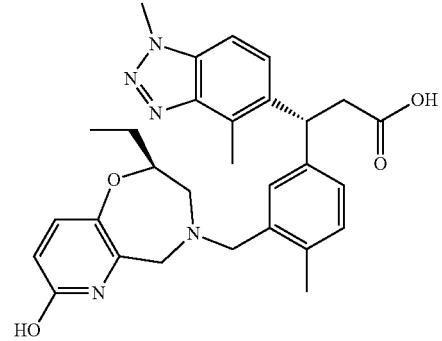

Example 7

Step A: Ethyl (R)-3-(1,4-dimethyl-1H-benzo[d][1,2,3]triazol-5-yl)-3-(3-(((S)-2-ethyl-7-hydroxy-2,3-dihydropyrido[2,3-f][1,4]oxazepin-4(5H)-yl)methyl)-4-methylphenyl)propanoate (XXVIII-18)

Compound XXVIII-18 was prepared according to Scheme F, step A, replacing compound XXVI-1 with XXV1-2 to afford a colorless foam (0.250 g, 84% yield). $^1$H NMR (DMSO-d$_6$) δ: 7.53-7.57 (m, 1H), 7.47-7.52 (m, 1H), 7.25 (d, J=9.1 Hz, 1H), 7.03-7.13 (m, 3H), 6.24 (br. s., 1H), 4.81 (t, J=8.0 Hz, 1H), 4.24 (s, 3H), 3.92 (q, J=7.1 Hz, 2H), 3.86 (d, J=14.7 Hz, 1H), 3.68 (d, J=13.7 Hz, 2H), 3.51 (d, J=4.3 Hz, 2H), 3.43-3.48 (m, 1H), 3.14 (d, J=7.9 Hz, 2H), 2.71 (s, 3H), 2.68 (s, 2H), 2.20 (s, 3H), 1.35 (br. s., 1H), 1.25 (br. s., 1H), 1.01 (t, J=7.1 Hz, 3H), 0.85 (t, J=5.8 Hz, 3H). LC-MS: rt=0.75 mins (UPLC), m/z=544.5 [M+H]$^+$

Step B: (R)-3-(1,4-dimethyl-1H-benzo[d][1,2,3]triazol-5-yl)-3-(3-(((S)-2-ethyl-7-hydroxy-2,3-dihydropyrido[2,3-f][1,4]oxazepin-4(5H)-yl)methyl)-4-methylphenyl)propanoic acid Example 7 was prepared according to Scheme F, step B, replacing compound XXVIII-1 with XXVIII-18 to afford a tan solid (0.182 g, 77% yield). $^1$H NMR (DMSO-d$_6$) δ: 11.77 (br. s., 2H), 7.54 (d, J=8.62 Hz, 1H), 7.47 (d, J=8.87 Hz, 1H), 7.25 (d, J=9.38 Hz, 1H), 6.96-7.13 (m, 3H), 6.24 (d, J=9.12 Hz, 1H), 4.79 (t, J=7.86 Hz, 1H), 4.23 (s, 3H), 3.79-3.87 (m, 1H), 3.60-3.73 (m, 2H), 3.41-3.58 (m, 2H), 2.92-3.10 (m, 2H), 2.71 (s, 3H), 2.54-2.70 (m, 2H), 2.20 (s, 3H), 1.30-1.45 (m, 1H), 1.10-1.21 (m, 1H), 0.82-0.92 (m, 3H). LC-MS: rt=0.62 mins (UPLC), m/z=516.5 [M+H]$^+$

Example 8

(S)-3-(1,4-dimethyl-1H-benzo[d][1,2,3]triazol-5-yl)-3-(3-(((R)-7-hydroxy-2-isopropyl-2,3-dihydropyrido[2,3-f][1,4]oxazepin-4(5H)-yl)methyl)-4-methylphenyl)propanoic acid

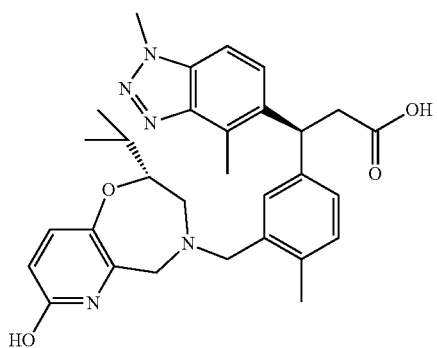

Example 8

Step A: Methyl (S)-3-(1,4-dimethyl-1H-benzo[d][1,2,3]triazol-5-yl)-3-(3-(((R)-7-hydroxy-2-isopropyl-2,3-dihydropyrido[2,3-f][1,4]oxazepin-4(5H)-yl)methyl)-4-methylphenyl)propanoate (XXVIII-9)

Compound XXVIII-9 was prepared according to Scheme F, step A, replacing compound XIV with XVIII, and compound XXVI-1 with XXVI-4-a to afford a white solid (0.263 g, 92% yield). $^1$H NMR (DMSO-$d_6$) δ: 7.51-7.56 (m, 1H), 7.43-7.49 (m, 1H), 7.23 (d, J=9.1 Hz, 1H), 7.08-7.13 (m, 1H), 7.02-7.08 (m, 2H), 6.14-6.33 (m, 1H), 4.80 (t, J=7.9 Hz, 1H), 4.16-4.28 (m, 3H), 3.85 (d, J=15.0 Hz, 1H), 3.69 (d, J=14.7 Hz, 1H), 3.43-3.56 (m, 6H), 3.14 (d, J=8.1 Hz, 2H), 2.59-2.74 (m, 5H), 2.13-2.26 (m, 3H), 1.39-1.53 (m, 1H), 0.82 (d, J=6.8 Hz, 3H), 0.69 (d, J=6.6 Hz, 3H). LC-MS: rt=0.76 mins (UPLC), m/z=544.5 [M+H]$^+$

Step B: (S)-3-(1,4-dimethyl-1H-benzo[d][1,2,3]triazol-5-yl)-3-(3-(((R)-7-hydroxy-2-isopropyl-2,3-dihydropyrido[2,3-f][1,4]oxazepin-4(5H)-yl)methyl)-4-methylphenyl)propanoic acid Example 8 was prepared according to Scheme F, step B, replacing compound XXVIII-1 with XXVIII-9 to afford a tan solid (0.178 g, 66% yield). $^1$H NMR (DMSO-$d_6$) δ: 11.56-11.84 (m, 2H), 7.53 (d, J=8.6 Hz, 1H), 7.45 (d, J=8.6 Hz, 1H), 7.23 (d, J=9.1 Hz, 1H), 7.10 (dd, J=7.9, 1.8 Hz, 1H), 7.02-7.07 (m, 2H), 6.23 (d, J=9.1 Hz, 1H), 4.78 (t, J=7.9 Hz, 1H), 4.17-4.29 (m, 3H), 3.84 (d, J=14.7 Hz, 1H), 3.68 (d, J=14.7 Hz, 1H), 3.41-3.55 (m, 3H), 2.94-3.09 (m, 2H), 2.59-2.77 (m, 5H), 2.13-2.27 (m, 3H), 1.40-1.54 (m, 1H), 0.82 (d, J=6.6 Hz, 3H), 0.70 (d, J=6.8 Hz, 3H). LC-MS:=0.68 mins (UPLC), m/z=530.5 [M+H]$^+$

Example 9

(S)-3-(1,4-dimethyl-1H-benzo[d][1,2,3]triazol-5-yl)-3-(3-(((S)-7-hydroxy-2-isopropyl-2,3-dihydropyrido[2,3-f][1,4]oxazepin-4(5H)-yl)methyl)-4-methylphenyl)propanoic acid

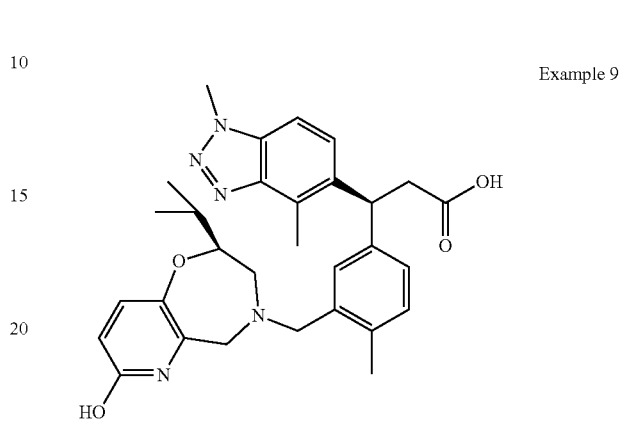

Example 9

Step A: Methyl (S)-3-(1,4-dimethyl-1H-benzo[d][1,2,3]triazol-5-yl)-3-(3-(((S)-7-hydroxy-2-isopropyl-2,3-dihydropyrido[2,3-f][1,4]oxazepin-4(5H)-yl)methyl)-4-methylphenyl)propanoate (XXVIII-10)

Compound XXVIII-10 was prepared according to Scheme F, step A, replacing compound XIV with XVIII, and compound XXVI-1 with XXVI-4-b to afford a white solid (0.267 g, 90% yield). $^1$H NMR (DMSO-$d_6$) δ: 7.52 (d, J=8.6 Hz, 1H), 7.41 (d, J=8.9 Hz, 1H), 7.23 (d, J=9.4 Hz, 1H), 7.09-7.15 (m, 1H), 7.02-7.08 (m, 2H), 6.10-6.36 (m, 1H), 4.82 (t, J=7.9 Hz, 1H), 4.16-4.29 (m, 3H), 3.85 (d, J=14.7 Hz, 1H), 3.68 (br d, J=15.2 Hz, 1H), 3.42-3.57 (m, 6H), 3.06-3.21 (m, 2H), 2.73 (s, 3H), 2.57-2.69 (m, 2H), 2.13-2.28 (m, 3H), 1.29-1.43 (m, 1H), 0.77 (br d, J=6.6 Hz, 3H), 0.65 (br d, J=6.6 Hz, 3H). LC-MS: rt=0.74 mins (UPLC), m/z=544.5 [M+H]$^+$

Step B: (S)-3-(1,4-dimethyl-1H-benzo[d][1,2,3]triazol-5-yl)-3-(3-(((S)-7-hydroxy-2-isopropyl-2,3-dihydropyrido[2,3-f][1,4]oxazepin-4(5H)-yl)methyl)-4-methylphenyl)propanoic acid Example 9 was prepared according to Scheme F, step B, replacing compound XXVI-1 with XXVIII-10 to afford a tan solid (0.198 g, 72% yield). $^1$H NMR (DMSO-$d_6$) δ: 11.53-11.92 (m, 2H), 7.52 (d, J=8.6 Hz, 1H), 7.40 (d, J=8.6 Hz, 1H), 7.23 (d, J=9.1 Hz, 1H), 7.08-7.13 (m, 1H), 7.02-7.07 (m, 2H), 6.23 (d, J=9.1 Hz, 1H), 4.79 (t, J=7.9 Hz, 1H), 4.22 (s, 3H), 3.85 (d, J=14.7 Hz, 1H), 3.68 (d, J=15.0 Hz, 1H), 3.42-3.57 (m, 3H), 2.93-3.07 (m, 2H), 2.72 (s, 3H), 2.59-2.69 (m, 2H), 2.21 (s, 3H), 1.29-1.43 (m, 1H), 0.77 (d, J=6.6 Hz, 3H), 0.65 (d, J=6.8 Hz, 3H). LC-MS: rt=0.67 mins (UPLC), m/z=530.5 [M+H]$^+$

Example 10

(S)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid

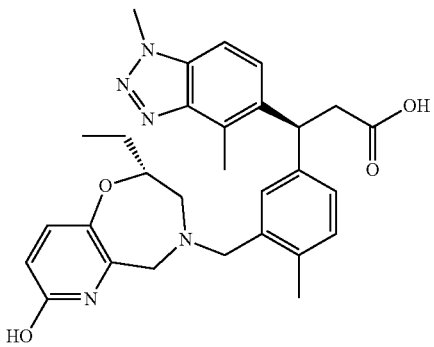

Example 10

Step A: Methyl (S)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoate (XXVIII-11)

Compound XXVIII-11 was prepared according to Scheme F, step A, replacing compound XIV with XVIII, and compound XXVI-1 with XXVI-2 to afford a white foam (0.150 g, 95% yield). $^1$H NMR (DMSO-d$_6$) δ: 7.47-7.58 (m, 2H), 7.26 (d, J=9.1 Hz, 1H), 7.03-7.13 (m, 3H), 6.25 (br. s., 1H), 4.81 (t, J=7.9 Hz, 1H), 4.24 (s, 3H), 3.87 (d, J=14.7 Hz, 1H), 3.69 (d, J=14.4 Hz, 2H), 3.51 (d, J=4.8 Hz, 2H), 3.48 (s, 3H), 3.34 (s, 1H), 3.17 (d, J=8.1 Hz, 2H), 2.72 (s, 3H), 2.54-2.69 (m, 2H), 2.47 (d, J=1.8 Hz, 1H), 2.21 (s, 3H), 1.35 (dd, J=14.6, 7.2 Hz, 1H), 1.12 (br. s., 1H), 0.85 (t, J=7.2 Hz, 3H). LC-MS: rt=0.71 mins (UPLC), m/z=530.3 [M+H]$^+$

Step B: (S)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid Example 10 was prepared according to Scheme F, step B, replacing compound XXVIII-1 with XXVIII-11 to afford a white solid (0.091 g, 61% yield). $^1$H NMR (DMSO-d$_6$) δ: 11.63 (br. s., 2H), 7.46-7.58 (m, 2H), 7.26 (d, J=9.1 Hz, 1H), 7.03-7.14 (m, 3H), 6.25 (d, J=9.4 Hz, 1H), 4.79 (t, J=7.9 Hz, 1H), 4.24 (s, 3H), 3.86 (d, J=15.0 Hz, 1H), 3.69 (d, J=14.4 Hz, 2H), 3.45-3.57 (m, 2H), 3.05 (dd, J=7.7, 2.9 Hz, 2H), 2.72 (s, 3H), 2.54-2.70 (m, 2H), 2.47 (d, J=1.8 Hz, 1H), 2.21 (s, 3H), 1.29-1.43 (m, 1H), 1.12 (ddd, J=13.9, 7.4, 4.3 Hz, 1H), 0.85 (t, J=7.4 Hz, 3H). LC-MS: rt=0.63 mins (UPLC), m/z=516.2 [M+H]$^+$

Example 11

(S)-3-(1,4-dimethyl-1H-benzo[d][1,2,3]triazol-5-yl)-3-(3-((7-hydroxy-2,2-dimethyl-2,3-dihydropyrido[2,3-f][1,4]oxazepin-4(5H)-yl)methyl)-4-methylphenyl)propanoic acid

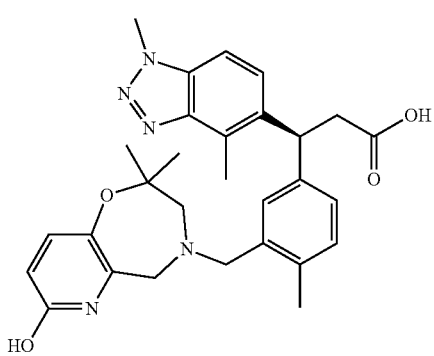

Example 11

Step A: Methyl (S)-3-(1,4-dimethyl-1H-benzo[d][1,2,3]triazol-5-yl)-3-(3-((7-hydroxy-2,2-dimethyl-2,3-dihydropyrido[2,3-f][1,4]oxazepin-4(5H)-yl)methyl)-4-methylphenyl)-propanoate (XXVIII-13)

Compound XXVIII-13 was prepared according to Scheme F, step A, replacing compound XIV with XVIII, and compound XXVI-1 with XXVI-5 to afford an orange oil (0.202 g, 100% yield). $^1$H NMR (DMSO-d$_6$) δ: 7.49-7.55 (m, 1H), 7.40-7.45 (m, 1H), 7.04-7.16 (m, 4H), 6.24 (br. s., 1H), 4.84 (t, J=7.9 Hz, 1H), 4.23 (s, 3H), 3.53 (d, J=7.4 Hz, 4H), 3.48 (s, 3H), 3.29-3.33 (m, 1H), 3.10-3.25 (m, 2H), 2.71 (s, 3H), 2.54 (s, 1H), 2.21 (s, 3H), 1.25 (br. s., 1H), 0.97 (d, J=11.4 Hz, 6H). LC-MS: rt=0.76 mins (UPLC), m/z=530.3 [M+H]$^+$

Step B: (S)-3-(1,4-dimethyl-1H-benzo[d][1,2,3]triazol-5-yl)-3-(3-((7-hydroxy-2,2-dimethyl-2,3-dihydropyrido[2,3-f][1,4]oxazepin-4(5H)-yl)methyl)-4-methylphenyl)propanoic acid Example 11 was prepared according to Scheme F, step B, replacing compound XXVIII-1 with XXVIII-13 to afford a light orange solid (0.165 g, 86% yield). $^1$H NMR (DMSO-d$_6$) δ: 11.61 (br. s., 2H), 7.49-7.54 (m, 1H), 7.42 (d, J=8.6 Hz, 1H), 7.03-7.16 (m, 4H), 6.24 (d, J=9.4 Hz, 1H), 4.81 (t, J=7.9 Hz, 1H), 4.23 (s, 3H), 3.53 (d, J=6.8 Hz, 4H), 2.97-3.14 (m, 2H), 2.71 (s, 3H), 2.54 (s, 2H), 2.21 (s, 3H), 0.97 (d, J=13.2 Hz, 6H). LC-MS: rt=0.67 mins (UPLC), m/z=516.4 [M+H]$^+$

Example 12

(S)-3-(1,4-dimethyl-1H-benzo[d][1,2,3]triazol-5-yl)-
3-(3-(((S)-2-ethyl-7-hydroxy-2,3-dihydropyrido[2,3-
f][1,4]oxazepin-4(5H)-yl)methyl)-4-methylphenyl)
propanoic acid

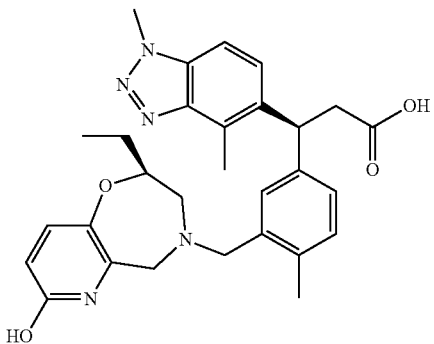

Example 12

Step A: Methyl (S)-3-(1,4-dimethyl-1H-benzo[d][1,2,3]triazol-5-yl)-3-(3-(((S)-2-ethyl-7-hydroxy-2,3-dihydropyrido[2,3-f][1,4]oxazepin-4(5H)-yl)methyl)-4-methylphenyl)propanoate (XXVIII-19)

Compound XXVIII-19 was prepared according to Scheme F, step A, replacing compound XIV with XVIII, and compound XXVI-1 with XXVI-2 to afford a colorless foam (0.300 g, 80% yield). $^1$H NMR (DMSO-$d_6$) δ: 7.54 (d, J=8.6 Hz, 1H), 7.44 (d, J=8.6 Hz, 1H), 7.25 (d, J=9.1 Hz, 1H), 7.03-7.15 (m, 3H), 6.24 (br. s., 1H), 4.83 (t, J=8.0 Hz, 1H), 4.23 (s, 3H), 3.86 (d, J=14.7 Hz, 1H), 3.63-3.74 (m, 2H), 3.40-3.57 (m, 5H), 3.31 (s, 1H), 3.16 (t, J=7.6 Hz, 2H), 2.74 (s, 3H), 2.54-2.69 (m, 2H), 2.21 (s, 3H), 1.33 (dd, J=14.1, 7.0 Hz, 1H), 0.79 (t, J=7.2 Hz, 3H). LC-MS: rt=0.70 mins (UPLC), m/z=530.6 [M+H]$^+$

Step B: (S)-3-(1,4-dimethyl-1H-benzo[d][1,2,3]triazol-5-yl)-3-(3-(((S)-2-ethyl-7-hydroxy-2,3-dihydropyrido[2,3-f][1,4]oxazepin-4(5H)-yl)methyl)-4-methylphenyl)propanoic acid Example 12 was prepared according to Scheme F, step B, replacing compound XXVIII-1 with XXVIII-19 to afford a tan solid (0.152 g, 56% yield). $^1$H NMR (DMSO-$d_6$) δ: 11.65 (br. s., 2H), 7.54 (d, J=8.62 Hz, 1H), 7.43 (d, J=8.62 Hz, 1H), 7.25 (d, J=9.12 Hz, 1H), 7.00-7.14 (m, 3H), 6.24 (d, J=9.38 Hz, 1H), 4.80 (t, J=7.73 Hz, 1H), 4.23 (s, 3H), 3.86 (d, J=14.70 Hz, 1H), 3.67 (d, J=14.45 Hz, 2H), 3.43-3.57 (m, 2H), 2.95-3.11 (m, 2H), 2.73 (s, 3H), 2.57-2.70 (m, 2H), 2.21 (s, 3H), 1.27-1.40 (m, J=7.20, 14.60 Hz, 1H), 1.04-1.13 (m, 1H), 0.74-0.83 (m, 3H). LC-MS: rt=0.63 mins (UPLC), m/z=516.5 [M+H]$^+$

Example 13

(S)-3-(1,4-dimethyl-1H-benzo[d][1,2,3]triazol-5-yl)-
3-(3-(((R)-2-ethyl-7-hydroxy-2,3-dihydropyrido[2,3-
f][1,4]oxazepin-4(5H)-yl)methyl)-4-methylphenyl)-
2,2-dimethyl propanoic acid

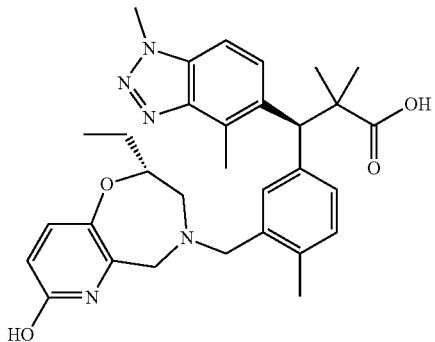

Example 13

Step A: Methyl (S)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)-2,2-dimethylpropanoate (XXVIII-2)

Compound XXVIII-2 was prepared according to Scheme F, step A, replacing compound XIV with XX to afford a yellow foam (0.187 g, 63% yield). $^1$H NMR (DMSO-$d_6$) δ: 11.40 (s, 1H), 7.61-7.67 (m, 1H), 7.54-7.59 (m, 1H), 7.26 (d, J=9.0 Hz, 1H), 7.01-7.15 (m, 3H), 6.24 (br. s., 1H), 4.73 (s, 1H), 4.25 (s, 3H), 3.88 (d, J=14.8 Hz, 1H), 3.59-3.76 (m, 2H), 3.52 (s, 2H), 3.37-3.43 (m, 4H), 2.65 (s, 3H), 2.55-2.62 (m, 1H), 2.21 (s, 3H), 1.25 (d, J=18.1 Hz, 6H), 1.10 (t, J=7.0 Hz, 2H), 0.83 (t, J=6.7 Hz, 3H). LC-MS: rt=1.15 mins (UPLC), m/z=558.2 [M+H]$^+$

Step B: (S)-3-(1,4-dimethyl-1H-benzo[d][1,2,3]triazol-5-yl)-3-(3-WR)-2-ethyl-7-hydroxy-2,3-dihydropyrido[2,3-f][1,4]oxazepin-4(5H)-yl)methyl)-4-methylphenyl)-2,2-dimethyl propanoic acid To a suspension of compound XXVIII-2 (0.167 g, 0.29 mmol) in methanol (2 mL) was added a solution of lithium hydroxide (0.143 g, 5.97 mmol) in water (1 mL) and the reaction mixture was heated at 120° C. under microwave irradiation for 1 h. The reaction mixture was cooled, the solvent evaporated to dryness, the residual solid dissolved in water (10 mL) and the pH of the solution adjusted with 1N HCl to pH 5-6. The white precipitate was extracted with ethyl acetate (3×), the extracts combined, washed with water, brine, dried over sodium sulfate, filtered and the solvent evaporated under reduced pressure. The crude solid was dissolved in dichloromethane, preabsorbed onto a silica gel packed precolumn and purified by silica gel chromatography (0-100% 3:1 EtOAc/EtOH-hexanes) to afford Example 13 as a white solid (0.143 g, 84% yield). $^1$H NMR (DMSO-$d_6$) δ: 11.77 (br. s., 2H), 7.70 (d, J=8.8 Hz, 1H), 7.57 (d, J=8.8 Hz, 1H), 7.27 (d, J=9.3 Hz, 1H), 7.01-7.12 (m, 3H), 6.26 (d, J=9.3 Hz, 1H), 4.74 (s, 1H), 4.25 (s, 3H), 3.88 (d, J=14.8 Hz, 1H), 3.58-3.74 (m, 2H), 3.51 (s, 2H), 2.55-2.68 (m, 6H), 2.22 (s, 3H), 1.27-1.37 (m, 1H), 1.19-1.27 (m, 6H), 1.03 (ddd, J=13.9, 7.4, 4.0 Hz, 1H), 0.83 (t, J=7.3 Hz, 3H). LC-MS: rt=0.83 mins (UPLC), m/z=544.6 [M+H]⁺

Example 14

(S)-3-(1,4-dimethyl-1H-benzo[d][1,2,3]triazol-5-yl)-3-(3-(((R)-7-hydroxy-2-methyl-2,3-dihydropyrido[2,3-f][1,4]oxazepin-4(5H)-yl)methyl)-4-methylphenyl)-2,2-dimethylpropanoic acid

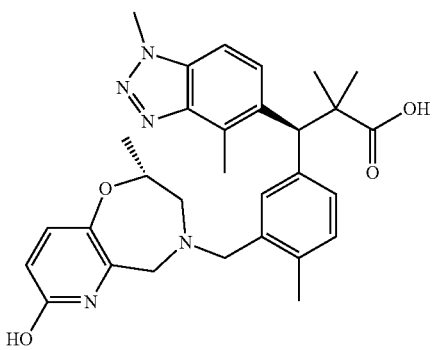

Example 14

Step A: Methyl (S)-3-(1,4-dimethyl-1H-benzo[d][1,2,3]triazol-5-yl)-3-(3-(((R)-7-hydroxy-2-methyl-2,3-dihydropyrido[2,3-f][1,4]oxazepin-4(5H)-yl)methyl)-4-methylphenyl)-2,2-dimethylpropanoate (XXVIII-3)

Compound XXVIII-3 was prepared according to Scheme F, step A, replacing compound XIV with XX and compound XXVI-1 with compound XXVI-3 to afford an orange foam (7.43 g, 99% yield). ¹H NMR (DMSO-d₆) δ: 11.11 (br. s., 1H), 7.64-7.70 (m, 1H), 7.55-7.61 (m, 1H), 7.26 (d, J=9.1 Hz, 1H), 7.16 (s, 1H), 7.01-7.11 (m, 2H), 6.25 (d, J=8.6 Hz, 1H), 4.74 (s, 1H), 4.26 (s, 3H), 3.92-4.00 (m, 1H), 3.88 (d, J=14.7 Hz, 1H), 3.71 (d, J=14.7 Hz, 1H), 3.53 (d, J=1.8 Hz, 2H), 3.42 (s, 3H), 2.66 (s, 4H), 2.54-2.64 (m, 2H), 2.21 (s, 3H), 1.27 (d, J=17.2 Hz, 6H), 0.97 (d, J=6.1 Hz, 3H). LC-MS: rt=0.75 mins (UPLC), m/z=544.2 [M+H]⁺

Step B: (S)-3-(1,4-dimethyl-1H-benzo[d][1,2,3]triazol-5-yl)-3-(3-(((R)-7-hydroxy-2-methyl-2,3-dihydropyrido[2,3-f][1,4]oxazepin-4(5H)-yl)methyl)-4-methylphenyl)-2,2-dimethylpropanoic acid Example 14 was prepared according to Scheme F, step B, replacing compound XXVIII-1 with XXVIII-3 to afford an orange-yellow foam (2.65 g, 36% yield). ¹H NMR (DMSO-d₆) δ: 11.78 (br. s., 2H), 7.73 (d, J=8.9 Hz, 1H), 7.58 (d, J=8.9 Hz, 1H), 7.28 (d, J=9.1 Hz, 1H), 7.13 (s, 1H), 7.02-7.11 (m, 2H), 6.26 (d, J=9.1 Hz, 1H), 4.75 (s, 1H), 4.26 (s, 3H), 3.91-4.00 (m, 1H), 3.88 (d, J=14.7 Hz, 1H), 3.69 (d, J=14.7 Hz, 1H), 3.52 (d, J=1.5 Hz, 2H), 2.65 (s, 4H), 2.53-2.61 (m, 1H), 2.21 (s, 3H), 1.24 (d, J=17.7 Hz, 6H), 0.96 (d, J=6.3 Hz, 3H). LC-MS: rt=0.69 mins (UPLC), m/z=530.3 [M+H]⁺

Example 15

(S)-3-(1,4-dimethyl-1H-benzo[d][1,2,3]triazol-5-yl)-3-(3-(((R)-7-hydroxy-2-isopropyl-2,3-dihydropyrido[2,3-f][1,4]oxazepin-4(5H)-yl)methyl)-4-methylphenyl)-2,2-dimethylpropanoic acid

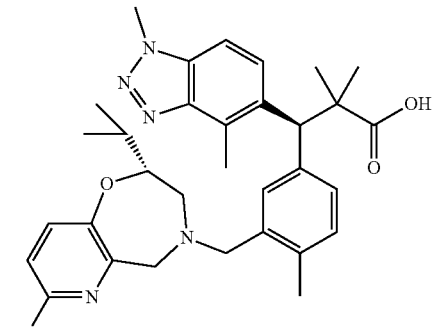

Example 15

Step A: Methyl (S)-3-(1,4-dimethyl-1H-benzo[d][1,2,3]triazol-5-yl)-3-(3-(((R)-7-hydroxy-2-isopropyl-2,3-dihydropyrido[2,3-f][1,4]oxazepin-4(5H)-yl)methyl)-4-methylphenyl)-2,2-dimethylpropanoate (XXVIII-7)

Compound XXVIII-7 was prepared according to Scheme F, step A, replacing compound XIV with XX and compound XXVI-1 with compound XXVI-4-a to afford a beige solid (0.284 g, 93% yield). ¹H NMR (DMSO-d₆) δ: 7.60-7.65 (m, 1H), 7.54-7.59 (m, 1H), 7.25 (d, J=9.4 Hz, 1H), 7.03-7.14 (m, 3H), 6.25 (br. s., 1H), 4.74 (s, 1H), 4.25 (s, 3H), 3.82-3.90 (m, 1H), 3.72 (d, J=14.7 Hz, 1H), 3.53 (s, 2H), 3.46 (d, J=5.1 Hz, 1H), 3.41 (s, 3H), 3.34 (s, 2H), 2.66 (s, 5H), 2.22 (s, 3H), 1.42 (d, J=5.8 Hz, 1H), 1.21-1.32 (m, 6H), 0.84-0.90 (m, 3H), 0.81 (d, J=6.6 Hz, 3H), 0.67 (d, J=6.6 Hz, 3H). LC-MS: rt=0.82 mins (UPLC), m/z=572.5 [M+H]⁺

Step B: (S)-3-(1,4-dimethyl-1H-benzo[d][1,2,3]triazol-5-yl)-3-(3-WR)-7-hydroxy-2-isopropyl-2,3-dihydropyrido[2,3-f][1,4]oxazepin-4(5H)-yl)methyl)-4-methylphenyl)-2,2-dimethylpropanoic acid Example 15 was prepared according to Scheme F, step B, replacing compound XXVIII-1 with XXVIII-7 to afford a white solid (0.201 g, 69% yield). ¹H NMR (DMSO-d₆) δ: 11.54-11.97 (m, 2H), 7.69 (d, J=8.9 Hz, 1H), 7.56 (d, J=8.6 Hz, 1H), 7.26 (d, J=9.1 Hz, 1H), 7.10-7.17 (m, 1H), 7.00-7.10 (m, 2H), 6.26 (d, J=9.4 Hz, 1H), 4.69-4.81 (m, 1H), 4.19-4.31 (m, 3H), 3.86 (d, J=15.0 Hz, 1H), 3.70 (d, J=15.0 Hz, 1H), 3.41-3.56 (m, 3H), 2.59-2.73 (m, 5H), 2.15-2.29 (m, 3H), 1.34-1.48 (m, 1H), 1.26 (s, 3H), 1.21 (s, 3H), 0.80 (d, J=6.8 Hz, 3H), 0.67 (d, J=6.8 Hz, 3H). LC-MS: rt=0.77 mins (UPLC), m/z=558.5 [M+H]⁺

Example 16

(S)-3-(1,4-dimethyl-1H-benzo[d][1,2,3]triazol-5-yl)-3-(3-(((S)-7-hydroxy-2-isopropyl-2,3-dihydropyrido[2,3-f][1,4]oxazepin-4(5H)-yl)methyl)-4-methylphenyl)-2,2-dimethylpropanoic acid

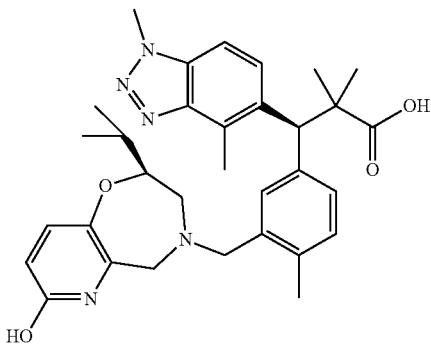

Example 16

Step A: Methyl (S)-3-(1,4-dimethyl-1H-benzo[d][1,2,3]triazol-5-yl)-3-(3-(((S)-7-hydroxy-2-isopropyl-2,3-dihydropyrido[2,3-f][1,4]oxazepin-4(5H)-yl)methyl)-4-methylphenyl)-2,2-dimethylpropanoate (XXVIII-8)

Compound XXVIII-8 was prepared according to Scheme F, step A, replacing compound XIV with XX and compound XXVI-1 with compound XXVI-4-b to afford a beige solid (0.305 g, 100% yield). $^1$H NMR (DMSO-d$_6$) δ: 7.49-7.58 (m, 2H), 7.23 (d, J=9.1 Hz, 1H), 7.07-7.14 (m, 2H), 7.01-7.07 (m, 1H), 6.12-6.34 (m, 1H), 4.75 (s, 1H), 4.17-4.29 (m, 3H), 3.84 (d, J=14.7 Hz, 1H), 3.70 (br d, J=14.7 Hz, 1H), 3.44-3.58 (m, 3H), 3.41 (s, 3H), 2.57-2.69 (m, 5H), 2.20 (s, 3H), 1.18-1.31 (m, 6H), 0.82-0.89 (m, 3H), 0.78 (br d, J=6.6 Hz, 3H), 0.69 (br d, J=6.6 Hz, 3H). LC-MS: rt=0.82 mins (UPLC), m/z=572.5 [M+H]$^+$

Step B: (S)-3-(1,4-dimethyl-1H-benzo[d][1,2,3]triazol-5-yl)-3-(3-(((S)-7-hydroxy-2-isopropyl-2,3-dihydropyrido[2,3-f][1,4]oxazepin-4(5H)-yl)methyl)-4-methylphenyl)-2,2-dimethylpropanoic acid Example 16 was prepared according to Scheme F, step B, replacing compound XXVIII-1 with XXVIII-8 to afford a white solid (0.222 g, 71% yield). $^1$H NMR (DMSO-d$_6$) δ: 11.69-11.90 (m, 2H), 7.59-7.66 (m, 1H), 7.51-7.57 (m, 1H), 7.25 (d, J=9.4 Hz, 1H), 7.14 (dd, J=7.7, 1.6 Hz, 1H), 7.02-7.09 (m, 2H), 6.24 (d, J=9.1 Hz, 1H), 4.77 (s, 1H), 4.18-4.30 (m, 3H), 3.85 (d, J=14.7 Hz, 1H), 3.67 (d, J=15.0 Hz, 1H), 3.43-3.57 (m, 3H), 2.59-2.71 (m, 5H), 2.15-2.27 (m, 3H), 1.30-1.40 (m, 1H), 1.26 (s, 3H), 1.14-1.21 (m, 3H), 0.78 (d, J=6.6 Hz, 3H), 0.69 (d, J=6.8 Hz, 3H). LC-MS: rt=0.77 mins (UPLC), m/z=558.5 [M+H]$^+$

Example 17

(S)-3-(1,4-dimethyl-1H-benzo[d][1,2,3]triazol-5-yl)-3-(3-((7-hydroxy-2,2-dimethyl-2,3-dihydropyrido[2,3-f][1,4]oxazepin-4(5H)-yl)methyl)-4-methylphenyl)-2,2-dimethylpropanoic acid

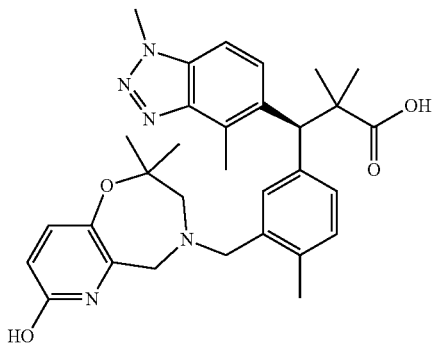

Example 17

Step A: Methyl (S)-3-(1,4-dimethyl-1H-benzo[d][1,2,3]triazol-5yl)-3-(3-((7-hydroxy-2,2-dimethyl-2,3-dihydropyrido[2,3-f][1,4]oxazepin-4(5H)-yl)methyl)-4-methylphenyl)-2,2-dimethylpropanoate (XXVIII-14)

Compound XXVIII-14 was prepared according to Scheme F, step A, replacing compound XIV with XX and compound XXVI-1 with compound XXVI-5 to afford a light orange solid (0.185 g, 96% yield). $^1$H NMR (DMSO-d$_6$) δ: 7.57-7.61 (m, 1H), 7.50-7.55 (m, 1H), 7.18 (s, 1H), 7.11 (d, J=9.1 Hz, 1H), 7.03-7.08 (m, 2H), 6.24 (br. s., 1H), 4.25 (s, 3H), 3.51-3.60 (m, 4H), 3.43 (s, 3H), 3.32 (s, 1H), 2.67 (s, 3H), 2.54 (br. s., 1H), 2.22 (s, 3H), 1.21-1.32 (m, 8H), 1.01 (s, 3H), 0.95 (s, 3H). LC-MS: rt=0.85 mins (UPLC), m/z=558.3 [M+H]$^+$

Step B: (S)-3-(1,4-dimethyl-1H-benzo[d][1,2,3]triazol-5-yl)-3-(3-((7-hydroxy-2,2-dimethyl-2,3-dihydropyrido[2,3-f][1,4]oxazepin-4(5H)-yl)methyl)-4-methylphenyl)-2,2-dimethylpropanoic acid Example 17 was prepared according to Scheme F, step B, replacing compound XXVIII-1 with XXVIII-14 to afford a light orange solid (0.121 g, 65% yield). $^1$H NMR (DMSO-d$_6$) δ: 11.66 (br. s., 2H), 7.64 (d, J=8.9 Hz, 1H), 7.52 (d, J=8.6 Hz, 1H), 7.02-7.19 (m, 4H), 6.23 (d, J=9.1 Hz, 1H), 4.78 (s, 1H), 4.25 (s, 3H), 3.35 (br. s., 4H), 2.65 (s, 3H), 2.53 (s, 1H), 2.22 (s, 3H), 1.16-1.30 (m, 6H), 0.97 (d, J=19.0 Hz, 6H). LC-MS: rt=0.79 mins (UPLC), m/z=544.4 [M+H]$^+$

Example 18

(S)-3-(1,4-dimethyl-1H-benzo[d][1,2,3]triazol-5-yl)-3-(3-(((S)-2-ethyl-7-hydroxy-2,3-dihydropyrido[2,3-f][1,4]oxazepin-4(5H)-yl)methyl)-4-methylphenyl)-2,2-dimethylpropanoic acid

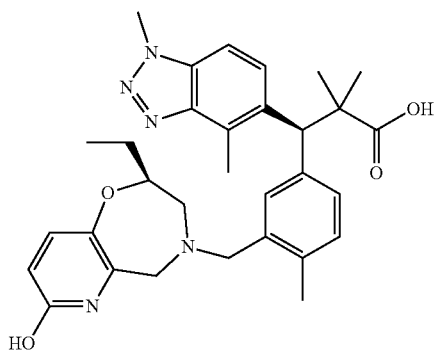

Example 18

Step A: Methyl (S)-3-(1,4-dimethyl-1H-benzo[d][1,2,3]triazol-5-yl)-3-(3-(((S)-2-ethyl-7-hydroxy-2,3-dihydropyrido[2,3-f][1,4]oxazepin-4(5H)-yl)methyl)-4-methylphenyl)-2,2-dimethylpropanoate (XXVIII-15)

Compound XXVIII-15 was prepared according to Scheme F, step A, replacing compound XIV with XX and compound XXVI-1 with compound XXVI-2 to afford a beige solid (0.079 g, 38% yield). $^1$H NMR (DMSO-d$_6$) δ: 7.52-7.67 (m, 2H), 7.27 (d, J=9.1 Hz, 1H), 7.02-7.16 (m, 3H), 6.25 (d, J=8.6 Hz, 1H), 4.76 (s, 1H), 4.25 (s, 3H), 3.89 (d, J=14.7 Hz, 1H), 3.65-3.75 (m, 2H), 3.40-3.60 (m, 5H), 2.69 (s, 3H), 2.54-2.66 (m, 2H), 2.21 (s, 3H), 1.21-1.40 (m, 7H), 0.85 (t, J=7.4 Hz, 3H). LC-MS: rt=0.79 mins (UPLC), m/z=558.5 [M+H]$^+$

Step B: (S)-3-(1,4-dimethyl-1H-benzo[d][1,2,3]triazol-5-yl)-3-(3-(((S)-2-ethyl-7-hydroxy-2,3-dihydropyrido[2,3-f][1,4]oxazepin-4(5H)-yl)methyl)-4-methylphenyl)-2,2-dimethylpropanoic acid Example 18 was prepared according to Scheme F, step B, replacing compound XXVIII-1 with XXVIII-15 to afford a white solid (0.035 g, 36% yield). $^1$H NMR (DMSO-d$_6$) δ: 11.77 (br. s., 2H), 7.52-7.68 (m, 2H), 7.29 (d, J=9.4 Hz, 1H), 7.03-7.16 (m, 3H), 6.26 (d, J=9.4 Hz, 1H), 4.78 (s, 1H), 4.25 (s, 3H), 3.90 (d, J=14.7 Hz, 1H), 3.64-3.75 (m, 2H), 3.45-3.60 (m, 2H), 2.68 (s, 3H), 2.55-2.66 (m, 2H), 2.22 (s, 3H), 1.33 (dd, J=15.0, 7.4 Hz, 1H), 1.18-1.30 (m, 6H), 1.05-1.16 (m, 1H), 0.84 (t, J=7.4 Hz, 3H). LC-MS: rt=0.74 mins (UPLC), m/z=544.4 [M+H]$^+$

Example 19

(S)-3-(1,4-dimethyl-1H-benzo[d][1,2,3]triazol-5-yl)-3-(3-(((S)-7-hydroxy-2-(trifluoromethyl)-2,3-dihydropyrido[2,3-f][1,4]oxazepin-4(5H)-yl)methyl)-4-methylphenyl)-2,2-dimethylpropanoic acid

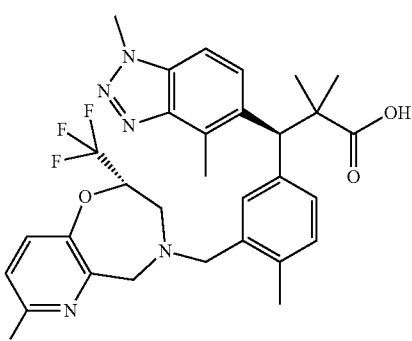

Example 19

Step A: Methyl (S)-3-(1,4-dimethyl-1H-benzo[d][1,2,3]triazol-5-yl)-3-(3-(((S)-7-hydroxy-2-(trifluoromethyl)-2,3-dihydropyrido[2,3-f][1,4]oxazepin-4(5H)-yl)methyl)-4-methylphenyl)-2,2-dimethylpropanoate (XXVIII-17)

Compound XXVIII-17 was prepared according to Scheme F, step A, replacing compound XIV with XX and compound XXVI-1 with compound XXVI-6 to afford a white solid (0.221 g, 66% yield). $^1$H NMR (DMSO-d$_6$) δ: 7.67 (d, J=8.87 Hz, 1H), 7.55 (d, J=8.62 Hz, 1H), 7.38 (d, J=9.38 Hz, 1H), 7.26 (d, J=1.27 Hz, 1H), 7.04-7.15 (m, 2H), 6.34 (br. s., 1H), 4.70-4.82 (m, 2H), 4.25 (s, 3H), 4.07 (d, J=15.21 Hz, 1H), 3.82 (d, J=15.21 Hz, 1H), 3.60 (d, J=3.80 Hz, 2H), 3.40 (s, 3H), 2.95 (d, J=5.58 Hz, 2H), 2.68 (s, 3H), 2.23 (s, 3H), 1.27 (d, J=4.82 Hz, 6H). LC-MS: rt=1.19 mins (UPLC), m/z=598.4 [M+H]$^+$

Step B: (S)-3-(1,4-dimethyl-1H-benzo[d][1,2,3]triazol-5-yl)-3-(3-(((S)-7-hydroxy-2-(trifluoromethyl)-2,3-dihydropyrido[2,3-f][1,4]oxazepin-4(5H)-yl)methyl)-4-methylphenyl)-2,2-dimethylpropanoic acid Example 19 was prepared according to Scheme F, step B, replacing compound XXVIII-1 with XXVIII-17 to afford a white solid (0.091 g, 42% yield). 1H NMR (DMSO-d$_6$) δ: 11.78 (br. s., 2H), 7.73 (d, J=8.62 Hz, 1H), 7.55 (d, J=8.87 Hz, 1H), 7.38 (d, J=9.38 Hz, 1H), 7.25 (s, 1H), 7.10-7.15 (m, 1H), 7.03-7.09 (m, 1H), 6.33 (d, J=9.13 Hz, 1H), 4.74 (s, 2H), 4.25 (s, 3H), 4.06 (d, J=15.21 Hz, 1H), 3.81 (d, J=14.95 Hz, 1H), 3.59 (d, J=4.56 Hz, 2H), 2.92-2.99 (m, 2H), 2.67 (s, 3H), 2.23 (s, 3H), 1.24 (d, J=4.82 Hz, 6H). LC-MS: rt=1.11 mins (UPLC), m/z=584.4 [M+H]$^+$

Example 20

(R)-3-(1,4-dimethyl-1H-benzo[d][1,2,3]triazol-5-yl)-3-(3-(((R)-7-hydroxy-2-(trifluoromethyl)-2,3-dihydropyrido[2,3-f][1,4]oxazepin-4(5H)-yl)methyl)-4-methylphenyl)propanoic acid

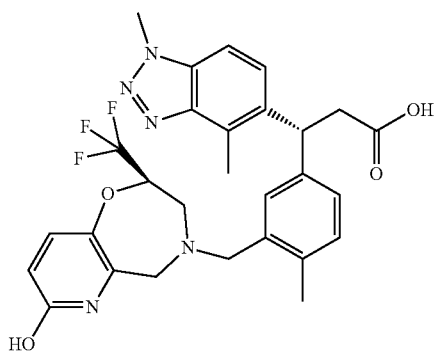

Example 20

Step A: Ethyl (R)-3-(1,4-dimethyl-1H-benzo[d][1,2,3]triazol-5-yl)-3-(3-(((R)-7-hydroxy-2-(trifluoromethyl)-2,3-dihydropyrido[2,3-f][1,4]oxazepin-4(5H)-yl)methyl)-4-methylphenyl)propanoate (XXVIII-20)

Compound XXVIII-20 was prepared according to Scheme F, step A, replacing compound XXVI-1 with XXV1-7 to afford a beige foam (0.600 g, 77% yield). $^1$H NMR (DMSO-d$_6$) δ: 7.42-7.53 (m, 2H), 7.38 (d, J=9.3 Hz, 1H), 7.27 (s, 1H), 7.06 (s, 2H), 6.33 (br. s., 1H), 4.82 (t, J=7.9 Hz, 2H), 4.23 (s, 3H), 4.05-4.12 (m, 1H), 3.91 (q, J=7.1 Hz, 2H), 3.80 (d, J=15.6 Hz, 1H), 3.59 (d, J=5.4 Hz, 2H), 3.14 (d, J=8.1 Hz, 2H), 2.94 (br. s., 2H), 2.76 (s, 3H), 2.22 (s, 3H), 1.18 (t, J=7.1 Hz, 1H), 0.99 (t, J=7.1 Hz, 3H). LC-MS: rt=1.06 mins (UPLC), m/z=584.4 [M+H]$^+$

Step B: (R)-3-(1,4-dimethyl-1H-benzo[d][1,2,3]triazol-5-yl)-3-(3-(((R)-7-hydroxy-2-(trifluoromethyl)-2,3-dihydropyrido[2,3-f][1,4]oxazepin-4(5H)-yl)methyl)-4-methylphenyl)propanoic acid Example 20 was prepared according to Scheme F, step B, replacing compound XXVIII-1 with XXVIII-20 to afford a tan solid (0.420 g, 74% yield). $^1$H NMR (DMSO-d$_6$) δ: 11.70 (br. s., 2H), 7.40-7.53 (m, 2H), 7.38 (d, J=9.3 Hz, 1H), 7.26 (s, 1H), 7.06 (s, 2H), 6.33 (d, J=9.3 Hz, 1H), 4.73-4.90 (m, 2H), 4.23 (s, 3H), 4.04-4.11 (m, 1H), 3.80 (d, J=15.2 Hz, 1H), 3.53-3.65 (m, 2H), 3.01-3.07 (m, 2H), 2.96 (d, J=5.9 Hz, 2H), 2.75 (s, 3H), 2.22 (s, 3H). LC-MS: rt=0.92 mins (UPLC), m/z=556.4 [M+H]$^+$

Example 21

(S)-3-(1,4-dimethyl-1H-benzo[d][1,2,3]triazol-5-yl)-3-(3-(((R)-7-hydroxy-2-(trifluoromethyl)-2,3-dihydropyrido[2,3-f][1,4]oxazepin-4(5H)-yl)methyl)-4-methylphenyl)-2,2-dimethylpropanoic acid

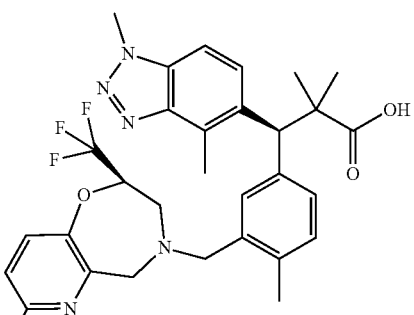

Example 21

Step A: Methyl (S)-3-(1,4-dimethyl-1H-benzo[d][1,2,3]triazol-5-yl)-3-(3-(((R)-7-hydroxy-2-(trifluoromethyl)-2,3-dihydropyrido[2,3-f][1,4]oxazepin-4(5H)-yl)methyl)-4-methylphenyl)-2,2-dimethylpropanoate (XXVIII-21)

Compound XXVIII-21 was prepared according to Scheme F, step A, replacing compound XIV with XX and compound XXVI-1 with compound XXVI-7 to afford a beige foam (0.270 g, 86% yield). LC-MS: rt=1.09 mins (UPLC), m/z=598.4 [M+H]$^+$

Step B: (S)-3-(1,4-dimethyl-1H-benzo[d][1,2,3]triazol-5-yl)-3-(3-(((R)-7-hydroxy-2-(trifluoromethyl)-2,3-dihydropyrido[2,3-f][1,4]oxazepin-4(5H)-yl)methyl)-4-methylphenyl)-2,2-dimethylpropanoic acid Example 21 was prepared according to Scheme F, step B, replacing compound XXVIII-1 with XXVIII-21 to afford a colorless solid (0.235 g, 89% yield). $^1$H NMR (DMSO-d$_6$) δ: 11.69-11.90 (m, 2H), 7.74-7.78 (m, 1H), 7.54-7.59 (m, 1H), 7.36-7.41 (m, 1H), 7.21-7.30 (m, 2H), 7.09-7.16 (m, 1H), 7.01-7.08 (m, 1H), 6.32 (d, J=9.3 Hz, 1H), 4.78-4.87 (m, 1H), 4.71-4.76 (m, 1H), 4.24 (s, 3H), 4.03-4.14 (m, 1H), 3.79 (d, J=14.7 Hz, 1H), 3.53-3.61 (m, 2H), 2.95 (br d, J=5.9 Hz, 2H), 2.63 (s, 3H), 2.22 (s, 3H), 1.23 (d, J=16.1 Hz, 6H). LC-MS: rt=1.12 mins (UPLC), m/z=584.4 [M+H]$^+$

Example 22

(R)-3-(1,4-dimethyl-1H-benzo[d][1,2,3]triazol-5-yl)-3-(3-(((R)-2-ethyl-8-fluoro-7-hydroxy-2,3-dihydropyrido[2,3-f][1,4]oxazepin-4(5H)-yl)methyl)-4-methylphenyl)propanoic acid Example 22

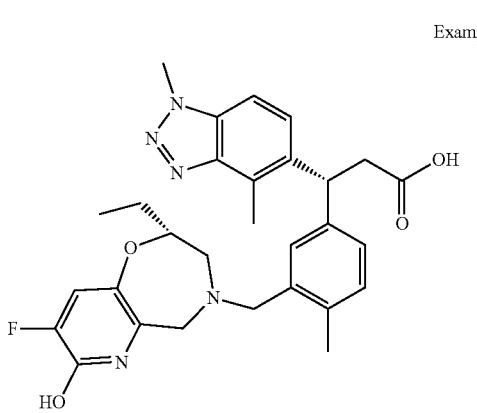

Step A: Ethyl (R)-3-(1,4-dimethyl-1H-benzo[d][1,2,3]triazol-5-yl)-3-(3-(((R)-2-ethyl-8-fluoro-7-hydroxy-2,3-dihydropyrido[2,3-f][1,4]oxazepin-4(5H)-yl)methyl)-4-methylphenyl)propanoate (XXVIII-22)

Compound XXVIII-22 was prepared according to Scheme F, step A, replacing compound XXVI-1 with XXVI-8 to afford a light yellow solid (0.157 g, 81% yield). $^1$H NMR (DMSO-$d_6$) δ: 12.02 (br. s., 1H), 7.42-7.56 (m, 3H), 7.34 (d, J=11.2 Hz, 1H), 7.04-7.14 (m, 3H), 4.82 (t, J=7.9 Hz, 1H), 4.23 (s, 3H), 3.92 (q, J=7.1 Hz, 2H), 3.64-3.88 (m, 3H), 3.45-3.56 (m, 2H), 3.13 (dd, J=8.1, 2.4 Hz, 2H), 2.74 (s, 3H), 2.61 (br. s., 2H), 2.20 (s, 4H), 1.24-1.40 (m, 1H), 1.00 (t, J=7.1 Hz, 3H), 0.77 (t, J=7.1 Hz, 3H). LC-MS: rt=0.78 mins (UPLC), m/z=562.4 [M+H]$^+$

Step B: (R)-3-(1,4-dimethyl-1H-benzo[d][1,2,3]triazol-5-yl)-3-(3-(((R)-2-ethyl-8-fluoro-7-hydroxy-2,3-dihydropyrido[2,3-f][1,4]oxazepin-4(5H)-yl)methyl)-4-methylphenyl)propanoic acid Example 22 was prepared according to Scheme F, step B, replacing compound XXVIII-1 with XXVIII-22 to afford a light yellow solid (0.114 g, 76% yield). $^1$H NMR (DMSO-$d_6$) δ: 12.00 (br. s., 2H), 7.54 (d, J=8.8 Hz, 1H), 7.42 (d, J=8.6 Hz, 1H), 7.34 (d, J=11.2 Hz, 1H), 7.03-7.14 (m, 3H), 4.80 (t, J=7.8 Hz, 1H), 4.23 (s, 3H), 3.65-3.92 (m, 3H), 3.44-3.56 (m, 2H), 2.95-3.11 (m, 2H), 2.74 (s, 3H), 2.53-2.69 (m, 2H), 2.21 (s, 3H), 1.22-1.38 (m, 1H), 0.98-1.13 (m, 1H), 0.77 (t, J=7.2 Hz, 3H). LC-MS: rt=0.65 mins (UPLC), m/z=534.3 [M+H]$^+$

Example 23

(S)-3-(1,4-dimethyl-1H-benzo[d][1,2,3]triazol-5-yl)-3-(3-(((S)-7-hydroxy-2-methyl-2,3-dihydropyrido[2,3-f][1,4]oxazepin-4(5H)-yl)methyl)-4-methylphenyl)-2,2-dimethylpropanoic acid Example 23

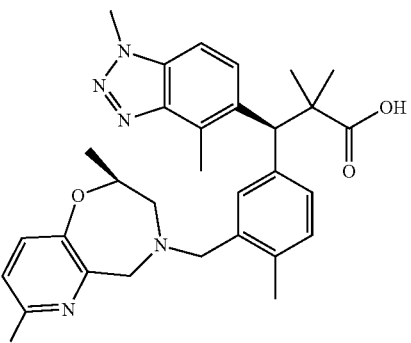

Step A: Methyl (S)-3-(1,4-dimethyl-1H-benzo[d][1,2,3]triazol-5-yl)-3-(3-(((S)-7-hydroxy-2-methyl-2,3-dihydropyrido[2,3-f][1,4]oxazepin-4(5H)-yl)methyl)-4-methylphenyl)-2,2-dimethylpropanoate (XXVIII-23)

Compound XXVIII-23 was prepared according to Scheme F, step A, replacing compound XIV with XX and compound XXVI-1 with compound XXVI-9 to afford a colorless oil (0.330 g, 100% yield). $^1$H NMR (DMSO-$d_6$) δ: 7.52-7.65 (m, 2H), 7.27 (d, J=9.3 Hz, 1H), 7.17 (s, 1H), 7.01-7.10 (m, 2H), 6.24 (br. s., 1H), 4.75 (s, 1H), 4.24 (s, 3H), 4.03 (q, J=7.1 Hz, 2H), 3.89 (d, J=14.4 Hz, 1H), 3.70 (d, J=14.7 Hz, 1H), 3.46-3.59 (m, 2H), 3.41 (s, 3H), 2.68 (s, 3H), 2.57-2.66 (m, 2H), 2.20 (s, 3H), 1.21-1.32 (m, 6H), 0.99-1.09 (m, 3H). LC-MS: rt=0.74 mins (UPLC), m/z=544.4 [M+H]$^+$

Step B: (S)-3-(1,4-dimethyl-1H-benzo[d][1,2,3]triazol-5-yl)-3-(3-(((S)-7-hydroxy-2-methyl-2,3-dihydropyrido[2,3-f][1,4]oxazepin-4(5H)-yl)methyl)-4-methylphenyl)propanoic acid Example 23 was prepared according to Scheme F, step B, replacing compound XXVIII-1 with XXVIII-23 to afford a colorless solid (0.230 g, 72% yield). $^1$H NMR (DMSO-$d_6$) δ: 11.78 (br s, 2H), 7.68 (d, J=8.8 Hz, 1H), 7.56 (d, J=8.8 Hz, 1H), 7.29 (d, J=9.3 Hz, 1H), 7.14 (s, 1H), 7.00-7.11 (m, 2H), 6.25 (d, J=9.3 Hz, 1H), 4.77 (s, 1H), 4.25 (s, 3H), 3.97-4.10 (m, 1H), 3.90 (d, J=14.7 Hz, 1H), 3.67 (d, J=15.2 Hz, 1H), 3.46-3.58 (m, 2H), 2.55-2.73 (m, 5H), 2.21 (s, 3H), 1.28 (s, 3H), 1.20 (s, 3H), 1.03 (d, J=6.4 Hz, 3H). LC-MS: rt=0.68 mins (UPLC), m/z=530.5 [M+H]$^+$

Example 24

(S)-3-(1,4-dimethyl-1H-benzo[d][1,2,3]triazol-5-yl)-3-(3-((7-hydroxy-2,3-dihydropyrido[2,3-f][1,4]oxazepin-4(5H)-yl)methyl)-4-methylphenyl)-2,2-dimethylpropanoic acid

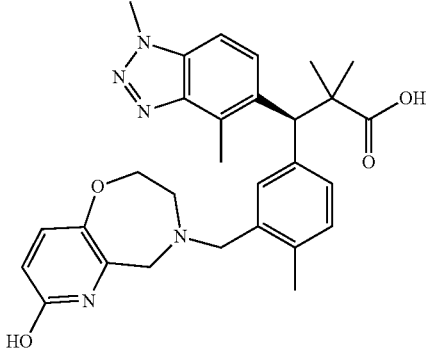

Example 24

Step A: Methyl (S)-3-(1,4-dimethyl-1H-benzo[d][1,2,3]triazol-5-yl)-3-(3-(((S)-7-hydroxy-2,3-dihydropyrido[2,3-f][1,4]oxazepin-4(5H)-yl)methyl)-4-methylphenyl)-2,2-dimethylpropanonate (XXVIII-24)

Compound XXVIII-24 was prepared according to Scheme F, step A, replacing compound XIV with XX and compound XXVI-1 with compound XXVI-10 to afford a light yellow solid (0.128 g, 98% yield). $^1$H NMR (DMSO-d$_6$) δ: 7.53-7.66 (m, 2H), 7.28 (d, J=9.0 Hz, 1H), 7.21 (s, 1H), 7.00-7.08 (m, 2H), 6.26 (br. s., 1H), 4.75 (s, 1H), 4.25 (s, 3H), 3.88-3.96 (m, 2H), 3.80 (s, 2H), 3.48-3.61 (m, 2H), 3.41 (s, 3H), 3.34 (s, 3H), 2.79 (br. s., 2H), 2.68 (s, 3H), 2.20 (s, 3H), 1.21-1.30 (m, 6H). LC-MS: rt=0.69 mins (UPLC), m/z=530.4 [M+H]$^+$

Step B: (S)-3-(1,4-dimethyl-1H-benzo[d][1,2,3]triazol-5-yl)-3-(3-(((S)-7-hydroxy-2,3-dihydropyrido[2,3-f][1,4]oxazepin-4(5H)-yl)methyl)-4-methylphenyl)-2,2-dimethylpropanoic acid Example 24 was prepared according to Scheme F, step B, replacing compound XXVIII-1 with XXVIII-24 to afford a white solid (0.071 g, 64% yield). $^1$H NMR (DMSO-d$_6$) δ: 11.78 (br. s, 2H), 7.69 (d, J=8.80 Hz, 1H), 7.57 (d, J=8.80 Hz, 1H), 7.30 (d, J=9.29 Hz, 1H), 7.19 (s, 1H), 7.01-7.09 (m, 2H), 6.27 (d, J=9.29 Hz, 1H), 4.77 (s, 1H), 4.25 (s, 3H), 3.89-3.93 (m, 2H), 3.79 (q, J=14.80 Hz, 2H), 3.54 (q, J=13.5 Hz, 2H), 2.79-2.84 (m, 2H), 2.67 (s, 3H), 2.21 (s, 3H), 1.26 (s, 3H), 1.20 (s, 3H). LC-MS: rt=0.64 mins (UPLC), m/z=516.3 [M+H]$^+$

Example 25

(S)-3-(1,4-dimethyl-1H-benzo[d][1,2,3]triazol-5-yl)-3-(3-(((S)-7-hydroxy-2-(trifluoromethyl)-2,3-dihydropyrido[2,3-f][1,4]oxazepin-4(5H)-yl)methyl)-4-methylphenyl)propanoic acid

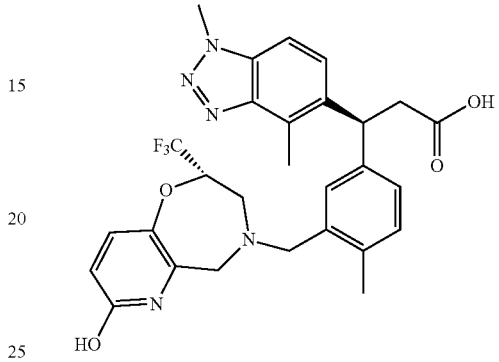

Example 25

Step A: Methyl (S)-3-(1,4-dimethyl-1H-benzo[d][1,2,3]triazol-5-yl)-3-(3-(((S)-7-hydroxy-2-(trifluoromethyl)-2,3-dihydropyrido[2,3-f][1,4]oxazepin-4(5H)-yl)methyl)-4-methylphenyl)propanoate (XXVIII-25)

Compound XXVIII-25 was prepared according to Scheme F, step A, replacing compound XIV with XVIII, and compound XXVI-1 with XXVI-6 to afford an off-white solid (0.248 g, 98% yield). $^1$H NMR (DMSO-d$_6$) δ: 7.47-7.54 (m, 1H), 7.36-7.46 (m, 2H), 7.27 (s, 1H), 7.03-7.11 (m, 2H), 6.33 (br. s., 1H), 4.78-4.89 (m, 3H), 4.23 (s, 3H), 4.08 (d, J=14.9 Hz, 1H), 3.80 (d, J=15.2 Hz, 1H), 3.53-3.66 (m, 2H), 3.46 (s, 3H), 3.16 (d, J=7.8 Hz, 2H), 2.95 (d, J=5.6 Hz, 2H), 2.76 (s, 3H), 2.22 (s, 3H). LC-MS: rt=1.00 mins (UPLC), m/z=570.3 [M+H]$^+$

Step B: (S)-3-(1,4-dimethyl-1H-benzo[d][1,2,3]triazol-5-yl)-3-(3-(((S)-7-hydroxy-2-(trifluoromethyl)-2,3-dihydropyrido[2,3-f][1,4]oxazepin-4(5H)-yl)methyl)-4-methylphenyl)propanoic acid Example 25 was prepared according to Scheme F, step B, replacing compound XXVIII-1 with XXVIII-25 to afford a white solid (0.092 g, 38% yield). $^1$H NMR (DMSO-d$_6$) δ: 11.88 (br. s., 1H), 7.46-7.53 (m, 1H), 7.35-7.44 (m, 2H), 7.27 (s, 1H), 7.01-7.10 (m, 2H), 6.32 (d, J=9.3 Hz, 1H), 4.72-4.92 (m, 2H), 4.23 (s, 3H), 3.99-4.09 (m, 1H), 3.78 (d, J=15.2 Hz, 1H), 3.52-3.65 (m, 2H), 2.91-3.13 (m, 4H), 2.75 (s, 3H), 2.22 (s, 3H). LC-MS: rt=0.90 mins (UPLC), m/z=556.3 [M+H]$^+$

Example 26

(R)-3-(1,4-dimethyl-1H-benzo[d][1,2,3]triazol-5-yl)-3-(3-(((R)-2-ethyl-7-hydroxy-2-methyl-2,3-dihydropyrido[2,3-f][1,4]oxazepin-4(5H)-yl)methyl)-4-methylphenyl)propanonic acid

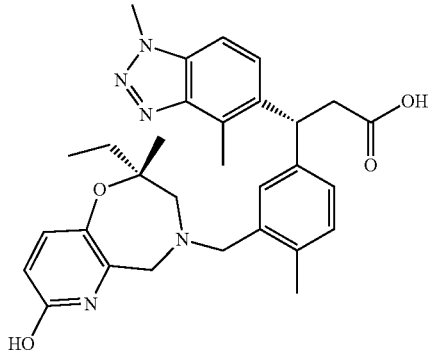

Example 26

Step A: Ethyl (R)-3-(1,4-dimethyl-1H-benzo[d][1,2,3]triazol-5-yl)-3-(3-(((R)-2-ethyl-7-hydroxy-2-methyl-2,3-dihydropyrido[2,3-f][1,4]oxazepin-4(5H)-yl)methyl)-4-methylphenyl)propanoate (XXVIII-26)

Compound XXVIII-26 was prepared according to Scheme F, step A, replacing compound XXVI-1 with XXVI-11-a to afford a light beige solid (0.177 g, 77% yield). $^1$H NMR (DMSO-$d_6$) δ: 10.61-11.63 (m, 1H), 7.47-7.56 (m, 1H), 7.37-7.46 (m, 1H), 6.98-7.18 (m, 4H), 6.23 (br. s., 1H), 4.83 (t, J=7.9 Hz, 1H), 4.23 (s, 3H), 3.93 (q, J=7.1 Hz, 2H), 3.45-3.58 (m, 4H), 3.06-3.23 (m, 2H), 2.70 (s, 3H), 2.41-2.49 (m, 1H), 2.21 (s, 3H), 1.22-1.38 (m, 1H), 1.09-1.21 (m, 1H), 1.02 (t, J=7.1 Hz, 3H), 0.86 (s, 3H), 0.53 (t, J=7.3 Hz, 3H). LC-MS: rt=0.84 mins (UPLC), m/z=558.4 [M+H]$^+$

Step B: (R)-3-(1,4-dimethyl-1H-benzo[d][1,2,3]triazol-5-yl)-3-(3-(((R)-2-ethyl-7-hydroxy-2-methyl-2,3-dihydropyrido[2,3-f][1,4]oxazepin-4(5H)-yl)methyl)-4-methylphenyl)propanonic acid Example 26 was prepared according to Scheme F, step B, replacing compound XXVIII-1 with XXVIII-26 to afford a light yellow solid (0.072 g, 46% yield). $^1$H NMR (DMSO-$d_6$) δ: 11.60 (br. s., 2H), 7.36-7.54 (m, 2H), 7.04-7.15 (m, 4H), 6.22 (d, J=9.0 Hz, 1H), 4.80 (t, J=7.9 Hz, 1H), 4.23 (s, 3H), 3.46-3.58 (m, 4H), 2.96-3.13 (m, 2H), 2.70 (s, 3H), 2.40-2.49 (m, 1H), 2.21 (s, 3H), 1.09-1.37 (m, 2H), 0.81-0.89 (m, 4H), 0.52 (t, J=7.5 Hz, 3H). LC-MS: rt=0.70 mins (UPLC), m/z=530.4 [M+H]$^+$

Example 27

(R)-3-(1,4-dimethyl-1H-benzo[d][1,2,3]triazol-5-yl)-3-(3-(((S)-2-ethyl-7-hydroxy-2-methyl-2,3-dihydropyrido[2,3-f][1,4]oxazepin-4(5H)-yl)methyl)-4-methylphenyl)propanonic acid

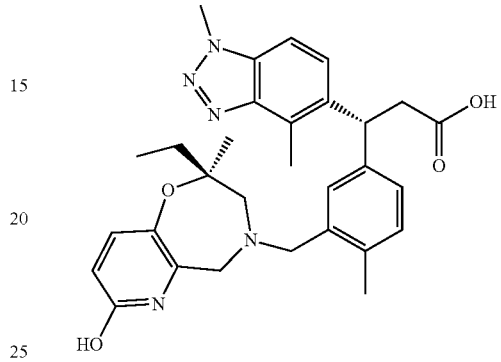

Example 27

Step A: Ethyl (R)-3-(1,4-dimethyl-1H-benzo[d][1,2,3]triazol-5-yl)-3-(3-(((S)-2-ethyl-7-hydroxy-2-methyl-2,3-dihydropyrido[2,3-f][1,4]oxazepin-4(5H)-yl)methyl)-4-methylphenyl)propanoate (XXVIII-27)

Compound XXVIII-27 was prepared according to Scheme F, step A, replacing compound XXVI-1 with XXVI-11-b to afford a light beige solid (0.161 g, 77% yield). $^1$H NMR (DMSO-$d_6$) δ: 7.40-7.55 (m, 2H), 7.02-7.15 (m, 4H), 6.23 (br. s., 1H), 4.82 (t, J=7.9 Hz, 1H), 4.23 (s, 3H), 3.93 (q, J=7.1 Hz, 2H), 3.44-3.59 (m, 4H), 3.06-3.23 (m, 2H), 2.70 (s, 3H), 2.46 (s, 1H), 2.21 (s, 3H), 1.31-1.43 (m, 1H), 1.12-1.25 (m, 1H), 1.02 (t, J=7.1 Hz, 3H), 0.83 (s, 3H), 0.53 (t, J=7.3 Hz, 3H). LC-MS: rt=0.84 mins (UPLC), m/z=558.4 [M+H]$^+$

Step B: (R)-3-(1,4-dimethyl-1H-benzo[d][1,2,3]triazol-5-yl)-3-(3-(((S)-2-ethyl-7-hydroxy-2-methyl-2,3-dihydropyrido[2,3-f][1,4]oxazepin-4(5H)-yl)methyl)-4-methylphenyl)propanonic acid Example 27 was prepared according to Scheme F, step B, replacing compound XXVIII-1 with XXVIII-27 to afford a beige solid (0.067 g, 46% yield). 1H NMR (DMSO-$d_6$) δ: 11.58 (br. s., 2H), 7.38-7.56 (m, 2H), 7.03-7.16 (m, 4H), 6.22 (d, J=9.0 Hz, 1H), 4.80 (t, J=7.7 Hz, 1H), 4.23 (s, 3H), 3.46-3.58 (m, 4H), 2.97-3.13 (m, 2H), 2.69 (s, 3H), 2.46 (s, 1H), 2.21 (s, 3H), 1.11-1.42 (m, 2H), 0.77-0.90 (m, 4H), 0.53 (t, J=7.5 Hz, 3H). LC-MS: rt=0.70 mins (UPLC), m/z=530.4 [M+H]$^+$

Example 28

(S)-3-(1,4-dimethyl-1H-benzo[d][1,2,3]triazol-5-yl)-3-(3-(((R)-7-hydroxy-2-(trifluoromethyl)-2,3-dihydropyrido[2,3-f][1,4]oxazepin-4(5H)-yl)methyl)-4-methylphenyl)propanoic acid

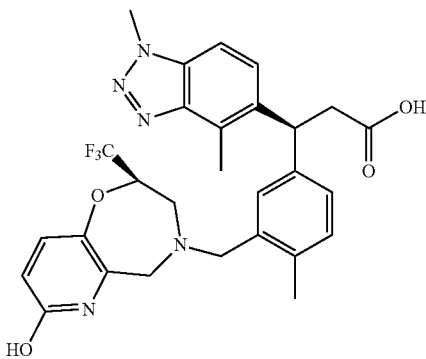

Example 28

Step A: Methyl (S)-3-(1,4-dimethyl-1H-benzo[d][1,2,3]triazol-5-yl)-3-(3-(((S)-7-hydroxy-2-(trifluoromethyl)-2,3-dihydropyrido[2,3-f][1,4]oxazepin-4(5H)-yl)methyl)-4-methylphenyl)propanoate (XXVIII-28)

Compound XXVIII-28 was prepared according to Scheme F, step A, replacing compound XIV with XVIII, and compound XXVI-1 with XXV1-7 to afford an off-white solid (0.228 g, 90% yield). $^1$H NMR (DMSO-$d_6$) δ: 11.37 (br. s., 1H), 7.47-7.59 (m, 2H), 7.38 (d, J=9.3 Hz, 1H), 7.28 (d, J=1.2 Hz, 1H), 7.02-7.15 (m, 2H), 6.33 (br. s., 1H), 4.75-4.88 (m, 2H), 4.23 (s, 3H), 4.03-4.12 (m, 1H), 3.78 (d, J=15.2 Hz, 1H), 3.51-3.66 (m, 2H), 3.46 (s, 3H), 3.06-3.26 (m, 2H), 2.94 (br. s., 2H), 2.69-2.80 (m, 3H), 2.22 (s, 3H). LC-MS: rt=1.00 mins (UPLC), m/z=570.3 [M+H]$^+$ Step B: (S)-3-(1,4-dimethyl-1H-benzo[d][1,2,3]triazol-5-yl)-3-(3-(((R)-7-hydroxy-2-(trifluoromethyl)-2,3-dihydropyrido[2,3-f][1,4]oxazepin-4(5H)-yl)methyl)-4-methylphenyl)propanoic acid Example 28 was prepared according to Scheme F, step B, replacing compound XXVIII-1 with XXVIII-28 to afford a white solid (0.051 g, 28% yield). $^1$H NMR (DMSO-$d_6$) δ: 11.71 (br. s., 2H), 7.53 (q, J=8.7 Hz, 2H), 7.38 (d, J=9.3 Hz, 1H), 7.26 (s, 1H), 7.02-7.12 (m, 2H), 6.32 (d, J=9.3 Hz, 1H), 4.75-4.89 (m, 2H), 4.23 (s, 3H), 3.73-4.10 (m, 2H), 3.58 (d, J=5.4 Hz, 2H), 2.89-3.15 (m, 4H), 2.73 (s, 3H), 2.22 (s, 3H). LC-MS: rt=0.74 mins (UPLC), m/z=556.3 [M+H]$^+$

Example 29

(R)-3-(1,4-dimethyl-1H-benzo[d][1,2,3]triazol-5-yl)-3-(3-((7'-hydroxy-3'H-spiro[cyclobutane-1,2'-pyrido[2,3-f][1,4]oxazepin-4'(5'H)-yl)methyl)-4-methylphenyl)propanonic acid

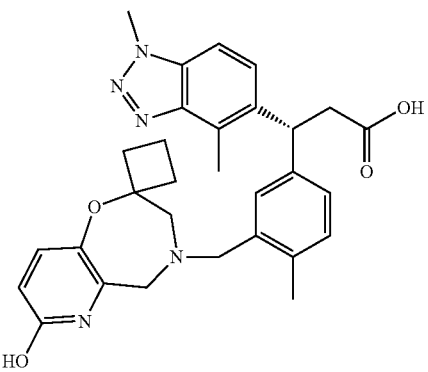

Example 29

Step A: Ethyl (R)-3-(1,4-dimethyl-1H-benzo[d][1,2,3]triazol-5-yl)-3-(3-((7'-hydroxy-3'H-spiro[cyclobutane-1,2'-pyrido[2,3-f][1,4]oxazepin-4'(5'H)-yl)methyl)-4-methylphenyl)propanoate (XXVIII-29)

Compound XXVIII-29 was prepared according to Scheme F, step A, replacing compound XXVI-1 with XXV1-12 to afford a light beige solid (0.117 g, 47% yield). $^1$H NMR (DMSO-$d_6$) δ: 11.20 (br. s., 1H), 8.14 (s, 1H), 7.42-7.57 (m, 2H), 7.23 (d, J=9.0 Hz, 1H), 7.16 (s, 1H), 7.03-7.14 (m, 2H), 6.24 (d, J=9.0 Hz, 1H), 4.84 (t, J=7.9 Hz, 1H), 4.23 (s, 3H), 3.93 (q, J=7.1 Hz, 2H), 3.57 (s, 2H), 3.34 (s, 2H), 3.07-3.22 (m, 2H), 2.71 (s, 3H), 2.65 (s, 2H), 2.21 (s, 3H), 1.71-1.86 (m, 2H), 1.46-1.67 (m, 3H), 1.02 (t, J=7.1 Hz, 3H). LC-MS: rt=0.80 mins (UPLC), m/z=556.4 [M+H]$^+$ Step B: (R)-3-(1,4-dimethyl-1H-benzo[d][1,2,3]triazol-5-yl)-3-(3-((7'-hydroxy-3'H-spiro[cyclobutane-1,2'-pyrido[2,3-f][1,4]oxazepin-4'(5'H)-yl)methyl)-4-methylphenyl)propanonic acid Example 29 was prepared according to Scheme F, step B, replacing compound XXVIII-1 with XXVIII-29 to afford a light yellow solid (0.028 g, 24% yield). $^1$H NMR (DMSO-$d_6$) δ: 11.52 (br. s., 1H), 7.41-7.55 (m, 2H), 7.23 (d, J=9.3 Hz, 1H), 7.16 (s, 1H), 7.04-7.14 (m, 2H), 6.24 (d, J=9.3 Hz, 1H), 4.82 (t, J=7.8 Hz, 1H), 4.22 (s, 3H), 3.55 (d, J=12.5 Hz, 4H), 2.96-3.13 (m, 2H), 2.71 (s, 3H), 2.66 (s, 2H), 2.21 (s, 3H), 1.71-1.86 (m, 2H), 1.45-1.68 (m, 3H), 0.95-1.11 (m, 1H). LC-MS: rt=0.66 mins (UPLC), m/z=528.4 [M+H]$^+$

Example 30

(R)-3-(3-(((R)-2-(tert-butyl)-7-hydroxy-2,3-dihydropyrido[2,3-f][1,4]oxazepin-4(5H)-yl)methyl)-4-methylphenyl)-3-(1,4-dimethyl-1H-benzo[d][1,2,3]triazol-5-yl)propanoic acid

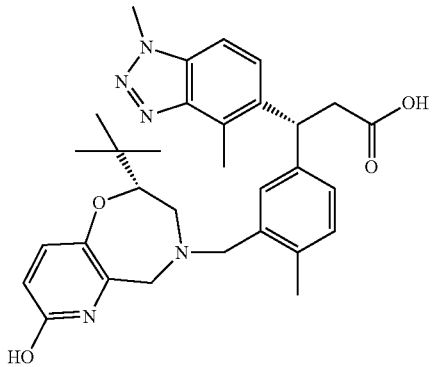

Example 30

Step A: Ethyl (R)-3-(3-((R)-2-(tert-butyl)-7-hydroxy-2,3-dihydropyrido[2,3-f][1,4]oxazepin-4(5H)-yl)methyl)-4-methylphenyl)-3-(1,4-dimethyl-1H-benzo[d][1,2,3]triazol-5-yl)propanoate (XXVIII-30)

Compound XXVIII-30 was prepared according to Scheme F, step A, replacing compound XXVI-1 with XXV1-13 to afford a beige solid (0.155 g, 83% yield). $^1$H NMR (DMSO-$d_6$) δ: 11.26 (br. s., 1H), 7.43-7.58 (m, 2H), 7.24 (d, J=9.3 Hz, 1H), 7.02-7.15 (m, 3H), 6.23 (d, J=8.3 Hz, 1H), 4.81 (t, J=8.1 Hz, 1H), 4.23 (s, 3H), 3.81-3.97 (m, 3H), 3.67-3.78 (m, 1H), 3.52 (s, 2H), 3.42 (d, J=9.5 Hz, 1H), 3.12 (d, J=8.1 Hz, 2H), 2.80 (d, J=13.9 Hz, 1H), 2.72 (s, 3H), 2.63 (dd, J=13.8, 10.1 Hz, 1H), 2.22 (s, 3H), 1.00 (t, J=7.1 Hz, 3H), 0.74 (s, 9H). LC-MS: rt=0.84 mins (UPLC), m/z=572.4 [M+H]$^+$

Step B: (R)-3-(3-((R)-2-(tert-butyl)-7-hydroxy-2,3-dihydropyrido[2,3-f][1,4]oxazepin-4(5H)-yl)methyl)-4-methylphenyl)-3-(1,4-dimethyl-1H-benzo[d][1,2,3]triazol-5-yl)propanoic acid Example 30 was prepared according to Scheme F, step B, replacing compound XXVIII-1 with XXVIII-30 to afford a white solid (0.105 g, 95% yield). $^1$H NMR (DMSO-$d_6$) δ: 11.66 (br. s., 2H), 7.57-7.42 (m, 2H), 7.24 (d, J=9.3 Hz, 1H), 7.13-7.03 (m, 3H), 6.24 (d, J=9.3 Hz, 1H), 4.79 (t, J=7.8 Hz, 1H), 4.23 (s, 3H), 3.91-3.68 (m, 2H), 3.51 (s, 2H), 3.42 (d, J=9.8 Hz, 1H), 3.01 (d, J=7.8 Hz, 2H), 2.81 (d, J=13.7 Hz, 1H), 2.71 (s, 3H), 2.63 (dd, J=10.3, 13.7 Hz, 1H), 2.22 (s, 3H), 0.74 (s, 9H). LC-MS: rt=0.74 mins (UPLC), m/z=544.2 [M+H]$^+$

Example 31

Crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid

Step A: Ethyl (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoate, amorphous Compound XXVIII-31, ethyl ester, was prepared according to Example 1, step A, to afford a beige solid (143.8 g, 65% yield). $^1$H NMR (DMSO-$d_6$) δ: 10.9-11.7 (m, 1H), 7.5-7.6 (m, 1H), 7.45 (d, 1H, J=8.6 Hz), 7.25 (d, 1H, J=9.4 Hz), 7.0-7.2 (m, 3H), 6.2-6.3 (m, 1H), 4.82 (t, 1H, J=8.0 Hz), 4.23 (s, 3H), 3.8-4.0 (m, 3H), 3.6-3.8 (m, 2H), 3.4-3.6 (m, 2H), 3.14 (dd, 2H, J=4.1, 7.9 Hz), 2.74 (s, 3H), 2.62 (br d, 2H, J=10.9 Hz), 2.20 (s, 3H), 1.3-1.4 (m, 1H), 1.0-1.2 (m, 1H), 1.01 (t, 3H, J=7.1 Hz), 0.79 (t, 3H, J=7.4 Hz). LCMS: rt=0.75 mins (UPLC), m/z=544.5 [M+H]$^+$

Step B: (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, amorphous Compound XXVIII-31, free acid, was prepared according to Example 1, step B, to afford a beige solid (122.9 g, 90% yield). $^1$H NMR (DMSO-$d_6$) δ: 11.5-11.9 (m, 2H), 7.54 (d, 1H, J=8.8 Hz), 7.43 (d, 1H, J=8.8 Hz), 7.26 (d, 1H, J=8.8 Hz), 7.0-7.1 (m, 3H), 6.24 (d, 1H, J=9.3 Hz), 4.80 (t, 1H, J=7.8 Hz), 4.23 (s, 3H), 3.87 (d, 1H, J=14.7 Hz), 3.6-3.7 (m, 2H), 3.4-3.6 (m, 2H), 3.03 (dd, 2H, J=7.8, 12.2 Hz), 2.74 (s, 3H), 2.5-2.7 (m, 2H), 2.21 (s, 3H), 1.33 (dd, 1H, J=7.1, 15.4 Hz), 1.0-1.1 (m, 1H), 0.79 (t, 3H, J=7.3 Hz). LCMS: rt=0.63 mins (UPLC), m/z=516.5 [M+H]$^+$

Step C: (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid, crystalline A mixture of XXVIII-31, free acid, amorphous (3.02 g, 5.58 mmol) and acetonitrile (30 mL) was heated at 50° C. for 20 min and then cooled to 25° C. over 4 h. The solid was collected by filtration, rinsed with acetonitrile (3×10 mL) and dried in a vacuum oven at 50° C. overnight to afford Example 31 as a crystalline white solid (2.55 g, 84% yield). $^1$H NMR (METHANOL-$d_4$) δ: 7.5-7.5 (m, 2H), 7.43 (d, 1H, J=9.8 Hz), 7.1-7.1 (m, 3H), 6.41 (d, 1H, J=9.8 Hz), 4.93 (s, 1H), 4.29 (s, 3H), 3.90 (d, 1H, J=15.2 Hz), 3.7-3.8 (m, 1H), 3.6-3.7 (m, 3H), 3.0-3.2 (m, 2H), 2.87 (s, 1H), 2.76 (s, 4H), 2.29 (s, 3H), 1.4-1.5 (m, 1H), 1.25 (s, 1H), 0.91 (t, 3H, J=7.6 Hz). LCMS: rt=0.64 mins (UPLC), m/z=516.4 [M+H]$^+$ The XRPD of this material is shown in FIG. 1 and the corresponding diffraction data is provided in Table 3.

Powder x-ray diffractograms for Examples 31 through 34 were acquired on a PANalytical X'Pert Pro diffractometer using Ni-filtered Cu Kα (45 kV/40 mA, 1.5406 Å wavelength) radiation and a step size of 0.03° 2θ with an X'celerator™ RTMS (Real Time Multi-Strip) detector. Configuration on the incident beam side: variable divergence slits (10 mm irradiated length), 0.04 rad Soller slits, fixed anti-scatter slit (0.50°), and 10 mm beam mask. Configuration on the diffracted beam side: variable anti-scatter slit (10 mm observed length) and 0.04 rad Soller slit. Samples were mounted flat on zero-background Si wafers.

TABLE 3

| Diffraction Angle (°2θ) | d-Spacing (Å) |
| --- | --- |
| 6.69 | 13.20 |
| 7.54 | 11.72 |
| 12.38 | 7.14 |
| 12.90 | 6.86 |
| 13.55 | 6.53 |
| 13.99 | 6.33 |
| 16.40 | 5.40 |
| 17.49 | 5.07 |
| 17.82 | 4.97 |
| 18.30 | 4.84 |
| 19.35 | 4.58 |
| 19.96 | 4.44 |
| 20.98 | 4.23 |
| 22.74 | 3.91 |
| 25.90 | 3.44 |
| 26.79 | 3.33 |
| 27.36 | 3.26 |

Figure 2:
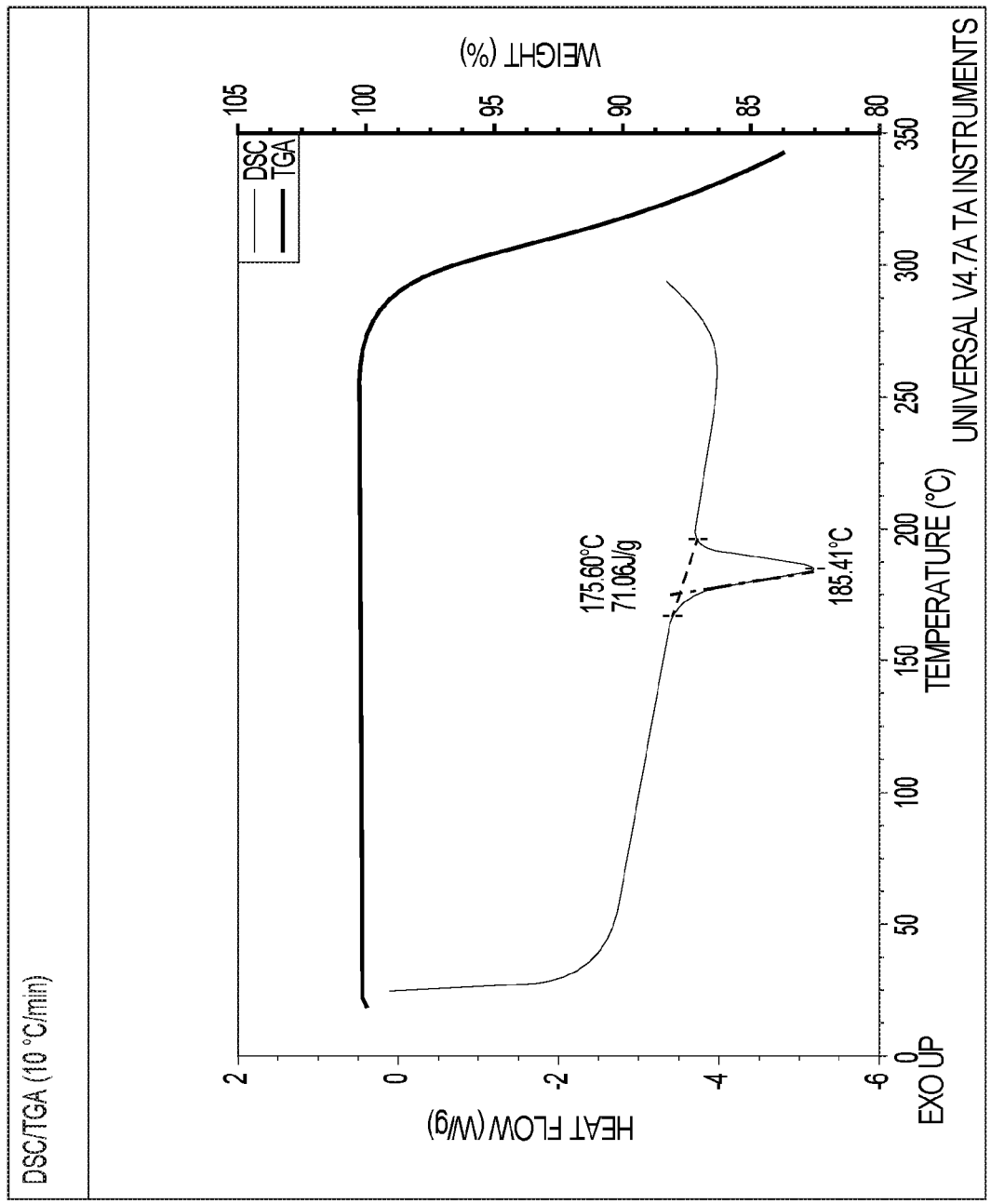
FIG. 2 depicts Differential Scanning calorimetry (DSC) and Thermogravimetric Analysis (TGA) curves of a crystalline form of anhydrous (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof.
Figure 3:
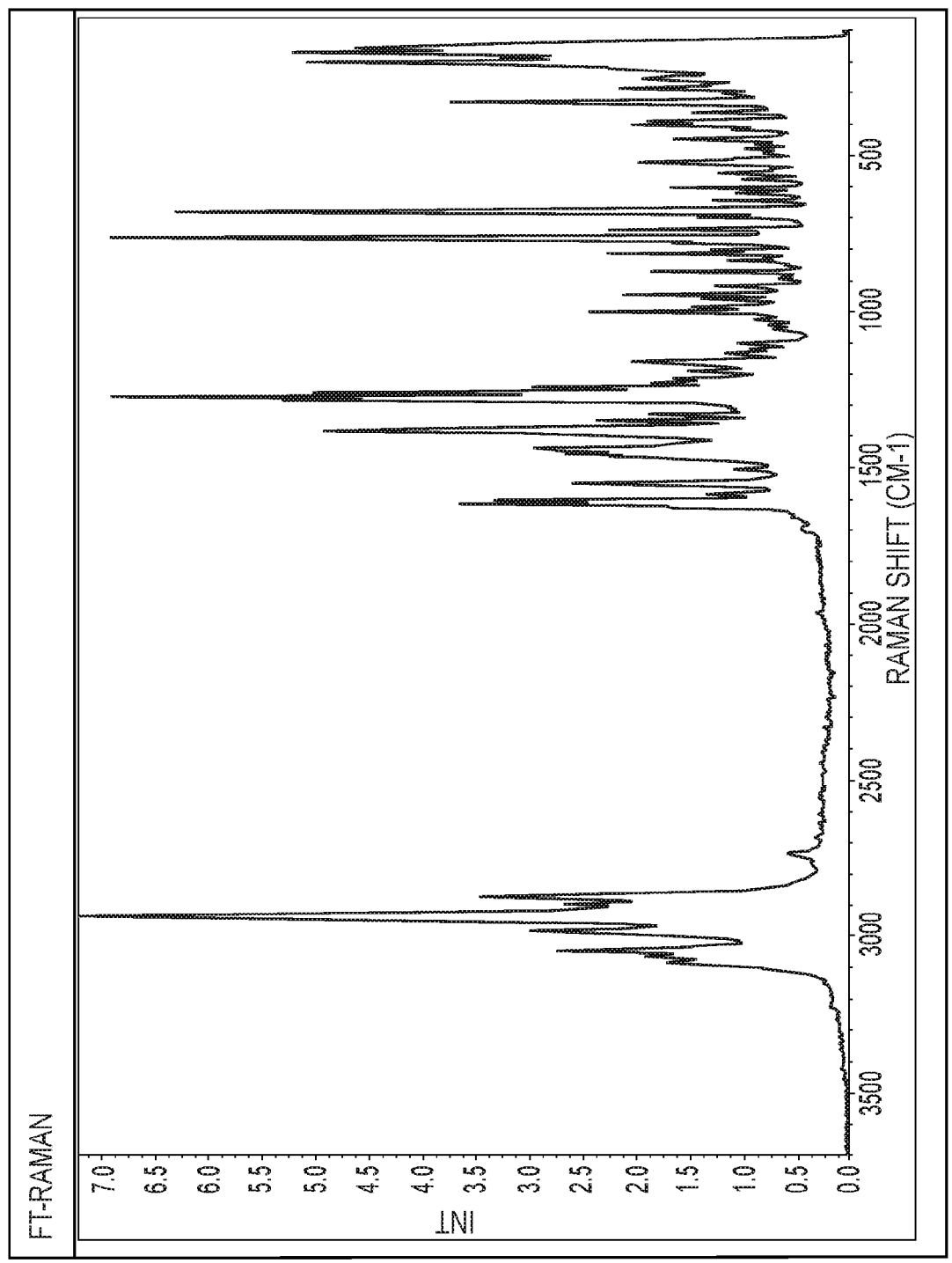
FIG. 3 depicts a Fourier-Transform Raman (FT-Raman) spectrum of a crystalline form of anhydrous (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4 (5H)-yl)methyl)-4-methylphenyl)propanoic acid (free form), or a tautomer thereof.

Other identifying spectra for crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid (free form), or a tautomer thereof, are shown in FIG. 2 (DSC and TGA) and FIG. 3 (FT-Raman).

Example 32

Crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid hydrate Example 32-1

Example 31 (39.1 mg, 0.076 mmol) was added to 1 mL of 20:80 ethanol water. The resulting suspension was continuously stirred while cycling the temperature between 40-5° C. for 48 h (heating and cooling at 2° C./min with 1 h hold at 40° C. and 5° C.). After 48 h, coming up from a 5° C. hold, the suspension was equilibrated with stirring at 20° C., and the resulting solids were harvested by filtration at room temperature and air-dried for 3 h. Solids were determined to be the crystalline Example 32-1 by XRPD, see FIG. 4, and were used as seed crystals for a larger scale-up batch described below.

Example 32-2

Figure 4:
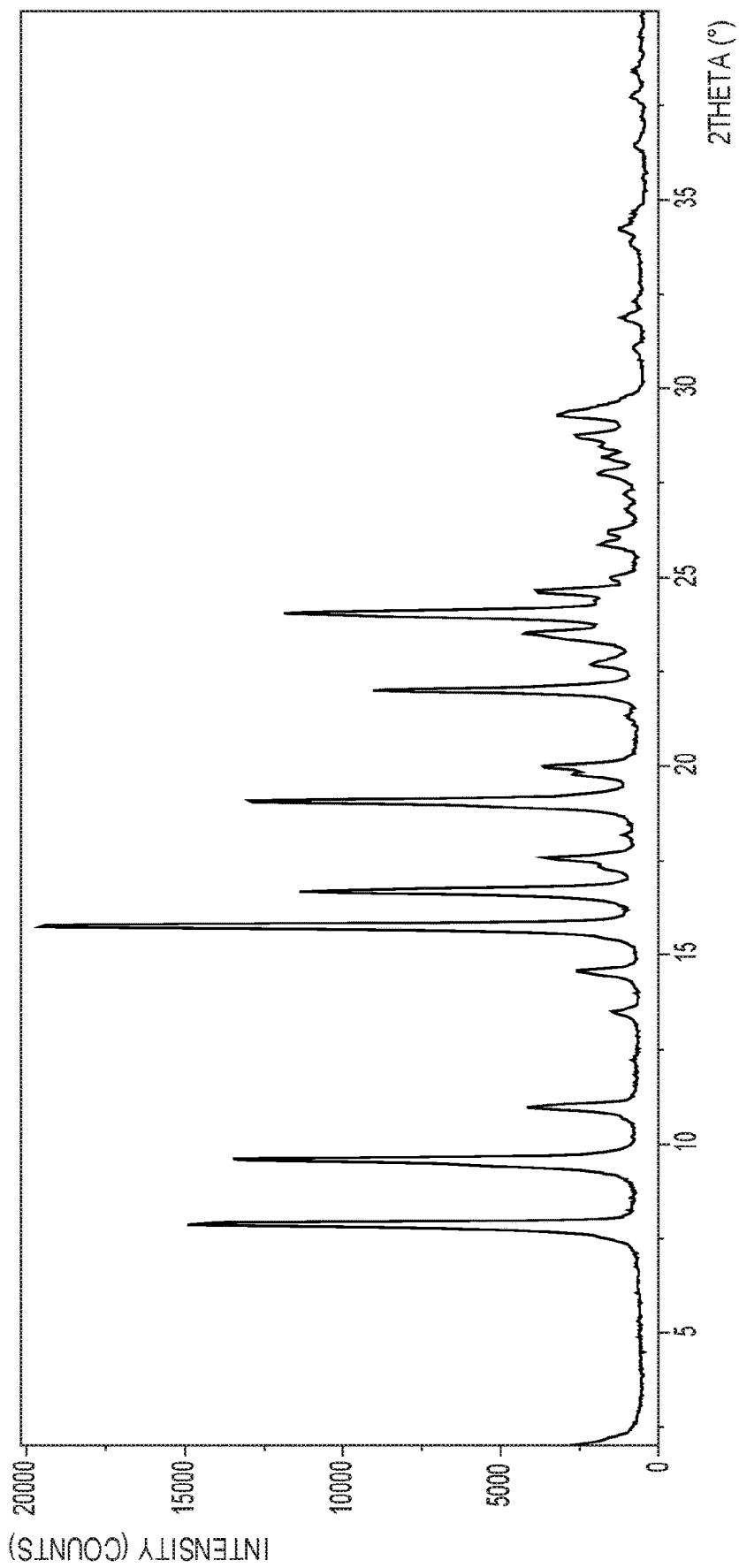
FIG. 4 depicts an XRPD of a crystalline hydrate form of (R)-3-(1,4-dimethyl-1H-benzo[d][1,2,3]triazol-5-yl)-3-(3-(((R)-2-ethyl-7-hydroxy-2,3-dihydropyrido[2,3-f][1,4] oxazepin-4(5H)-yl)methyl)-4-methylphenyl)propanoic acid hydrate, or a tautomer thereof.

Example 31 (300.8 mg, 0.583 mmol) was combined with ethanol:water (20:80) (95:5 v:v, 10 mL). The slurry was stirred at RT for 1 h, then seeded with Example 32-1, (6 mg, 0.011 mmol). The suspension was stirred while cycling the temperature between 40-5° C. for 2 h and then stirred at RT for 2 days. The solids were isolated by vacuum filtration on a Büchner funnel and air-dried for 3 h to afford Example 32-2 (305.4 mg, 68%). $^1$H NMR (METHANOL-d4) δ 7.5-7.6 (m, 2H), 7.43 (d, 1H, J=9.3 Hz), 7.0-7.1 (m, 3H), 6.42 (d, 1H, J=9.3 Hz), 4.94 (t, 1H, J=7.8 Hz), 4.29 (s, 3H), 3.90 (d, 1H, J=15.2 Hz), 3.7-3.8 (m, 1H), 3.6-3.7 (m, 3H), 3.0-3.2 (m, 2H), 2.8-2.9 (m, 1H), 2.7-2.8 (m, 4H), 2.30 (s, 3H), 1.45 (td, 1H, J=7.1, 8.3 Hz), 1.24 (ddd, 1H, J=4.4, 7.5, 14.1 Hz), 0.91 (t, 3H, J=7.3 Hz). LCMS: rt=0.77 mins (UPLC), m/z=516.4 [M+H]$^+$ The XRPD of this material is shown in FIG. 4 and the corresponding diffraction data is provided in Table 4.

TABLE 4

| Diffraction Angle (°2θ) | d-Spacing (Å) |
| --- | --- |
| 7.86 | 11.24 |
| 9.58 | 9.22 |
| 10.97 | 8.06 |
| 15.76 | 5.62 |
| 16.69 | 5.31 |
| 17.57 | 5.04 |
| 19.07 | 4.65 |
| 19.98 | 4.44 |
| 22.01 | 4.04 |
| 23.50 | 3.78 |
| 24.05 | 3.70 |
| 24.63 | 3.61 |
| 28.73 | 3.10 |
| 29.32 | 3.04 |

Figure 5:
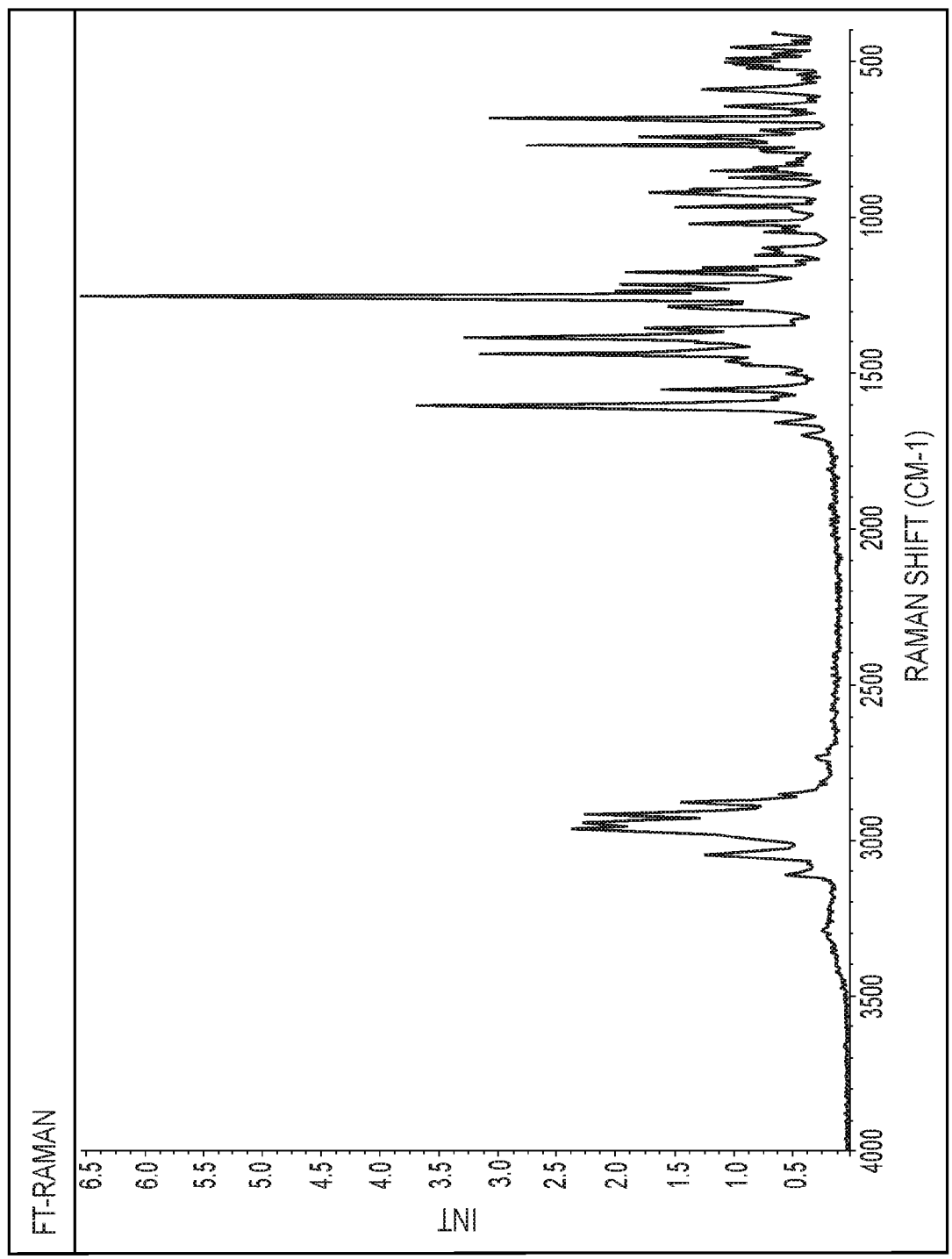
FIG. 5 depicts an FT-Raman spectrum of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4] oxazepin-4(5H)-yl)methyl)-4-methylphenyl)propanoic acid hydrate, or a tautomer thereof.
Figure 6:
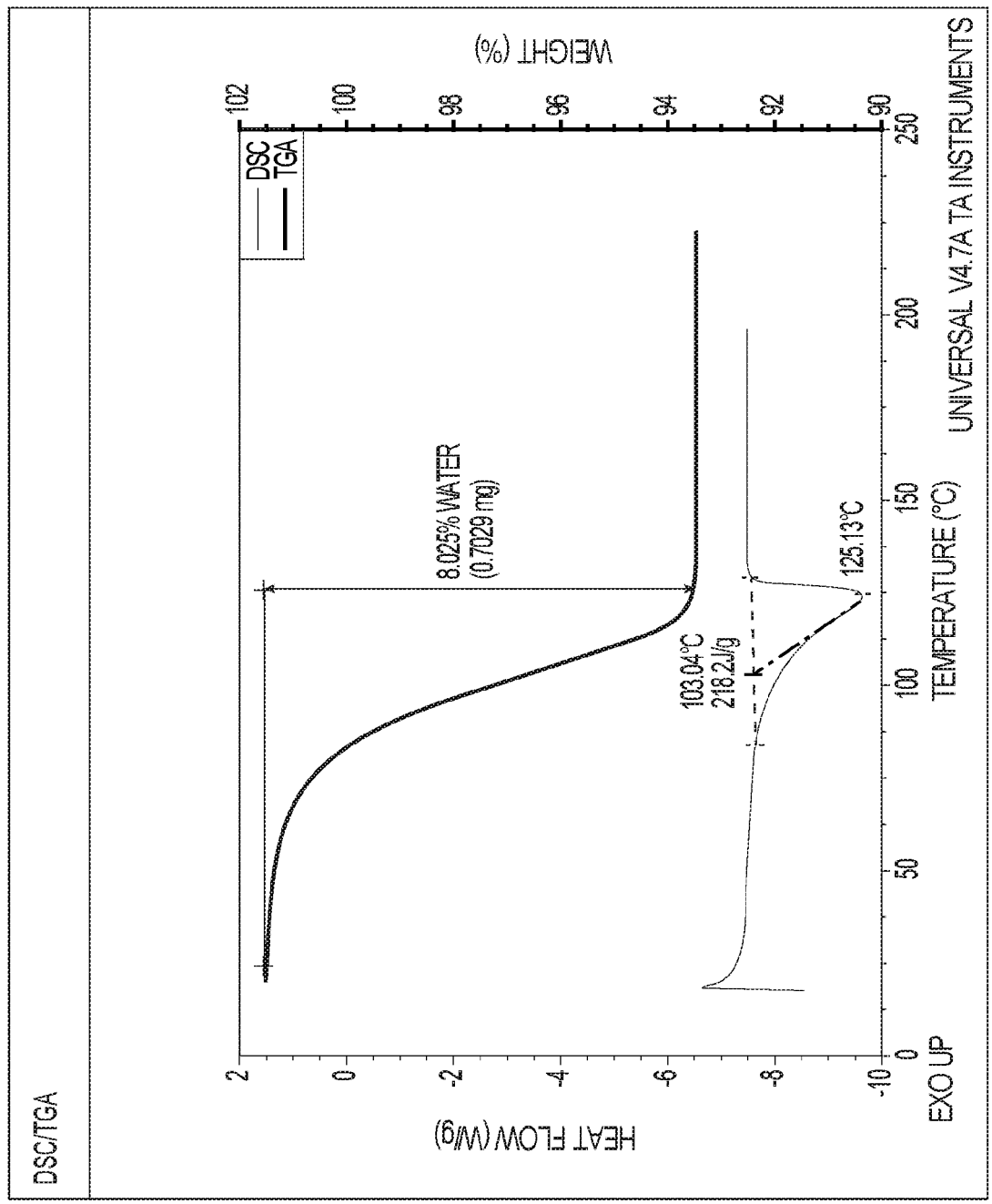
FIG. 6 depicts DSC and TGA curves of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4 (5H)-yl)methyl)-4-methylphenyl)propanoic acid hydrate, or a tautomer thereof.

Other identifying spectra for crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid hydrate, or a tautomer thereof, are shown in FIG. 5 (FT-Raman) and FIG. 6 (DSC and TGA).

Example 33

Crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid besylate salt Example 33-1

Compound XXVIII-31, free acid (19.2 mg, 0.037 mmol) was dispensed into a 2 mL vial into which was added 2-propanol (400 µL) followed by a solution of 3M aq. benzenesulfonic acid (12.4 µL). The resulting mixture was continuously stirred while cycling the temperature between 40-5° C. for 48 h (heating and cooling at 2° C./min with 1 h hold at 40° C. and 5° C.). After 48 h, coming up from a 5° C. hold, the suspension was equilibrated with stirring at 20° C. for 30 min, and the resulting solids were harvested by filtration at room temperature and air-dried for 4 h to afford Example 33-1, besylate salt, with 1:1 stoichiometry by XRPD, see FIG. 8.

Example 33-2

Figure 8:
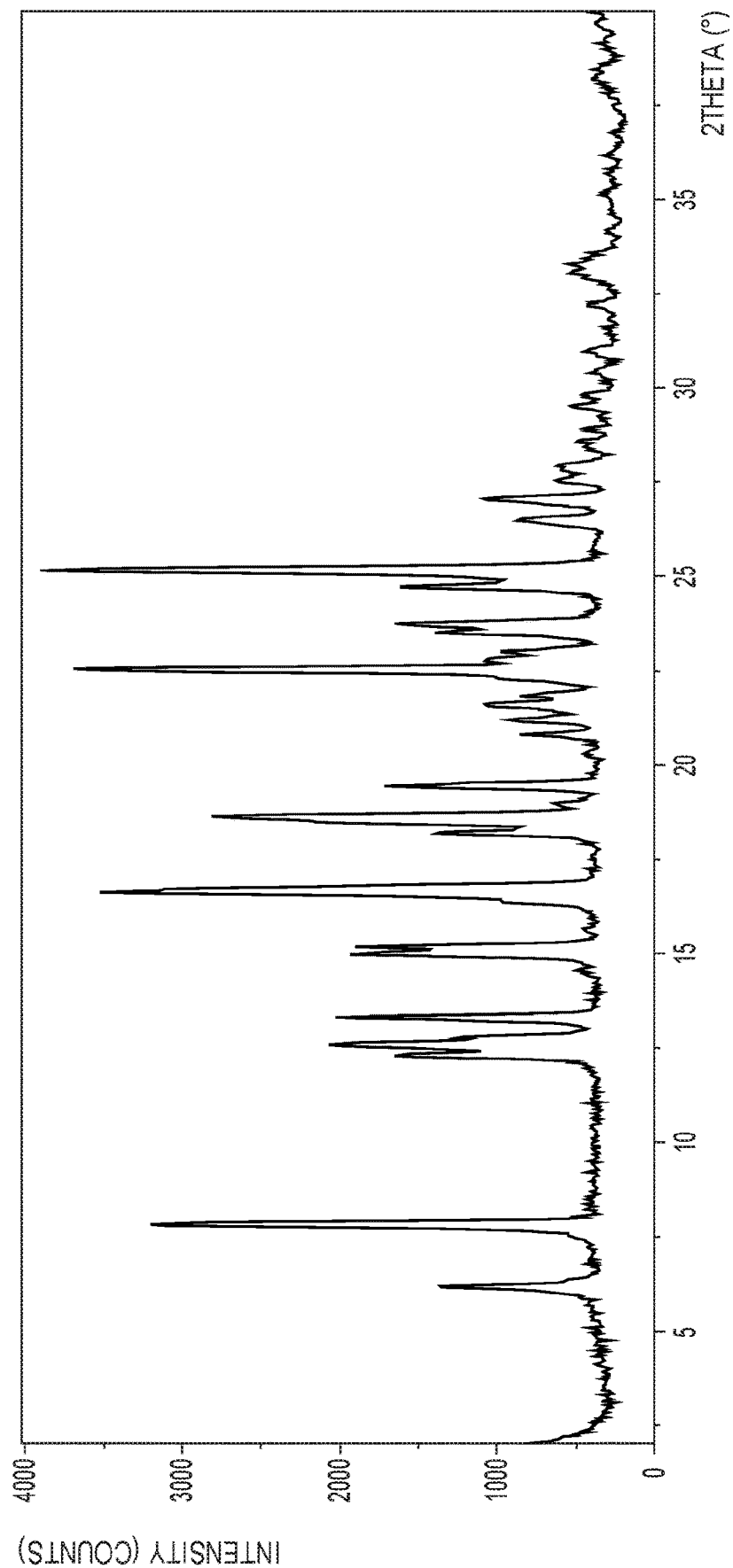
FIG. 8 depicts an XRPD of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl) methyl)-4-methylphenyl)propanoic acid besylate salt, or a tautomer thereof.

To Compound XXVIII-31, free acid (738 mg; 1.43 mmol) was added 2-propanol (14.8 mL; 20 vol), followed by a solution of 3M aq. benzenesulfonic acid (477 µL, 1.43 mmol) and seeds of Example 33-1. The mixture was heated to 40° C. for 2 h then slowly cooled at 0.1° C./min to 20° C. and stirred for several hours. The mixture was very thin, so the temperature was reduced to 5° C. and stirred overnight (~20 h). An aliquot of the slurry/gum was filtered and was determined to be amorphous by XRPD. Stirring was discontinued, the slurry/gum allowed to settle to the bottom of the vial, then the light-yellow supernatant was decanted. Fresh 2-propanol (14.8 mL) was added to the slurry/gum, the mixture heated to 40° C., and most solids were observed to have dissolved. The mixture was temperature-cycled from 40-5° C. in 1 h blocks overnight, resulting in a thick mixture. A second aliquot of the slurry was filtered and matched the desired besylate salt by XRPD. The solids were filtered and air-dried for 30 min, then dried in a vacuum oven at 40° C. with nitrogen bleed for 2 h to afford Example 33-2, besylate salt (609 mg, 63% yield), consistent with the besylate salt by XRPD analysis. $^1$H NMR (METHANOL-d4) δ 7.8-7.9 (m, 2H), 7.5-7.6 (m, 3H), 7.4-7.5 (m, 5H), 7.3-7.4 (m, 1H), 6.62 (d, 1H, J=8.8 Hz), 5.03 (t, 1H, J=8.1 Hz), 4.60 (br s, 1H), 4.50 (br s, 2H), 4.3-4.4 (m, 1H), 4.27 (s, 3H), 3.8-4.1 (m, 1H), 3.5-3.7 (m, 2H), 3.1-3.3 (m, 2H), 2.83 (s, 3H), 2.43 (s, 3H), 1.65 (s, 1H), 1.4-1.6 (m, 1H), 1.07 (t, 3H, J=7.3 Hz). LCMS: rt=0.76 mins (UPLC), m/z=516.3 [M+H]$^+$ The XRPD of this material is shown in FIG. 8 and the corresponding diffraction data is provided in Table 5.

TABLE 5

| Diffraction Angle (°2θ) | d-Spacing (Å) |
|---|---|
| 6.18 | 14.29 |
| 7.82 | 11.30 |
| 12.32 | 7.18 |
| 12.60 | 7.02 |
| 13.31 | 6.65 |
| 15.01 | 5.90 |
| 15.21 | 5.82 |
| 16.66 | 5.32 |
| 18.20 | 4.87 |
| 18.63 | 4.76 |
| 19.46 | 4.56 |
| 22.53 | 3.94 |
| 23.54 | 3.78 |
| 23.73 | 3.75 |
| 24.72 | 3.60 |
| 25.18 | 3.53 |
| 27.04 | 3.29 |

Figure 7:
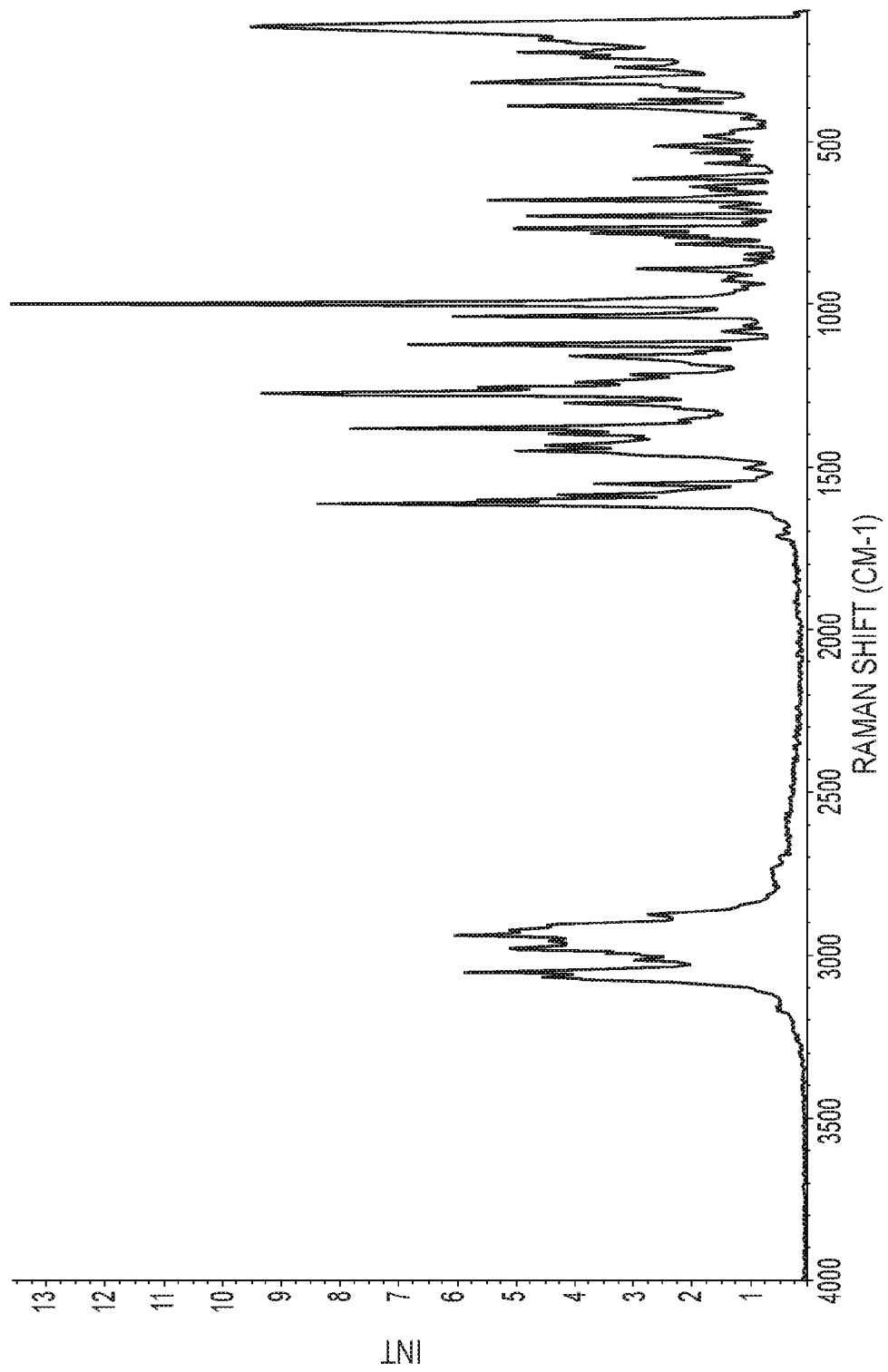
FIG. 7 depicts an FT-Raman spectrum of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4] oxazepin-4(5H)-yl)methyl)-4-methylphenyl)propanoic acid besylate salt, or a tautomer thereof.

Another identifying spectra for crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4 (5H)-yl)methyl)-4-methylphenyl)propanoic acid besylate salt, or a tautomer thereof, is shown in FIG. 7 (FT-Raman).

Example 34

Crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid mesylate salt hydrate Example 34-1

Compound XXVIII-31, free acid (19.5 mg; 0.038 mmol) was dispensed into a 2 mL vial, to which was added ethyl acetate (400 μL), followed by 3M aq methanesulfonic acid (12.6 μL, 0.042 mmol). The resulting slurry was continuously stirred while cycling the temperature between 40-5° C. for 48 h (heating and cooling at 2° C./min with 1 h hold at 40° C. and 5° C.). After 48 h, coming up from a 5° C. hold, the suspension was equilibrated with stirring at 20° C. for 30 min, and the resulting solids were harvested by filtration at room temperature and air-dried for 4 h to afford Example 34-1, mesylate salt hydrate, with 1:1 API:mesylate stoichiometry as determined by NMR.

Example 34-2

Figure 9:
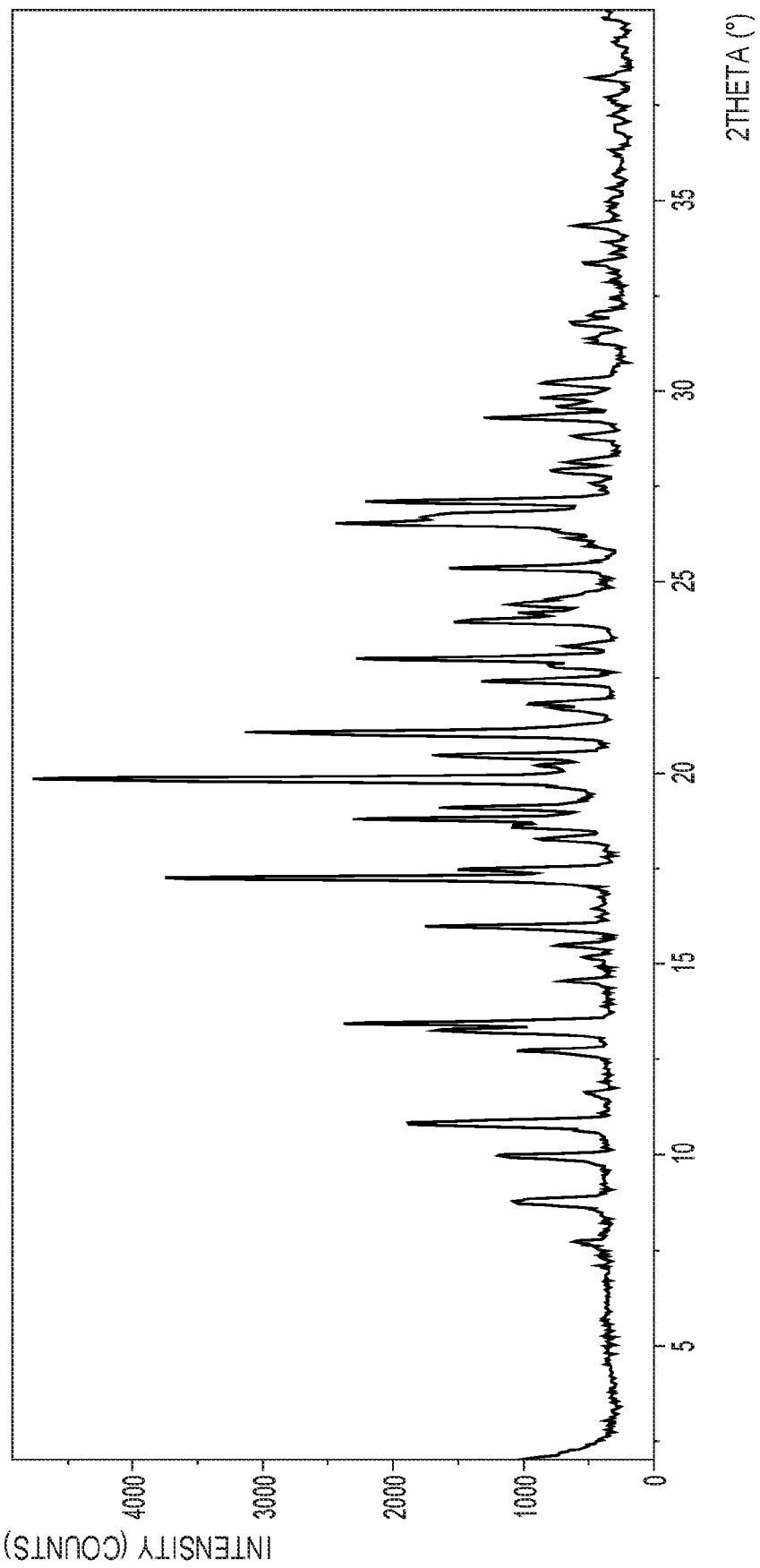
FIG. 9 depicts an XRPD of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl) methyl)-4-methylphenyl)propanoic acid mesylate salt hydrate, or a tautomer thereof.

To Compound XXVIII-31, free acid (623 mg; 1.21 mmol) was added ethyl acetate (12.5 mL; 20 vol) followed by 3M aq. methanesulfonic acid (403 μL, 1.34 mmol) and seeds of Example 34-1. The mixture was heated to 40° C. for 2 h then slowly cooled at 0.1° C./min to 20° C. and stirred overnight (~20 h). The solids were dried in a vacuum oven at 40° C. with nitrogen bleed for 2 h to afford Example 34-2, mesylate salt hydrate, (710 mg, 90% yield), and were consistent with the mesylate salt hydrate, by XRPD analysis. $^1$H NMR (METHANOL-d4) δ 7.4-7.6 (m, 4H), 7.4-7.4 (m, 1H), 7.3-7.4 (m, 1H), 6.65 (d, 1H, J=8.8 Hz), 5.04 (t, 1H, J=8.1 Hz), 4.62 (s, 1H), 4.52 (br s, 2H), 4.3-4.4 (m, 1H), 4.29 (s, 3H), 3.97 (td, 1H, J=3.3, 6.1 Hz), 3.5-3.7 (m, 2H), 3.1-3.3 (m, 2H), 2.84 (s, 3H), 2.71 (s, 3H), 2.44 (s, 3H), 1.68 (br dd, 1H, J=7.6, 14.9 Hz), 1.56 (br d, 1H, J=3.9 Hz), 1.09 (t, 3H, J=7.3 Hz). LCMS: rt=0.77 mins (UPLC), m/z=516.4 [M+H]$^+$ The XRPD of this material is shown in FIG. 9 and the corresponding diffraction data is provided in Table 6.

TABLE 6

| Diffraction Angle (°2θ) | d-Spacing (Å) |
|---|---|
| 8.78 | 10.06 |
| 9.97 | 8.86 |
| 10.82 | 8.17 |
| 12.72 | 6.95 |
| 13.29 | 6.66 |
| 13.45 | 6.58 |
| 15.98 | 5.54 |
| 17.25 | 5.14 |
| 17.47 | 5.07 |
| 18.80 | 4.72 |
| 19.10 | 4.64 |
| 19.84 | 4.47 |
| 20.46 | 4.34 |
| 21.06 | 4.22 |
| 22.41 | 3.96 |
| 23.00 | 3.86 |
| 23.98 | 3.71 |
| 25.38 | 3.51 |
| 26.54 | 3.36 |
| 27.11 | 3.29 |
| 29.31 | 3.04 |

Figure 10:
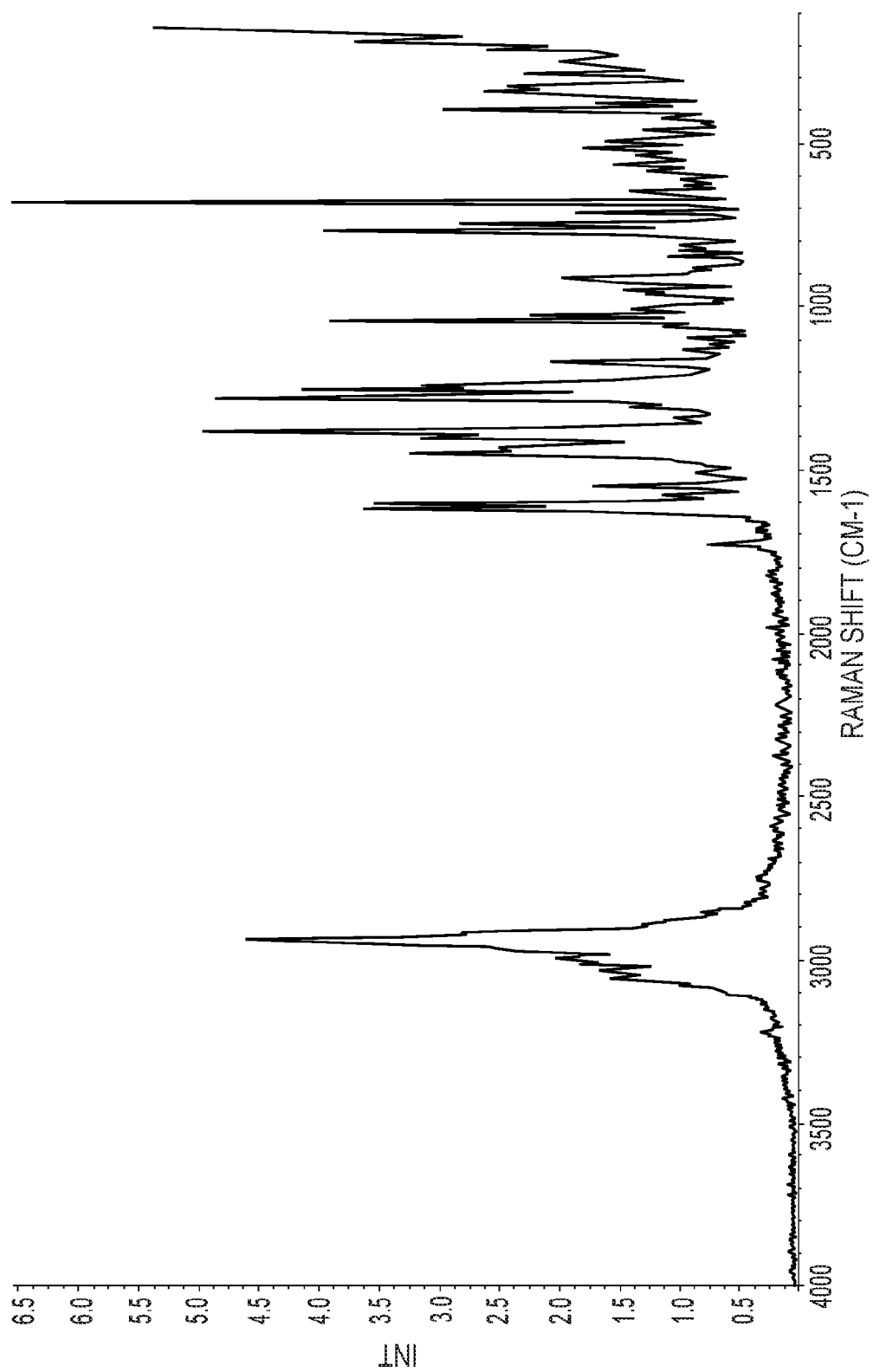
FIG. 10 depicts an FT-Raman spectrum of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4] oxazepin-4(5H)-yl)methyl)-4-methylphenyl)propanoic acid mesylate salt hydrate, or a tautomer thereof.
Figure 11:
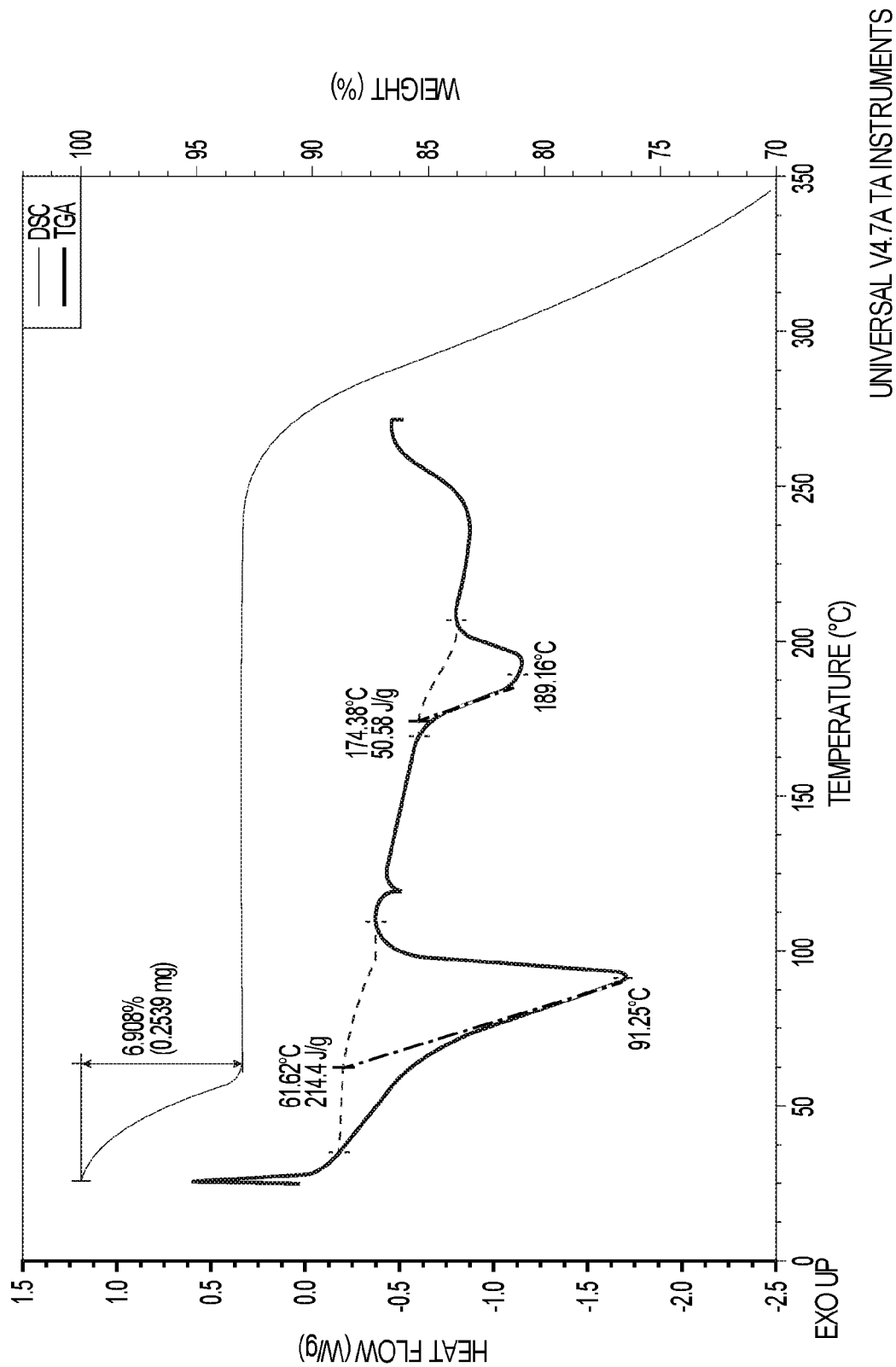
FIG. 11 depicts DSC and TGA curves of crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4] oxazepin-4(5H)-yl)methyl)-4-methylphenyl)propanoic acid mesylate salt hydrate, or a tautomer thereof.

Other identifying spectra for crystalline (R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl) methyl)-4-methylphenyl)propanoic acid mesylate salt hydrate, or a tautomer thereof, are shown in FIG. 10 (FT-Raman) and FIG. 11 (DSC and TGA).

What is claimed is:
1. A compound of Formula (I):

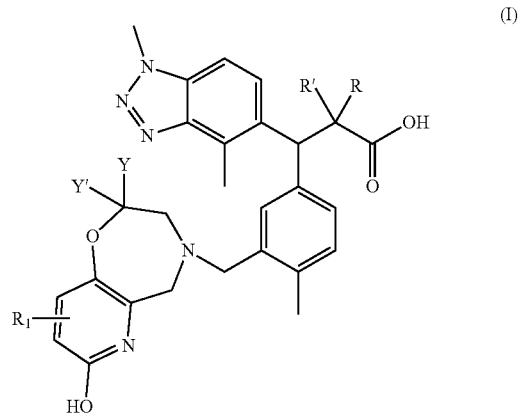

(I)

wherein:
R is hydrogen or methyl;
R' is hydrogen or methyl;

R₁ is hydrogen, —OH, —C₁₋₃alkyl, —CF₃, difluoromethyl, or halo;
Y is hydrogen, —C₁₋₅alkyl, —C₃₋₇cycloalkyl, —CF₃, —CHF₂, —CH₂CF₃; and
Y' is hydrogen, —C₁₋₅alkyl, —C₃₋₇cycloalkyl, —CF₃, —C$_H$F₂, —CH₂CF₃; or Y and Y' form —C₃₋₇cycloalkyl;
or a pharmaceutically acceptable salt thereof, or a tautomer thereof, or a hydrate thereof.

2. The compound according to claim 1, wherein
R is hydrogen or methyl;
R' is hydrogen or methyl;
R₁ is hydrogen, —C₁₋₃alkyl or halo;
Y is independently —C₁₋₅alkyl, —C₃₋₅cycloalkyl or —CF₃; and
Y' is hydrogen;
or a pharmaceutically acceptable salt thereof, or a tautomer thereof, or a hydrate thereof.

3. The compound according to claim 1, wherein
R is hydrogen or methyl;
R' is hydrogen or methyl;
R₁ is hydrogen, —C₁₋₃alkyl or halo;
Y is —C₁₋₅alkyl, —C₃₋₅cycloalkyl or —CF₃; and
Y' is methyl;
or a pharmaceutically acceptable salt thereof, or a tautomer thereof, or a hydrate thereof.

4. The compound according to claim 1, wherein
R is methyl;
R' is methyl;
R₁ is hydrogen;
Y is methyl, ethyl or isopropyl; and
Y' is hydrogen;
or a pharmaceutically acceptable salt thereof, or a tautomer thereof, or a hydrate thereof.

5. The compound according to claim 1, wherein
R is hydrogen;
R' is hydrogen;
R₁ is hydrogen;
Y is methyl, ethyl or isopropyl; and
Y' is hydrogen;
or a pharmaceutically acceptable salt thereof, or a tautomer thereof, or a hydrate thereof.

6. A compound which is:
(R)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid;
(R)-3-(1,4-dimethyl-1H-benzo[d][1,2,3]triazol-5-yl)-3-(3-(((S)-7-hydroxy-2-isopropyl-2,3-dihydropyrido[2,3-f][1,4]oxazepin-4(5H)-yl)methyl)-4-methylphenyl)propanoic acid;
(R)-3-(1,4-dimethyl-1H-benzo[d][1,2,3]triazol-5-yl)-3-(3-(((R)-7-hydroxy-2-isopropyl-2,3-dihydropyrido[2,3-f][1,4]oxazepin-4(5H)-yl)methyl)-4-methylphenyl)propanoic acid;
(R)-3-(1,4-dimethyl-1H-benzo[d][1,2,3]triazol-5-yl)-3-(3-(((R)-7-hydroxy-2-methyl-2,3-dihydropyrido[2,3-f][1,4]oxazepin-4(5H)-yl)methyl)-4-methylphenyl)propanoic acid;
(R)-3-(1,4-dimethyl-1H-benzo[d][1,2,3]triazol-5-yl)-3-(3-((7-hydroxy-2,2-dimethyl-2,3-dihydropyrido[2,3-f][1,4]oxazepin-4(5H)-yl)methyl)-4-methylphenyl)propanoic acid;
(R)-3-(1,4-dimethyl-1H-benzo[d][1,2,3]triazol-5-yl)-3-(3-(((S)-7-hydroxy-2-(trifluoromethyl)-2,3-dihydropyrido[2,3-f][1,4]oxazepin-4(5H)-yl)methyl)-4-methylphenyl)propanoic acid;
(R)-3-(1,4-dimethyl-1H-benzo[d][1,2,3]triazol-5-yl)-3-(3-(((S)-2-ethyl-7-hydroxy-2,3-dihydropyrido[2,3-f][1,4]oxazepin-4(5H)-yl)methyl)-4-methylphenyl)propanoic acid;
(S)-3-(1,4-dimethyl-1H-benzo[d][1,2,3]triazol-5-yl)-3-(3-(((R)-7-hydroxy-2-isopropyl-2,3-dihydropyrido[2,3-f][1,4]oxazepin-4(5H)-yl)methyl)-4-methylphenyl)propanoic acid;
(S)-3-(1,4-dimethyl-1H-benzo[d][1,2,3]triazol-5-yl)-3-(3-(((S)-7-hydroxy-2-isopropyl-2,3-dihydropyrido[2,3-f][1,4]oxazepin-4(5H)-yl)methyl)-4-methylphenyl)propanoic acid;
(S)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)propanoic acid;
(S)-3-(1,4-dimethyl-1H-benzo[d][1,2,3]triazol-5-yl)-3-(34(7-hydroxy-2,2-dimethyl-2,3-dihydropyrido[2,3-f][1,4]oxazepin-4(5H)-yl)methyl)-4-methylphenyl)propanoic acid;
(S)-3-(1,4-dimethyl-1H-benzo[d][1,2,3]triazol-5-yl)-3-(3-(((S)-2-ethyl-7-hydroxy-2,3-dihydropyrido[2,3-f][1,4]oxazepin-4(5H)-yl)methyl)-4-methylphenyl)propanoic acid;
(S)-3-(1,4-dimethyl-1H-benzo[d][1,2,3]triazol-5-yl)-3-(3-(((R)-2-ethyl-7-hydroxy-2,3-dihydropyrido[2,3-f][1,4]oxazepin-4(5H)-yl)methyl)-4-methylphenyl)-2,2-dimethyl propanoic acid;
(S)-3-(1,4-dimethyl-1H-benzo[d][1,2,3]triazol-5-yl)-3-(3-(((R)-7-hydroxy-2-methyl-2,3-dihydropyrido[2,3-f][1,4]oxazepin-4(5H)-yl)methyl)-4-methylphenyl)-2,2-dimethylpropanoic acid;
(S)-3-(1,4-dimethyl-1H-benzo[d][1,2,3]triazol-5-yl)-3-(3-(((R)-7-hydroxy-2-isopropyl-2,3-dihydropyrido[2,3-f][1,4]oxazepin-4(5H)-yl)methyl)-4-methylphenyl)-2,2-dimethylpropanoic acid;
(S)-3-(1,4-dimethyl-1H-benzo[d][1,2,3]triazol-5-yl)-3-(3-(((S)-7-hydroxy-2-isopropyl-2,3-dihydropyrido[2,3-f][1,4]oxazepin-4(5H)-yl)methyl)-4-methylphenyl)-2,2-dimethylpropanoic acid;
(S)-3-(1,4-dimethyl-1H-benzo[d][1,2,3]triazol-5-yl)-3-(3-((7-hydroxy-2,2-dimethyl-2,3-dihydropyrido[2,3-f][1,4]oxazepin-4(5H)-yl)methyl)-4-methylphenyl)-2,2-dimethylpropanoic acid;
(S)-3-(1,4-dimethyl-1H-benzo[d][1,2,3]triazol-5-yl)-3-(3-(((S)-2-ethyl-7-hydroxy-2,3-dihydropyrido[2,3-f][1,4]oxazepin-4(5H)-yl)methyl)-4-methylphenyl)-2,2-dimethylpropanoic acid;
(S)-3-(1,4-dimethyl-1H-benzo[d][1,2,3]triazol-5-yl)-3-(3-(((S)-7-hydroxy-2-(trifluoromethyl)-2,3-dihydropyrido[2,3-f][1,4]oxazepin-4(5H)-yl)methyl)-4-methylphenyl)-2,2-dimethylpropanoic acid;
(R)-3-(1,4-dimethyl-1H-benzo[d][1,2,3]triazol-5-yl)-3-(3-(((R)-7-hydroxy-2-(trifluoromethyl)-2,3-dihydropyrido[2,3-f][1,4]oxazepin-4(5H)-yl)methyl)-4-methylphenyl)propanoic acid;
(S)-3-(1,4-dimethyl-1H-benzo[d][1,2,3]triazol-5-yl)-3-(3-(((R)-7-hydroxy-2-(trifluoromethyl)-2,3-dihydropyrido[2,3-f][1,4]oxazepin-4(5H)-yl)methyl)-4-methylphenyl)-2,2-dimethylpropanoic acid;
(R)-3-(1,4-dimethyl-1H-benzo[d][1,2,3]triazol-5-yl)-3-(3-(((R)-2-ethyl-8-fluoro-7-hydroxy-2,3-dihydropyrido[2,3-f][1,4]oxazepin-4(5H)-yl)methyl)-4-methylphenyl)propanoic acid;

(S)-3-(1,4-dimethyl-1H-benzo[d][1,2,3]triazol-5-yl)-3-
(3-(((S)-7-hydroxy-2-methyl-2,3-dihydropyrido[2,3-f]
[1,4]oxazepin-4(5H)-yl)methyl)-4-methylphenyl)-2,2-
dimethylpropanoic acid;

(S)-3-(1,4-dimethyl-1H-benzo[d][1,2,3]triazol-5-yl)-3-
(3-((7-hydroxy-2,3-dihydropyrido[2,3-f][1,4]oxaze-
pin-4(5H)-yl)methyl)-4-methylphenyl)-2,2-dimethyl-
propanoic acid;

(S)-3-(1,4-dimethyl-1H-benzo[d][1,2,3]triazol-5-yl)-3-
(3-(((S)-7-hydroxy-2-(trifluoromethyl)-2,3-dihydro-
pyrido[2,3-f][1,4]oxazepin-4(5H)-yl)methyl)-4-meth-
ylphenyl)propanoic acid;

(R)-3-(1,4-dimethyl-1H-benzo[d][1,2,3]triazol-5-yl)-3-
(3-(((R)-2-ethyl-7-hydroxy-2-methyl-2,3-dihydro-
pyrido[2,3-f][1,4]oxazepin-4(5H)-yl)methyl)-4-meth-
ylphenyl)propanonic acid;

(R)-3-(1,4-dimethyl-1H-benzo[d][1,2,3]triazol-5-yl)-3-
(3-(((S)-2-ethyl-7-hydroxy-2-methyl-2,3-dihydro-
pyrido[2,3-f][1,4]oxazepin-4(5H)-yl)methyl)-4-meth-
ylphenyl)propanonic acid;

(S)-3-(1,4-dimethyl-1H-benzo[d][1,2,3]triazol-5-yl)-3-
(3-(((R)-7-hydroxy-2-(trifluoromethyl)-2,3-dihydro-
pyrido[2,3-f][1,4]oxazepin-4(5H)-yl)methyl)-4-meth-
ylphenyl)propanoic acid;

(R)-3-(1,4-dimethyl-1H-benzo[d][1,2,3]triazol-5-yl)-3-
(3-((7'-hydroxy-3'H-spiro[cyclobutane-1,2'-pyrido[2,
3-t][1,4]oxazepin-4'(5'H)-yl)methyl)-4-methylphenyl)
propanonic acid; and (R)-3-(3-(((R)-2-(tert-butyl)-7-hydroxy-2,3-dihydro-
pyrido[2,3-f][1,4]oxazepin-4(5H)-yl)methyl)-4-meth-
ylphenyl)-3-(1,4-dimethyl-1H-benzo[d][1,2,3]triazol-
5-yl)propanoic acid;

or a pharmaceutically acceptable salt thereof, or a tau-
tomer thereof, or a hydrate thereof.

7. A compound, or a pharmaceutically acceptable salt thereof, or a tautomer thereof, or a hydrate thereof, which is

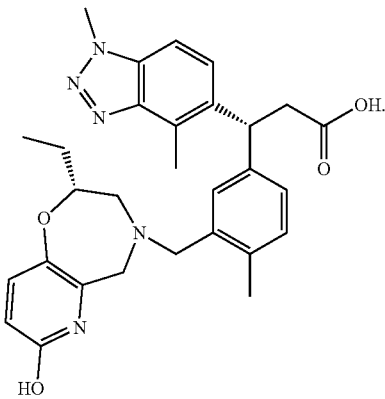 [SMILES: CC[C@@H]1CN(Cc2cc([C@@H](CC(=O)O)c3ccc4c(nnn4C)c3C)ccc2C)Cc2nc(O)ccc2O1]

8. A crystalline form of (R)-3-(1,4-dimethyl-1H-benzo[d]
[1,2,3]triazol-5-yl)-3-(3-(((R)-2-ethyl-7-hydroxy-2,3-dihy-
dropyrido[2,3-f][1,4]oxazepin-4(5H)-yl)methyl)-4-meth-
ylphenyl)propanoic acid hydrate, or a tautomer thereof,
having an x-ray powder diffraction pattern comprising peaks
at 15.76°, 7.86°, 9.58°, and 19.07°±0.2° 2θ as measured by
x-ray powder diffraction using an x-ray wavelength of
1.5406 Å.

9. The compound according to claim 1 which is (R)-3-
(1,4-dimethyl-1H-benzo[d][1,2,3]triazol-5-yl)-3-(3-(((R)-2-
ethyl-7-hydroxy-2,3-dihydropyrido[2,3-f][1,4]oxazepin-4
(5H)-yl)methyl)-4-methylphenyl)propanoic acid besylate
salt, or a tautomer thereof.

10. A crystalline form of (R)-3-(1,4-dimethyl-1H-benzo
[d][1,2,3]triazol-5-yl)-3-(3-(((R)-2-ethyl-7-hydroxy-2,3-di-
hydropyrido[2,3-f][1,4]oxazepin-4(5H)-yl)methyl)-4-meth-
ylphenyl)propanoic acid besylate salt, or a tautomer thereof,
having an x-ray powder diffraction pattern comprising peaks
at 25.18°, 22.53°, 16.66°, and 7.82°±0.2° 2θ as measured by
x-ray powder diffraction using an x-ray wavelength of
1.5406 Å.

11. The compound according to claim 1 which is (R)-3-
(1,4-dimethyl-1H-benzo[d][1,2,3]triazol-5-yl)-3-(3-(((R)-2-
ethyl-7-hydroxy-2,3-dihydropyrido[2,3-f][1,4]oxazepin-4
(5H)-yl)methyl)-4-methylphenyl)propanoic acid mesylate
salt hydrate, or a tautomer thereof.

12. A crystalline form of (R)-3-(1,4-dimethyl-1H-benzo
[d][1,2,3]triazol-5-yl)-3-(3-(((R)-2-ethyl-7-hydroxy-2,3-di-
hydropyrido[2,3-f][1,4]oxazepin-4(5H)-yl)methyl)-4-meth-
ylphenyl)propanoic acid mesylate salt hydrate, or a tautomer
thereof, having an x-ray powder diffraction pattern compris-
ing peaks at 19.84°, 17.25°, 21.06°, and 13.45°±0.2° 2θ as
measured by x-ray powder diffraction using an x-ray wave-
length of 1.5406 Å.

13. A crystalline form of (R)-3-(1,4-dimethyl-1H-benzo
[d][1,2,3]triazol-5-yl)-3-(3-(((R)-2-ethyl-7-hydroxy-2,3-di-
hydropyrido[2,3-f][1,4]oxazepin-4(5H)-yl)methyl)-4-meth-
ylphenyl)propanoic acid (free form), or a tautomer thereof.

14. A crystalline form of (R)-3-(1,4-dimethyl-1H-benzo
[d][1,2,3]triazol-5-yl)-3-(3-(((R)-2-ethyl-7-hydroxy-2,3-di-
hydropyrido[2,3-f][1,4]oxazepin-4(5H)-yl)methyl)-4-meth-
ylphenyl)propanoic acid (free form), or a tautomer thereof,
which is characterized by an x-ray powder diffraction pat-
tern substantially in accordance with that shown in FIG. 1.

15. A crystalline form of (R)-3-(1,4-dimethyl-1H-benzo
[d][1,2,3]triazol-5-yl)-3-(3-(((R)-2-ethyl-7-hydroxy-2,3-di-
hydropyrido[2,3-f][1,4]oxazepin-4(5H)-yl)methyl)-4-meth-
ylphenyl)propanoic acid (free form), or a tautomer thereof,
having an x-ray powder diffraction pattern comprising peaks
at 12.38°, 25.90°, 19.35°, and 7.54°±0.2° 2θ as measured by
x-ray powder diffraction using an x-ray wavelength of
1.5406 Å.

16. Isolated crystalline (R)-3-(1,4-dimethyl-1H-benzo[d]
[1,2,3]triazol-5-yl)-3-(3-(((R)-2-ethyl-7-hydroxy-2,3-dihy-
dropyrido[2,3-f][1,4]oxazepin-4(5H)-yl)methyl)-4-meth-
ylphenyl)propanoic acid (free form), or a tautomer thereof.

17. A substantially pure crystalline form of (R)-3-(1,4-
dimethyl-1H-benzo[d][1,2,3]triazol-5-yl)-3-(3-(((R)-2-
ethyl-7-hydroxy-2,3-dihydropyrido[2,3-f][1,4]oxazepin-4
(5H)-yl)methyl)-4-methylphenyl)propanoic acid (free
form), or a tautomer thereof.

18. The crystalline form according to claim 13, wherein
the crystalline compound is characterized by having at least
five peaks selected from the diffraction pattern comprising
peaks at 6.69°, 7.54°, 12.38°, 12.90°, 13.55°, 13.99°, 16.40°,
17.49°, 17.82°, 18.30°, 19.35°, 19.96°, 20.98°, 22.74°,
25.90°, 26.79°, and 27.36°−±0.2° 2θ as measured by x-ray
powder diffraction using an x-ray wavelength of 1.5406 Å.

19. A pharmaceutical composition comprising a com-
pound, or a pharmaceutically acceptable salt thereof, or a
tautomer thereof, or a hydrate thereof, according to claim 1
and one or more pharmaceutically acceptable excipients.

20. A method of treating an Nrf2-regulated disease or
disorder selected from COPD, asthma, ALI, ARDS, fibrosis,
chronic asthma and acute asthma, lung disease secondary to
environmental exposures, acute lung infection, chronic lung
infection, al antitrypsin disease, cystic fibrosis, autoimmune
diseases, diabetic nephropathy, chronic kidney disease, sep-
sis-induced acute kidney injury, acute kidney injury (AKI),
kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, heart failure with preserved ejection fraction, heart failure with reduced ejection fraction, diabetic cardiomyopathy, SCD, Progeria and cardiorenal syndrome (CRS), Parkinson's disease (PD), Alzheimer's disease (AD), Friedreich's Ataxia (FA), amyotrophic lateral sclerosis (ALS), multiple sclerosis (MS), Huntington's disease (HD), spinal cord injury, traumatic brain injury, ischemic stroke, stroke, Creutzfeldt-Jakob Disease, fatal familial insomnia, Gerstmann-Sträussler-Scheinker syndrome, and related prion diseases, progressive supranuclear palsy, chronic traumatic encephalopathy (CTE), neurodegeneration, dementias, frontotemporal dementias, tauopathies, retinitis pigmentosa, Pick's disease, Neimann-Pick's disease, amyloidosis, cognitive impairment, inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease, viral hepatitis, cirrhosis, psoriasis, dermatitis/topical effects of radiation, immunosuppression due to radiation exposure, Preeclampsia, and high altitude sickness which comprises administering to a subject in need thereof, a therapeutically effective amount of a compound according to claim 1, or a pharmaceutically acceptable salt thereof, or a tautomer thereof, or a hydrate thereof.

21. The method according to claim 20 wherein the compound, or a pharmaceutically acceptable salt thereof, or a tautomer thereof, or a hydrate thereof, is administered orally.

22. The method according to claim 20 wherein the compound, or a pharmaceutically acceptable salt thereof, or a tautomer thereof, or a hydrate thereof, is administered intravenously.

23. The method according to claim 20 wherein the compound, or a pharmaceutically acceptable salt thereof, or a tautomer thereof, or a hydrate thereof, is administered by inhalation.

24. The method according to claim 20 wherein the disease is COPD.

25. The method according to claim 20 wherein the disease is heart failure.

26. The method according to claim 20 wherein the disease is heart failure with reduced ejection fraction.

27. The method according to claim 20 wherein the disease is heart failure with preserved ejection fraction.

28. A pharmaceutical composition comprising a compound, or a pharmaceutically acceptable salt thereof, or a tautomer thereof, or a hydrate thereof, according to claim 7, and one or more pharmaceutically acceptable excipients.

29. A method of treating an Nrf2-regulated disease or disorder which is heart failure, which comprises administering to a subject in need thereof, a therapeutically effective amount of a compound according to claim 7, or a pharmaceutically acceptable salt thereof, or a tautomer thereof, or a hydrate thereof.

30. The method according to claim 29, wherein the disease or disorder is heart failure with reduced ejection fraction.

31. The method according to claim 29, wherein the disease or disorder is heart failure with preserved ejection fraction.

* * * * *